United States Patent [19]

Okayama et al.

[11] Patent Number: 5,747,339

[45] Date of Patent: May 5, 1998

[54] NON-A, NON-B HEPATITIS VIRUS GENOMIC CDNA AND ANTIGEN POLYPEPTIDE

[75] Inventors: Hiroto Okayama, Minoo; Isao Fuke, Takamatsu; Chisato Mori, Kanonji; Akihisa Takamizawa, Kanonji; Iwao Yoshida, Kanonji, all of Japan

[73] Assignee: Research Foundation for Microbial Diseases of Osaka, Osaka, Japan

[21] Appl. No.: 324,977

[22] Filed: Oct. 18, 1994

Related U.S. Application Data

[60] Continuation of Ser. No. 99,706, Jul. 30, 1993, abandoned, which is a division of Ser. No. 769,996, Oct. 2, 1991, abandoned, which is a continuation-in-part of Ser. No. 635,451, Dec. 28, 1990, abandoned.

[30] Foreign Application Priority Data

| Jun. 25, 1990 | [JP] | Japan | 2-167466 |
| Aug. 31, 1990 | [JP] | Japan | 2-230921 |
| Nov. 9, 1990 | [JP] | Japan | 2-305605 |

[51] Int. Cl.⁶ .................. A61K 39/29; A61K 39/00; A61K 39/12; C07K 14/00
[52] U.S. Cl. .................. 435/350; 424/184.1; 424/486.1; 424/189.1; 424/204.1; 424/228.1; 435/71; 435/69.1; 435/69.3; 530/350; 530/403; 930/223
[58] Field of Search ............... 424/184.5, 186.1, 424/189.1, 204.1, 228.1; 435/69.1, 69.3; 530/350, 403; 930/223

[56] References Cited

U.S. PATENT DOCUMENTS

| 4,542,016 | 9/1985 | Trepo | 424/86 |
| 5,350,671 | 9/1994 | Houghton et al. | 435/5 |

OTHER PUBLICATIONS

Farci et al., "Lack of Protective Immunity Against Reinfection with Hepatitis C Virus", Science 258, 135–140, 1992.

Kato et al., "Molecular cloning of the human hepatitis C virus genome from Japanese patients with non–A, non–B hepatitis", Proc. Natl. Acad. Sci. 87, 9524–9528, 1990.

*Primary Examiner*—Marian C. Knode
*Assistant Examiner*—Henry E. Auer
*Attorney, Agent, or Firm*—Armstrong, Westerman, Hattori, McLeland & Naughton

[57] ABSTRACT

Disclosed is an isolated non-A, non-B hepatitis virus genomic cDNA covering the entire region of the virus gene nucleotide sequence from the 1st to 9416th nucleotides shown in FIG. 2(1) through FIG. 2(16) hereof, wherein the coding region is from the 333rd to 9362nd nucleotides, and the 5'- and 3'-noncoding sequences contain 332 nucleotides and 54 nucleotides, respectively. Part of the cDNA and an antigen polypeptide as an expression product thereof are useful as a diagnostic reagent for non-A, non-B hepatitis. The antigen polypeptide is also useful as an active ingredient for a non-A, non-B hepatitis virus vaccine.

2 Claims, 18 Drawing Sheets

FIG. 2(1)

```
  1  CGATTGGGGGCGACACTCCACCATAGATCACTCCCCTGTGAGGAACTACTGTCTTCACGCAGAAAGCGTCTAGCCATGGGGTTAGTATGAGTTGTCGTGCAGCCTCCAGGACCCCCCTCC
     GCTAACCCCCGCTGTGAGGTGGTATCTAGTGAGGGACACTCCTTGATGACAGAAGTGCGTCTTTGCAGATGGTACGCAATCATACTCACAGCACGTCGGAGGTCCTGGGGGGAGG

121  CGGGAGAGCCATAGTGGTCTGCGGAACGGTGAGTAGTAGTACACCGGAGTACACCGGAGTCCTTCTTGGATCAACCGGCTCAATGCCTGGAGATTGGGGGTGCCCCGCGAGACTG
     GCCCTCTCGGTATCACCCAGAGCGCCTGGCCTCATGGGCCACTCAATCGGTCCTGCTGGCCCAGGAAGAACCTAGTGGGCGAGTTACGGACCTCTAAACCGCACGGGGGCGCTCTGAC

MetSerThrAsnProLysProGlnArgLys
241  CTAGCCGAGTAGTCGTTGGGTGCGCGAAAGGCCTTGTGGTGCCTGATAGGGTGTTGCGAGTGCCCGAGTGCTCTCGTAGACCGTGCACCATGAGCACGAATCCTAAACCTCAAAGAA
     GATCGGCTCATCACAACCCAGCGCTTTCCGGAACTTCCCACAGGACTATCCCACAGAAGCTCACGGGCCCTCCAGAGCATCGTCCAGACATCTGCTACTCGTGCTTAGGATTTGGAGTTTCTT

ThrLysArgAsnThrArgArgProGlnAspValLysPheProGlyGlyGlyGlnIleValGlyGlyValTyrLeuLeuProArgArgGlyProArgLeuGlyValArgAlaProArg
361  AAACCAAACGTAACACCAACCGCCGCCACCAAGCTTCCGGGACGTCAAGTTCCCGGGACCGGTTGCATGGTTGCAGATGTTGGTGAGTTACCGTGTTGCCGCCAAGGCCCAGGTTGGGTGCCGCGCCA
     TTTGGTTTGCATTGTGTTGGCGGCGGTGGTTCGAAGGCCCTGCAGCATGACAACGGGGTCCCCGGGTCCAACCCACACGCGCGGGT

LysThrSerGluArgSerGlnProArgGlyArgArgGlnProIleProLysAlaArgArgProGluGlyArgThrAlaGlnProGlyTyrProLeuTyrProGlyAsnGluGly
481  GAAGACTTCCAGCGGTCGCAACCTCGTGAAGGCGACAACCTATCCCCAAGGCTCCGCCGCCCAGAGGCTGGGCTCAGCCCGGTACCCTGGCCTCTCTATGGCAATGAGG
     CCTTCTGAAGGCTCGCCAGCGGTTGGAGCACCTTCGCGTCTTGTTTGAATAGGGGTTCGAGCGGCGGCGGGCTCCGTCCTGACCGAGTCGGCCCATGGGAACCGGAGAGATACCGTTACTCC
```

FIG. 2(2)

```
         LeuGlyTrpAlaGlyTrpLeuLeuSerProArgGlySerArgProArgArgArgSerArgAsnLeuGlyLysValIleAspThrCysGlyPhe
     GCTTAGGGTGGGCAGGATGGCTCTGTCACCCGGCTCCCGGCTCCCGGCCTAGTTGGGCCCCACGGACCCCGGGTAGTCGGTAATTTGGGTAAGGTCATCGATACCCTCACATGCGGCT
601  CGAATCCCACCACCCGTCCTACCGAGGACAGTGGGCCCGATCAACCCGGGGCCGAGGGCCCGATCAACCCGGGCTGCCTGGGGCCCGGGTGCCTCCAGCGCATTAACCCATTCCAGTAGCTATGGAGTGTACGCCGA

AlaAspLeuMetGlyTyrIleProLeuValGlyAlaProLeuGlyGlyAlaLeuAlaArgAlaLeuAlaHisGlyValLeuGluAsnTyrAlaThrGlyValAsnLeuPro
     TGGCCGATCTCATGGGTACATTCCGGTCGTCGGCCCCCCTGGGGCGCTGCCAGGGCCCTGCACATGGTGTCCGGTTCTGGAGGACGGCTGAACTATGCAACAGGAATCTGC
721  AGCGGCTAGAGTACCCCATGTAAGGCGAGCAGCCGGGGGACCCCGGGAGGGTCCGGACGTGTACCACAGGCCAAGACCTCTGCCGCACTTGATAGTTGTCCCTTAGACG

GlyCysSerPheLeuLeuAlaLeuLeuSerCysLeuThrProAlaSerAlaTyrGluValHisAsnValSerGlyIleTyrHisValThrAsnAspCysSerAsnAla
     CCGGTTGCTCTTTTCTATCTCCCTTCGGCTCTGCTCCTGCTCCTGACCCCAGTTCCGTTCACCACCCCAGCCCCAGTGTCCGGATATATCATGTCCGGAGTCCACAAGTGCACAAGTGCACCAAGACTGCTCAACG
841  GGCCAAGCGAGAAAAGATAGAAGGAGAACGGAGACACAGGATGGTCGGGTGAAGGGAATGCTTCAGGTGCTTGAAGGGAATGCTTCAGGTGTTGCACAGCCCTATAGTACAGTGTCTGCTGAGGAGGTTGC

SerIleValTyrGluAlaAlaAlaAspLeuIleMetHisThrProGlyCysValProCysValArgGluGlyAsnSerSerArgCysTrpValAlaLeuThrProThrLeuAlaAlaArgAsn
     CAAGCATTGTGTATGAGGCAGCAGCGGACTTGATCATGCATACCCCTGGTTGCGTGCCCTGCGTTCGGGAAGCAACTCCTCCGGCTGCTCACTCCCAGCTCGCAGCCAGGA
961  GTTCGTAACACATACTCCGTCCTGAACTACTGTATGAGGACGCACCCAGCACGACAAGCCCTTCCGTTGAGGAGGGCGACACCCATGCAGTGAGGGTGCGAGGTCGTCCT

ValThrIleProThrThrIleArgArgHisValAspLeuLeuValGlySerLeuCysGlySerAlaMetTyrValGlyAspLeuCysGlySerValPheLeuValSerGlnLeu
     ACGTCACCATCCCACCACCACGATACGAGCCACGTGATCTGCTCGTTGGGGCGGCTGCTTTCTGTTCCGCTATGTAGTGGGGACCTTCTGGGACTTGGGGATCTGTTTTCCTGTCTCAGC
1081 TGCAGTGGTAGGGGTGGTCGTCCTATGCTGCCGGTGCCAGCTAGACGAGCTAGACGAGCAACCCGCACGAAAGACAAGGCGATACATGCACCCCTGGAGACGCCTAGACGCTAGAGACAAAGGAGCAGAGAGTCG
```

FIG. 2(3)

```
                PheThrPheSerProArgArgIleValThrLeuGlnAspCysAsnCysSerIleTyrProGlyIleValSerGlyIleHisArgMetAlaTrpAspMetMetAsnTrpSerProThrThr
1201  TGTTCACCTTCTCGCCTCGCCGGCATGTGACATTACAGGAGACTGTAACTGCTCAATTTATCCCGGCATTGTGGGTTCACCGTATGGCTTGGGACATGATGAATTGGAGTCCGACCACAA
      ACAAGTGGAAGAGGCGGAGGGCGGCCGTACACTGTAATGTCCTGACATTGACGAGTTAAATAGGGCCGTACACAGCCAGTGGCATACGGAACCCTGTACTACTGACCAGGGGTGTT

AlaLeuValSerGlnLeuLeuArgIleProGlnAlaValAlaValAspMetValAlaGlyLeuAlaGlyLeuAlaTyrSerMetAlaGlyLeuAsnTrpAlaLys
1321  CAGCCCTAGTGTGTGCAGTTACTCCGGATCCCACAAGGCGTCGTGGACATGGTGGCGGGGCCTTGCTGGGGAGTCCTGGCGGCCTTGCCTACTATTCCATGGCGGGAACTGGCTA
      GTCGGGATCACCACAGGGTCAATGAGGGCTAGGGTGTTCCGGCAGCACCTGTACCACCGCGGGTTCCGGACCCCTCAGGACGCCCGGAACGGATGATAAGTACCGCCCCTTGACCGAT

ValLeuIleValMetLeuLeuPheAlaGlyValAspGlyValAlaGlnAlaSerMetPheAsnArgLeuValSerMetPheAlaSerGlyProSerGlnLys
1441  AGGTTCTGATTGTGATGCTACTTTTTGCTGGGTTGACGGGATACCCAACGCTGACAGGGGGCAAGCCAAACACCAACAGGCTCGTGTCCATGTTCGCAAGTGGGCCGTCTCAGA
      TCCAAGACTAACACTACGATGAAAAACGACGACCCAACTGCCCCCGGTTCTGCCACGTCCCCGTTTGGTTGTCGAGCAGGTACAAGGGTTCACCGGCAGAGTCT

IleGlnLeuIleAsnThrAsnGlySerTrpHisIleAsnArgThrAlaLeuAsnCysAsnAspSerLeuGlnThrGlyPheLeuAlaAlaLeuPheTyrThrHisSerPheAsnSerSer
1561  AATCCAGCTTATAAACACCAATGGGAGTTGGCACATCAACAGGACTGCCCTGAACTGACTCTCTCCAGACTGGTTTCTTGCGCGCTGTTCTTACACATAGTTTCAACTCGT
      TTTAGGTCGAATATTTGTGGTTACCCTCAACGGTGTAGTTGTCCTGACGTGACTTGACTGAGTTGACCGCAAAGAAGGGCGACAAGATGTGTATCAAGTTGAGCA

GlyCysProGluArgMetAlaGlnCysArgMetAlaGlnCysArgIleThrIleThrTyrAlaGluSerSerArgSerAspGlnArgProCysTrpHisTyrPro
1681  CCGGGTGCCCAGAGCGCATGGCCCAGTGCCGCAGTGCCGCAGTTGACCAAGTTGACACGGATGGGTCCCATTACTTATGCTGAGTCTAGCAGATCAGACCAGGCCATATTGCTGCACTACC
      GGCCCACGGGTCTCGGTACCGGGTCACGGGTGTAACTGTTCAAGCTGGTCCCTACCCAGGTAATGAATACGACTCAGATGTCTAGTCTCGGTCTCGGTAAGACGGTGATGG
```

FIG. 2(4)

```
      ProProGlnCysThrIleValProAlaSerGluValCysGlyProValTyrCysPheThrProSerProValValValGlyThrThrAspArgPheGlyValProThrTyrArgTrpGly
1801  CACCTCCACAATGTACCATCGTCCTGCGGAGTGTGCGGAGCCCAGTGTGCGGCCAGCCTGCTTCACCCCAAGCCCTGTCGTGGGAGACCGATCGTTTCGGTGTCCCTAGTATAGATGGG
      GTGGAGGTGTTACATGGTAGCATGGACGGCAGCCTCCACAGCCCGGTCACAGCAGCAGGAGTGGGGTTCGGACAGCAGGAGTGGGGTTCGACACACCCTGGCTAGCAGAAGCCACAGGGATGCATATCTACCC

GluAsnGluThrAspValLeuLeuAsnAsnThrArgProProGlnGlyAsnTrpPheGlyCysThrTrpMetAsnSerThrGlyPheThrLysThrCysGlyGlyProProCysAsn
1921  GGGAACGAGACTGACGTGCTGCTCAACAACACGGGCCCCGGCCAAGGCAACTGGTTCGGCTGCACATGAATGAATAGCACCGGGTTCACCAAGACATGTGGGGGCCCCCCGTGTA
      CCCTCTTGCTCTGACTGACGACGACGAGTTGTTGTGCCCGGGGCCGGTTCCGTTGACCAAGCCGAGCGTGTACCTAGTTATGTGGCCCAAGTGGTTCTGTACACCCCCCGGGGGACAT

IleGlyGlyValGlyAsnAsnThrLeuThrCysProThrAspCysPheArgLysHisProGluAlaThrTyrThrLysCysGlySerGlyProLeuThrProArgCysMetValAsp
2041  ACATGGGGGGTGGGCAACAACACCCTGACCTGCCCCACGGACTGCTTCCGGAAGCACCCCGAGGCTACCTACACAAATGTGGTTCGGGCCTTGGCCTGACACTAGGTGCATGGTTG
      TGTAGCCCCCCCAGCCGTTGTTGTGCCAGCGGGGTGCCTGACGAAGGCCTTCGTGGGGACTGGATGTGTTTTACACCAAGCCCGAACGACTGTGATCCACGTACCAAC

TyrProTyrArgLeuTrpHisTyrProCysThrValAsnPheThrIlePheLysValArgMetTyrValGlyValGluHisArgLeuAsnAlaAlaCysAsnTrpThrArgGlyGlu
2161  ACTATCCATACAGGCTCTGGCATTACCCCTGCACTGTTAACTTTACCATCTTCAAGGTTAGGATGTATGTGGGGGGGTGGAGCACAGCTCAATGCTGCATGCAATTGACCGAGGAG
      TGATAGGTATGTCCGAGACCGTAATGGGACGTGACAATTGAAAATGGTAGAAGTTCCAATCCTACATACACCCCCCACCTGTGTCCGAGTTAGAGTTAACCTGGCTCCTC

ArgCysAspLeuGluAspArgAspArgProGluLeuLeuSerProPheThrThrGluTrpGlnValLeuProCysSerPheThrThrGlyAlaLeuSerThrThrGlyLeuIle
2281  AGGTGTGACTTGGAGGACAGGGATAGGCCGGAGCTCAGCCCGTTCACACAGAGTGGCAGGTACTGCCCTGTTCCTTCCTCACCACCTGTTCGGTGGACAGGAGTGGAGACAGGTGACCGAACT
      TGCAACACTGAACCTCCTGCTCCGACAGGGAGAGGAGACAGATGTTGTCTCACGTCCATGACGGGACAAGGAAGTGGTGGACATGGTGGAGACAGGTGACCGAACT
```

FIG. 2(5)

```
          HisLeuHisGlnAsnIleValAspValGlnTyrLeuTyrGlyIleGlySerAlaValValSerPheAlaIleLysTrpGluTyrValLeuLeuLeuPheLeuLeuAlaAspAlaArg
2401 TTCACCTCCATCAGAACATCGTGACGTGCAATACCTACGGTATAGGGTCAGCGGTTGTCCTTTGCAATCAAATGGAGTATGTCCTGTTCCTGTTTCCTTTCCTTCTCCTAGCGACGGCAAC
     AGTCGAGTAGTCTTGTACACCTGCAGCTTCTTGCCATATATGGATATGCCATATCCAGTCGCCAACAGAGGAAACGTTAGTTTACCTCATACAGGACACGCAAAAGGAAGAGGATCGCCTGCGTG
          ValCysAlaCysLeuTrpMetMetLeuLeuIleAlaGlnAlaAlaAlaLeuAsnSerAlaSerValAlaGlyAlaHisGlyIleLeuSerPheLeuVal
2521 GTGTCTGTGCCTGCCTGTGTGATGATGCTGCTGATAGCCCAGGCCGCTTGGAGAACCTGGTCCTCAATTGGGTCTCTGGCCGGCCACATGGCATCCTCTCCTTCCTTG
     CACAGACACGGACGAACACTACTACGACGACTACGGGTCCGGGCTCCGGCCGACACCGCAGACACCGGCCGGCCGGCCGGTGTACGTGTAGGAGAGGAGGAAC
          PhePheCysAlaAlaTrpTyrTyrIleLysGlyArgLeuValProGlyAlaThrTyrAlaLeuTyrGlyValTrpProLeuLeuLeuLeuAlaLeuProProArgAlaTyrAlaMet
2641 TGTTCTTCTGTGCCGCTGCCTGGTACATCCAAAGGCAGGCTGGTCCCTGGGGCGACATATGCTCTTATGCGGTGCCGCCTGCTGTGCTGGCATTACCACCGCGAGCTTACGCCA
     ACAAGAAGACACGGCGGACGGACGGACCATGTAGTTTCCGTGCGCCAGGAGACCCGTGTATACGAGAAATACGCACACGGGAGGAGAGAACGACCGTAATGGTGGGGCTCGAATGCGGT
          AspArgGluMetAlaAlaAlaSerCysGlyGlyAlaValPheLeuValLeuLeuThrLeuSerProTyrTyrLysValPheLeuAlaArgLeuIleTrpTrpLeuGlnTyrPheThr
2761 TGGACCGGGAGATGGCTGCATCGTGCGAGCGCCGCCGGTTTTGTGGTCTGGTACTCCCTGACTTGTCACGTATACTACAAGGTGTTCCTGCTAGGCTCATATGGTGGTTACAATATTTTA
     ACCTGGCCCTCTACCGACGTAGCACGCCTCCGCGCCAAAAACACCCAGAGGACTGAAACAGTGGTATGATGTTCCACAAGGAGGATCCGAGTATACCAGTATACCACCAATGTTATAAAAT
          ThrArgAlaGluAlaAspLeuHisValTrpIleProProLeuAsnAlaArgGlyGlyArgAspAlaIleIleLeuMetCysAlaValHisProGluLeuIleThrLys
2881 CCACCAGAGCGAGGCGAGGGGACTTACATGTGGATCCCGCCCCCTCAACGTCGGGGAGGCCGGATGCCATCATCCTCATGTGCCAGTCCATCCAGAGCTAATCTTTGACATCACCA
     GGTGGTCTCGGCTCCGCTCACACTTACACACACCGTAGGGGGGGGAGTGGAGCCCCTCCGGCGCAGCCCCCCCAGGGGGAGTAGGAGGAGTACACGGTCAGGTAGGTCTGATTAGAAACTGTAGTGGT
```

FIG. 2(6)

```
          LeuLeuIleAlaIleLeuGlyProLeuMetValLeuGlnAlaGlyIleThrArgValProTyrPheValArgAlaGlnGlyLeuIleHisAlaCysMetLeuValArgLysValAlaGly
3001  AACTTCTAATTGCCATACTCGGTCCGTCATGGTGCTCCATGGTGCTCCAAGCTGGCATAACCAGAGTGCCGTACTTCGTGCGCGCTCAAGGGCTCATTCATGCATGTTAGTGCGGAAGTCGCTG
      TTGAAGATTAACGGTATGAGCCAGGCCAGTCCACGAGGTTCGACCGTATTGGTCTCACGGCAGTAAGCACGGCACGCGCGAGTAAGTACGTACAATCACGCTTCCAGCGAC
          GlyHisTyrValGlnMetAlaPheMetLysLeuGlyThrTyrIleTyrAsnHisLeuThrProLeuArgAspTrpProArgAlaGlyLeuArgAspLeuAlaValAlaAla
3121  GGGGTCATTTATGTCCAAATGGCCTTCATGAAGCTGGGCACGTACATTACAACCATCTTACCCGCTACGGATTGGCCACGCGGCGGGCCTAGGAGACCTTGCGGTGG
      CCCCAGTAATACAGGTTTACGGAAGTACTTCGACGCGCGACTGTCCGTGCCGACTGTAAATGTTGGTAGAATGGGCGATGCCCTAACCGGTGCGCGCCCGATGCTCTGGAACGCCACC
          ValGluProValValPheSerAspMetGluThrLysIleIleLeuThrTrpGlyAlaAspThrAlaAlaCysGlyAspIleIleLeuGlyLeuProValSerAlaArgArgGlyLysGluIle
3241  CAGTGGAGCCGGTCGTCTTCTCCGACATGGAGACCAAGATCATCACCTGGGGAGCCAGACACGGGCGTGTGGGACATCATCTTGGGTCTGCCCGTCTCCGCCCGAAGGGGAAAGGAGA
      GTCACCTCGGCCAGGCAGAGAAGAGAGGCTGTACTCTGGTTCTAGTAGTGGCTGCACAGCCCCTGTAGTAGAACCCAGAGGGCAGAGGCGGGCTTCCCTTTCCTCT
          LeuLeuGlyProAlaAspSerLeuGluArgGlyLeuLeuLeuGlyLysIleIleThrSerLeuThrGlyArg
3361  TACTCTGGGCCGGCCCGATAGTCTTGAAGGGCGGGGGTTGGACTCCTGGGACTCACGGCCTACTCCAACAGACCGGGCCTACTTGGTTGCATCATCACTAGCCTTACAGGCC
      ATGAGACCCGGCGGCCGGCTATCAGAAGTTCCCGCCCAACGCTGAGGAGCGGGGTAGTGCGAGCAACCAACGTAGTAGTGATGATGATCGGAATGTCCGG
          AspLysAsnGlnValGlnGlyGluValGlnValValSerThrAlaThrCysGlnSerPheLeuAlaThrCysValAsnGlyValCysTrpThrValTyrHisGlyAlaGlySerLysThrLeu
3481  GGGACAAGAACCAGTCGAGGGAGGAGAGTTCAGGTGGTTTCCACCGCAACACAATCTTCCTGGGACCTGCTCAACGGCGTGGTGTTGGACGTTACCATGGTGCTGGCTCAAAGACCT
      CCCTGTTCTTGGTCAGTCCAGCTCCCTCTCCAAGTCCACCAAAGGTTCCATTTGAGGACACGCTGCGACTGCAACTGGCAAATGGTACCACGACCGAGTTTCTGGA
```

FIG. 2(7)

```
     AlaAlaProLysGlyProIleThrGlnMetTyrThrAsnValAspGlnLeuValGlyTrpProLysProProGlyAlaArgSerLeuThrProCysThrGlySerSerAspLeu
3601 TAGCCGCGCCAAAGGGCCAATCACCCAGATGTACACTAATGTGGACCAGGACCTGGTTGGCTGGCCAAGCCCCCGGGGGCGGTTCCTTGACACCGTGCACCTGTGCAGCTCAGACC
     ATGGGCGGTTTCCCCGGTTAGTGGTCTACATGTGATTGTGGACCAGGAACTGTGGTACGTGGACACCGTGGACACCGTGAGTCTGG

TyrLeuValThrArgHisAlaAspValIleProValArgArgArgGlyAspSerArgGlySerLeuLeuSerProArgProValSerTyrLeuLysGlyGlyProLeuLeu
3721 TTTACTTGGTCACGAGACATGCTGACGTCATTCCGGTGGGCCGGGGGGACAGTAGGGGGAGCCTGTCTCTCCCCAGGCTCTGTCTACTTGAAGGGCTCTTGGGTGGTCCACTGC
     AAATGAACCAGTGCTCTGTACGACTGCAGTAAGGCCACGGCACCCGGCCCGCGCCCGGGTCCGGACAGAGGATGAACTTCCCGAGAAGCCCACCAGGTGACG

CysProPheGlyHisAlaValGlyIleProArgAlaAlaValCysThrArgGlyValAlaLysAlaAlaValAspPheValProValGluSerMetGluThrThrMetArgSerProValPhe
3841 TCTGCCCCTTCGGGCACGCTGTGGGCATCTTCCGGGCTGCCGTATGCACCCGGGGTTGCGAAGGCGGTTGGACTTTGTGCCGTAGAGTCCATGGAAACTACTATGGGTCTCCGGTCT
     AGAGGGGAAGCCGTGCCGACACCGGTGGAGGCCGTAGAAGGCCCGAGCGGCATCTCAGGTACGTCTTTGATGATACGGCCAGAGCCCAGA

ThrAspAsnSerProProAlaValProGlnSerPheGlnValAlaHisLeuHisAlaProThrGlySerGlyLysSerThrLysValProAlaAlaAlaGlnGlyTyrLys
3961 TCACGGACAACTCATCATCCCCCGGCCGTACCGCAGTCATTTCAAGTGGCCCACTGCCACTGCAGCGGGAAGAGTACTAAAGTGCCGGCTGCATATGCAGCCCAAGGTACA
     AGTGCCTGTTGAGTAGGGGCCGGCATGGGGTGAGTAAAGTTCACCGGGTGACGTGCCGTTCTCATGATTTCACGGCCGACGTATACGTGGGGTCCCATGT

ValLeuValLeuAsnProSerValAlaAlaThrLeuGlyPheGlyAlaTyrMetSerLysAlaHisGlyIleAspProAsnIleArgThrGlyValArgThrIleThrThrGlyAlaPro
4081 AGGTGCTCGTCCTCAATCCGTCCGTTGCCGCTACCTTAGGGTTTGGGGCGTATATGTCTAAGGCACACGGTATTGACCCCAACATCAGAACTCAGAACTGGGTAAGGACCATTACCACAGGCGCC
     TCCACGAGCAGGAGTTAGGCAGCAACGGCATGGAATCCCAAACCCGCATATACAGATTCGTGTGCCATAACTGGGTTGTAGTCTTGAGTCTTGACCCCATTCCTGGTAATGGTTCGGGG
```

FIG. 2(8)

```
        ValThrTyrSerThrTyrGlyLysPheLeuAlaAspGlyGlyCysSerGlyGlyAlaTyrAspIleIleIleCysAspGluCysIleIleSerThrThrIleLeuGlyIleGly
4201    CCGTCACATACTCTACCTATGGCAAGTTTCTTGCCATGGTGGTTGCTCTGGGGGCCTTATGACATCATAATATGTGACGAATCTGACTGACTGAACTGACAATCTGGGCATCG
        GGCAGTGTGATGAGATGGATACCGTTCAAAGAACGGCTACCAACCAGGAGACCCCGGAATACTGTAGTATTATACACTACTCACGTAGTTGACTGAGCTGATGTTAGAACCGTAGC

ThrValLeuAspGlnAlaGluThrAlaGlyAlaArgLeuValValLeuAlaThrProProGlySerValProHisProAsnIleGluValAlaLeuSerAsnThr
4321    GCACAGTCCTGGACCAAGCGGAGAGGGCTGGAGCGCGCCTTGTGCTGGCCACCCCGGATGGTCACCGTGCCACACCCAAACATGGAGGAGGTGGCCCTGTCTAATA
        CGTGTCAGGACCTGGTTCGCCTCTCGCGCGACCTCGCGCCGAACAGCACGACGGTGGCGATGCGGAGGCCTAGCCAGTGGCAGGGTGTGGGTTTGTAGCTCCTCACCGGACAGATTAT

GlyGluIleProPheTyrGlyLysLeuAlaIleProIleGluAlaIleArgGlyGlyArgHisLeuIlePheCysHisSerLysLysCysAspGluLeuAlaAlaLysLeuSerGlyLeu
4441    CTGGAGAGATCCCCCTTCTATGGCAAAGCTGCCATCCCCATTGAAGCCATCAGGGGGGAAGGCATTCATTTTCTGTCATTCCAAGAGAAGTGCGACGAGCTCGCCGCAAAGCTGTCAGGCC
        GACCTCTCTAGGGGAAGATACCGTTTCGACGGTAGGGGTAACTTCGGTAGTCCCCCCCTTCCGTAGTAAAAGACAGTAAGTTCTTCTTCACGCTGCTCGAGCGGCGTTTGACAGTCGG

GlyIleAsnAlaValAlaAlaTyrTyrArgGlyLeuAspValSerValIleProThrIleGlyAspValValValAlaThrAspAlaLeuMetThrGlyTyrThrGlyPheAspSer
4561    TCGGAATCAACGCTGTGGCGTATTACCGGGGGCTGATGTGTCCGTCATACCAACTATGGAGACGTCGTTGTCGTGGCAACAGACGCTCTGATGACGGCGTATACGGCGACTTTGACT
        AGCCTTAGTTGCGACACCGCATAATGGCCCCCGAGCTACACAGGCATGGTTGATAGCCTGCAGCAACAGACCGTTGTCTGCGAGACTACTGCCGATATGCCGCTGAAACTGA

ValIleAspCysAsnThrCysValThrGlnThrValAspPheSerLeuAspProThrPheThrIleGluThrThrValProGlnAspAlaValSerArgSerGlnArgArgGlyArg
4681    CAGTGATCGACTGTAACACATGTGTACACAGTAGACTTCAGCTTGGATCCCACCTTCACCATTGAGACGACGGTGCCTCAAGACGCAGTGTCCGCTCCAGCGCGCGGGGTA
        GTCACTAGCTGACATTGTGTACACATGTGTCAGATCGAACAGTCGAAGTCGAACCTAGGGTGGAAGTGGTAACTCTGCTGGCACGGAGTTCGCGTCACAGGCGGAGCTCGCCGCCCAT
```

FIG. 2(9)

```
     ThrGlyArgArgGlyIleTyrArgPheValThrProGlyGluArgProSerGlyMetPheAspSerSerValLeuCysGluCysTyrAspAlaGlyTyrGluLeu
4801 GGACTGGCAGGGGTAGGAGAGGCATCTACAGGTTTGTGACTCCGGGAGAACGGCCCTGGGATGTTCGATTCCTCGGTCCTGTGAGTGCTATGACGCGGGCTGTGCTTGGTACGAGC
     CCTGACCGTTCCCATCCTCTCGTAGATGTCCAAACACTGAGGCCCTCTTGCCGGAGCCGTACAGCTAACGAGCCAGGACCCGTACAACTGGCCGACAGGAACCATGCTCG

ThrProAlaGluThrSerValArgLeuArgAlaTyrLeuAsnThrProGlyLeuProValCysGlnAspHisLeuGluPheTrpGluSerValPheThrGlyLeuThrHisIleAspAla
4921 TCACCCCGGCCGAGACCTCGGTTAGGTTGCGGGCTACTGAACACACCAGGGTTGCCGTTTGCCAGGACCACCTGAGTTCTGGAGACCTCACAGGCCTCACCCATAGATG
     AGTGGGGCCGGCTCTGGAGCCAATCCAACGCCCGATGACTTGTGTGGTCCCAAACGGGCAAACGGTCCTGGTGGAACTTCAAGACCCTCTCACAGAAGTGTCGGAGTGGTATATCTAC

HisPheLeuSerGlnThrLysGlnAlaGlyAspAsnPheProTyrLeuValAlaTyrGlnAlaThrValCysAlaArgAlaGlnAlaProProSerTrpAspMetTrpLysCys
5041 CACACTTCTTGTCCCAGACCAAGCAGCAGGAGACAACTTCCCCTACCTGGTAGCAGTCCGTGTGCGCCAGGGCTCAGGCCCCACCTCCATCATGGGATCAAATGTGGAAGT
     GTGTGAAGAACAGGGTCTCGTTCGTCCTCTGTTGAAGGGATGGACCATGTCATGGTTCGGTGCCACAGCGGTCCGAGTCCGGGGTGGAGGTAGTACCCTAGTTTACACCTTCA

LeuIleArgLeuLysProThrLeuHisGlyProThrProLeuLeuTyrArgLeuTyrLeuAlaValGlnAsnGluValThrThrProIleThrLysTyrIleMetAlaCysMetSer
5161 GTTCTCATACGGCTGAAACCTGCAAACCTAGCTGCACGGCCAACACCTGCTGTACAGGCTGGAGCCGTCAGAATGAGGTCACCTCACCCCATAACCAAATACATCATGGCATGCATGT
     CAGAGTATGCCGACTTTGGATGGACGTGCCCGGTTGTGGACACGATGTCCGACCCTCGGCCAGGTCTTACTCCAGTGGGTATTGGTTATGTAGTACCGTACGTACA

AlaAspLeuGluValThrSerThrTrpValLeuValGlyValLeuAlaAlaLeuAlaAlaTyrCysLeuThrThrGlySerValValIleValArgIleIleLeuSerGly
5281 CGGCTGACCTGACGTGCAGTGGCCCTGGTCTGAGCACCTGGGCTGCTGGTGGCGGAGTCCTTGCGCGCTCTGGCCGCGTATTGCCCTGACAACAGGCAGTGTGGTCATTGTGGTAGGATTATCTTGTCCG
     GCCGACTGGACCTGACGTGATCGTGACCCACGACCACCCGGACCCGCCCCATAACGAGACGTCCGAGACCGGACGATAACCGCATAACCAGTAACACCAGTAACACCCATCCTAATAGAACAGGC
```

FIG. 2(10)

```
                ArgProAlaIleValProAspArgGluLeuLeuTyrGlnGluPheAspGluMetGluGlnGlyMetGlnLeuAlaAlaGluAlaGlnPheLysGln
5401   GGAGGCGGCCATTGTTCCCGACAGGGAGCTTCTCTACCAGGAGTTCGATGAAATGGAGCAGGGAATGCAGCTCGCCGAGCAATTCAAGC
       AGAGTGAAGAGTGGCCCTCGCACCTCCTTACATCGAGCAGGGAATGCAGCTCGCCGAGCAATTCG
       CCTCCGGCCGGTAACAAGGGCTGTCCCTGGCAGCTACTTCTCCAAGCTACTTCTCACCGCGAGGGTGAGGAGGAATGTAGCTCGTCCCTTAGTCGAGGGGCTCGTTAAGTTCG

LysAlaLeuGlyLeuLeuGlnThrAlaThrLysGlnAlaAlaGluAlaProValGluSerLysTrpArgAlaLeuGluPheAlaLysHisMetTrpAsnPheIleSer
5521   AGAAAGCCCTCGGTTACTGCAAACAGCCACCAAACAGGGAGCCTGTGCTCCCGTGGTGAGTCCAAGTGGCGAGCCCTTGAGACATTCTGGCGAAGCACATGTGGAATTTCATCA
       TCTTTCGGAGCCCAATGACGTTTGTCGGTGTTGTTCGCCTCCGACGACGAGGCACCACTCAGGTTCACCGTCGGGAACTCTGTAAGACCCGTCTTGTGTACACCTTAAAGTAGT

GlyIleGlnTyrLeuTyrLeuAlaGlyLeuSerThrLeuProGlyAsnProAlaIleAlaSerLeuMetAlaThrAlaPheAlaSerIleThrSerProLeuLeuPheAsn
5641   GCGGGATACAGTACTTACGCAGGCTTATCCACTCTGCCTGGAAACCCCGCCAATAGCATTCAGAGCATTGATGGCATTCACCAGCCGCTCACCACCAAAGTACCCTCCTGTTTA
       CGCCTATGTCATGAATCGTCCGAATAGGTGAGAGGACCCTTGGGGCGTTATCGTAAGTCAGTAGTGTCGATAGTCGGGCGAGTGGTGTGGGTTCATGGGAGGACAAAT

IleLeuGlyGlyTrpValAlaAlaGlnLeuAlaProSerAlaAlaSerAlaAlaPheValGlyAlaGlyIleAlaGlyAlaAlaValGlySerIleGlyLeuGlyLysValLeuValAsp
5761   ACATCTTGGGGGGGGTGGCTGTCCTCCCAACTCGCCCCCCCAGCGCCCTTGGCGTTCGTTGGGGCCCGGCATGCGGTGGGCGTTGGCAGCCCTTGGCAGCATAGGCCTTGGGAAGGTTGTTGTGG
       TGTAGAACCCCCCCACCGACCGGGTTGAGCGGGGAGGGGTGGCGGGAGCCGAAGCCAGCCGAGGCTAGCCCGACACGCTGTATCGGAACCCTTCCAGACACC

IleLeuValAlaGlyTyrGlyAlaLeuValAlaLeuValAlaPheLysValMetSerGlyMetProSerThrGluAspLeuValAsnLeuLeuProAlaIleLeuSerProGly
5881   ACATTCTGGCGGGGTTATGGAGCAGGAGTGGCCGGGCGGCCGCTCGGTGGCCTTTAAGGTCATGAGCGGGCGAGATGCCCTCCACGGAGGACCTGGTCAATCTACTTCCTGCCATCTCTCCTG
       TGTAAGACCGCCCAATACCTGTCCTCACCGGCGCCGGCGCGCGAGCACCGGAAATTCCAGTACTCGCCGCTCTACGGGAGTGGCTCCTGACCAGTTAGATGAAGGACGGTAGGAGAGGAC
```

FIG. 2(11)

```
                   AlaLeuValValGlyValValCysAlaAlaAlaIleLeuArgArgHisValGlyProGlyGluGlyAlaValGlnTrpMetAsnArgLeuIleAlaPheAlaSerArgGlyAsnHisValSer
6001  GCGCCCTCGTCGTCGGGGTCGTGTGTGCAGCAGCAATACTGCCTCGACACGTGGGTCCGGAGAGGGGCTGTGCAGTGGATGAACCGGCTGATAGCGTTCGCCTCGCGGGTAATCATGTTT
      CGCGGGACCAGCAGCCCCAGCACACAGTCGTTATGACGCAGCAGTTGTGCACCCAGACAGTCACCTACTCGCCGACTATCGCAAGCGAGCGAGCGCCCATTAGTACAAA

ProThrHisTyrValProGluSerGlyAspAlaAlaAlaArgValThrGlnIleLeuLeuSerSerLeuThrIleThrGlnLeuLeuLysArgLeuHisGlnTrpIleAsnGluAspCysSerThr
6121  CCCCCACGGACTATGTGCCTGAGAGCGAGCCGCAGCGGGTGTTACTCAGATCCTCCAGCTTACCATCACTCAGCTGCTGAAAAGGCTCCACCAGTGATTAATGAAGACTGCTCA
      GGGGGTGCCTGATACACGGACTCTCGCTCGGGGTCGCCCAGCACTCTAGGAGAGGTCGAATGAGTGAAGCACCTTTCCGAGGTGGTCACCTAATTACTTCTGAGGAGGT

ProCysSerGlySerTrpLeuArgAspValTrpAspPheLysThrValLeuThrAspPheCysThrValLeuThrAspPheLysSerLysLeuLeuProGlyValProPheSer
6241  CACCGTGTTCCGGCTCGTGGCTAAGGGATGTTTGGGACTGGATATGCACGGTTGACTTCAAGACCGTGCCTCCAGTCCTGCCGCAGCTACCTGAGTCCCTTTTTCT
      GTGGCACAAGGCCGAGCGCATTCCCTACAAACCCTGACTATACGTGCCACAACTGACTGAAGTTCTGGACCGAGGTCAGTTCGAGGACGGGTCGATGGACTCAGGGAAAAAGA

CysGlnArgGlyTyrLysGlyValTrpArgGlyAspGlyIleMetGlnThrThrCysProCysGlyAlaGlnIleThrGlyHisValLysAsnGlySerMetArgIleValGlyProLys
6361  CGTGCCAACGCGGGTACAAGGGAGTCTGGCGGGGAGACGGCATCATGCAAACCACCTGCCCATGTGAGCACAGATCACCGACATGTCAAAAACGGTTCCATGAGGATCGTCGGCCTA
      GCACGGTTGCGCCCATGTTCCCTCAGACGCCGCCTCTGCCGTAGTACGTTGGTGAGCGGTACACCTGTCTAGTGCCTGCCTAGACGTTTTGCCAAGGTACTCCTAGCAGCCGGAT

ThrCysSerAsnThrTrpHisGlyThrThrProIleAsnAlaTyrThrThrProSerProAlaProAsnTyrSerArgAlaLeuTrpArgValAlaAlaGluTyr
6481  AGACCTGCAGCAACACGTGCACGTGGCATGAACATTCCCATCAACGCATACACCACCACGTCCCGGGCCCCTGCACACCTCTCCAGCGCCAAACTATTCTAGGGCGCTGTGGCGGTGGCCGCTGAGGAGT
      TCTGGACGTCGTTGTGCACGTGCACCGTACCTTGTAAGGGGTAGTTGCGTATGTGGTGCCCGGGACGTGTGGAGAGGTCGCGAGAGGTCGGCGGTTCGGCGTTGATAAGATCCCGGACACCGCCACCGGCGACTCCTCA
```

FIG. 2(12)

```
         ValGluValThrArgValGlyAspPheIleTyrValThrGlyMetThrThrAspAsnValLysCysProCysGlnValProAlaProGluPhePheSerGluValAspGlyValArgLeu
6601  AGTGGAGGTCACGCGGGTGGGGATTTCCACTACGTGACGGGCATGACCACTGACAACGTAAAGTGCCCATGCCCAGGTTCGGCTCCTGAATTCTTCTCGGAGGTGGACGGAGTGCGGT
      TCACCTCCAGTGCGCCACCCCCTAAAGGTGATGCACTGCCCGTACTGGTGACTGTTGCATTTCACGGGTACGGTCCAAGGCGAGCCTTCCACGTCCTCAGCCA

HisArgTyrAlaProAlaCysArgProLeuLeuArgGluValThrPheGlnValThrPheGlnLeuProCysGlnLeuProCysGluProGluProCysValAlaVal
6721  TGCACAGTAGCTCCGGCTGCAGCCTCTCCTACGGAGGAGAGTTACATTCCAGGTGCGGCTCAACCAATACCTGGTTGGTCACAGTGCTACCACCATGGAGCCGAACCGGATGTAGCAG
      ACGTGTCCATGCGAGGCGCCACGTCGGAGGAGATGCCCTCCTCCAATGAAGGTCCAGCCGAGTTGGTTATGGACCAACCAGTGTCGATGGTAGCCTCGGCTTGGCCTACATCGTC

LeuThrSerMetLeuThrAspProSerHisIleThrAlaGluThrAlaLysArgLeuAlaArgGlySerProProSerLeuAlaSerGlnLeuSerAlaProSer
6841  TGCTCACTTCCATGCTCACGACCCTCACACATCCCACATCTCCCACGCTCACGAGAAACGGCTAAGGGTAGGTTGGCCAGGGTCTCCCCCTCCTTGGCCAGTCCTTCAGCTAGCCAGTTGTCTGGCCTT
      ACGAGTGAAGGTACGAGTGCTGGGAGGGTAGTGTGGTCTTTGCCGATTGGCATCCAACCGGTCCCCAGAGGGGAGGAACCGGTCGAGAAGTCGATCGGTCAACAGACGCGGAA

LeuLysAlaThrCysThrThrHisValSerProAspAlaAspLeuIleGluAlaAsnLeuLeuTrpArgGlnGluMetGlyGlyAsnIleGluSerGluAsnLysVal
6961  CCTTGAGGGGACATGCACTGACTACCACCATGCTCTCCGGACGCTGACCTCATGGAGCCAACCTCCTGTGCGGCAGGAGATGGCCGGAACATCACCCGGTGGAGTCGGAGAACAAGG
      GGAACTTCCGCTGTACGGTGATGGTGTGGTAGTCAGAGAGGCCTGCGACTGGAGTAGCTCCGGTTGGAGGACACCGCCGTCCTCTACCGGCCACTCAGCCTTCTTGTTCC

ValValLeuAspSerPheAspProLeuArgAlaGluAspGluArgGluIleLeuArgLysSerLysPheProAlaAlaMetProIleTrpAlaArg
7081  TGGTAGTCCTGGACTCTTTGACCGCTCGAGCCGGAGGATGAGAGGAGAAGTATCCGTTCCGGCGGAGATCCTGCGGAAATCCAAGAAGTTCCCCGCAGCGATGCCCATCTGGGCGC
      ACCATCAGGACCTGAGAAAGCTGGAGCTCGGCGCTCAGGCCGGTCCTTAGGAGGCTTTAGTTCTTCAAGGGCGTCGCTACGGGTAGACCCCG
```

FIG. 2(13)

```
                  ProAspTyrAsnProProLeuGluSerTrpLysAspProProValHisGlyCysProLeuProProIleLysAlaProProIleProProProArgArgLys
7201 GCCCGGATTACAACCCTCCACTGTTAGAGTCCTGGAAGGACCCGGACTACGTCCCTCCGTTGTGACGGGTGCCCGTTGCCACCTATCAAGGCCCCTCCAATACCACCTCCAGGAGAA
     CGGGCCTAATGTTGGGAGGTGACAATCTCAGGACCTTCCTGGGCTCAGGGAGGAGGCCACAGGGCAAGGTGGATAGTTCCGGGAGGTTATGGTGGAGGTGCCTCTT

ArgThrValLeuThrGluSerSerValSerSerAlaLeuLeuAlaGluLeuAlaThrLysThrPheGlySerSerGlyThrAlaValAspSerGlyThrAlaLeuProAsp
7321 AGAGGACGGTTGTCCTAACAGAGTCCTCCGTGTCTTCGCCTTAGCGGAGCTGCTACTAAGACCTTCGGCAGCTGCTACTAAGACCTTCGGCAGCTCGAATCATCGGCCGTCGACAGGGCACGGGGACGGCCTTCCTG
     TCTCCTGCCAACAGGATTGTCTCAGGAGCACAGAGAAGCGGAATGCCTTAGTGAGGCGTGAGCGTTAGTAGCCGGCAGCTGTCGCCGTCGCCGTCGGCGGAAGGAC

GlnAlaSerAspAspGlyAspLysGlySerTyrSerAspValGluSerTyrSerSerMetProProLeuGluGlyProAspGlyLeuProAsnGlySerTrpSerGlu
7441 ACCAGGCCTCCGACGACGGTGACAAAGGATCCGAGTTGAGTGTACTCCTCAGATGGAGCTCTCGATGGGGGACCCCTTGAGGGGGAACCGGAGGGGAACCGGAGGGGACCCGATCTCAGTGACGGGTCTTGGTCTACCGTGAGCG
     TGGTCCGGAGGCTGCTGCCACTGTTTCCTAGGCTGCAACTCAGAGTCTGCAACTCAGAGGAGTACGGGGGAACTCCCCTTGGCCCCTCAGAGTCACTGCCCAGAACCAGATGGCACTGGC

GluAlaSerGluAspValValCysCysSerMetSerTyrThrTrpThrGlyAlaAlaLeuIleThrProCysAlaAlaLeuGluSerLysLeuProIleAsnAlaLeuSerAsnLeuLeu
7561 AGGAAGCTAGTGAGGATGTCGTCTGCTGCTCAATGTCCTACACAGTGGACAGGGCCTTGATCACGCCATGGCTGCGGAGGAAAGCAACGTGCCATCAACGCGTTGAGCAACTCTTTGC
     TCCTTCGATCACTCACTCCTACAGCAGACGAGTTACAGGATGTGTACCTGTCCCGGAACTAGTGCGGTACGCGACGCCTCCTTCGTTCGACGGGTAGTTGCGCAACTCGTTGAGAAACG

ArgHisHisAsnMetValTyrAlaThrThrSerArgSerAlaGlyLeuArgGlnLeuLysValThrPheAspArgLeuGlnValLeuLysGluMet
7681 TGGCCACCATAACATGTTTATGCCACAACATCTCCAGGCAGGCTGGGCAGAAGAAGGTCACCTTTGACAGACTGCAAGTCCTGGACGACACTACGGGACGTGCTCAAGGAGA
     ACCGGTGGTATTGTACCAAATACGGTGTTGTAGAGGTGGGTCGGTCGGGACGGGTCCGGACGCGTCTTCTTCCAGTGGAAACTGTCTGACGTTCAGGACCTGCTGGTGATGGCCCTGCAGTTCCTCT
```

FIG. 2(14)

```
       LysAlaLysAlaSerThrValLysAlaLysLeuLeuSerValGluAlaAlaCysLysLeuThrProProHisSerAlaLysSerLysPheGlyTyrGlyAlaLysAspValArgAsnLeu
       TGAAGGCAAGCCGTCCACAGTTAAGCTAAACTCCTATCCGTAGAGGAAGCCTGCAAGCTGACCCCCACATTCGGCAAATCCAAGTTTGGCTATGGGCAAAGGACGTCCGGAACC
7801
       ACTTCCGCTTCCGCAGGTGTGTCAGGATAGCCATCTCCTTCGGACGTTCGACTGGGGGGTGTAAGCCGGTTTAGTTCAAACCGATACCCGTTTCCTGGAGGCCTTGG

SerSerLysAlaValAsnHisIleHisSerValTrpLysAspLeuLeuGluAspThrThrIleMetAlaLysAsnGluValPheCysValGlnProGluLys
       TATCCAGCAAGGCCGTTAACCACATCCACTCCGTGTGGAAGGACTTGCTGGAAGACACTGACACCACCATCATGGCAAAAAATGAGGTTTTCTGTGTCAACCAGAGA
7921
       ATAGGTGGTTCCGGCAATTGGTAGGTGAGGCACACCTTCCTGAACGACCTTCTGTGACACTGTGGTGGTAGTACGTTTTTACTCCAAAGACACAGGTTGGTCTCT

GlyGlyArgLysProAlaArgLeuIleValPheProAspLeuValLysMetAlaLeuTyrAspValValSerThrLeuProGlnValValMetGlySerSerTyr
       AAGGAGGCCTAAGCCAGCCCGCCTATCCTATTCCCAGATCTGGAGTCCGTGTATGCGAGAAGATGGCCCTCTATGATGTGTCCACCCTTCCTCAGGTCGTGATGGGCTCCTCAT
8041
       TTCCTCCGGCATTCGGTCGGCGCGAATAGCATAAGGGTCTAGACCCTCAGGCACATACGCTCTTCTACCGGAGATACTACACCAGAGGTGGGAAGGAGTCCAGCACTACCCGAGGAGTA

GlyPheGlnTyrSerProGlyGlnArgValGluPheLeuValAlaAsnThrTrpLysSerLysAsnProMetGlyPheSerTyrAspThrArgCysPheAspSerPheValThrGluAsn
       ACGGATTCCAGTACTCTCCTGGGCAGCAGTGAGTTCCTGGTGAATACCTGGAAATCAAAGAAAAACCCATGGGCTTTTCATGACACTCGCTGTTTGACTCAAGCGTCACGAGA
8161
       TGCCTAAGGTCATGAGAGTACCCGTCGTCACTCAGCTCAAGGACCACTTATGGAACCTTTAGTTTCTTTTTGGGTACCCGAAAAGTATACTGTGAGCGACAAAGCTGAGTGTGCCAGTGGCTCT

AspIleArgValGluGluSerIleTyrGlnCysCysAspLeuAlaProGluAlaArgGlnAlaIleLysSerLeuThrGluArgLeuTyrIleGlyProLeuThrAsnSerLysGly
       ACGACATCCGTGTTGAGGAGTCAATTTACCAATGTTGTGACTTGGCCCCCGAAGCCAGACAGGCCATAAAATGCTCACAGAGCGGCTTATATCGGGGTCCTCTGACTAATTCAAAAG
8281
       TGCTGTAGGCACCAACTCCTCAGTTAAATGGTTACAACACTGAACCGGGGGGCTTCGGTCTGTCTGCCGGTATTTAGCGAGTGTCGCGAAATATAGCCCCCAGGAGACTGATTAAGTTTTC
```

FIG. 2(15)

```
         GlnAsnCysGlyTyrArgArgCysArgAlaSerGlyValLeuThrThrSerCysGlyAsnThrLeuThrCysTyrLeuLysAlaSerAlaAlaCysArgAlaAlaLysLeuGlnAspCys
8401     GGCCAACTGCGGTTATCGCCGGTGCCCGGTGCCCCCGAGCGGGTGCTGACGGGTGCTGCGACTAGCTGCGGTAACACCCTCACATGTTACTTGAAGGCCTCTGCAGCCTGCGAAGCTCCAGGACT
         CCGTCTTGACGCCAATAGCGGCCACGGCCCGGCTGCCGCACGACTGCTGATGACGACGACTGATCGACGGATTGTGGAGTGTACAATGAACTTCCGGAGAGTGCACAGCTCGACGCTTGAGGTCCTGA

ThrMetLeuValAsnGlyAspAspLeuValIleCysGluSerAlaGlyThrGlnGluAspAlaAlaSerLeuArgValPheThrGluAlaMetThrArgTyrSerAlaProProGly
8521     GCACGATGCTCGTGAACGACGACGACCTCGTCGTTATCTGTGAAAGCGCGGGAACCCAAGAGGAGCGGGAGCCTACGAGTCTTCAGGAGGCTATGACTCGATACTCGGCGCCCCCCG
         CGTGCTACGAGCACTTGCCTCTGCAGCAGCAATAGACACTTTCGCGCCCTGCGGTTCCTGGTGTCTCAGAAGTCCTCGATGCTCGATACTGATCCATGAGGCGGGGGGC

AspProGlnProGluTyrAspLeuGluLeuIleThrSerCysSerSerAsnValSerValAlaHisAspAlaSerGlyLysArgValTyrTyrLeuThrArgAspProThrPro
8641     GGGACCCCCCAACCAGATACGACGTTGGAGCTGGAACTCATGTTCCTCAATGTGTCGGTGCCCAAGATGCATCAGGCAAAGGGTGTACTACCTCACCGTGACTCCCACCACCC
         CCCTGGGGGGGTTGGTCTTATGCTGAACCTCGACTTCGACACAAGGAGTTACACAGCCACAGCCACGGGTGCTAGTAGTCCGTTTTCCACATGATGAGTGGCACTAGGGTGGTGGG

LeuAlaAlaAlaTrpGluThrAlaArgHisThrProValAsnSerTrpLeuGlyAsnIleIleMetTyrAlaProThrLeuProGlyAlaArgMetIleLeuMetThrHisPhePheSer
8761     CCCTAGCACGGGCTGCGTGGGAGACAGCTAGACACACTCCAGTTAACTCCTGGCTAGGCAACATTATTATGTATGCCCCACTTTGTGGGCAAGGATGATTCTGATGACTCACTTCTCT
         GGGATCGTGCCCGACGCACCCTCTGTCGATCGATCGTCTGTGAGGTCAATTGAGGACCGATCCGTTGTAATAATACATACGGGTGAAACACCCGTTCCTACTACTAAGACTACTGAGTGAAGAGA

IleLeuLeuAlaGlnGluGlnLeuGluLysAspCysGlnIleTyrGlyAlaCysTyrSerIleGluProLeuAspLeuAlaArgLeuHisGlyLeuSerAla
8881     CCATCCTTCTAGCGCAGGAGCAACTTGAAAAAGCCCTGGACTGCCAGATCTACGGGGCCTGTTACTCCATTGAGCCACTTGACCTACCTCAGATCATTGAACGACTCCATGGCCTAGCG
         GGTAGGAAGATCGCGTCCTCGTTGAACTTTTTCGGACCTGACGGTCTAGATGCCCGGACACTGACGGTCTAGATGCCCGGGACTGTAACTCGGTGAACTGGATGAGTCTAGTAACTTCTGAGGTACCGGAATGC
```

FIG. 2(16)

```
                                                                                                    PheSerLeuHisSerTyrSerProGlyGluIleAsnArgValAlaSerCysLeuArgLysArgLeuGlyValProProLeuArgValTrpArgHisArgAlaArgSerValArgAlaArgLeu
9001  CATTTCACTCACTTCATATAGTTACTCCAGGTGAGTCAATAGGGTGGCTTCATGCCTCAGGAAACTTCGGGTACCTCAGGAGTCTGGAGAGTCTGGAGCATCGGGCGGCCAGGAGGTCCGGCGGCTAGCC
      GTAAAGTGAGGTATCAATGAGAGGTCCACTCAGTTATCCACCGAGTACGGAGTCCTTTGAACCCATGTCGGAACGCTCAGACCTCTGTAGCCCGGTCGTCGAGGCGGCGATCCG

LeuSerGlnGlyArgAlaAlaThrCysGlyLysTyrLeuPheAsnTrpAlaValLysThrLysLeuLysLeuThrProIleProAlaAlaSerArgLeuAspLeuSerGlyTrpPhe
9121  TACTGTCCCAGGGAGGGAGGGCCCCACTTGTGGCAAGTACCTCTTCAACTGGGCAGTAAAAACCAAACTTAAACTCACTCCAATCCCGGCTGCGTCCGGCTGGACTTGTCCGGCTGGT
      ATGACAGGGTCCCTCCCTCCGCGGGTGAACACCGGTTAATGGAGAGTTGACCGTCATTTTGGTTTGAATTTGAGTGAGGTTAGGGCCGACGCAGGCCGACCTGAACAGGCCGACCA

ValAlaGlyTyrSerGlyGlyAspAlaTyrHisSerLeuSerArgAlaArgProArgTrpPheMetLeuCysLeuLeuLeuSerValGlyValGlyIleTyrLeuLeuProAsnArg
9241  TGGTTGCTGGTTACAGCGGGGAGGAGACATATATCACAGGCCTGTCTCGTCGCCGACCCGTTGGTTCATGCTGCCTACTTCTGTAGGGTAGGCATCTACCTGTCCCAACC
      AGCAACGACCAATGTCGCCCCTCTGCGCCCCTCGTATAGTGCGGACAGAGCACCGGGCTGGGGCAACCAAGTACGACACGATGAAGGATGAAAGACATCCCATCCGTAGATGAGAGGGGTTGG

9361  GATGAACGGGAGGAGATAAACACTCCAGGCCAATAGGCCATCCCCTTTTTTTTTT
      CTACTTGCCCTCTATTTGTGAGGTCCGGTTATCCGGTAGGCGGAAAAAAAAAAA
```

NON-A, NON-B HEPATITIS VIRUS GENOMIC cDNA AND ANTIGEN POLYPEPTIDE

This application is a continuation of application Ser. No. 08/099,706, abandoned, filed Jul. 30, 1993, which was a division of application Ser. No. 07/769,996, abandoned, filed Oct. 2, 1991, which was a continuation-in-part of application Ser. No. 07/635,451, abandoned, filed Dec. 28, 1990 now abandoned.

BACKGROUND OF THE INVENTION

1. Field of the Invention

The present invention relates to a non-A, non-B hepatitis virus genomic cDNA and a non-A, non-B hepatitis virus antigen polypeptide. More particularly, the present invention is concerned with a non-A, non-B hepatitis virus genomic cDNA which is useful for producing a non-A, non-B hepatitis virus antigen polypeptide and with a non-A, non-B hepatitis antigen polypeptide which is an expression product thereof. The non-A, non-B hepatitis virus genomic cDNA of the present invention is also useful for genetically diagnosing non-A, non-B hepatitis. Further, the non-A, non-B hepatitis antigen polypeptide of the present invention is useful for producing a vaccine for non-A, non-B hepatitis, an immunoglobulin, a polyclonal or monoclonal antibody, an immunological diagnostic reagent, an agent for screening blood for transfusion and an agent for use in affinity chromatography for removing non-A, non-B hepatitis virus from blood for transfusion.

2. Discussion of Related Art

Definition of non-A, non-B hepatitis virus:

The viral hepatitis is a liver disease caused by the infection of a hepatitis virus. Heretofore, hepatitis A virus, hepatitis B virus and hepatitis D (delta) virus have been isolated and identified. The hepatitis D virus (delta-hepatitis virus) is a deficient virus which cannot multiply by itself and requires for its multiplication the co-presence of hepatitis B virus as a helper virus. Therefore, the hepatitis D virus is present only in a patient having hepatitis B. In 1974, it was reported that there were many patients having hepatitis caused by a factor other than the infection with either hepatitis A virus or hepatitis B virus. Such a hepatitis was named "non-A, non-B hepatitis", and researches on the non-A, non-B hepatitis virus have been made extensively and intensively throughout the world. Heretofore, it has been found that a plurality of types of non-A, non-B hepatitis viruses exist. Results of the researches up to now show that the non-A, non-B hepatitis virus is classified into two types according to the infection route, that is, an epidemic hepatitis virus, namely an enterically-transmitted non-A, non-B hepatitis virus, which is spread through water and food; and a blood transmitted non-A, non-B hepatitis virus which is spread through blood by transfusion, etc. Of the non-A, non-B hepatitis viruses, only an enterically-transmitted non-A, non-B hepatitis virus which spreads over the areas of Africa, India and Southeast Asia has been virologically identified, but the blood-transmitted non-A, non-B hepatitis virus has not yet been identified.

Hereinbelow, the blood-transmitted non-A, non-B hepatitis is often referred to simply as "NANB hepatitis", and the blood-transmitted non-A, non-B hepatitis virus is often referred to simply as "NANBV".

Current situation of the studies on NANB hepatitis and problems:

With respect to the epidemiology, clinical examination, diagnosis, treatment and prevention of the NANB hepatitis, virological studies have been made in the world by the comparison of NANBV with the other hepatitis viruses, based on the knowledge of diagnostics, histopathology, immunology, molecular biology and the like ["Japan Medical Journal", No. 3320, pp. 3–10, 1987; "Igaku-no Ayumi (Progress of medicine)", 151(13), pp. 735–923, 1989; "Kan Tan Sui (Liver, Gallbladder, Pancreas)", 21(1), pp. 5–113, 1990; "Jikken Igaku (Experimental Medicine)", 8(3), pp. 201–233, 1990]. With respect to the NANB hepatitis, the following findings have been reported.

(1) Epidemiology: In Japan, according to the estimation by the Ministry of Health and Welfare, about 60% of chronic hepatitis patients (namely about 720 thousand patients), about 40% of hepatocirrhosis patients (namely about 100 thousand patients) and about 40% of liver cancer patients (namely about 7 thousand patients) are patients having NANB hepatitis. Further, the mortality attributed to the above-mentioned NANB hepatitis reaches 16 thousand per year. In U.S.A., the number of post-transfusion hepatitis patients reaches 150 to 300 thousand per year and 90% of the post-transfusion hepatitis patients are patients having NANB hepatitis. Further, it is considered that 1 to 6% of the blood donors are NANBV carriers. Further, it is estimated that in the other countries also, the incidence of NANB hepatitis and the ratio of the NANBV carrier are equal to or higher than those in U.S.A. and Japan. Therefore, prevention, early diagnosis and early treatment of the NANB hepatitis are of global importance.

(2) Virology: The NANBV heretofore reported comprises an envelope and assumes a viral particle having a spherical shape of about 50 nm in diameter. The taxonomic observations suggest that the known NANBV is a virus similar to a togavirus or a flavivirus, or a virus of new type different from the togavirus or flavivirus. Further, the results of pathological observations of the cytoplasm of hepatocytes of a plurality of chimpanzees injected with serum of a patient having NANBV hepatitis show that the formation of a tubular structure occurs in the cytoplasm of a hepatocyte of some of the chimpanzees, but does not occur in the cytoplasm of a hepatocyte of the other chimpanzees, and that an intranuclear particle is formed in the cytoplasm of a hepatocyte of some of the chimpanzees. These results and the results of the epidemiological observations, tests on the presence or absence of the chloroform sensitivity and immunological diagnosis suggest that a plurality of types of NANBV-sexist (see, for example, "Science", Vol. 205, pp. 197–200, 1979, "Journal of Infectious Disease", Vol. 148, pp. 254–265, 1983, and "Biseibutsu" (Microorganism), Vol. 5, No. 5, pp. 463–475, 1989). The amount of the NANBV present in the blood of a patient having NANB hepatitis is extremely small as compared to either the amount of a hepatitis A virus present in the feces of a patient having hepatitis A or the amount of a hepatitis B virus present in the blood of a patient having a hepatitis B. For example, the amount of hepatitis B virus in the blood of the patient is $10^8$ to $10^9$ per ml in terms of Chimpanzee Infectious dose (CID), whereas the amount of NANBV in the blood of the patient is only $10^4$ to $10^5$ per ml in terms of CID (Bradley, D. W.: Research perspectives in post-transfusion non-A, non-B hepatitis, in "Infection, Immunity and Blood Transfusion", edited by Dodd, R. Y. & Barker, L. F., published by Alan R. Liss, Inc., New York (1985) pp. 81–97). Further, it is known that except for human, there are no animals except chimpanzee that are sensitive to NANBV and that in the cytoplasm of the hepatocyte, a typical tubular structure is occasionally formed by NANBV infection. Since only chimpanzee can be used as an animal for experiment of the NANBV infection, a large number of chimpanzees are required to be used for the study of NANBV. However, the chimpanzee is not easily available and expensive. Therefore, the study of NANBV by, for example, experimental infection by NANBV, identification of NANBV and search for a useful marker for NANBV, is necessarily restricted and delayed. In order to solve these problems, various attempts have been made for the study of NANBV. For example, in an attempt, an NANBV genomic cDNA [(referred to as "hepatitis C virus (HCV)"] was cloned from blood plasma of chimpanzees suffering from NANB hepatitis (Science, Vol. 244, pp. 359–362, 1989), and it was confirmed that the antigen (referred to as "C-100") obtained by expressing the cDNA exhibited an antigen-antibody reaction with the antibody in the blood of an NANB hepatitis patient (Science, Vol. 244, pp. 362–364, 1989). Further, in another attempt, a chimpanzee was not used and an NANBV genomic cDNA was cloned from the blood plasma of NANB hepatitis patients, and it was confirmed that the antigen obtained by expressing the cDNA exhibited an antigen-antibody reaction with the antibody in the serum of an NANB hepatitis patient (Gastroenterologia Japonica, Vol. 24, pp. 540–544 and pp. 545–548, 1989).

(3) Clinical observations: Hepatitis is generally classified either into epidemic hepatitis and sporadic hepatitis according to the number and frequency of the occurrences of hepatitis, or into acute hepatitis, fulminant hepatitis, subacute hepatitis, persistent hepatitis and chronic hepatitis according to the severeness and stage of the hepatitis patients. The latent period of the NANB hepatitis is 2 to 26 weeks. The symptom of NANB hepatitis in the early stage is mild as compared to that of hepatitis B. For example, a patient having NANB hepatitis only becomes feverish and complains of languor. Further, 70% of the patients have anicteric symptom. Therefore, the NANB hepatitis is frequently overlooked. However, the NANB hepatitis is very dangerous because the NANB hepatitis is likely to become chronic and, then, to progress to liver cirrhosis. Illustratively stated, 40 to 50% of the patients having NANB hepatitis whose serum exhibits an increased aminotransferase activity develop chronic hepatitis. 10 to 20% of the cases of chronic hepatitis suffer from liver cirrhosis. Further, 0.5 to 1% of blood recipients per year becomes liver cirrhosis patients without subjective symptoms. More seriously, the liver cirrhosis may further progress to liver cancer or hepatoma. Therefore, for preventing biohazard caused by blood transfusion and bleeding, eradication of the NANB hepatitis is a matter of global importance from the viewpoint of public health.

(4) Diagnosis: As mentioned above, the NANBV (blood-transmitted type) has not yet been identified and a viral marker, such as an NANBV antigen, which is useful for the diagnosis of NANB hepatitis has not been known. Therefore, diagnosis of NANB hepatitis has been conducted by examining the titer of the antibody in serum of a patient, which is specific for each of the known pathogenic viruses, such as hepatitis A virus, hepatitis B virus, cytomegalovirus, EB virus, varicella virus and herpes simplex virus, and diagnosing the patient whose serum is negative with respect to the antibody specific for any of the above-mentioned viruses, as having NANB hepatitis, or by performing a histopathological examination through a biopsy of the liver ("Disease of the Liver and biliary system", 8th edition, S. Shenlock, pp. 326–333, 1989, Blackwell Scientific Publications). At the same time, another diagnosis method has also been used. For example, there have been used a method in which the activity of an enzyme in serum, such as GPT [glutamic-pyruvic transaminase, also known as "ALT" (alanine aminotransaminase)], GOT [glutamic-oxalo-acetic transaminase, also known as "AST" (aspartate aminotransferase)], and guanine deaminase (also known as "guanase") is determined ("Kan Tan Sui (Liver, Gallbladder, Pancreas)", Vol. 14, pp. 519–522, 1987). With respect to the GPT or GOT in serum mentioned above, a standard for the diagnosis of NANB hepatitis in which lasting and abnormally high activities of GPT and GOT are utilized as a criterion for the diagnosis of NANB hepatitis, is employed in Japan ("Journal of Blood Transfusion Society in Japan", Vol. 31, No. 4, pp. 316–320, 1985; and "Nippon Rinsho", Vol. 46, p. 2635–2638, 1988). Regarding the immunological diagnosis, in the present situation in which the isolation and identification of NANBV are difficult, an antigen-antibody reaction between an antigen obtained by expression of NANBV cDNA clone (which has been isolated using the techniques of genetic engineering and the knowledge of immunology) and the serum of an NANB hepatitis patient is used as a criterion. Examples of known antigens include an expression product of an NANBV cDNA prepared from the plasma of an NANB hepatitis patient (European Patent Application Publication No. 363025), an expression product of "HCV" cDNA prepared from the plasma of a chimpanzee having the symptoms of NANB hepatitis (European Patent Application Publication No. 318216 and Japanese Patent Application Laid-Open Specification No. 2-500880), an expression product of an NANBV cDNA derived from the liver of an NANBV-infected chimpanzee (European Patent Application Publication No. 293274, Japanese Patent Publication Specification No. 64-2576 and Japanese Patent Application Laid-Open Specification No. 1-124387). As a method for determining the antigen-antibody reaction, RIA (radioimmunoassay) and EIA (enzyme immunoassay) are generally used. However, these expression products are different in antigenicity. The antigen which is an expression product of HCV cDNA (that is, the C-100 antigen mentioned above) can be some criterion or yardstick for the diagnosis of chronic hepatitis caused by the HCV infection. However, since the region in which the antigen (C-100) exhibits its antigenicity is limited ("Biseibutsu (Microorganism)", Vol. 5, pp. 463–475, 1989; "Kan Tan Sui (Liver, Gallbladder, Pancreas)", Vol. 20, pp. 47–51, 1990; and "Igaku-no Ayumi (Progress of Medicine)", Vol. 151, p. 871, 1989), this antigen is unsatisfactory from the viewpoint of accurate diagnosis of NANB hepatitis and NANBV infection and from the viewpoint of accurate determination of the progress of a patient suffering from chronic hepatitis and acute hepatitis for treatment thereof. Therefore, it has been desired to obtain a reliable method for the diagnosis and prognosis of the NANB hepatitis.

(5) Therapy and Prevention: Recently, the usefulness of $\alpha$- and $\beta$-interferons in the treatment of chronic NANB hepatitis have been reported ("Kan Tan Sui (Liver, Gallbladder, Panceras)" vol. 20, pp. 59–64, 1990; "Igaku-no Ayumi (Progress of Medicine)", vol. 151, pp. 871–876, 1989). However, a suitable dose of $\alpha$- and $\beta$-interferons and a suitable period for administration thereof have not yet been established.

On the other hand, for prevention of NANB hepatitis, various vaccines are used in which the above-mentioned conventional expression products of NANBV cDNAs (European Patent Application Publication No. 363025) or HCV cDNAs (European Patent Application Publication No. 318216) are used as an antigen. However, as is apparent from the fact that the NANBV itself has not yet been isolated and identified before completion of the present invention, it has been impossible to specify an antigen useful for NANBV vaccines from the above-mentioned expression products each having a variety of antigenic determinants (epitopes) and determine the effectiveness and safety of such a specific antigen so that the antigen can be clinically used. Accordingly, there is no NANBV vaccine which can be advantageously put into practical use.

SUMMARY OF THE INVENTION

The present inventors have made extensive and intensive studies with a view toward solving the above-mentioned problems by developing a novel NANBV genomic cDNA. As a result, the present inventors have surprisingly succeeded in cloning an NANBV genomic cDNA, which not only has excellent reliability as compared to the known NANBV cDNA but also is larger in length than any known NANBV cDNAs and contains the entire region of the open reading frame of the NANBV genome, and expressing this NANBV cDNA to thereby obtain an NANBV antigen peptide which can reliably exhibit an antigen-antibody reaction specific for not only sera from patients having chronic NANB hepatitis but also sera from patients having acute NANB hepatitis. This success is attributed to a unique technique of the present inventors such that in order to obtain an authentic NANBV genome, NANBV RNAs are extracted directly from NANBV particles contained in whole blood of a patient having NANB hepatitis or a resected liver of a patient having NANB hepatitis and liver cancer in combination, without multiplying the NANBV in a chimpanzee having unknown factors which are considered to have rendered difficult the isolation of NANBV, although the amount of NANBV in the blood or resected liver is extremely small, that is, as small as about 1/10,000 that of a hepatitis A virus or a hepatitis B virus, but with paying minute care in the operating procedure so that the NANBV and its genome do not undergo cleavage and/or decomposition by the action of body fluids or blood enzymes during the storage of fresh materials for NANBV genome. RNAs thus prepared from fresh human materials are then converted to double-stranded cDNA by means of a reverse transcriptase to obtain a cDNA library. In order to screen an NANBV genome from the cDNA library, the cDNAs are individually inserted in lambda gt11 phage vectors and then expressed on the phage plaques at high concentration, followed by screening of NANBV genomic cDNAs by repeatedly conducting enzyme immunoassay (EIA) in which both serum from a convalescent patient having acute NANB hepatitis and serum from a patient having chronic NANB hepatitis are used. Thus, safe production of the NANBV antigen polypeptide with high purity on a large scale at low cost without biohazard, has for the first time been realized by expressing the cDNA of the present invention by recombinant DNA techniques. Based on the above, the present invention has been completed.

Therefore, it is an object of the present invention to provide an NANB hepatitis virus genomic cDNA.

It is another object of the present invention to provide an NANB hepatitis virus antigen polypeptide which is useful as an active ingredient for a diagnostic reagent and a vaccine for NANB hepatitis.

It is still another object of the present invention to provide a method for producing an NANBV antigen polypeptide.

It is a further object of the present invention to provide a diagnostic reagent for NANB hepatitis.

It is still a further object of the present invention to provide a vaccine for NANB hepatitis.

The foregoing and other objects, features and advantages of the present invention will be apparent from the following detailed description, appended claims taken in connection with the accompanying drawings.

BRIEF DESCRIPTION OF THE DRAWINGS

In the Drawings:

FIG. 2(1) through FIG. 2(16) show the nucleotide sequence of the entire region of the NANBV genomic cDNA according to the present invention and the amino acid sequence coded for by the nucleotide sequence.

DETAILED DESCRIPTION OF THE INVENTION

Figure 1:
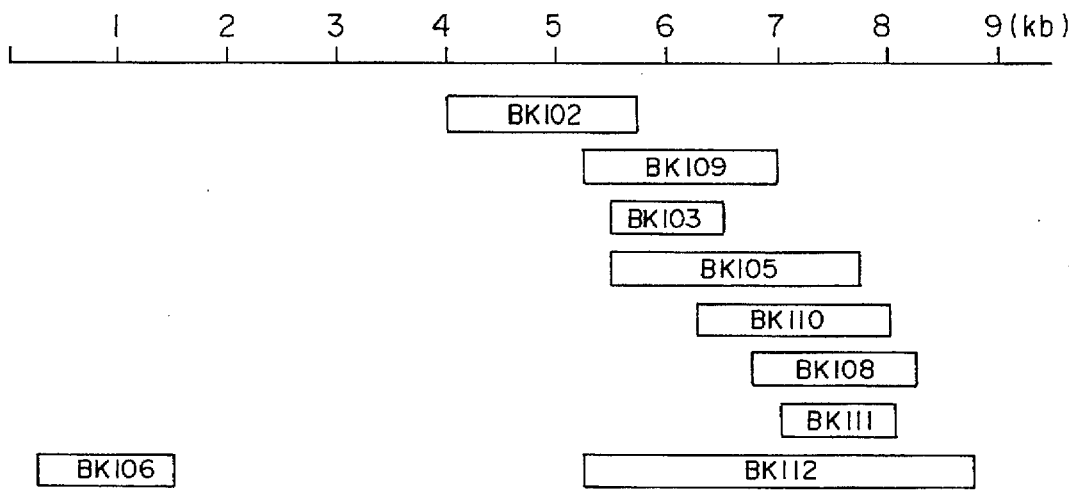
FIG. 1(1) and FIG. 1(2) are diagrams showing the relationships between the cDNA clones of the NANBV gene of the present invention, shown relative to the entire region of the NANBV genome.
Figure 1:
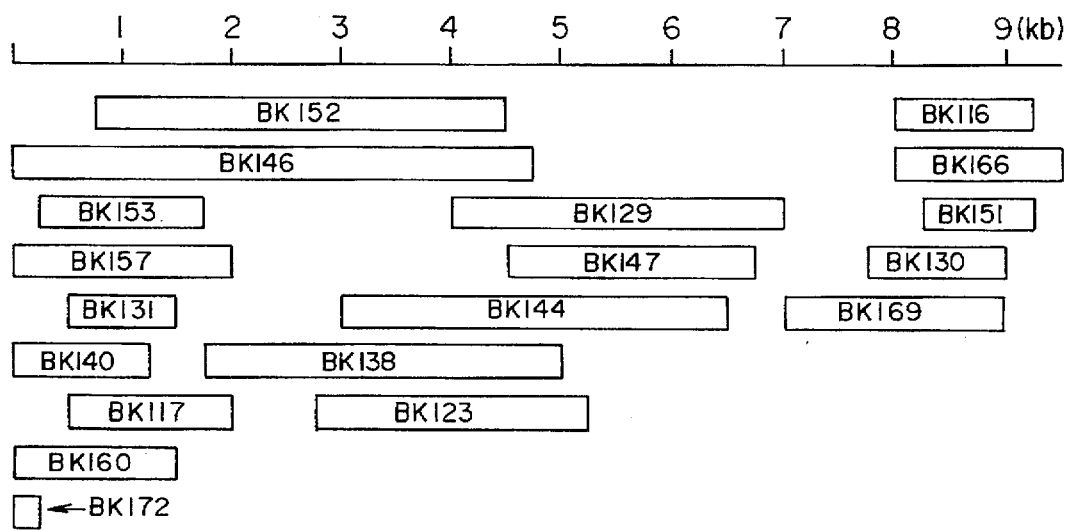

Essentially, according to the present invention, there is provided an isolated deoxyribonucleic acid comprising at least one nucleotide sequence selected from the group consisting of a nucleotide sequence comprising at least part of the non-A, non-B hepatitis virus entire nucleotide sequence from the 1st to 9416th nucleotides shown in FIG. 2(1) through FIG. 2(16) hereof and a nucleotide sequence complementary to said nucleotide sequence, or comprising at least one nucleotide sequence obtained by substituting at least one nucleotide of said nucleotide sequence in accordance with the degeneracy of the genetic code.

In another aspect of the present invention, there is provided an isolated antigen polypeptide comprising at least one amino acid sequence comprising at least part of an amino acid sequence coded for by a deoxyribonucleic acid comprising a coding region from the 333rd to 9362nd nucleotides of the non-A, non-B hepatitis virus nucleotide sequence shown in FIG. 2(1) through FIG. 2(16) hereof.

In the present invention, unless otherwise specified, the left end and right end of the sequence of deoxyribonucleotides are the 5' end and 3' end, respectively. Further, unless otherwise specified, the left end and right end of the amino acid sequences of peptides are the N-terminus and C-terminus, respectively.

The NANBV genomic cDNA of the present invention and the NANBV antigen polypeptide as an expression product thereof can be prepared and identified in accordance with the following steps (I) to (VII).

Step (I): Selection and collection of a material for extracting an NANBV RNA.

As a material for extracting the NANBV RNA, there may be used, for example, blood, lymph, ascites and. hepatocyte of an NANBV carrier, or of a human or a chimpanzee suffering from NANB hepatitis, and hepatocyte of a patient suffering from NANB hepatitis and liver cancer or hepatoma in combination. Since the materials derived from a chimpanzee may contain NANBV in a relatively small amount as compared to the materials derived from a human and a chimpanzee has unknown factors which are considered to have rendered difficult the isolation of NANBV, the use of the materials derived from a human is preferred. Of blood, lymph, ascites and hepatocytes from a human, blood can most easily be obtained in a large amount. For example, blood which is not acceptable for use as blood for transfusion is available from a blood bank in a large amount. Such blood can advantageously be used as a material for extracting an NANBV RNA. When blood is used as a material, blood is separated into plasma and erythrocytes. The thus obtained plasma is examined to determine whether or not the plasma is negative to the surface antigen of hepatitis B virus (WHO expert committee on viral hepatitis: Advances in viral hepatitis, WHO Technical Report Series, 602, 28–33, 1977) and negative to a genomic DNA of hepatitis B virus (Brechot, C., Hadchouel, M., Scotto, J., Degos, F., Charnay, P., Trepo, C., Tiollais, P.: Detection of hepatitis B virus DNA in liver and serum: a direct appraisal of the chronic carrier state. Lancet 2: 765–768, 1981). Further, the plasma is examined with respect to the activities of enzymes, such as GPT (Wroblewski, F. & LaDue, J. S.: Serum glutamic-pyruvic transaminase in cardiac and hepatic disease, Proc. Soc. Exp. Biol. Med., 91, 569, 1956), GOT, guanase and the like, which are employed as the criterion for the diagnosis of NANB hepatitis. The above-mentioned procedures of the separation of blood into plasma and erythrocytes and the examination of the plasma are conducted with respect to blood of different lots. The plasma which is negative to both surface antigen and genomic cDNA of hepatitis B virus and exhibits extremely high activities of the above-mentioned enzymes, for example, a GPT activity of 35 IU/ml or more, is pooled.

The number of the NANB hepatitis virus particles in blood is extremely small as compared to that of the hepatitis B virus particles as mentioned hereinbefore. From the results of the infection experiment, the number of the NANB hepatitis virus particles in blood is estimated to be about 1/10,000 of the number of the hepatitis B virus particles (Bradley, D. W., (1985): Research perspectives in post-transfusion non-A, non-B hepatitis, in "Infection, Immunity and Blood Transfusion", edited by Dodd, R. Y. & Barker, L. F., published by Alan R. Liss, Inc., New York, pp. 81–97). Therefore, for the extraction of the RNA, it is preferred to use blood in a large amount, for example, in an amount as large as about 3 to 10 liters. Fresh whole blood to be used as a material for extracting an NANB RNA from NANBV particles is stored at 1° to 5° C. in order to prevent NANBV and its gene from being denatured and to prevent its gene from being cleaved or decomposed by the action of an enzyme. It is also desirable to complete the preparation of NANBV RNAs by Step (II) within 48 to 72 hours from the collection of the fresh whole blood. When a hepatocyte is used as a material, about 1 to 3 g of a non-cancerous or a cancerous portion of a liver tissue resected from a patient having hepatoma or liver cancer which is a complication of a chronic NANB hepatitis may advantageously be used. Hepatocyte to be used as a material is stored in a frozen state at −70° C.

Step (II): Preparation of the NANBV RNA

From the material obtained in Step (I), the RNA may be extracted and purified by conventional methods. For example, when fresh whole blood is used as the material, about 2 to 10 liters of fresh whole blood is subjected to low-speed centrifugation to collect a plasma fraction as a supernatant. The virus fraction is obtained from the plasma through purification for use in the subsequent procedure for the extraction and purification of the RNA.

On the other hand, when hepatocyte is used as a material for extracting the NANBV RNA, about 5 to 30-fold volume of a diluent containing ribonuclease inhibitor is added to the liver tissue. Then, according to the conventional method using a homogenizer and the like, the liver tissue is crushed or disrupted to obtain a homogenate of hepatocyte. As a diluent, 10 to 150 mM of a conventional buffer may be used. Then, the homogenate is subjected to low-speed centrifugation to collect a supernatant. The collected supernatant is used as an original solution for the extraction and purification of the NANBV RNA. The extraction and purification of the NANBV RNA may be conducted by the conventional method, for example, an extraction method in which a mixture of a ribonuclease inhibitor, such as heparin, diethyl pyrocarbonate and guanidine thiocyanate, with a surfactant, a chelating agent, or a reducing agent capable of enhancing the denaturation of a protein, is used; a method in which fractionation is conducted by density gradient centrifugation using sucrose, cesium chloride, cesium trichloroacetate, Ficoll (Pharmacia Fine Chemicals AB, Sweden) or the like as a solute of a gradient; a method in which separation is conducted by affinity column utilizing the 3'-terminal poly A chain which an mRNA specifically has; a separation method in which an mRNA-bonded polysome is obtained by the immunoprecipitation using an antibody specific for a protein synthesized on the polysome; a phenol extraction method based on a principle of two-phase separation; a precipitation method by the use of a polyethylene glycol, a dextran sulfate, an alcohol or the like. The above-mentioned methods may be used individually or in combination. The above-mentioned procedure for extracting and purifying the NANBV RNA may preferably be conducted at pH 3 to 10 in order to prevent the irreversible denaturation of the RNA.

Step (III): Preparation of a double-stranded cDNA from the NANBV RNA

Using the above-obtained NANBV RNA as a template, a cDNA may be prepared by a customary method. That is, using an oligodeoxythymidine and a random hexanucleotide primer as primers and using a reverse transcriptase, a cDNA complementary to the NANBV RNA is synthesized using the NANBV RNA as a template to obtain a double-strand comprising the cDNA and the NANBV RNA which are complementarily bonded to each other. Then, the thus obtained double-strand is reacted with ribonuclease H so that the NANBV RNA is decomposed and removed from the cDNA. Thus, a single-stranded cDNA is obtained. Using the obtained single-stranded cDNA as a template, a double-stranded cDNA is synthesized by means of a DNA synthase. The double-stranded cDNA synthesis may easily be conducted using a commercially available kit for cDNA synthesis, for example, cDNA Synthesis System Plus® (manufactured and sold by Amersham, England), cDNA System Kit® (manufactured and sold by Pharmacia LKB, Sweden), cDNA Synthesis Kit® (manufactured and sold by Boehringer Mannheim GmbH, West Germany), and the like. When the quantity of the synthesized cDNA is small, the cDNA can be amplified using a conventional method, such as PCR (polymerase chain reaction) method ("PCR Technology", edited by H. A. Erlich, published by Stockton Press, 1989) using a PCR kit, such as AmpliTaq (manufactured and sold by Perkin Elmer Cetus, U.S.A.).

Step (IV): Preparation of a cDNA library

Using the cDNA prepared in Step (III), a cDNA library is prepared by a customary method. That is, the cDNA prepared in Step (III) is cut into fragments having different lengths and the resultant various cDNA fragments are individually ligated to replicable cloning vectors, to thereby obtain a cDNA library. As a replicable cloning vector, any known or commercially available vectors, such as phage genes, cosmids, plasmids and animal virus genes may be used. When a phage gene or a cosmid is used as a replicable vector, in order to attain high stability and high transforming ability of the vector after each of the cDNA fragments has been individually inserted therein, the in vitro packaging of each of the cDNA-inserted vectors is conducted by a customary method. Thus, the cDNA-inserted vectors are obtained in the form of a recombinant phage particle. The obtained phage particles are used as a cDNA library for cDNA cloning. On the other hand, when a plasmid is used as a replicable vector, the above-mentioned cDNA fragments are individually inserted in the plasmid vectors and the resultant cDNA-inserted vectors are then individually introduced into host cells, such as cells of *Escherichia coli, Bacillus subtilis*, yeast or the like, according to a customary method. The thus obtained transformants are used as a cDNA library for cDNA cloning. Further when the animal virus gene is used as a replicable vector, the above-mentioned cDNA fragments are individually inserted in the virus gene vectors and the resultant recombinant viruses are then individually transfected into sensitive animal cells according to a standard method and multiplied in the cells. In the case of the recombinant virus, the obtained recombinant viruses as such are used as a cDNA library.

The preparation of the cDNA library may easily be conducted using a commercially available kit, for example, a cDNA cloning system lambda gt10 and lambda gt11 (manufactured and sold by Amersham, England; BRL Inc., U.S.A.; and Stratagene Inc., U.S.A.), an in vitro packaging system (manufactured and sold by Amersham, England; BRL Inc., U.S.A.; and Stratagene Inc., U.S.A.) and the like.

Step (V): Cloning of a cDNA containing an NANBV gene from the cDNA library

In this step, a cDNA clone containing an NANBV gene is obtained. When the cDNA library is comprised of transformants, the transformants are cultured on a standard agar medium to form colonies. On the other hand, when the cDNA library is comprised of recombinant phage particles or recombinant viruses, these phage particles or recombinant viruses are used to infect known sensitive host cells, such as *Escherichia coli, Bacillus subtilis*, yeast, animal cell culture and the like, and cultured to form a plaque, or to multiply the infected cells. The above-obtained transformant colonies, plaques or infected cells are subjected to immunoassay by at least one of the standard methods individually using serum from a convalescent patient having acute NANB hepatitis, serum from a patient having chronic NANB hepatitis, and serum from chimpanzee infected with an NANBV irrespective of whether or not the NANBV is of the type which causes a tubular structure to be formed in the cytoplasm of the hepatocyte of the chimpanzee, so that colonies, plaques or infected cells which have produced an NANBV antigen specifically reacted with at least one of the above-mentioned sera are selected and isolated. For the strict selection of the colonies, plaques and infected cells, it is preferred that the above procedure be repeated. From each of the thus selected and isolated colonies, plaques or the infected cells, a cDNA clone containing an NANBV gene is isolated according to a standard method described in T. Maniatis et al., Molecular Cloning, A Laboratory Manual, published by Cold Spring Harbor Laboratory, U.S.A., pp. 309–433 (1982). The immunoassay may be conducted by, for example, an enzyme-labeled antibody technique in which an antibody labeled with an enzyme, such as peroxidase and alkaline phosphatase is used; and a fluorescent antibody technique in which an antibody labeled with fluorescein isothiocyanate, europium or the like is used. It is preferred that the immunoassay by the above-mentioned technique be conducted by an indirect method because with the indirect method, high sensitivity immunoassay can be attained even by the use of an extremely small amount of serum from a patient. As a primary antibody to be used in the indirect method, serum from a patient having NANB hepatitis or serum from a chimpanzee having NANB hepatitis may preferably be employed because these sera contain an antibody specific for an NANBV antigen in relatively large amount. As a secondary antibody to be used in the indirect method, a commercially available anti-human Ig (immunoglobulin) antibody labeled with an enzyme, a fluorescent substance or the like may be used.

A specimen to be subjected to immunoassay may be prepared according to a conventional method, for example, a blotting method in which nucleic acids and proteins of the colonies, plaques and infected cells are adsorbed on a filter membrane, a method in which a microplate or a slide glass for microscopy is used, or the like. When the blotting method is used in combination with an indirect, enzyme-labeled antibody technique, the selection of the intended colonies, plaques or infected cells from an extremely large number of the original colonies, original plaques or original infected cells can be conducted easily and promptly. In this case, blotting is conducted by contacting a commercially available filter made of nitrocellulose, cellulose acetate, nylon or the like, with the colonies, plaques or infected cells.

The above-obtained cDNA clone is a part of the NANBV gene. Therefore, in order to obtain cDNA clones covering the entire region of the NANBV gene, it is requisite to extend the cNDA clone by a method in which cDNA fragments adjacent to the cDNA clone are isolated by using 3'- and 5'- terminals of the cDNA clone as a probe. In this case, the technique which is known as "gene walking" (also known as "genomic walking" or "chromosome walking") may be employed ("DNA cloning volume III", edited by D. M. Glover, pp. 37–39, IRL Press, 1987; "Molecular Cloning—a laboratory manual" 2nd edit., T. Maniatis et al, 3.21–3.23, 1989). By the repetition of the cloning procedure and the gene walking, the entire region of the NANBV gene can be obtained in the form of cDNA clones.

In this step, it is preferred to determine the nucleotide sequence of each of the obtained cDNA clones. The determination of the nucleotide sequence of the cDNA clone may generally be conducted according to a conventional method, for example, the Maxam-Gilbert method, the dideoxy chain termination method (Analytical Biochemistry, 152, 232–238, 1986), or the like.

Based on the determined nucleotide sequence, the amino acid sequence can be determined. The sequencing of the amino acids is conducted from the location of the initiation codon (ATG on the cDNA or AUG on the mRNA). Important portions of the amino acid sequence, for example, a hydrophilic portion, which is considered to constitute an epitope, can be identified by synthesizing a peptide corresponding to each hydrophilic portion and purifying the synthesized polypeptide by high performance liquid chromatography (HPLC), followed by subjecting the purified peptide to enzyme immunoassay (EIA) or radioimmunoassay (RIA).

The cDNA clones are preferably classified into groups according to the respective properties of the NANBV antigen polypeptides coded for by the cDNA clones in order to distinguishing clones from one another. In this connection, the location of each cDNA clone on the restriction map of the NANBV gene can be used as a yardstick for the classification [see FIG. 1(1) and FIG. 1(2)]. Further, it has been found that some of NANBVs have the ability to cause a tubular structure to be formed in the cytoplasm of a hepatocyte of a chimpanzee, and some of NANBV do not have such ability (Science, 205, pp. 197–200, 1979). Therefore, the cDNA clones may be identified and classified by examining the serological reactivity of each cDNA clone with serum from a chimpanzee infected with an NANBV of the type which causes a tubular structure to be formed in the cytoplasm of the hepatocyte of the chimpanzee and with serum from a chimpanzee infected with an NANBV of the type which does not cause a tubular structure to be formed in the cytoplasm of the hepacyte of the chimpanzee. The examination of this serological reactivity may be conducted by immunoassay mentioned above.

In the present invention, as shown in FIGS. 1(1) and 1(2), the cDNA clones of the NANBV gene of the present invention are identified with prefix "BK".

FIG. 1(1) is a diagram showing the relationships between the cDNA clones of the NANBV gene of the present invention, shown relative to the entire region of the NANBV gene, and FIG. 1(2) is a diagram showing the relationships between the cDNA clones obtained by gene walking, shown relative to the entire region of the NANBV gene.

These BK NANBV cDNA clones include, for example, *Escherichia coli* BK 108 (deposited at Fermentation Research Institute, Japan under the accession number FERM BP-2971), *Escherichia coli* BK 129 (deposited at Fermentation Research Institute, Japan under the accession number FERM BP-2972), *Escherichia coli* BK 138 (deposited at Fermentation Research Institute, Japan under the accession number FERM BP-2973), *Escherichia coli* BK 153 (deposited at Fermentation Research Institute, Japan under the accession number FERM BP-2974), *Escherichia coli* BK 157, *Escherichia coli* BK 166 (deposited at Fermentation Research Institute, Japan under the accession number FERM BP-2975), and *Escherichia coli* BK 172 (deposited at Fermentation Research Institute, Japan under accession number FERM BP-2976). These seven BK NANBV cDNA clones are considered to cover at least the entire region of the open reading frame of the NANBV gene and probably the entire region of the NANBV gene.

The nucleotide sequence of the entire region of the NANBV gene which is covered by the above-mentioned BK NANBV cDNA clones and the amino acid sequence which is coded for by this nucleotide sequence are shown in FIG. 2(1) through FIG. 2(16). Based on the entire NANBV nucleotide sequence and the entire NANBV amino acid sequence shown in FIG. 2(1) through FIG. 2(16), various studies and observations can be made with respect to the homology of the nucleotide sequence and amino acid sequence of the NANBV gene to those of other virus genes, the hydrophobicity index (hydrophobicity/hydrophilicity profile), the structure of the NANBV gene, the regions of epitopes (antigenic determinants) and the like.

With respect to the homology, studies can be made by comparison of the nucleotide sequence and amino acid sequence of the NANBV gene with those of various viruses whose genes are well known (Japanese Patent Application Laid-Open specification No. 62-286930 and "Virology", Vol. 161, pp. 497–510, 1987) and those of other viruses, such as bovine virus diarrhea-mucosal disease virus ("Virology", Vol. 165, pp. 497–510, 1988), swine cholera virus ("Virology", Vol. 171, pp. 555–567, 1989), tobacco vein mottling virus ("Nucleic Acid Research, Vol. 165, pp. 5417–5430, 1986), etc.

With respect to the analysis of the hydrophobicity index, studies can be made by techniques using, for example, a genetic information processing software, SDC-Genetyx (manufactured and sold by SDC Software Co., Ltd., Japan), Doolittle's program (Journal of Molecular Biology, Vol. 157, pp. 105–132, 1982) and the like.

Figure 3:
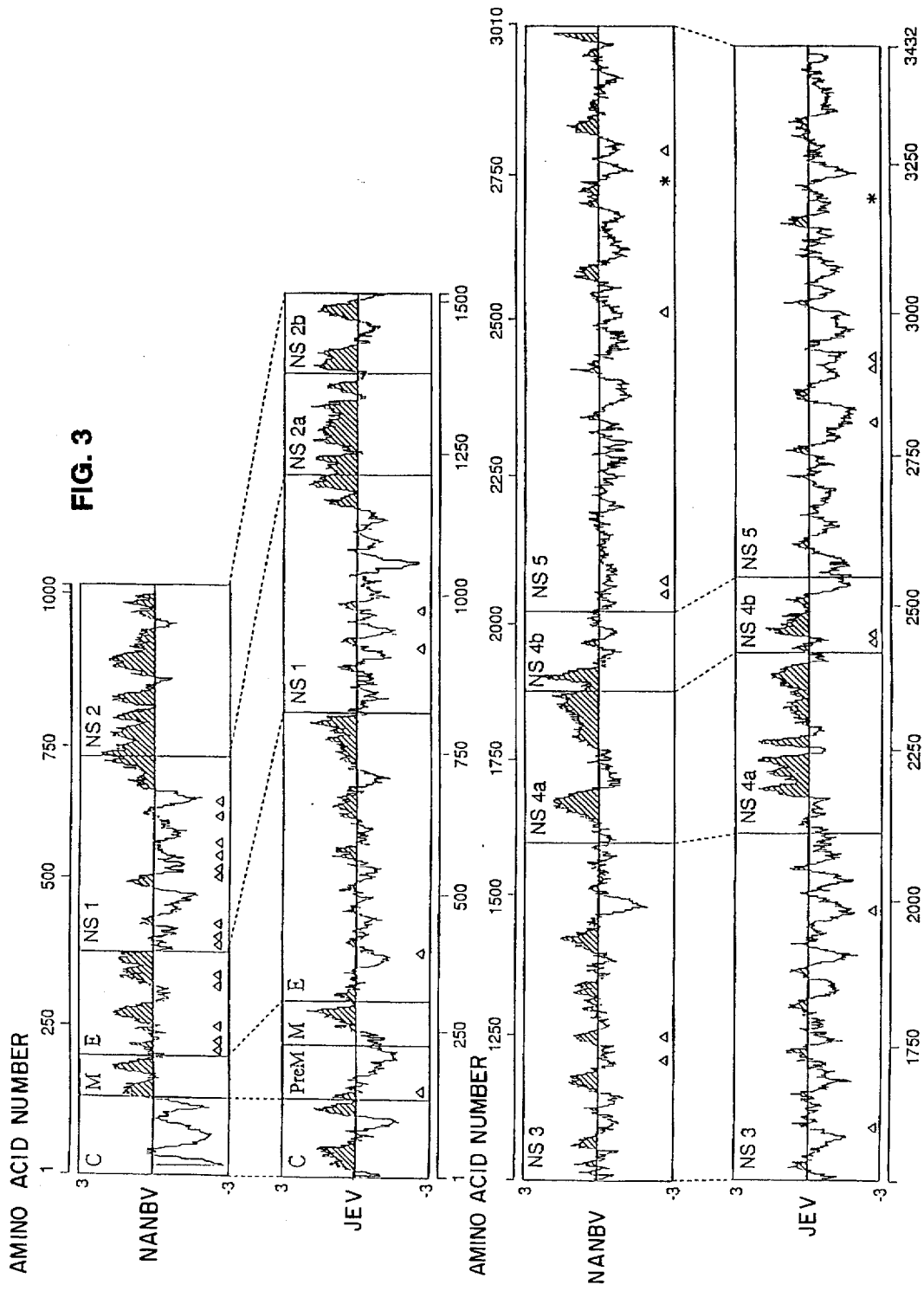
FIG. 3 is a diagram showing the hydrophobicity profiles of both of the NANBV of the present invention and the Japanese encephalitis virus (JEV), in which the hydrophobicity index of the NANBV is compared with that of the JEV.

FIG. 3 is a diagram showing the hydrophobic profiles of both of the NANBV of the present invention and the Japanese encephalitis virus (JEV), in which the respective hydrophobic indexes of both viruses are compared with each other. A significant similarity is found between the gene structure of the NANBV gene and that of the JEV gene. As shown in FIG. 3, the polypeptide of the NANBV of the present invention contains three structural proteins, namely, core protein (C), pre-matrix protein (PreM) that is further processed to matrix protein (M) and envelope protein (E), and seven nonstructural proteins, NS1, NS2a, NS2b, NS3, NS4a, NS4b and NS5. These proteins are, respectively, coded for by the following nucleotide sequences.

| | |
|---|---|
| C protein: | from the 333rd to 677th nucleotides |
| M protein: | from the 678th to 905th nucleotides |
| E protein: | from the 906th to 1499th nucleotides |
| NS1 protein: | from the 1500th to 2519th nucleotides |
| NS2 protein: | from the 2520th to 3350th nucleotides |
| NS3 protein: | from the 3351st to 5177th nucleotides |
| NS4a protein: | from the 5178th to 5918th nucleotides |
| NS4b protein: | from the 5919th to 6371th nucleotides |

NS5 protein: from the 6372nd to 9362nd nucleotides

These nucleotide sequences are useful for the diagnosis of NANB hepatitis. Polypeptides respectively coded for by these nucleotide sequences are useful as antigens for not only vaccines but also diagnostic reagents for NANB hepatitis.

The above-mentioned three structural proteins are represented by the 1st(Met) to 389th(Gly) amino acids shown in FIG. 2(1) through FIG. 2(3). The 1st methionine residue is the residue that is coded for by the initiation codon.

By further studies by the present inventors, it has been found that the following nucleotide sequences contain epitopes which are reactive to an anti-NANBV antibody: nucleotide sequences respectively of the 333rd to 422nd nucleotides, of the 333rd to 1499th nucleotides, of the 333rd to 6371st nucleotides, of the 474th to 563rd nucleotides, of the 906th to 953rd nucleotides, of the 1020th to 1046th nucleotides, of the 1020th to 1121st nucleotides, of the 1194th to 1232nd nucleotides, of the 1209th to 1322nd nucleotides, of the 4485th to 4574th nucleotides and of the 5544th to 5633rd nucleotides.

As described hereinbelow, the above-mentioned nucleotide sequences or nucleotide sequences containing such nucleotide sequences as part of the whole sequences, can be effectively used not only for producing NANBV antigen polypeptides by recombinant DNA technique or chemical synthesis but also for diagnosing NANB hepatitis by hybridization or polymerase chain reaction (PCR).

Further, it has been found that a first nucleotide sequence comprising at least six nucleotides of the entire region from the 1st to 9416th nucleotides shown in FIG. 2(1) through FIG. 2(16) is useful as a probe for hybridization or as a primer for polymerase chain reaction in the diagnosis of NANB hepatitis and that a polypeptide comprising at least four amino acids, which is coded for by a nucleotide sequence of at least twelve nucleotides of the nucleotide sequence of the 333rd to 9362nd nucleotides is effective as an antigen not only for a vaccine but also for a diagnostic reagent for NANB hepatitis. Further, as is well known in the art, a second nucleotide sequence complementary to the first nucleotide sequence is also useful as a probe for hybridization or as a primer for polymerase chain reaction in the diagnosis of NANB hepatitis. Further, a nucleotide sequence obtained by substituting at least one nucleotide of at least part of the coding region of the first nucleotide sequence of the NANBV in accordance with the degeneracy of the genetic code can also be used for producing the antigen polypeptide of the present invention by recombinant DNA technique.

Accordingly, the isolated deoxyribonucleic acid of the present invention comprises at least one nucleotide sequence selected from the group consisting of a first nucleotide sequence comprising at least part of the non-A, non-B hepatitis virus entire nucleotide sequence from the 1st to 9416th nucleotides shown in FIG. 2(1) through FIG. 2(16) hereof and a second nucleotide sequence complementary to the first nucleotide sequence, or comprises at least one nucleotide sequence obtained by substituting at least one nucleotide of the first nucleotide sequence in accordance with the degeneracy of the genetic code.

In one preferred embodiment of the present invention with respect to the deoxyribonucleic acid, the first nucleotide sequence comprises at least six nucleotides of the non-A, non-B hepatitis virus entire nucleotide sequence from the 1st to 9416th nucleotides shown in FIG. 2(1) through FIG. 2(16) hereof.

In another preferred embodiment of the present invention with respect to the deoxyribonucleic acid, the first nucleotide sequence comprises at least one nucleotide sequence selected from the group consisting of a nucleotide sequence of the 333rd to 422nd nucleotides, a nucleotide sequence of the 333rd to 677th nucleotides a nucleotide sequence of the 333rd to 1499th nucleotides, a nucleotide sequence of the 333rd to 6371st nucleotides, a nucleotide sequence of the 474th to 563rd nucleotides, a nucleotide sequence of the 678th to 905th nucleotides, a nucleotide sequence of the 906th to 953rd nucleotides, a nucleotide sequence of the 906th to 1499th nucleotides, a nucleotide sequence of the 1020th to 1046th nucleotides, a nucleotide sequence of the 1020th to 1121st nucleotides, a nucleotide sequence of the 1194th to 1232nd nucleotides, a nucleotide sequence of the 1209th to 1322nd nucleotides, a nucleotide sequence of the 1500th to 2519th nucleotides, a nucleotide sequence of the 2520th to 3350th nucleotides, a nucleotide sequence of the 3351st to 5177th nucleotides, a nucleotide sequence of the 4485th to 4574th nucleotides, a nucleotide sequence of the 5178th to 5918th nucleotides, a nucleotide sequence of the 5544th to 5633rd nucleotides, a nucleotide sequence of the 5919th to 6371st nucleotides, a nucleotide sequence of the 6372nd to 9362nd nucleotides and a nucleotide sequence from the 1st to 9416th nucleotides.

The isolated antigen polypeptide of the present invention comprises at least one amino acid sequence comprising at least part of an amino acid sequence coded for by a deoxyribonucleic acid comprising a coding region from the 333rd to 9362nd nucleotides of the non-A, non-B hepatitis virus nucleotide sequence shown in FIG. 2(1) through FIG. 2(16) hereof.

In one preferred embodiment of the present invention with respect to the antigen polypeptide, the antigen polypeptide comprises at least one amino acid sequence of at least four amino acids, which is coded for by a nucleotide sequence of at least twelve nucleotides of the nucleotide sequence of the 333rd to 9362nd nucleotides.

In another preferred embodiment of the present invention with respect to the antigen polypeptide, the antigen polypeptide comprises an amino acid sequence coded for by a nucleotide sequence selected from the group consisting of a nucleotide sequence of the 333rd to 422nd nucleotides, a nucleotide sequence of the 333rd to 677th nucleotides, a nucleotide sequence of the 333rd to 1499th nucleotides, a nucleotide sequence of the 333rd to 6371st nucleotides, a nucleotide sequence of the 474th to 563rd nucleotides, a nucleotide sequence of the 678th to 905th nucleotides, a nucleotide sequence of the 906th to 953rd nucleotides, a nucleotide sequence of the 906th to 1499th nucleotides, a nucleotide sequence of the 1020th to 1046th nucleotides, a nucleotide sequence of the 1020th to 1121st nucleotides, a nucleotide sequence of the 1194th to 1232nd nucleotides, a nucleotide sequence of the 1209th to 1322nd nucleotides, a nucleotide sequence of the 1500th to 2519th nucleotides, a nucleotide sequence of the 2520th to 3350th nucleotides, a nucleotide sequence of the 3351st to 5177th nucleotides, a nucleotide sequence of the 4485th to 4574th nucleotides, a nucleotide sequence of the 5178th to 5918th nucleotides, a nucleotide sequence of the 5544th to 5633rd nucleotides, a nucleotide sequence of the 5919th to 6371st nucleotides, a nucleotide sequence of the 6372nd to 9362nd nucleotides and a nucleotide sequence of the 333rd to 9362nd nucleotides.

Furthermore, it should be noted that since a polypeptide coded for by the entire coding region of the NANBV shown in FIG. 2(1) through FIG. 2(16), such a polypeptide has a broad antigen-antibody reaction spectrum and therefore can react to a wide variety of antibodies produced by infection with NANB hepatitis virus as compared to an antigen containing a single epitope, so that it has high sensitivity in detecting NANB hepatitis.

Step (VI): Expression of the NANBV genomic cDNA clone and a mass production of an NANBV antigen polypeptide.

In order to express the cloned cDNA of an NANBV antigen gene to produce an NANBV antigen polypeptide on a commercial scale, part or whole of the cloned cDNA present in the cDNA clone is taken out from the replicable cloning vector and recombined with a replicable expression vector. Illustratively stated, part or whole of the cDNA of each cDNA clone is cut off using a restriction enzyme to obtain a DNA fragment containing an NANBV antigen gene (hereafter referred to as "NANBV DNA fragment"). The NANBV DNA fragment is then inserted in a replicable expression vector by a customary method. When one DNA fragment is inserted in an expression vector, one type of antigen polypeptide can be produced by gene expression. When two or more of different DNA fragments are inserted in sequence in an expression vector, an antigen polypeptide can be produced by gene expression in the form of a fused polypeptide comprising polypeptides coded for by the inserted DNA fragments.

As the replicable expression vector which may be used in this step, any conventionally known or commercially available expression vector can be used. Examples of expression vectors include plasmid vector pSN508 for enterobacteria (U.S. Pat. No. 4,703,005), plasmid vector pBH103 for yeast, and its series (Japanese Patent Application Laid-Open Specification No. 63-22098), plasmid pJM105 (Japanese Patent application Laid-Open Specification No. 62-286930), an attenuated chicken pox virus gene (Japanese Patent Application Laid-Open Specification No. 53-41202), an attenuated Marek's disease virus (The Journal of Japanese Society of Veterinary, 27, 20–24 (1974), and Gan Monograph on Cancer Research, 10, 91–107 (1971)), plasmid pTTQ series (manufactured and sold by Amersham, England), plasmid pSLV series (manufactured and sold by Pharmacia LKB, Sweden), and the like.

The NANBV DNA-inserted expression vectors are individually introduced or transfected into host cells sensitive to the vector according to a conventional method, to obtain transformants. Then, from the transformants, the transformant(s) which has produced an NANBV antigen polypeptide or an NANBV particle is selected. The production of an NANBV antigen polypeptide (or an NANBV particle) may be detected by the immunoassay mentioned above in Step (V). When an animal virus gene is used as an expression vector, a recombinant virus having an NANBV antigen polypeptide on the surface thereof may be obtained. Such a recombinant virus may advantageously be used as a raw material for a multifunctional vaccine having not only an antigenicity inherent in the virus vector but also an antigenicity of the NANBV.

By culturing the transformant or recombinant virus obtained above according to a customary method, an NANBV antigen polypeptide can be produced in the culture of the transformant or recombinant virus on a commercial scale. With respect to the details of the method in which an animal virus gene is used as an expression vector, reference may be made to European patent Application Publication No. 0 334 530 A1.

Accordingly, in still another aspect of the present invention, there is provided a method for producing a non-A, non-B hepatitis virus antigen polypeptide, which comprises:

(a) inserting a deoxyribonucleic acid into a replicable expression vector selected from a plasmid and an animal virus gene to obtain a replicable recombinant DNA comprising the plasmid and the deoxyribonucleic acid inserted therein when the replicable expression vector is a plasmid or obtain a recombinant virus comprising the animal virus gene and the deoxyribonucleic acid inserted therein when the expression vector is an animal virus gene, the deoxyribonucleic acid comprising a nucleotide sequence selected from the group consisting of a first nucleotide sequence comprising at least part of a region from the 1st to 1499th nucleotides or at least part of a region from the 1500th to 9416th nucleotides of the non-A, non-B hepatitis virus entire nucleotide sequence shown in FIG. 2(1) through FIG. 2(16) hereof and a nucleotide sequence obtained by substituting at least one nucleotide of the first nucleotide sequence in accordance with the degeneracy of the genetic code;

(b) transfecting cells of a microorganism or eukaryotic cell culture with the recombinant DNA when the replicable expression vector used in step (a) is a plasmid, to thereby form a transformant, followed by selection of the transformant from parent cells of the microorganism or eukaryotic cell culture;

(c) culturing the transformant obtained in step (b) to thereby express the deoxyribonucleic acid and produce a non-A, non-B hepatitis virus antigen peptide, or culturing the recombinant virus obtained in step (a) to thereby express the deoxyribonucleic acid and the animal virus gene and produce a non-A, non-B hepatitis virus antigen peptide in the form of a multiplied recombinant virus comprising an animal virus and a non-A, non-B hepatitis virus antigen peptide contained on the surface thereof; and (d) isolating the non-A, non-B hepatitis virus antigen peptide alone or in the form of the multiplied recombinant virus.

Furthermore, by using part or whole of the cDNA of FIG. 2(1) through FIG. 2(16) as a template, an RNA or mRNA corresponding thereto can be synthesized by in vitro transcription according to a standard method. For example, an RNA or mRNA corresponding to the entire region of the cDNA of FIG. 2(1) through FIG. 2(16) can synthesized using as a template the entire region of the cDNA which is prepared by digesting plasmid pDM-18 (constructed in Example 2) with restriction enzyme HindIII, followed by in vitro transcription by means of T7 RNA polymerase and cap analog. The thus synthesized RNA or mRNA covers the entire region of NANBV gene, that is, the RNA or mRNA is substantially naked NANBV genome. Therefore, when the mRNA is transfected into animal cells, an infectious NANBV particle can be obtained. The above-mentioned mRNA can be synthesized by means of, for example, a commercially available mRNA Capping Kit (manufactured and sold by Stratagene, U.S.A.) in a conventional manner. With respect to the details of the operating procedure for the synthesis, reference may be made to "Current Protocols in Molecular Biology", 10.17.1–10.17.5, published by John Wiley & Sons, 1989). The RNA which can be obtained using part or whole of the cDNA of FIG. 2(1) through FIG. 2(16), is part or whole of the NANBV genome and, therefore, it is useful for studying NANBV and infectious disease caused thereby.

Step (VII): Purification of an NANBV antigen polypeptide

The NANBV antigen polypeptide produced in the culture of the transformant or recombinant virus may be purified using an appropriate combination of customary techniques selected from, for example, salting-out; adsorption and desorption using a silica gel, an activated carbon or the like; precipitation by an organic solvent; fractionation by ultracentrifugation; separation by ion exchange chromatography or affinity column chromatography; fractionation by high-performance liquid chromatography or electrophoresis, and the like.

When the NANBV antigen polypeptide is purified from the culture of an E. coli transformant or a yeast transformant, from the viewpoint of effective removal of allergens derived from E. coli and yeast which cause the quality of the final product of the NANBV antigen polypeptide to be markedly lowered, it is preferred that the purification be conducted by, for example, the steps of (1) adsorption and desorption using a silica gel, removal of impurities by adsorption on an activated carbon and (2) fractionation by density gradient centrifugation in this order (Japanese Patent Application Laid-Open Specification No. 63-297). When the NANBV antigen polypeptide is purified from the culture of a recombinant virus, e.g., the culture of a recombinant virus-infected cells, a high purity NANBV antigen polypeptide can be obtained by subjecting a crude solution containing the antigen to purification by ultracentrifugation and density gradient centrifugation repeatedly.

Thus, a solution containing a purified NANBV antigen polypeptide of the present invention is obtained. If desired, the solution may be lyophilized to obtain a purified NANBV antigen polypeptide in a dry form.

The mixed antigen polypeptide of the present invention may be obtained by mixing at least two different types of the NANBV antigen polypeptides obtained by gene expression of at least two different types of cDNAs having different nucleotide sequences.

As described above, the core protein (C protein), matrix protein (M protein) and envelope protein (E protein) of the NANBV are included in the region from the 1st (Met) to 389th (Gly) amino acids shown in FIG. 2(1) through FIG. 2(3). Therefore, the above-mentioned epitopes contained in this region, especially epitopes coded for by nucleotide sequences respectively of the 906th to 953rd nucleotides, of the 1020th to 1046th nucleotides and of the 1194th to 1232nd nucleotides, are extremely useful as antigens. The epitopes may be obtained by polypeptide synthesis. The polypeptide synthesis can be conducted by means of a commercially available polypeptide synthesizer, such as polypeptide synthesizer COUPLER 2100 (manufactured and sold by Du Pont, USA) and polypeptide synthesizer 430A (manufactured and sold by Applied Biosystems, USA). The synthesized antigen polypeptide may be used, for example, for producing a vaccine, a diagnostic reagent and an antibody.

In a further aspect of the present invention, there is provided a replicable recombinant comprising a replicable expression vector selected from a plasmid and an animal virus gene and a deoxyribonucleic acid comprising a nucleotide sequence selected from the group consisting of the first nucleotide sequence comprising at least part of a region from the 1st to 1499th nucleotides or at least part of a region from the 1500th to 9416th nucleotides of the non-A, non-B hepatitis virus nucleotide sequence shown in FIG. 2(1) through FIG. 2(16) hereof and a nucleotide sequence obtained by substituting at least one nucleotide of the first nucleotide sequence in accordance with the degeneracy of the genetic code.

The replicable recombinant can be used not only for producing the NANBV antigen polypeptide of the present invention but also for amplifying the NANBV genomic cDNA of the present invention by replication.

In a preferred embodiment of the present invention with respect to the replicable recombinant for amplifying the NANBV genomic cDNA by replication, the first nucleotide sequence comprises at least six nucleotides of the nucleotide sequence of the 1st to 1499th nucleotides or at least six nucleotides of the nucleotides sequence of the 1500th to 9416th nucleotides.

In a preferred embodiment of the present invention with respect to the replicable recombinant for producing the NANB antigen polypeptide, the first nucleotide sequence comprises at least twelve nucleotides of the nucleotide sequence of the 333rd to 1499th nucleotides or at least twelve nucleotides of the nucleotide sequence of the 1500th to 9362nd nucleotides.

In another preferred embodiment of the present invention with respect to the replicable recombinant for producing the NANBV antigen polypeptide, the first nucleotide sequence is selected from the group consisting of a nucleotide sequence of the 333rd to 422nd nucleotides, a nucleotide sequence of the 333rd to 677th nucleotides, a nucleotide sequence of the 333rd to 1499th nucleotides, a nucleotide sequence of the 474th to 563rd nucleotides, a nucleotide sequence of the 678th to 905th nucleotides, a nucleotide sequence of the 906th to 953rd nucleotides, a nucleotide sequence of the 906th to 1499th nucleotides, a nucleotide sequence of the 1020th to 1046th nucleotides, a nucleotide sequence of the 1020th to 1121st nucleotides, a nucleotide sequence of the 1194th to 1232nd nucleotides, a nucleotide sequence of the 1209th to 1322nd nucleotides, a nucleotide sequence of the 1500th to 2519th nucleotides, a nucleotide sequence of the 2520th to 3350th nucleotides, a nucleotide sequence of the 3351st to 5177th nucleotides, a nucleotide sequence of the 4485th to 4574th nucleotides, a nucleotide sequence of the 5178th to 5918th nucleotides, a nucleotide sequence of the 5544th to 5633rd nucleotides, a nucleotide sequence of the 5919th to 6371st nucleotides and a nucleotide sequence of the 6372nd to 9362nd nucleotides.

The purified NANBV antigen polypeptide of the present invention is useful as a diagnostic reagent for detecting NANB hepatitis.

The NANBV antigen polypeptide of the present invention can be formulated into a diagnostic reagent as follows. The purified NANBV antigen polypeptide solution obtained above is dispensed in a vessel, such as a vial and an ampul, and sealed. The antigen polypeptide solution put in a vessel may be lyophilized before the sealing, in the same manner as mentioned above. The amount of the NANBV antigen polypeptide put in a vessel is generally about 1 µg to about 10 mg. Alternatively, the NANBV antigen polypeptide may also be adsorbed on the surface of a customarily employed support, such as a microplate, polyethylene beads, filter paper or a membrane.

The determination of the reactivity of the serum with the NANBV antigen polypeptide may be conducted in substantially the same manner as described in Step (V) mentioned above. That is, the determination of the reactivity may be conducted by a conventional immunoassay method, such as radioimmunoassay (RIA), enzyme-linked immunosorbent assay (ELISA), fluorescent antibody technique (FA), passive haemagglutination (PHA), reversed passive haemagglutination (rPHA) and the like. The amount of the NANBV antigen polypeptide to be used for the above immunoassay is generally from about 0.1 to about 100 mg/ml of serum. Particularly, the amounts of the NANBV antigen polypeptide to be used for RIA, ELISA, FA, PHA and rPHA are generally from 0.1 to 1 mg/ml, from 0.1 to 1 mg/ml, from 1 to 100 mg/ml, from 1 to 50 mg/ml and from 1 to 50 mg/ml, respectively.

The NANBV antigen polypeptide of the present invention may also be used for screening blood for transfusion. The screening method consists in:

a) isolating serum from whole blood;

b) contacting serum of an unknown blood with an isolated NANBV antigen polypeptide comprising at least one amino acid sequence comprising at least part of an amino acid sequence coded for by a deoxyribonucleic acid comprising a coding region from the 333rd to 9362nd nucleotides of the NANBV nucleotide sequence shown in FIG. 2(1) through FIG. 2(16);

c) determining whether the serum reacts with the NANBV antigen polypeptide;

d) classifying the serum as positive or negative to non-A, non-B hepatitis based on the reactivity; and e) effecting separation of the blood in accordance with the identification.

The contact of serum of an unknown blood with the NANBV antigen polypeptide of the present invention, and the determination of the reactivity of the serum of the blood with the NANBV antigen polypeptide may be conducted in the same manner as mentioned above with respect to the method for diagnosing NANB hepatitis. By the above method, a blood for transfusion free from the NANBV can be selected.

The polyclonal antibody and monoclonal antibody specific for the NANBV antigen polypeptide of the present invention may be used as an agent for removing NANBV from blood for transfusion. That is, NANBV, present in blood can efficiently be removed by the polyclonal antibody or the monoclonal antibody by antigen-antibody reaction.

Further, the NANBV antigen polypeptide of the present invention may advantageously be used as an active ingredient of a vaccine for NANB hepatitis. The vaccine for NANB hepatitis may be prepared as follows. The culturing of a transformant containing a recombinant phage or plasmid carrying the cDNA coding for the NANBV antigen polypeptide, or a cell infected with the recombinant virus carrying the cDNA coding for the NANBV antigen polypeptide is conducted in the same manner as described above to thereby produce the NANBV antigen polypeptide in the culture. For detoxifying the NANBV antigen polypeptide in the culture to secure the safety of the antigen polypeptide and for fixing the antigen polypeptide to stabilize the immunogenicity and the antigenicity of the antigen polypeptide, it is preferred to add a conventional inactivating agent to the culture of the transformant or recombinant virus-infected cell, or to a culture medium obtained by removing the transformant cells or the recombinant virus-infected cell. For example, an inactivating agent, such as formalin, may be added in an amount of from 0.0001 to 0.001 v/v%, followed by incubation at 4° to 37° C. for 5 to 90 days. Then, the resultant culture or culture medium is subjected to purification in the same manner as mentioned above. Thus, an original NANB hepatitis vaccine solution containing the purified NANBV antigen polypeptide is obtained.

The original NANB hepatitis vaccine solution is filtered using a microfilter by a standard method to sterilize the solution. The filtrate is diluted with physiological saline so that the protein concentration is about 1 to about 500 µg/ml as measured by the Lowry method. To the resultant solution is then added aluminum hydroxide gel as an adjuvant so that the concentration of the added gel becomes about 0.1 to about 1.0 mg/ml. As an adjuvant, there may also be employed precipitating depositary adjuvants such as calcium phosphate gel, aluminum phosphate gel, aluminum sulfate, alumina and bentonite, and antibody-production inducing adjuvants such as muramyl peptide derivatives, polynucleotides, Krestin® (manufactured and sold by Kureha Chemical Industry Co., Ltd., Japan) and picibanil (both of which are an antineoplastic agent). Further, to the mixture, at least one stabilizing agent may be added. As the stabilizing agent, any commercially available stabilizing agent may be used. Examples of stabilizing agents include gelatin and hydrolysates thereof, albumin, saccharides such as glucose, fructose, galactose, sucrose and lactose, and amino acids such as glycine, alanine, lysine, arginine and glutamine.

Then, the thus obtained NANB hepatitis vaccine solution containing a gel-adsorbed NANBV antigen polypeptide is dispensed into a small vessel, such as an ampul and a vial, and sealed. Thus, there is obtained a purified adsorbed NANB hepatitis vaccine comprising an adsorbed NANBV antigen polypeptide.

The NANB hepatitis vaccine solution thus obtained may be lyophilized to obtain the NANB hepatitis vaccine in a dried form so that the product can be transported to and stored at a place of severe climate, for example, in an area in the tropics. The lyophilization may generally be conducted according to a standard method after the liquid adsorbed NANB hepatitis vaccine is dispensed in a vessel such as a vial and an ampul. After lyophilization, a nitrogen gas is introduced in the vessel containing the dried vaccine, followed by sealing. Incidentally, the quality of the vaccine produced is examined in accordance with "Adsorbed Hepatitis B Vaccine", "Dried Japanese Encephalitis Vaccine", and "Adsorbed Pertussis Vaccine" provided for in Notification No. 159 of the Ministry of Health and Welfare, Japan, "Minimum Requirements for Biological Products".

The NANB hepatitis vaccine may be prepared in the form of a mixed vaccine which contains an adsorbed NANBV antigen polypeptide mentioned above and at least one antigen other than the present NANBV antigen polypeptide. As the antigen other than the present NANBV antigen polypeptide, there may be employed any antigens that are conventionally used as active ingredients of the corresponding vaccines insofar as the side effects and adverse reactions caused by such other antigens and the NANBV antigen polypeptide are not additively or synergistically increased by the use of the NANBV antigen polypeptide and such other antigens in combination and the antigenicities and immunogenicities of the NANBV antigen polypeptide and such other antigens are not reduced by the interference between the NANBV antigen polypeptide and other antigens. The number and the types of the antigens which may be mixed with the NANBV antigen polypeptide are not limited insofar as the side effects and adverse reactions are not increased additively or synergistically and the antigenicity and immunogenicity of each of the NANBV antigen polypeptide and such antigens are not reduced as mentioned above. Generally, two to six types of antigens may be mixed with the NANBV antigen polypeptide. Examples of antigens which may be mixed with the present NANBV antigen polypeptide, include detoxified antigens, inactivated antigens or toxoids which are derived from Japanese encephalitis virus, HFRS (hemorrhagic fever with renal syndrome) virus, influenza virus, parainfluenza virus, hepatitis B virus, dengue fever virus, AIDS virus, *Bordetella pertussis*, diphtheria bacillus, tetanus bacillus, meningococcus, pneumococcus and the like.

Generally, the vaccine comprising the NANBV antigen polypeptide of the present invention may be contained and sealed in a vial, an ampul or the like. The vaccine of the present invention may generally be administered in the form of a liquid or suspension. In the case where the vaccine is in a dried form, the vaccine is dissolved or suspended in sterilized distilled water before administration, the amount of the distilled water being such that the volume becomes the original volume before being subjected to lyophilization. Generally, the vaccine may be administered subcutaneously. The dose of the vaccine per person may generally be about 0.5 ml. In general, the dose of the vaccine per child may be half as much as that of the vaccine per adult. The vaccine may generally be administered twice at an interval of about one week to one month and then, about half a year later, administered once more.

Further, the NANBV antigen polypeptide may be used for preparing an antibody, such as a polyclonal antibody and a monoclonal antibody, specific for the NANBV antigen polypeptide. For example, a polyclonal antibody specific for the NANBV antigen polypeptide may be prepared by a conventional method as follows. The purified NANBV antigen polypeptide of the present invention is inoculated subcutaneously, intramuscularly, intraperitoneally or intravenously to an animal, such as mouse, guinea pig and rabbit. The inoculation of the NANBV antigen polypeptide is generally conducted several times at intervals of 1 to 4 weeks, to thereby completely immunize the animal. In order to enhance the immunizing effect, a conventional and commercially available adjuvant may be used. Then, blood serum is collected from the immunized animal and an anti-NANBV antigen polypeptide polyclonal antibody is isolated and purified from the blood serum according to a standard method.

On the other hand, a monoclonal antibody specific for the NANBV antigen polypeptide may be prepared by a conventional method as described, for example, in Cell Technology, 1, 23-29 (1982). For example, splenic cells obtained from a mouse immunized with the purified NANBV antigen polypeptide are fused with commercially available mouse myeloma cells by cell fusion technique, to obtain hybridomas. The hybridomas are screened to obtain a hybridoma capable of producing an antibody reactive with the NANBV antigen polypeptide. The obtained hybridoma is cultured in a standard method. From the supernatant of the culture, an anti-NANBV antigen polypeptide monoclonal antibody is isolated and purified by a standard method.

The above-mentioned polyclonal antibody and monoclonal antibody may also be used as a diagnostic reagent for diagnosing NANB hepatitis. The diagnosis of NANB hepatitis using the antibody may be conducted by immunoassay in substantially the same manner as mentioned above with respect to the diagnosis of NANB hepatitis using the NANBV antigen polypeptide. By the use of the polyclonal antibody or the monoclonal antibody, the identification and quantification of the NANBV antigen polypeptide present in a liver tissue and blood can be conducted.

The NANBV genomic cDNA of the present invention can be prepared by digesting the NANBV genomic cDNA clone defined in the present invention with an appropriate restriction enzyme. Also, the NANBV genomic cDNA of the present invention can be prepared by the technique of DNA synthesis in accordance with the nucleotide sequence shown in FIG. 2(1) to FIG. 2(16) of the present application. The preparation of the NANBV genomic cDNA by way of DNA synthesis can be performed by means of a customary DNA synthesizer, such as DNA synthesizer Model 380B (manufactured and sold by Applied Biosystem, U.S.A.) and DNA Synthesizer Model 8700 (manufactured and sold by Biosearch, U.S.A.). The NANBV genomic cDNA of the present invention can be used to conduct the genetic diagnosis of NANBV infection. That is, the NANBV genomic cDNA of the present invention can be used as a primer for polymerase chain reaction (PCR) in the detection of an NANBV gene in the body fluid or cells from a patient. For the diagnosis by polymerase chain reaction, the NANBV genomic cDNA is used in an amount of 10 to 100 ng.

The NANBV genomic cDNA of the present invention may also be used for diagnosing NANB hepatitis by hybridization technique. That is, the NANBV genomic cDNA is labeled with, for example, biotin, alkaline phosphatase, radioisotope $^{32}P$ or the like and used as a probe for hybridization. The cDNA to be used for the diagnosis by hybridization technique may be prepared by a standard method, for example, as follows. The recombinant phage containing the NANBV cDNA obtained in Step (V) mentioned above is digested with an appropriate restriction enzyme to cut off the DNA fragment containing the NANBV cDNA. The obtained DNA fragment is ligated to a commercially available replicable cloning plasmid to obtain a recombinant plasmid containing the DNA fragment. The recombinant plasmid is introduced in a host cell to form a transformant and the transformant is cultured to multiply the recombinant plasmid. The multiplied recombinant plasmid is isolated from the transformant and digested with a restriction enzyme. The resultant digest is subjected to low-melting point agarose gel electrophoresis to isolate and purify the cDNA coding for the NANBV antigen polypeptide. The thus obtained cDNA is labeled with biotin, alkaline phosphatase, radioisotope $^{32}P$ or the like. The labeling of the cDNA may be conducted by using a commercially available nick translation kit or multiprime DNA labeling system (manufactured and sold by, for example, Amersham, England; Nippon Gene Co., Ltd., Japan; and the like). The labeled cDNA is put in a vessel having a volume of about 5 to 20 ml, such as a vial or an ampul, and sealed. The amount of the labeled cDNA put in a vessel is generally 1 to 100 µg per vessel. The labeled cDNA may be contained in the vessel in the form of a solution. Alternatively, the labeled cDNA may be contained in the vessel in a lyophilized state. The diagnosis of NANB hepatitis by the use of the labeled cDNA is conducted by a standard hybridization method. That is, plasma, serum or leukocytes obtained from a patient is placed in contact with the labeled cDNA and an RNA hybridized with the labeled cDNA is detected. The detection of the RNA hybridized with the labeled cDNA may be conducted by a standard method. When the cDNA is labeled with an enzyme, the detection is conducted by enzyme immunoassay. When the cDNA is labeled with a radioisotope, the detection is conducted by, for example, scintillation counting.

The NANBV genomic cDNA of the present invention is excellent in reliability and contains the entire region of the open reading frame of the NANBV gene.

The NANBV antigen polypeptide of the present invention is specifically reactive with the NANBV. Therefore, when the NANBV antigen polypeptide is used as a diagnostic reagent, the diagnosis of NANB hepatitis can be conducted easily with high reliability. Further, when the NANBV antigen polypeptide of the present invention is used for screening blood for transfusion, blood which is infected by NANBV can be selected easily with high reliability and removed from blood not infected by NANBV. Therefore, the post-transfusion NANB hepatitis can be prevented.

Further, the NANBV antigen polypeptide of the present invention may advantageously be used as an active ingredient of a vaccine for preventing NANB hepatitis.

Further, by the use of the NANBV antigen polypeptide of the present invention, an antibody, particularly monoclonal antibody, specific for NANBV can easily be prepared. The antibody specific for NANBV can advantageously be used as not only a diagnostic reagent for detecting NANB hepatitis, but also an agent for removing NANBV from blood for transfusion.

Furthermore, it should be noted that the NANBV antigen polypeptide of the present invention is not produced by the infection of an animal with a virus, but produced by gene expression of the DNA coding for the present antigen polypeptide in a host cell. Hence, the possibility of infection during the steps for production of the present antigen polypeptide is substantially eliminated. Also, the production cost can be decreased. Moreover, since all of the materials used in the production process, e.g., medium for the incubation system, are well-known in respect of the composition thereof, purification is facile and an antigen polypeptide product having high purity can be obtained.

PREFERRED EMBODIMENT OF THE INVENTION

The present invention will now be described in detail with reference to the following Examples, which should not be construed to be limiting the scope of the present invention.

EXAMPLE 1

Step 1 (Preparation of a plasma-derived RNA for producing cDNA, which is complementary to NANBV genome RNA)

In order to obtain NANBV from plasma, 4.8 liters of human plasma exhibiting a glutamic-pyruvic transaminase (GPT) activity of 35 IU/ or more (as measured by the method of Wroblewski, F. & J. S. LaDue: Serum glutamic-pyruvic transaminase in cardiac and hepatic disease. Proc. Soc. Exp. Biol. Med., 91:569, 1956) was superposed on a 30% (w/w) aqueous sucrose solution, and subjected to centrifugation under 48,000×g at 4° C. and for 13 hours to obtain a precipitate. The precipitate was suspended in an aqueous solution containing 50 mM Tris.HCl (pH 8.0) and 1 mM EDTA, and once more subjected to centrifugation under 250,000×g at 4° C. and for 3 hours to thereby obtain a precipitate. The obtained precipitate was dissolved in 75 ml of 5.5M GTC solution containing 5.5M quanidine thiocyanate, 20 mM sodium citrate (pH 7.0), 0.05% sarkosyl (sodium lauryl sarcosinate) and 0.1M 2-mercaptoethanol. The resultant solution was superposed on 16 ml of CsTFA-0.1M EDTA solution (ρ=1.51), and subjected to centrifugation under 140,000×g at 15° C. and for 20 hours to thereby obtain a precipitate of RNA. The supernatant containing proteins and DNA was removed by suction, and the precipitate was dissolved in 200 μl of TE 10 mM Tris.HCl, pH 8.0 and 1 mM EDTA solution. 20 μl of 3M sodium chloride and ethanol were added to the solution, and allowed to stand still at −70° C. for 90 minutes. The mixture was centrifuged under 12,000×g at 4° C. and for 30 minutes to obtain a precipitate. The precipitate was dissolved in TE, and sodium chloride and ethanol were added in the same manner as mentioned above. The mixture was allowed to stand still at −70° C. to obtain a precipitate. The precipitate was dissolved in 10 μl of TE to thereby obtain a purified RNA.

Step 2 (Preparation of a liver-derived RNA for producing a cDNA, which is complementary to NANBV genome RNA)

NANBV genome RNA was prepared from a liver tissue cut off from a NANBV hepatitis patient by the method of Okayama et al. (see H. Okayama, M. Kawaichi, M. Brownstein, F. Lee, T. Yokota, and K. Arai: High-Efficiency Cloning of Full-Length cDNA; Construction and Screening of cDNA Expression Libraries for Mammalian Cells, Methods in Enzymology 154.3–28, 1987).

Illustratively stated, 1 g of liver tissue was cut into small pieces. The small pieces were suspended in 100 ml of 5.5M GTC solution as used in Step 1, and homogenized by means of a Teflon-glass homogenizer. Subsequently, the introduction of the homogenate into a syringe having #18 needle and the discharge of the homogenate from the syringe through the needle were repeated to thereby mechanically split DNA. The resultant homogenate was centrifuged under 1,500×g (lower centrifugal force) at 4° C. and for 15 minutes to thereby obtain a supernatant. The supernatant was superposed on CsTFA solution and centrifuged in substantially the same manner as described in Step 1 to thereby obtain a precipitate as an RNA fraction. The thus obtained precipitate was suspended in 0.4 ml of 4M GTC solution. 10 μl of 1M acetic acid and 300 μl of ethanol were added to the suspension, and allowed to stand still at a temperature of −20° C. for at least 3 hours to thereby obtain a precipitate of RNA. The precipitate was separated by centrifugation under 12,000×g at a temperature of 4° C. and for 10 minutes, and dissolved in 1 ml of TE solution. 100 μl 2M sodium chloride solution and 3 ml of ethanol were added to the solution, and the mixture was allowed to stand at −20° C. for 3 hours. The resultant precipitate was collected by centrifugation and dissolved in 10 μl of TE to thereby obtain a purified, liver-derived RNA.

Step 3 (Preparation of a double-stranded cDNA using a cDNA synthesis kit)

A double-stranded cDNA was prepared using a commercially available cDNA synthesis kit (manufactured and sold by Amersham International, England).

Illustratively stated, 0.75 μg of the purified RNA obtained in Step 1 and 2 μl of random hexanucleotide primer and 2 μl of reverse transcriptase taken from the reagents included in the kit were put in a reaction tube. Then, distilled water was added in an amount such that the total volume of the resultant mixture became 20 μl. The mixture was incubated at 42° C. for 40 minutes, thereby preparing a first strand of cDNA. Subsequently, a second strand of cDNA was synthesized while cooling the reaction mixture in ice water, as follows. To 20 μl of the reaction mixture were added 37.5 μl of buffer for second strand synthetic reaction, 1 μl of *E. coli* ribonuclease H and 6.6 μl of DNA polymerase I, which were taken from the reagents included in the kit, followed by addition of 34.9 μl of distilled water. The mixture was incubated at 12° C. for 60 minutes, 22° C. for 60 minutes and at 70° C. for 10 minutes. Then, the mixture was once more cooled with ice water. 1 μl of T4 DNA polymerase was added, incubated at a temperature of 37° C. for 10 minutes, and 4 μl of 0.25M EDTA (pH 8.0) was added to thereby terminate the reaction. The reaction mixture was mixed well with a mixture of phenol and chloroform, and centrifuged under 12,000×g for one minute to thereby separate an aqueous layer. The aqueous layer was again subjected to the same extraction as mentioned above, and an equal amount of chloroform was added. The mixture was agitated well and centrifuged to separate an aqueous layer. Subsequently, an equal amount of 4M ammonium acetate and a two-fold amount of ethanol were added to the aqueous layer, and the mixture was cooled to −70° C., thereby obtaining a precipitate of purified double-stranded cDNA. The precipitate was dissolved in 50 μl of 2M ammonium acetate. To the mixture, 100 μl of ethanol was added, and the resultant mixture was cooled to −70° C. to thereby obtain a precipitate. The precipitate was collected by centrifugation under 12,000×g for ten minutes. The collected precipitate was dried and then, dissolved in 20 μl of TE.

Step 4 (Preparation of a double-stranded cDNA by the Polymerase Chain Reaction (PCR) method)

The cDNAs which were prepared by means of a reverse transcriptase using as templates the RNAs prepared in Step 1 and Step 2, were individually amplified by the PCR method (see Saiki, R. K., Gelfand, D. H., Stoffer, S., Scharf, S. J., Higuchi, R., Horn, G. T., Mullis, K. B., and Erlich, H. A., Primer-directed enzymatic amplification of DNA with a thermostable DNA Polymerase, Science 239:487–491, 1988). That is, 5 to 1,000 ng of the RNA was incubated in 20 μl of a reverse transcriptase solution containing 50 mM Tris.HCl (pH 8.3), 40 mM KCl, 6 mM $MgCl_2$, 1 μM 3'-primer [synthesized oligonucleotide comprised of 25 nucleotides of nucleotide numbers 7949 to 7973 in FIG. 2(14)], 10 mM dNTP, and 0.5 unit of reverse transcriptase (product of New England Bio Lab., U.S.A.) at 37° C. for 30 minutes. To the resultant mixture was added 80 μl of a PCR reaction solution containing 18 mM Tris.HCl (pH 8.3), 48 mM KCl, 1.5 mM $MgCl_2$, 0.6 μM each of 5'-primer [synthesized oligonucleotide comprised of 25 nucleotides of nucleotide numbers 7612 to 7636 in FIG. 2(13)] and the above-mentioned 3'-primer, 10 mM dNTP and 2.5 units of Taq DNA polymerase (manufactured and sold by Perkin Elmer Cetus Co., Ltd., U.S.A.). The mixture was subjected to incubation at 94° C. for one minute, at 50° C. for 2 minutes and at 72° C. for 3 minutes. This incubation was repeated 40 times. The resultant mixture was subjected to electrophoresis using agarose gel, thereby obtaining amplified cDNA. The amplified cDNA was subjected to phenol treatment, ethanol precipitation and drying. The dried cDNA was dissolve in 10 µl of TE.

Step 5 (Preparation of a cDNA library using lambda g11)

Using a commercially available cDNA cloning kit (manufactured and sold by Amersham International, England), a cDNA library was prepared. That is, to 130 ng of cDNA prepared in Step 3 were added 2 µl of L/K buffer, 2 µl of EcoRI adaptor and 2 µl of T4 DNA ligase, which were taken from the reagents included in the cloning kit. Distilled water was added to the solution in an amount such that the total volume of the resultant mixture became 20 µl. The mixture was incubated at a temperature of 15° C. for a period of from 16 to 20 hours, and 2 µl of 0.25M EDTA was added thereto, to thereby terminate the reaction. Subsequently, the mixture was passed through a size fractionating column included in the kit, thereby removing EcoRI adaptors which were not ligated to the cDNA. To 700 µl of the cDNA having EcoRI adaptor ligated thereto were added 83 µl of L/K buffer and 8 µl of T4 polynucleotidekinase. The mixture was incubated at a temperature of 37° C. for 30 minutes. The resultant mixture was subjected to phenol extraction twice, concentration to 350 to 400 µl by means of butanol and then ethanol precipitation, thereby obtaining a precipitate. The precipitate was dissolved in 5 µl of TE.

Subsequently, in order to insert the cDNA having EcoRI adaptor ligated thereto to the EcoRI site of cloning vector lambda gt11, 1 µl of L/K buffer, 2 µl (1 µg) of lambda gt11 arm DNA and 2 µl of T4 DNA ligase were added to 1 µl (10 ng) of the above-mentioned cDNA having EcoRI adaptor ligated thereto. Distilled water was added to the mixture in an amount such that the total volume of the mixture became 10 µl. The mixture was incubated at a temperature of 15° C. for a period of from 16 to 20 hours. Thus, a recombinant lambda gt11 DNA solution was prepared. Further, a recombinant lambda phage was obtained by in vitro packaging using a commercially available in vitro packaging kit (manufactured and sold by Stratagene Co., Ltd., U.S.A.) including Gigapack II Gold solutions A and B, SM buffer and chloroform. That is, 10 µl of Gigapack II Gold solution A and 15 µl of Gigapack II Gold solution B were added to 4 µl of the above-mentioned recombinant lambda gt11 DNA solution. The mixture was incubated at 22° C. for 2 hours. After the incubation, 470 µl of SM buffer and 10 µl of chloroform were added to thereby obtain a recombinant phage, which was stored at 4° C.

Step 6 (Cloning of cDNA using E. coli plasmid pUC19)

Using a commercially available DNA ligation kit (manufactured and sold by Takara Shuzo Co., Ltd., Japan) including solutions A and B, the cDNA was inserted in E. coli plasmid pUC19 (C. Yanishi-Perron, J. Vieira, J. Messing, Gene 33, 103, 1985), and cloned in E. coli. That is, 40 µl of solution A and 10 µl of solution B were added to 5 µl of the cDNA prepared by polymerase chain reaction (PCR) in Step 4 and 5 µl (50 ng) of plasmid pUC19 DNA which had been digested with restriction enzyme SmaI and dephosphorylated. The mixture was incubated at a temperature of 15° C. for 16 hours. E. coli strain JM 109 (see Messing, J., Crea, R., and Seeburg, P. H., Nucleic Acids Res. 9, 309, 1981) was transformed with the above-obtained plasmid DNA according to the calcium chloride method (see Mandel, M. and A. Higa, J. Mol. Biol., 53, 154, 1970). Thus, a transformed E. coli containing the plasmid having the cDNA ligated thereto was obtained.

Step 7 (Screening of clone having NANBV gene from a cDNA library)

E. coli strain Y 1090 (see Richard A. Young and Ronald W. Davis, Science, 222, 778, 1983) was cultured in 50 ml of LBM medium containing 1% tryptone, 0.5% yeast extract, 1% sodium chloride, 50 µg/ml ampicillin and 0.4% maltose at a temperature of 37° C. The E. coli cells in a logarithmic growth phase were suspended in 15 ml of 10 mM magnesium sulfate cooled with ice. The phage solution obtained in Step 5 was diluted with SM buffer containing 0.1M sodium chloride, 8 mM magnesium sulfate, 50 mM Tris.HCl (pH 7.5) and 0.01% gelatin. 0.1 ml of the diluted phage solution was mixed with an equal volume of the above-mentioned E. coli cell suspension, and the mixture was incubated at a temperature of 37° C. for 15 minutes. To the mixture was added 4 ml of soft agar medium heated to 45° C. and containing 1% tryptone, 0.5% yeast extract, 0.5% sodium chloride, 0.25% magnesium sulfate and 0.7% agar (pH 7.0). The mixture was spread on L-agar plate containing 1% tryptone, 0.5% yeast extract, 1% sodium chloride, 1.5% agar and 100 µg/ml ampicillin (pH 7.0), and incubated at a temperature of 42° C. for 3 hours. Subsequently, 10 mM IPTG (isopropyl β-D-thiogalactopyranoside) was infiltrated into a nitrocellulose filter, and the nitrocellulose filter was dried and closely contacted with the L-agar plate. The plate was incubated at a temperature of 37° C. for 3 hours. The filter was separated, and washed with TBS buffer three times. The washed filter was immersed in 2% bovine serum albumin solution, and incubated at room temperature for one hour. 1/20 volume of E. coli lysate solution included in a commercially available immunoscreening kit (manufactured and sold by Amersham International, England) was added to pooled serum from NANB hepatitis patients, and incubated at room temperature for 30 minutes. Thereafter, the serum was diluted to 50-fold with 0.2% bovine serum albumin-added TBS buffer, and the filter was immersed in the diluted serum solution, and incubated at room temperature for one hour.

The resultant filter was washed four times with a TBS buffer containing 0.05% Tween 20. The washed filter was immersed in an antibody solution which had been prepared by diluting a peroxidase-labeled antihuman IgG (manufactured and sold by Cappel Co., Ltd., Germany) 1,000-fold for one hour. The filter was washed with the above-mentioned Tween-TBS buffer, and immersed in a solution prepared by adding 0.4 ml of DAB (3,3'-diaminobenzidine tetrahydrochloride) and 15 µl of a 30% aqueous hydrogen peroxide solution to 50 ml of a TBS buffer, followed by incubation at room temperature for 5 to 30 minutes to allow color development. The resultant filter was completely washed with distilled water to terminate the reaction.

By the above-mentioned procedure, the obtained plaques were purified. As a result, 9 positive clones were isolated, which were, respectively, designated as BK 102, BK 103, BK 105, BK 106, BK 108, BK 109, BK 110, BK 111 and BK 112. All of these clones did not react with serum from a healthy human, but reacted with serum from a patient suffering from NANB hepatitis. See Table 1.

TABLE 1

Reactivity between the serum obtained from a patient suffering from NANB hepatitis and the recombinant lambda gt11 phage clone

| Clone | Serum from healthy person | Serum from NANB hepatitis patient |
|---|---|---|
| BK 102 | 0/10* | 10/11 |
| BK 103 | 0/10 | 9/11 |
| BK 105 | 0/10 | 11/11 |
| BK 106 | 0/10 | 11/11 |
| BK 108 | 0/10 | 9/11 |
| BK 109 | 0/10 | 9/11 |
| BK 110 | 0/10 | 9/11 |
| BK 111 | 0/10 | 9/11 |
| BK 112 | 0/10 | 10/11 |

*the number of positive samples/the number of specimens.

Step 8 (Determination of the nucleotide sequence of the obtained clones)

Recombinant phage DNAs of clones BK 102 to BK 112 were collected, and the collected DNAs were digested with restriction enzyme EcoRI. Then, cDNA fragments of NANBV were isolated and the isolated cDNAs were individually inserted into plasmid pUC19 at EcoRI site. Using the plasmids, E. coli strain JM 109 was transformed in substantially the same manner as in Step 7. Plasmid DNAs were obtained from the transformed E. coli and purified. The nucleotide sequence of each of the NANBV cDNAs was determined using 7-DEAZA sequencing kit (manufactured and sold by Takara Shuzo Co., Ltd., Japan; see Mizusawa, S., Nishimura, S. and Seela, F. Nucleic Acids Res., 14, 1319, 1986). The relationship between the nucleotide sequences of the obtained cDNA clones is shown in FIG. 1(1).

Step 9 (Cloning of NANBV cDNA clones from a cDNA library by Genomic walking)

Probes were prepared by labeling with $^{32}$P-dCTP the cDNA fragments of clone BK 102, clone BK 106 and clone BK 112 which were obtained in Step 8. Using the probes, phage clones containing NANBV cDNAs were obtained by hybridization from the cDNA library of cloning vector lambda gt11 obtained in Step 5 and the above-mentioned probes. That is, plasmid DNAs were prepared from the transformed E. coli with clone BK 102, clone BK 106 and clone BK 112 obtained in Step 8 by the alkali method (see T. Maniatis, E. F. Fritsch, and J. Sambrook: Isolation of Bacteriophage λ and Plasmid DNA: "Molecular Cloning", Cold Spring Harbor Lab., pp 75–96.).

Plasmid DNA of clone BK 102 was digested with restriction enzymes NcoI and HincII, and the resultant 0.7 kb fragments having been on the 5'-terminus side of the DNA were subjected to electrophoresis with agarose gel, and collected. Plasmid DNAs of clone BK 106 and clone BK 112 were digested with restriction enzyme NcoI. In the same manner as mentioned above, 1.1 kb DNA fragments were collected from clone BK 106, and 0.7 kb fragments having been on the 3'-terminus side were collected from clone BK 112. 25 ng to 1 µg of DNA fragments were incubated with [α-$^{32}$P]dCTP (3000 Ci/mmol; manufactured by Amersham Co., Ltd., England) at a temperature of 37° C. for a period of from 3 to 5 hours, using commercially available DNA labeling kit (manufactured by Nippon Gene Co., Ltd.). Thus, probes for hybridization were prepared.

Subsequently, the cDNA library phage obtained in Step 5 was incubated at a temperature of 42° C. in L-agar medium for 3 hours, as described in Step 7. Further, the phage was incubated at a temperature of 37° C. for 3 hours, and was cooled. A nitrocellulose filter was disposed on the mixture, and was allowed to stand still for a period of from 30 to 60 seconds. Thus, the phage was adsorbed onto the filter.

The filter was subjected to alkali denaturation for a period of from 1 to 5 minutes using an aqueous solution containing 0.5N sodium hydroxide and 1.5M sodium chloride and to the neutralization with an aqueous solution containing 0.5M Tris.HCl (pH 8.0) and 1.5M sodium chloride for a period of from 1 to 5 minutes. The filter was washed with 2×SSC solution containing 0.3M sodium chloride and 0.03M sodium citrate, air dried, and baked at a temperature of 80° C. for 2 hours.

The filter was incubated at a temperature of 42° C. for 6 hours in a solution for hybridization containing 50% formamide, 5×SSC, 5×Denhart solution, 50 mM phosphoric acid-citric acid buffer (pH 6.5), 100 µg/ml trout sperm DNA and 0.1% SDS. Then, the filter was immersed in 300 ml of the hybridization solution having 1 ml of the above-mentioned probe of about 4×10$^8$ cpm/ml added thereto, and incubated at a temperature of 42° C. for 16 to 20 hours. The filter was washed with an SDS solution containing 0.1% 2×SSC four times and with an SDS solution containing 0.1% 0.1×SSC twice. After the washing, the filter was dried, and was subjected to autoradiography. Thus, hybridization positive clones were isolated. As a result, 27 clones being reactive with the probe derived from clone BK 102, 14 clones being reactive with the probe derived from clone BK 106 and 13 clones being reactive with the probe derived from clone BK 112, were obtained, which were respectively designated as BK 114 to BK 169.

The nucleotide sequence of each of clones BK 114 to BK 169 was determined according to the method described in Step 8, followed by mapping for each of the clones. As a result, a map of nucleotide sequence having a length of about 9.5 kb considered to be the approximately total length of the NANBV genome was obtained [see FIG. 1(2)].

Clone BK 157 located on the 5' terminus side was digested with restriction enzyme KpnI to thereby collect a 0.55 kb fragment having been on the 5'-terminus side. Also, clone BK 116 located on the extreme 3'-terminus side was digested with restriction enzymes HpaI and EcoRI to thereby collect a 0.55 kb fragment having been on the 3'-terminus side. A probe labeled with $^{32}$P was prepared in the same manner as described above, and the cDNA library phage obtained in Step 5 was subjected to plaque hybridization. As a result, three new additional clones were separated by the probe derived from the clone BK 157. These new clones were, respectively, designated as clones BK 170, BK 171 and BK 172.

Step 10 (Analysis of the nucleotide sequence of cDNA)

The entire nucleotide sequence of NANBV gene was determined from the nucleotide sequences of the clones obtained in Steps 8 and 9, and shown in FIGS. 2(1) to 2(16). From the Figures, it was assumed that the cloned genomic cDNAs of NANBV were composed of 9416 nucleotides, wherein there was an open reading frame composed of 9030 nucleotides coding for a protein composed of 3010 amino acid residues. The hydrophilicity/hydrophobicity pattern of this protein was similar to that of flavivirus as already reported (see H. Sumiyoshi, C. Mori, I. Fuke et al., Complete Nucleotide Sequence of the Japanese Encephalitis Virus Genome RNA. Virology, 161, 497–510, 1987). Clone BK 157 covers nucleotide numbers 1 to 1962 of FIGS. 2(1) to 2(16), clone BK 172 covers nucleotide numbers 5 to 366, clone BK 153 covers nucleotide numbers 338 to 1802, clone BK 138 covers nucleotide numbers 1755 to 5124, clone BK 129 covers nucleotide numbers 4104 to 6973, clone BK 108 covers nucleotide numbers 6886 to 8344 and clone BK 166 covers nucleotide numbers 8082 to 9116. They are preserved as *Escherichia coli* BK 108 (deposited at Fermentation Research Institute, Japan under accession number FERM BP-2971), BK 129 (deposited at Fermentation Research Institute, Japan under accession number FERM BP-2972), BK 138 (deposited at Fermentation Research Institute, Japan under accession number FERM BP-2973), BK 153 (deposited at Fermentation Research Institute, Japan under accession number FERM BP-2974), BK 157, BK 166 (deposited at Fermentation Research Institute, Japan under accession number FERM BP-2975), and BK 172 (deposited at Fermentation Research Institute, Japan under accession number FERM BP-2976), respectively.

Step 11 (Production of NANBV-related antigens in *E. coli*, which antigens are related with the antibody-response accompanying NANBV infection)

Respective cDNAs of clone BK 106, clone BK 111 and clone BK 112 each obtained in Step 8 and cDNA of clone BK 147 obtained in Step 9 were individually inserted into plasmids, and the thus obtained plasmid DNAs were collected by the conventional alkali method. Subsequently, the collected DNA of clone BK 106 was digested with restriction enzymes EcoRI and ClaI to thereby obtain 0.5 µg of a DNA fragment of 0.34 kb in length. The thus obtained DNA fragment was incubated at 37° C. for 60 minutes in a T4 DNA polymerase solution containing 67 mM Tris.HCl (pH 8.8), 6.7 mM magnesium chloride, 16.6 mM ammonium sulfate, 10 mM 2-mercaptoethanol, 6.7 µM EDTA, 0.02% bovine serum albumin, 0.3 mM dNTP and 2–5 units of T4 DNA polymerase, thereby rendering both terminals blunt. The DNA of clone BK 102 was digested with restriction enzyme BamHI to thereby collect 0.5 µg of a DNA fragment of 0.7 kb in length, and the terminals of the DNA fragment were rendered blunt using T4 DNA polymerase in substantially the same manner as mentioned above. The DNA of clone BK 147 was digested with restriction enzyme Sau3AI to thereby obtain 0.5 µg of a DNA fragment of 1 kb in length and the terminals of the DNA fragment were rendered blunt in the same manner as mentioned above. Also, the DNA of clone BK 111 was digested with restriction enzyme EcoRI to thereby obtain 0.5 µg of a DNA fragment of 1 kb in length, and the terminals of the DNA fragment were rendered blunt in substantially the same manner as mentioned above. Subsequently, the DNA of expression vector pKK 233-2 (Amann, E. and J. Brosius. ATG vector for regulated high-level expression of cloned genes in *Escherichia coli*. Gene, Vol. 40, 183, 1985) was digested with restriction enzyme HindIII. 2 µg of the resultant DNA was incubated at 37° C. for 20 minutes in a S1 nuclease solution containing 0.3M sodium chloride, 50 mM sodium acetate (pH 4.5), 1 mM zinc sulfate and 100–200 units of S1 nuclease, and the reaction was terminated by adding 1/10 volume of each of 0.12M EDTA and 1M Tris.HCl solution (pH 9.0). Then, phenol extraction was performed, and the vector DNA having blunt terminals was precipitated by ethanol and collected. On the other hand, the DNA of vector pKK 233-2 was digested with restriction enzyme PstI, and the digested DNA was purified by extraction with phenol and precipitation from ethanol. The terminals of 2 µg of the purified vector DNA which had been cleaved by restriction enzyme PstI were rendered blunt by the above-mentioned T4 DNA polymerase reaction. The thus obtained DNA fragments derived from clone BK 106 and clone BK 111 were each cleaved with restriction enzyme HindIII. 0.5 µg of each of the cleaved DNA fragments was mixed with 0.5 µg of a vector DNA having blunt terminals. The DNA fragments derived from clone BK 102 and clone BK 147 were each cleaved with restriction enzyme PstI. 0.5 µg of each of the cleaved DNA fragments was mixed with 0.5 µg of a vector DNA having terminals thereof rendered blunt. The volume of each of the mixtures was adjusted to 20 µl by adding 2 µl of 10× ligation solution containing 500 mM Tris.HCl (pH 7.5), 100 mM magnesium chloride, 100 mM DTT and 10 mM ATP, 300–400 units of T4 DNA ligase and distilled water. The mixtures were incubated at 14° C. for 12–18 hours, thereby obtaining plasmids, which were respectively designated as pCE-06, pE-11, pB-02 and pS-09. Using each of these plasmid DNAs, *E. coli* strain JM 109 was transformed in substantially the same manner as described in Step 6, thereby obtaining transformed *E. coli*. The transformed *E. coli* was cultured at 37° C. in LB medium (pH 7.5) containing 1 (w/v) % trypton, 0.5 (w/v) % yeast extract and 1 (w/v) % sodium chloride, and when it was in logarithmic growth phase, 1 mM IPTG (isopropyl-β-D-thiogalactopyranoside) was added to the medium. The culturing was further continued for 3 hours. Then, *E. coli* cells were collected by centrifugation (10,000×g for 15 minutes), and the collected cells were lysed in 50 mM Tris.HCl (pH 8.0). The mixture was subjected to ultrasonic treatment (20 Hz, 600 W, 5 minutes), and centrifuged at 10,000×g 15 minutes to thereby obtain a supernatant fraction and a precipitate fraction. Each of the fractions was dissolved in a sample buffer containing of 20 (v/v)% glycerol, 0.1M Tris.HCl (pH 6.8), 2 (w/v)% SDS, 2 (v/v)% 2-mercaptoethanol and 0.02% BPB, heated at 100° C. for 3 minutes, and subjected to electrophoresis using 0.1% SDS-7.5% polyacrylamide gel to separate protein. After the electrophoresis, the protein was transferred to a nitrocellulose filter by trans blot cell (manufactured and sold by BIO.RAD Co., Ltd., U.S.A.). The filter was immersed in 3% gelatin solution, and allowed to stand still for 60 minutes. The filter was incubated together with serum from a patient suffering from NANB hepatitis, which had been diluted 100-fold, for 2 to 3 hours at room temperature. The filter was washed with distilled water and then with TTBS solution containing 0.02M Tris.HCl (pH 7.5), 0.5M sodium chloride and 0.05 (v/v)% Tween 20. Subsequently, the washed filter was immersed in a 2,000 fold-diluted solution of peroxidase-labeled anti-human IgG antibody, and incubated at room temperature for 90 minutes. The filter was washed with distilled water and then with TTBS solution. The washed filter was immersed in a buffer having, added thereto, coloring agent DAB and 30%, based on substrate, hydrogen peroxide as described in Step 7 for 5 to 30 minutes, following by washing with water, to terminate the reaction.

As a result, as shown in Table 2, all of the antigens produced by the plasmids specifically react with serum from a patient suffering from NANB hepatitis, thereby demonstrating that the proteins produced by the cDNAs inserted in the plasmids are clinically important.

TABLE 2

Reactivity evaluated by the Western blot method between proteins produced by various plasmids and sera from a patient suffering from NANB hepatitis.

| Plasmid | origin of cDNA | Extract | Serum from NANB hepatitis patient | Serum from healthy human |
|---------|----------------|---------|-----------------------------------|--------------------------|
| pCE-066 | BK 106 | S | ± | − |
|         |        | P | + | − |
| pE-11-89 | BK 111 | S | ± | − |
|          |        | P | + | − |
| pB-02-10 | BK 102 | S | + | − |
|          |        | P | − | − |
| ps-09-07 | BK 109 | S | ± | − |
|          |        | P | + | − |
| pKK233-3 | — | S | − | − |
|          |   | P | − | − |

S: Supernatant by centrifugation
P: Precipitate by centrifugation
+: positive
±: slightly positive
−: negative Step 12 (Purification of NANBV-related antigens produced by *E. coli* and reactivity thereof with serum from a patient suffering from hepatitis)

The usefulness of the protein produced by the cDNA which was inserted into an expression vector was demonstrated by purifying the protein and using the purified protein as an antigen for ELISA or radioimmunoassay. That is, the lysate of the transformed *E. coli* which was obtained in Step 11 was subjected to centrifugation at 10,000×g for 15 minutes, thereby obtaining a supernatant and a precipitate. For example, the precipitate obtained from transformant JM 109/pCE 066 was suspended in a solution of 100 mM Tris.HCl (pH 8.0) and 0.1% Triton X-100, and the resultant suspension was subjected to ultrasonic treatment at a frequency of 20 KHz (600 W) for one minute, followed by centrifugation at 21,000×g for 15 minutes, thereby obtaining a precipitate. The precipitate was re-suspended in a solution of 100 mM Tris.HCl (pH 8.0) and 6M urea, and then subjected to ultrasonic treatment followed by centrifugation.

The resultant supernatant was dialyzed against a solution of 10 mM phosphoric acid buffer (pH 7.5) and 6M urea to thereby obtain an antigen solution. 20 ml of the antigen solution was passed through a column 21.5× 250 mm) packed with hydroxyapatite, which had been equilibrated with the above-mentioned buffer, to cause the antigen to be adsorbed onto the packing material. The column was subjected to high speed liquid chromatography (HPLC) wherein elution was performed with the above-mentioned buffer having, added thereto, sodium chloride, the concentration of which was varied from 0 to 2M with a linear concentration gradient, thereby obtaining a fraction containing an antigen. The obtained fraction was dialyzed against a solution of 50 mM carbonate buffer (pH 9.6) and 0.05% sodium dodecyl sulfate (SDS).

Further, the supernatant obtained by centrifugation (at 10,000 g for 15 minutes) of the lysate of transformant JM 109/pB-02-10 was treated with 35% saturated ammonium sulfate, and the obtained precipitate was dissolved in a solution of 50 mM Tris.HCl (pH 8.5) and 100 mM 2-mercaptoethanol. The resultant solution was dialyzed against the above-mentioned buffer. Subsequently, 100 ml of the dialysed solution was passed through a column (22.0× 200 mm) packed with DEAE cellulose, which had been equilibrated with the above-mentioned buffer, to cause the antigen to be adsorbed onto the packing material. The column was subjected to high performance liquid chromatography wherein elution was performed with a solution of 50 mM Tris.HCl (pH 8.5) and 100 mM 2-mercaptoethanol having, added thereto, sodium chloride, the concentration of which was varied from 0 to 2M with a linear concentration gradient, thereby pooling a fraction containing the antigen.

The fraction was dialyzed against a solution of 10 mM phosphate buffer (pH 6.8) and 100 mM 2-mercaptoethanol. The dialyzed solution was passed through the column of hydroxyapatite for high performance liquid chromatography, which had been equilibrated by the above-mentioned buffer, to cause the antigen to be adsorbed onto the packing material. The column was subjected to high speed liquid chromatography wherein elution was performed with phosphoric acid, the concentration of which was varied with a linear concentration gradient from 10 to 400 mM, thereby pooling a fraction containing the antigen. The resultant fraction was dialyzed against a solution of 50 mM carbonate buffer (pH 9.6) and 0.05% SDS.

The precipitate obtained by centrifugation of the lysate of transformant JM 109/pE-11-89 was suspended in 10 mM phosphate buffer (pH 5.5). The suspension was subjected to the above-mentioned ultrasonic treatment for one minute, and then subjected to centrifugation at 21,000×g for 15 minutes. The resultant precipitate was suspended in a solution of 100 mM carbonate buffer (pH 10.5), 500 mM sodium chloride and 10 mM EDTA. The resultant suspension was again subjected to the ultra sonic treatment for one minute, followed by centrifugation. The resultant supernatant was dialyzed against a solution of 30 mM phosphate buffer and 6M urea. Subsequently, 20 ml of the dialyzed solution was passed through a CM cellulose column (22×200 mm) for high performance liquid chromatography (HPLC), which had been equilibrated with the same buffer as used for the above-mentioned dialysis, to thereby cause the antigen to be adsorbed onto the packing material. The column was subjected to high performance liquid chromatography wherein elution was performed with the above-mentioned buffer having, added thereto, sodium chloride, the concentration of which was varied from 0 to 1.5M with a linear concentration gradient, obtaining a fraction containing the antigen. The fraction was dialyzed against a solution containing 50 mM carbonate buffer (pH 9.6) and 0.05% SDS, thereby obtaining a solution containing the antigen.

The antigens prepared above were used as an antigen for ELISA for the clinical diagnosis of infection with non-A, non-B hepatitis virus. The protein concentration of each of the above-mentioned purified antigens was adjusted to 1 μg/ml, and put in each well of Microplate Immulone 600 (manufactured and sold by Greiner, Co., Ltd., Germany) in an amount of 100 ml for use in ELISA, which well was allowed to stand still at 4° C. overnight. The contents of the individual wells were washed well three times with PBS-T buffer containing 10 mM phosphate buffer (pH 7.2), 0.8% sodium chloride and 0.05% Tween 20, and sample serum diluted with the PBS-T buffer was added in an amount of 100 μl/well, followed by reaction at 37° C. for one hour. The contents of the individual wells were washed three times with the PBS-T buffer, and a peroxidase-labeled anti-human IgG antibody (manufactured and sold by Cappel Co., Ltd., Germany) which had been diluted 8000-fold with PBS-T buffer containing 10% fetal calf serum was added in an amount of 100 μl/well. The individual well contents were reacted at 37° C. for one hour, and washed with the PBS-T buffer four times. A substrate coloring agent solution composed of 9 ml of 0.05M citric acid-phosphate buffer and, contained therein, 0.5 μg of o-phenylenediamine and 20 μl of aqueous hydrogen peroxide, was added in an amount of 100 μl/well. The plate was light shielded, and allowed to stand still at room temperature for 60 minutes. 75 μl of 4N sulfuric acid was added to each of the wells, and the absorbance at 490 nm was determined. The results are shown in Table 3. As apparent from the table, all of the antigens derived from the transformants specifically react with the serum from NANB hepatitis patient, thereby attesting to the usefulness in clinical diagnosis of the antigens produced by the transformants.

TABLE 3

Reactivity in ELISA between the purified antigens from various transformed *Escherichia coli* and the serum from NANB hepatitis patient

| origin of antigen (transformed *Escherichia coli*) | Serum from blood transfused patient of hepatitis | | | | healthy human serum |
|---|---|---|---|---|---|
| | acute | chronic | hepato-cirrhosis | hepatoma | |
| JM109/pCE-066 | 2/3* | 7/8 | 3/4 | 3/3 | 0/10 |
| JM109/pB-02-10 | 2/3 | 8/8 | 4/4 | 3/3 | 0/10 |
| JM109/pE-11-89 | 2/3 | 8/8 | 2/4 | 3/3 | 0/10 |

*the number of positive samples/the number of samples examined

The same results as shown in Table 3 were also obtained by radioimmunoassay using the above-mentioned antigens. That is, a polystyrene ball of ¼ inch in diameter (manufactured and sold by Pesel Co., Ltd., Germany) was put in 0.2 ml of each of the above-mentioned purified antigen solutions of 1 μ/ml in concentration, and allowed to stand still at 4° C. overnight. Then, the polystyrene ball was washed five times with the same PBS-T buffer as used in the above-mentioned ELISA, and a sample serum diluted 20 to 2500-fold with the PBS-T buffer was added in an amount of 200 μl/ball. Reaction was performed at 37° C. for 60 min. The polystyrene ball was washed five times with the PBS-T buffer, and $^{125}$I-labeled anti-human IgG antibody was added in an amount of 200 μl/ball. Reaction was performed at 37° C. for one hour and the ball was washed five times with the PBS-T buffer. The cpm of $^{125}$I bound to the polystyrene ball was measured, thereby obtaining the same results as shown in Table 3. Thus, the usefulness of the purified antigens obtained above in the clinical diagnosis of infection with NANB hepatitis virus, was demonstrated.

Application Example 1
(Assay of the reactivity of synthetic polypeptide)

The antibody molecule reacts with a specific region structure known as "epitope" which exists on the antigen molecule, to thereby form a bonding therebetween. Such a specific region can be found in the hydrophilic region of the antigen molecule. The antigen polypeptide having such a specific region is believed to be useful for easily preparing a valuable clinical diagnostic reagent with high reaction specificity. The NANBV epitope is presumed from the hydrophilicity/hydrophobicity pattern of the amino acid sequence coded for by the NANBV genomic cDNA shown in FIGS. 2(1) to 2(16) Namely, polypeptides BKP-106-1, BKP-106-2, BKP-102-1 and BKP-147-1 were prepared, which were respectively comprised of amino acid residues coded for by nucleotide numbers 333 to 422 shown FIG. 2(1), nucleotide numbers 474 to 563 shown in FIG. 2(1) through FIG. 2(2), nucleotide numbers 4485 to 4574 shown in FIG. 2(8), and nucleotide numbers 5544 to 5633 shown in FIG. 2(10). The concentration of each of the prepared polypeptides was adjusted to 1 μg/ml, applied to a microplate for ELISA according to the same method as described in Step 12 to thereby form a solid phase, and examined with respect to the reactivity thereof with the serum from NANB hepatitis patient by the method of ELISA. The results are shown in Table 4. As apparent from the table, all of the prepared polypeptides specifically reacted with the serum from NANB hepatitis patient, thereby demonstrating the importance in clinical diagnosis of the particular regions of nucleotide sequences described above.

TABLE 4

Reactivity of synthetic polypeptides with the serum from NANB hepatitis patient

| synthetic polypeptides | serum from NANB hepatitis patient | | healthy human |
|---|---|---|---|
| | acute | chronic | |
| BKP-106-1 | 2/5 | 5/5 | 0/5 |
| BKP-106-2 | 2/5 | 5/5 | 0/5 |
| BKP-102-1 | 3/5 | 5/5 | 0/5 |
| BKP-147-1 | 2/5 | 5/5 | 0/5 |

Moreover, presuming the epitopes of the envelop protein of NANBV, three types of proteins were prepared. That is, proteins coded for by nucleotide numbers 906 to 953 shown in FIG. 2(2), nucleotide numbers 1020 to 1046 shown in FIG. 2(2) and nucleotide numbers 1194 to 1232 shown in FIG. 2(2) through FIG. 2(3), were prepared. All of the thus prepared polypeptides correspond to the regions of the envelop where antigenic variation is believed to occur depending on the type of the NANBV strain, and the reactivity thereof in ELISA with the serum from a NANB hepatitis patient was confirmed. These attest to the importance and usefulness of the above-mentioned proteins in immunological survey, clinical diagnosis and vaccination.

Application Example 2
[Detection of NANBV nucleic acid according to PCR (Polymerase Chain Reaction) method]

For preventing NANB hepatitis caused by blood transfusion, it is important to determine whether or not any NANBV infection exists in the blood supplied for transfusion. Further, for diagnosing hepatitis, it is extremely clinically important to study whether or not any NANBV infection exists in liver tissue. The NANBV cDNA of the present invention can be advantageously used for producing a primer for polymerase chain reaction (PCR) useful for detecting NANB hepatitis. That is, as described in Step 1, the purification of RNA and the preparation of cDNA were performed from 1 ml of serum. Likewise, cDNA was prepared from liver cells as described in Step 2. Subsequently, as described in Step 4, PCR and electrophoresis were conducted. According to the customary procedure, whether or not the amplified cDNA was derived from NANBV, was investigated by Southern hybridization using $^{32}$P-labeled probe prepared from the cDNA derived from NANBV cDNA clone BK 108.

The results are shown in Table 5. From the table, it is apparent that the NANBV nucleic acid in serum can be detected and the serum infection with NANBV can be diagnosed by the use of the primer prepared from the nucleotide sequence of the NANBV cDNA obtained according to the present invention and the fragment of cloned NANBV cDNA as a probe.

TABLE 5

Detection of NANBV nucleic acid by PCR

| sample | antibody against NANBV | PCR |
|---|---|---|
| serum from chronic hepatitis patient | | |
| NANB | | |
| 1 | + | + |
| 2 | + | + |
| HBV carrier | | |
| 1 | − | − |
| 2 | − | − |
| healthy human | | |
| 1 | − | − |
| 2 | − | − |
| excised liver | + | |

TABLE 5-continued

Detection of NANBV nucleic acid by PCR

| sample | antibody against NANBV | PCR |
|---|---|---|
| from NANB hepatoma-1 | | |
| cancerous site | | + |
| non-cancerous site | | + |
| excised liver | + | |
| from NANB hepatoma-2 | | |
| cancerous site | | + |
| non-cancerous site | | + |

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:
  ( A ) LENGTH: 9416 base pairs
  ( B ) TYPE: nucleic acid
  ( C ) STRANDEDNESS: single
  ( D ) TOPOLOGY: linear ( i i ) MOLECULE TYPE: cDNA from genomic RNA ( i x ) FEATURE:
  ( A ) NAME/KEY: CDS
  ( B ) LOCATION: 333..9362

( x i ) SEQUENCE DESCRIPTION: SEQ ID NO:1:

```
CGATTGGGGG CGACACTCCA CCATAGATCA CTCCCCTGTG AGGAACTACT GTCTTCACGC      60

AGAAAGCGTC TAGCCATGGC GTTAGTATGA GTGTCGTGCA GCCTCCAGGA CCCCCCCTCC     120

CGGGAGAGCC ATAGTGGTCT GCGGAACCGG TGAGTACACC GGAATTGCCA GGACGACCGG     180

GTCCTTTCTT GGATCAACCC GCTCAATGCC TGGAGATTTG GGCGTGCCCC CGCGAGACTG     240

CTAGCCGAGT AGTGTTGGGT CGCGAAAGGC CTTGTGGTAC TGCCTGATAG GGTGCTTGCG     300

AGTGCCCCGG GAGGTCTCGT AGACCGTGCA CC ATG AGC ACG AAT CCT AAA CCT      353
                                  Met Ser Thr Asn Pro Lys Pro
                                   1               5

CAA AGA AAA ACC AAA CGT AAC ACC AAC CGC CGC CCA CAG GAC GTC AAG      401
Gln Arg Lys Thr Lys Arg Asn Thr Asn Arg Arg Pro Gln Asp Val Lys
         10              15                  20

TTC CCG GGC GGT GGT CAG ATC GTT GGT GGA GTT TAC CTG TTG CCG CGC      449
Phe Pro Gly Gly Gly Gln Ile Val Gly Gly Val Tyr Leu Leu Pro Arg
     25                  30                  35
```

| | | | | | | | | | | | | | | | | |
|---|---|---|---|---|---|---|---|---|---|---|---|---|---|---|---|---|
| AGG | GGC | CCC | AGG | TTG | GGT | GTG | CGC | GCG | CCC | AGG | AAG | ACT | TCC | GAG | CGG | 497 |
| Arg | Gly | Pro | Arg | Leu | Gly | Val | Arg | Ala | Pro | Arg | Lys | Thr | Ser | Glu | Arg | |
| 40 | | | | 45 | | | | | 50 | | | | | | 55 | |
| TCG | CAA | CCT | CGT | GGA | AGG | CGA | CAA | CCT | ATC | CCC | AAG | GCT | CGC | CGG | CCC | 545 |
| Ser | Gln | Pro | Arg | Gly | Arg | Arg | Gln | Pro | Ile | Pro | Lys | Ala | Arg | Arg | Pro | |
| | | | | 60 | | | | | 65 | | | | | 70 | | |
| GAG | GGC | AGG | ACC | TGG | GCT | CAG | CCC | GGG | TAC | CCT | TGG | CCT | CTC | TAT | GGC | 593 |
| Glu | Gly | Arg | Thr | Trp | Ala | Gln | Pro | Gly | Tyr | Pro | Trp | Pro | Leu | Tyr | Gly | |
| | | | 75 | | | | | 80 | | | | | 85 | | | |
| AAT | GAG | GGC | TTA | GGG | TGG | GCA | GGA | TGG | CTC | CTG | TCA | CCC | CGC | GGC | TCC | 641 |
| Asn | Glu | Gly | Leu | Gly | Trp | Ala | Gly | Trp | Leu | Leu | Ser | Pro | Arg | Gly | Ser | |
| | | 90 | | | | | 95 | | | | | 100 | | | | |
| CGG | CCT | AGT | TGG | GGC | CCC | ACG | GAC | CCC | CGG | CGT | AGG | TCG | CGT | AAT | TTG | 689 |
| Arg | Pro | Ser | Trp | Gly | Pro | Thr | Asp | Pro | Arg | Arg | Arg | Ser | Arg | Asn | Leu | |
| 105 | | | | | 110 | | | | | 115 | | | | | | |
| GGT | AAG | GTC | ATC | GAT | ACC | CTC | ACA | TGC | GGC | TTC | GCC | GAT | CTC | ATG | GGG | 737 |
| Gly | Lys | Val | Ile | Asp | Thr | Leu | Thr | Cys | Gly | Phe | Ala | Asp | Leu | Met | Gly | |
| 120 | | | | | 125 | | | | | 130 | | | | | 135 | |
| TAC | ATT | CCG | CTC | GTC | GGC | GCC | CCC | CTG | GGG | GGC | GCT | GCC | AGG | GCC | CTG | 785 |
| Tyr | Ile | Pro | Leu | Val | Gly | Ala | Pro | Leu | Gly | Gly | Ala | Ala | Arg | Ala | Leu | |
| | | | | 140 | | | | | 145 | | | | | 150 | | |
| GCA | CAT | GGT | GTC | CGG | GTT | CTG | GAG | GAC | GGC | GTG | AAC | TAT | GCA | ACA | GGG | 833 |
| Ala | His | Gly | Val | Arg | Val | Leu | Glu | Asp | Gly | Val | Asn | Tyr | Ala | Thr | Gly | |
| | | | 155 | | | | | 160 | | | | | 165 | | | |
| AAT | CTG | CCC | GGT | TGC | TCT | TTT | TCT | ATC | TTC | CTC | TTG | GCT | CTG | CTG | TCC | 881 |
| Asn | Leu | Pro | Gly | Cys | Ser | Phe | Ser | Ile | Phe | Leu | Leu | Ala | Leu | Leu | Ser | |
| | | 170 | | | | | 175 | | | | | 180 | | | | |
| TGC | CTG | ACC | ACC | CCA | GCT | TCC | GCT | TAC | GAA | GTG | CAC | AAC | GTG | TCC | GGG | 929 |
| Cys | Leu | Thr | Thr | Pro | Ala | Ser | Ala | Tyr | Glu | Val | His | Asn | Val | Ser | Gly | |
| 185 | | | | | 190 | | | | | 195 | | | | | | |
| ATA | TAT | CAT | GTC | ACG | AAC | GAC | TGC | TCC | AAC | GCA | AGC | ATT | GTG | TAT | GAG | 977 |
| Ile | Tyr | His | Val | Thr | Asn | Asp | Cys | Ser | Asn | Ala | Ser | Ile | Val | Tyr | Glu | |
| 200 | | | | | 205 | | | | | 210 | | | | | 215 | |
| GCA | GCG | GAC | TTG | ATC | ATG | CAT | ACT | CCT | GGG | TGC | GTG | CCC | TGC | GTT | CGG | 1025 |
| Ala | Ala | Asp | Leu | Ile | Met | His | Thr | Pro | Gly | Cys | Val | Pro | Cys | Val | Arg | |
| | | | | 220 | | | | | 225 | | | | | 230 | | |
| GAA | GGC | AAC | TCC | TCC | CGC | TGC | TGG | GTA | GCG | CTC | ACT | CCC | ACG | CTC | GCA | 1073 |
| Glu | Gly | Asn | Ser | Ser | Arg | Cys | Trp | Val | Ala | Leu | Thr | Pro | Thr | Leu | Ala | |
| | | | 235 | | | | | 240 | | | | | 245 | | | |
| GCC | AGG | AAC | GTC | ACC | ATC | CCC | ACC | ACG | ACA | ATA | CGA | CGC | CAC | GTC | GAT | 1121 |
| Ala | Arg | Asn | Val | Thr | Ile | Pro | Thr | Thr | Thr | Ile | Arg | Arg | His | Val | Asp | |
| | | 250 | | | | | 255 | | | | | 260 | | | | |
| CTG | CTC | GTT | GGG | GCG | GCT | GCT | TTC | TGT | TCC | GCT | ATG | TAC | GTG | GGG | GAC | 1169 |
| Leu | Leu | Val | Gly | Ala | Ala | Ala | Phe | Cys | Ser | Ala | Met | Tyr | Val | Gly | Asp | |
| 265 | | | | | 270 | | | | | 275 | | | | | | |
| CTC | TGC | GGA | TCT | GTT | TTC | CTC | GTC | TCT | CAG | CTG | TTC | ACC | TTC | TCG | CCT | 1217 |
| Leu | Cys | Gly | Ser | Val | Phe | Leu | Val | Ser | Gln | Leu | Phe | Thr | Phe | Ser | Pro | |
| 280 | | | | | 285 | | | | | 290 | | | | | 295 | |
| CGC | CGG | CAT | GTG | ACA | TTA | CAG | GAC | TGT | AAC | TGC | TCA | ATT | TAT | CCC | GGC | 1265 |
| Arg | Arg | His | Val | Thr | Leu | Gln | Asp | Cys | Asn | Cys | Ser | Ile | Tyr | Pro | Gly | |
| | | | | 300 | | | | | 305 | | | | | 310 | | |
| CAT | GTG | TCG | GGT | CAC | CGT | ATG | GCT | TGG | GAC | ATG | ATG | ATG | AAC | TGG | TCG | 1313 |
| His | Val | Ser | Gly | His | Arg | Met | Ala | Trp | Asp | Met | Met | Met | Asn | Trp | Ser | |
| | | | 315 | | | | | 320 | | | | | 325 | | | |
| CCC | ACA | ACA | GCC | CTA | GTG | GTG | TCG | CAG | TTA | CTC | CGG | ATC | CCA | CAA | GCC | 1361 |
| Pro | Thr | Thr | Ala | Leu | Val | Val | Ser | Gln | Leu | Leu | Arg | Ile | Pro | Gln | Ala | |
| | | 330 | | | | | 335 | | | | | 340 | | | | |
| GTC | GTG | GAC | ATG | GTG | GCG | GGG | GCC | CAC | TGG | GGA | GTC | CTG | GCG | GGC | CTT | 1409 |
| Val | Val | Asp | Met | Val | Ala | Gly | Ala | His | Trp | Gly | Val | Leu | Ala | Gly | Leu | |
| 345 | | | | | 350 | | | | | 355 | | | | | | |

| | | | | | | | | | | | | | | | | |
|---|---|---|---|---|---|---|---|---|---|---|---|---|---|---|---|---|
| GCC | TAC | TAT | TCC | ATG | GCG | GGG | AAC | TGG | GCT | AAG | GTT | CTG | ATT | GTG | ATG | 1457 |
| Ala 360 | Tyr | Tyr | Ser | Met | Ala 365 | Gly | Asn | Trp | Ala 370 | Lys | Val | Leu | Ile | Val | Met 375 | |
| CTA | CTT | TTT | GCT | GGC | GTT | GAC | GGG | GAT | ACC | CAC | GTG | ACA | GGG | GGG | GCG | 1505 |
| Leu | Leu | Phe | Ala | Gly 380 | Val | Asp | Gly | Asp | Thr | His 385 | Val | Thr | Gly | Gly | Ala 390 | |
| CAA | GCC | AAA | ACC | ACC | AAC | AGG | CTC | GTG | TCC | ATG | TTC | GCA | AGT | GGG | CCG | 1553 |
| Gln | Ala | Lys | Thr 395 | Thr | Asn | Arg | Leu | Val 400 | Ser | Met | Phe | Ala | Ser 405 | Gly | Pro | |
| TCT | CAG | AAA | ATC | CAG | CTT | ATA | AAC | ACC | AAT | GGG | AGT | TGG | CAC | ATC | AAC | 1601 |
| Ser | Gln | Lys 410 | Ile | Gln | Leu | Ile | Asn 415 | Thr | Asn | Gly | Ser | Trp 420 | His | Ile | Asn | |
| AGG | ACT | GCC | CTG | AAC | TGC | AAT | GAC | TCT | CTC | CAG | ACT | GGG | TTT | CTT | GCC | 1649 |
| Arg | Thr 425 | Ala | Leu | Asn | Cys | Asn 430 | Asp | Ser | Leu | Gln | Thr 435 | Gly | Phe | Leu | Ala | |
| GCG | CTG | TTC | TAC | ACA | CAT | AGT | TTC | AAC | TCG | TCC | GGG | TGC | CCA | GAG | CGC | 1697 |
| Ala 440 | Leu | Phe | Tyr | Thr | His 445 | Ser | Phe | Asn | Ser | Ser 450 | Gly | Cys | Pro | Glu | Arg 455 | |
| ATG | GCC | CAG | TGC | CGC | ACC | ATT | GAC | AAG | TTC | GAC | CAG | GGA | TGG | GGT | CCC | 1745 |
| Met | Ala | Gln | Cys | Arg 460 | Thr | Ile | Asp | Lys | Phe 465 | Asp | Gln | Gly | Trp | Gly 470 | Pro | |
| ATT | ACT | TAT | GCT | GAG | TCT | AGC | AGA | TCA | GAC | CAG | AGG | CCA | TAT | TGC | TGG | 1793 |
| Ile | Thr | Tyr | Ala 475 | Glu | Ser | Ser | Arg | Ser 480 | Asp | Gln | Arg | Pro | Tyr 485 | Cys | Trp | |
| CAC | TAC | CCA | CCT | CCA | CAA | TGT | ACC | ATC | GTA | CCT | GCG | TCG | GAG | GTG | TGC | 1841 |
| His | Tyr | Pro 490 | Pro | Pro | Gln | Cys | Thr 495 | Ile | Val | Pro | Ala | Ser 500 | Glu | Val | Cys | |
| GGC | CCA | GTG | TAC | TGC | TTC | ACC | CCA | AGC | CCT | GTC | GTC | GTG | GGG | ACG | ACC | 1889 |
| Gly | Pro 505 | Val | Tyr | Cys | Phe | Thr 510 | Pro | Ser | Pro | Val | Val 515 | Val | Gly | Thr | Thr | |
| GAT | CGT | TTC | GGT | GTC | CCT | ACG | TAT | AGA | TGG | GGG | GAG | AAC | GAG | ACT | GAC | 1937 |
| Asp 520 | Arg | Phe | Gly | Val | Pro 525 | Thr | Tyr | Arg | Trp | Gly 530 | Glu | Asn | Glu | Thr | Asp 535 | |
| GTG | CTG | CTG | CTC | AAC | AAC | ACG | CGG | CCG | CCG | CAA | GGC | AAC | TGG | TTC | GGC | 1985 |
| Val | Leu | Leu | Leu | Asn 540 | Asn | Thr | Arg | Pro | Pro 545 | Gln | Gly | Asn | Trp | Phe 550 | Gly | |
| TGC | ACA | TGG | ATG | AAT | AGC | ACC | GGG | TTC | ACC | AAG | ACA | TGT | GGG | GGG | CCC | 2033 |
| Cys | Thr | Trp | Met 555 | Asn | Ser | Thr | Gly | Phe 560 | Thr | Lys | Thr | Cys | Gly 565 | Gly | Pro | |
| CCG | TGT | AAC | ATC | GGG | GGG | GTC | GGC | AAC | AAC | ACC | CTG | ACC | TGC | CCC | ACG | 2081 |
| Pro | Cys | Asn 570 | Ile | Gly | Gly | Val | Gly 575 | Asn | Asn | Thr | Leu | Thr 580 | Cys | Pro | Thr | |
| GAC | TGC | TTC | CGG | AAG | CAC | CCC | GAG | GCT | ACC | TAC | ACA | AAA | TGT | GGT | TCG | 2129 |
| Asp | Cys 585 | Phe | Arg | Lys | His | Pro 590 | Glu | Ala | Thr | Tyr | Thr 595 | Lys | Cys | Gly | Ser | |
| GGG | CCT | TGG | CTG | ACA | CCT | AGG | TGC | ATG | GTT | GAC | TAT | CCA | TAC | AGG | CTC | 2177 |
| Gly 600 | Pro | Trp | Leu | Thr | Pro 605 | Arg | Cys | Met | Val | Asp 610 | Tyr | Pro | Tyr | Arg | Leu 615 | |
| TGG | CAT | TAC | CCC | TGC | ACT | GTT | AAC | TTT | ACC | ATC | TTC | AAG | GTT | AGG | ATG | 2225 |
| Trp | His | Tyr | Pro | Cys 620 | Thr | Val | Asn | Phe | Thr 625 | Ile | Phe | Lys | Val | Arg 630 | Met | |
| TAT | GTG | GGG | GGG | GTG | GAG | CAC | AGG | CTC | AAT | GCT | GCA | TGC | AAT | TGG | ACC | 2273 |
| Tyr | Val | Gly | Gly 635 | Val | Glu | His | Arg | Leu 640 | Asn | Ala | Ala | Cys | Asn 645 | Trp | Thr | |
| CGA | GGA | GAG | CGT | TGT | GAC | TTG | GAG | GAC | AGG | GAT | AGG | CCG | GAG | CTC | AGC | 2321 |
| Arg | Gly | Glu | Arg 650 | Cys | Asp | Leu | Glu | Asp 655 | Arg | Asp | Arg | Pro | Glu 660 | Leu | Ser | |
| CCG | CTG | CTG | CTG | TCT | ACA | ACA | GAG | TGG | CAG | GTA | CTG | CCC | TGT | TCC | TTC | 2369 |
| Pro | Leu 665 | Leu | Leu | Ser | Thr | Thr 670 | Glu | Trp | Gln | Val | Leu 675 | Pro | Cys | Ser | Phe | |

| | | | | | | | | | | | | | | | | |
|---|---|---|---|---|---|---|---|---|---|---|---|---|---|---|---|---|
| ACC | ACC | CTA | CCA | GCT | CTG | TCC | ACT | GGC | TTG | ATT | CAC | CTC | CAT | CAG | AAC | 2417 |
| Thr | Thr | Leu | Pro | Ala | Leu | Ser | Thr | Gly | Leu | Ile | His | Leu | His | Gln | Asn | |
| 680 | | | | 685 | | | | | 690 | | | | | | 695 | |
| ATC | GTG | GAC | GTG | CAA | TAC | CTA | TAC | GGT | ATA | GGG | TCA | GCG | GTT | GTC | TCC | 2465 |
| Ile | Val | Asp | Val | Gln | Tyr | Leu | Tyr | Gly | Ile | Gly | Ser | Ala | Val | Val | Ser | |
| | | | | 700 | | | | | 705 | | | | | 710 | | |
| TTT | GCA | ATC | AAA | TGG | GAG | TAT | GTC | CTG | TTG | CTT | TTC | CTT | CTC | CTA | GCG | 2513 |
| Phe | Ala | Ile | Lys | Trp | Glu | Tyr | Val | Leu | Leu | Leu | Phe | Leu | Leu | Leu | Ala | |
| | | | 715 | | | | | 720 | | | | | 725 | | | |
| GAC | GCA | CGT | GTC | TGT | GCC | TGC | TTG | TGG | ATG | ATG | CTG | CTG | ATA | GCC | CAG | 2561 |
| Asp | Ala | Arg | Val | Cys | Ala | Cys | Leu | Trp | Met | Met | Leu | Leu | Ile | Ala | Gln | |
| | | 730 | | | | | 735 | | | | | 740 | | | | |
| GCC | GAG | GCC | GCC | TTG | GAG | AAC | CTG | GTG | GTC | CTC | AAT | TCG | GCG | TCT | GTG | 2609 |
| Ala | Glu | Ala | Ala | Leu | Glu | Asn | Leu | Val | Val | Leu | Asn | Ser | Ala | Ser | Val | |
| 745 | | | | | 750 | | | | | 755 | | | | | | |
| GCC | GGC | GCA | CAT | GGC | ATC | CTC | TCC | TTC | CTT | GTG | TTC | TTC | TGT | GCC | GCC | 2657 |
| Ala | Gly | Ala | His | Gly | Ile | Leu | Ser | Phe | Leu | Val | Phe | Phe | Cys | Ala | Ala | |
| 760 | | | | | 765 | | | | | 770 | | | | | 775 | |
| TGG | TAC | ATC | AAA | GGC | AGG | CTG | GTC | CCT | GGG | GCG | ACA | TAT | GCT | CTT | TAT | 2705 |
| Trp | Tyr | Ile | Lys | Gly | Arg | Leu | Val | Pro | Gly | Ala | Thr | Tyr | Ala | Leu | Tyr | |
| | | | | 780 | | | | | 785 | | | | | 790 | | |
| GGC | GTG | TGG | CCG | CTG | CTC | CTG | CTC | TTG | CTG | GCA | TTA | CCA | CCG | CGA | GCT | 2753 |
| Gly | Val | Trp | Pro | Leu | Leu | Leu | Leu | Leu | Leu | Ala | Leu | Pro | Pro | Arg | Ala | |
| | | | 795 | | | | | 800 | | | | | 805 | | | |
| TAC | GCC | ATG | GAC | CGG | GAG | ATG | GCT | GCA | TCG | TGC | GGA | GGC | GCG | GTT | TTT | 2801 |
| Tyr | Ala | Met | Asp | Arg | Glu | Met | Ala | Ala | Ser | Cys | Gly | Gly | Ala | Val | Phe | |
| | | 810 | | | | | 815 | | | | | 820 | | | | |
| GTG | GGT | CTG | GTA | CTC | CTG | ACT | TTG | TCA | CCA | TAC | TAC | AAG | GTG | TTC | CTC | 2849 |
| Val | Gly | Leu | Val | Leu | Leu | Thr | Leu | Ser | Pro | Tyr | Tyr | Lys | Val | Phe | Leu | |
| | 825 | | | | | 830 | | | | | 835 | | | | | |
| GCT | AGG | CTC | ATA | TGG | TGG | TTA | CAA | TAT | TTT | ACC | ACC | AGA | GCC | GAG | GCG | 2897 |
| Ala | Arg | Leu | Ile | Trp | Trp | Leu | Gln | Tyr | Phe | Thr | Thr | Arg | Ala | Glu | Ala | |
| 840 | | | | | 845 | | | | | 850 | | | | | 855 | |
| GAC | TTA | CAT | GTG | TGG | ATC | CCC | CCC | CTC | AAC | GCT | CGG | GGA | GGC | CGC | GAT | 2945 |
| Asp | Leu | His | Val | Trp | Ile | Pro | Pro | Leu | Asn | Ala | Arg | Gly | Gly | Arg | Asp | |
| | | | | 860 | | | | | 865 | | | | | 870 | | |
| GCC | ATC | ATC | CTC | CTC | ATG | TGC | GCA | GTC | CAT | CCA | GAG | CTA | ATC | TTT | GAC | 2993 |
| Ala | Ile | Ile | Leu | Leu | Met | Cys | Ala | Val | His | Pro | Glu | Leu | Ile | Phe | Asp | |
| | | | 875 | | | | | 880 | | | | | 885 | | | |
| ATC | ACC | AAA | CTT | CTA | ATT | GCC | ATA | CTC | GGT | CCG | CTC | ATG | GTG | CTC | CAA | 3041 |
| Ile | Thr | Lys | Leu | Leu | Ile | Ala | Ile | Leu | Gly | Pro | Leu | Met | Val | Leu | Gln | |
| | | 890 | | | | | 895 | | | | | 900 | | | | |
| GCT | GGC | ATA | ACC | AGA | GTG | CCG | TAC | TTC | GTG | CGC | GCT | CAA | GGG | CTC | ATT | 3089 |
| Ala | Gly | Ile | Thr | Arg | Val | Pro | Tyr | Phe | Val | Arg | Ala | Gln | Gly | Leu | Ile | |
| 905 | | | | | 910 | | | | | 915 | | | | | | |
| CAT | GCA | TGC | ATG | TTA | GTG | CGG | AAG | GTC | GCT | GGG | GGT | CAT | TAT | GTC | CAA | 3137 |
| His | Ala | Cys | Met | Leu | Val | Arg | Lys | Val | Ala | Gly | Gly | His | Tyr | Val | Gln | |
| 920 | | | | | 925 | | | | | 930 | | | | | 935 | |
| ATG | GCC | TTC | ATG | AAG | CTG | GGC | GCG | CTG | ACA | GGC | ACG | TAC | ATT | TAC | AAC | 3185 |
| Met | Ala | Phe | Met | Lys | Leu | Gly | Ala | Leu | Thr | Gly | Thr | Tyr | Ile | Tyr | Asn | |
| | | | | 940 | | | | 945 | | | | | 950 | | | |
| CAT | CTT | ACC | CCG | CTA | CGG | GAT | TGG | CCA | CGC | GCG | GGC | CTA | CGA | GAC | CTT | 3233 |
| His | Leu | Thr | Pro | Leu | Arg | Asp | Trp | Pro | Arg | Ala | Gly | Leu | Arg | Asp | Leu | |
| | | | 955 | | | | | 960 | | | | | 965 | | | |
| GCG | GTG | GCA | GTG | GAG | CCC | GTC | GTC | TTC | TCC | GAC | ATG | GAG | ACC | AAG | ATC | 3281 |
| Ala | Val | Ala | Val | Glu | Pro | Val | Val | Phe | Ser | Asp | Met | Glu | Thr | Lys | Ile | |
| | | | 970 | | | | | 975 | | | | | 980 | | | |
| ATC | ACC | TGG | GGA | GCA | GAC | ACC | GCG | GCG | TGT | GGG | GAC | ATC | ATC | TTG | GGT | 3329 |
| Ile | Thr | Trp | Gly | Ala | Asp | Thr | Ala | Ala | Cys | Gly | Asp | Ile | Ile | Leu | Gly | |
| | 985 | | | | | 990 | | | | | 995 | | | | | |

```
CTG CCC GTC TCC GCC CGA AGG GGA AAG GAG ATA CTC CTG GGC CCG GCC     3377
Leu Pro Val Ser Ala Arg Arg Gly Lys Glu Ile Leu Leu Gly Pro Ala
1000                1005                1010                1015

GAT AGT CTT GAA GGG CGG GGG TTG CGA CTC CTC GCG CCC ATC ACG GCC     3425
Asp Ser Leu Glu Gly Arg Gly Leu Arg Leu Leu Ala Pro Ile Thr Ala
            1020                1025                1030

TAC TCC CAA CAG ACG CGG GGC CTA CTT GGT TGC ATC ATC ACT AGC CTT     3473
Tyr Ser Gln Gln Thr Arg Gly Leu Leu Gly Cys Ile Ile Thr Ser Leu
        1035                1040                1045

ACA GGC CGG GAC AAG AAC CAG GTC GAG GGA GAG GTT CAG GTG GTT TCC     3521
Thr Gly Arg Asp Lys Asn Gln Val Glu Gly Glu Val Gln Val Val Ser
    1050                1055                1060

ACC GCA ACA CAA TCC TTC CTG GCG ACC TGC GTC AAC GGC GTG TGT TGG     3569
Thr Ala Thr Gln Ser Phe Leu Ala Thr Cys Val Asn Gly Val Cys Trp
1065                1070                1075

ACC GTT TAC CAT GGT GCT GGC TCA AAG ACC TTA GCC GCG CCA AAG GGG     3617
Thr Val Tyr His Gly Ala Gly Ser Lys Thr Leu Ala Ala Pro Lys Gly
1080                1085                1090                1095

CCA ATC ACC CAG ATG TAC ACT AAT GTG GAC CAG GAC CTC GTC GGC TGG     3665
Pro Ile Thr Gln Met Tyr Thr Asn Val Asp Gln Asp Leu Val Gly Trp
            1100                1105                1110

CCC AAG CCC CCC GGG GCG CGT TCC TTG ACA CCA TGC ACC TGT GGC AGC     3713
Pro Lys Pro Pro Gly Ala Arg Ser Leu Thr Pro Cys Thr Cys Gly Ser
        1115                1120                1125

TCA GAC CTT TAC TTG GTC ACG AGA CAT GCT GAC GTC ATT CCG GTG CGC     3761
Ser Asp Leu Tyr Leu Val Thr Arg His Ala Asp Val Ile Pro Val Arg
    1130                1135                1140

CGG CGG GGC GAC AGT AGG GGG AGC CTG CTC TCC CCC AGG CCT GTC TCC     3809
Arg Arg Gly Asp Ser Arg Gly Ser Leu Leu Ser Pro Arg Pro Val Ser
1145                1150                1155

TAC TTG AAG GGC TCT TCG GGT GGT CCA CTG CTC TGC CCC TTC GGG CAC     3857
Tyr Leu Lys Gly Ser Ser Gly Gly Pro Leu Leu Cys Pro Phe Gly His
1160                1165                1170                1175

GCT GTG GGC ATC TTC CGG GCT GCC GTA TGC ACC CGG GGG GTT GCG AAG     3905
Ala Val Gly Ile Phe Arg Ala Ala Val Cys Thr Arg Gly Val Ala Lys
            1180                1185                1190

GCG GTG GAC TTT GTG CCC GTA GAG TCC ATG GAA ACT ACT ATG CGG TCT     3953
Ala Val Asp Phe Val Pro Val Glu Ser Met Glu Thr Thr Met Arg Ser
        1195                1200                1205

CCG GTC TTC ACG GAC AAC TCA TCC CCC CCG GCC GTA CCG CAG TCA TTT     4001
Pro Val Phe Thr Asp Asn Ser Ser Pro Pro Ala Val Pro Gln Ser Phe
    1210                1215                1220

CAA GTG GCC CAC CTA CAC GCT CCC ACT GGC AGC GGC AAG AGT ACT AAA     4049
Gln Val Ala His Leu His Ala Pro Thr Gly Ser Gly Lys Ser Thr Lys
1225                1230                1235

GTG CCG GCT GCA TAT GCA GCC CAA GGG TAC AAG GTG CTC GTC CTC AAT     4097
Val Pro Ala Ala Tyr Ala Ala Gln Gly Tyr Lys Val Leu Val Leu Asn
1240                1245                1250                1255

CCG TCC GTT GCC GCT ACC TTA GGG TTT GGG GCG TAT ATG TCT AAG GCA     4145
Pro Ser Val Ala Ala Thr Leu Gly Phe Gly Ala Tyr Met Ser Lys Ala
            1260                1265                1270

CAC GGT ATT GAC CCC AAC ATC AGA ACT GGG GTA AGG ACC ATT ACC ACA     4193
His Gly Ile Asp Pro Asn Ile Arg Thr Gly Val Arg Thr Ile Thr Thr
        1275                1280                1285

GGC GCC CCC GTC ACA TAC TCT ACC TAT GGC AAG TTT CTT GCC GAT GGT     4241
Gly Ala Pro Val Thr Tyr Ser Thr Tyr Gly Lys Phe Leu Ala Asp Gly
    1290                1295                1300

GGT TGC TCT GGG GGC GCT TAT GAC ATC ATA ATA TGT GAT GAG TGC CAT     4289
Gly Cys Ser Gly Gly Ala Tyr Asp Ile Ile Ile Cys Asp Glu Cys His
1305                1310                1315
```

| | |
|---|---|
| TCA ACT GAC TCG ACT ACA ATC TTG GGC ATC GGC ACA GTC CTG GAC CAA<br>Ser Thr Asp Ser Thr Thr Ile Leu Gly Ile Gly Thr Val Leu Asp Gln<br>1320                   1325              1330               1335 | 4337 |
| GCG GAG ACG GCT GGA GCG CGG CTT GTC GTG CTC GCC ACC GCT ACG CCT<br>Ala Glu Thr Ala Gly Ala Arg Leu Val Val Leu Ala Thr Ala Thr Pro<br>             1340              1345               1350 | 4385 |
| CCG GGA TCG GTC ACC GTG CCA CAC CCA AAC ATC GAG GAG GTG GCC CTG<br>Pro Gly Ser Val Thr Val Pro His Pro Asn Ile Glu Glu Val Ala Leu<br>         1355               1360               1365 | 4433 |
| TCT AAT ACT GGA GAG ATC CCC TTC TAT GGC AAA GCC ATC CCC ATT GAA<br>Ser Asn Thr Gly Glu Ile Pro Phe Tyr Gly Lys Ala Ile Pro Ile Glu<br>         1370               1375               1380 | 4481 |
| GCC ATC AGG GGG GGA AGG CAT CTC ATT TTC TGT CAT TCC AAG AAG AAG<br>Ala Ile Arg Gly Gly Arg His Leu Ile Phe Cys His Ser Lys Lys Lys<br>         1385               1390               1395 | 4529 |
| TGC GAC GAG CTC GCC GCA AAG CTG TCA GGC CTC GGA ATC AAC GCT GTG<br>Cys Asp Glu Leu Ala Ala Lys Leu Ser Gly Leu Gly Ile Asn Ala Val<br>1400                   1405              1410               1415 | 4577 |
| GCG TAT TAC CGG GGG CTC GAT GTG TCC GTC ATA CCA ACT ATC GGA GAC<br>Ala Tyr Tyr Arg Gly Leu Asp Val Ser Val Ile Pro Thr Ile Gly Asp<br>                1420              1425               1430 | 4625 |
| GTC GTT GTC GTG GCA ACA GAC GCT CTG ATG ACG GGC TAT ACG GGC GAC<br>Val Val Val Val Ala Thr Asp Ala Leu Met Thr Gly Tyr Thr Gly Asp<br>                1435              1440               1445 | 4673 |
| TTT GAC TCA GTG ATC GAC TGT AAC ACA TGT GTC ACC CAG ACA GTC GAC<br>Phe Asp Ser Val Ile Asp Cys Asn Thr Cys Val Thr Gln Thr Val Asp<br>         1450               1455               1460 | 4721 |
| TTC AGC TTG GAT CCC ACC TTC ACC ATT GAG ACG ACG ACC GTG CCT CAA<br>Phe Ser Leu Asp Pro Thr Phe Thr Ile Glu Thr Thr Thr Val Pro Gln<br>1465                   1470              1475 | 4769 |
| GAC GCA GTG TCG CGC TCG CAG CGG CGG GGT AGG ACT GGC AGG GGT AGG<br>Asp Ala Val Ser Arg Ser Gln Arg Arg Gly Arg Thr Gly Arg Gly Arg<br>1480                   1485              1490               1495 | 4817 |
| AGA GGC ATC TAC AGG TTT GTG ACT CCG GGA GAA CGG CCC TCG GGC ATG<br>Arg Gly Ile Tyr Arg Phe Val Thr Pro Gly Glu Arg Pro Ser Gly Met<br>                1500              1505               1510 | 4865 |
| TTC GAT TCC TCG GTC CTG TGT GAG TGC TAT GAC GCG GGC TGT GCT TGG<br>Phe Asp Ser Ser Val Leu Cys Glu Cys Tyr Asp Ala Gly Cys Ala Trp<br>                1515              1520               1525 | 4913 |
| TAC GAG CTC ACC CCG GCC GAG ACC TCG GTT AGG TTG CGG GCC TAC CTG<br>Tyr Glu Leu Thr Pro Ala Glu Thr Ser Val Arg Leu Arg Ala Tyr Leu<br>                1530              1535               1540 | 4961 |
| AAC ACA CCA GGG TTG CCC GTT TGC CAG GAC CAC CTG GAG TTC TGG GAG<br>Asn Thr Pro Gly Leu Pro Val Cys Gln Asp His Leu Glu Phe Trp Glu<br>         1545               1550               1555 | 5009 |
| AGT GTC TTC ACA GGC CTC ACC CAT ATA GAT GCA CAC TTC TTG TCC CAG<br>Ser Val Phe Thr Gly Leu Thr His Ile Asp Ala His Phe Leu Ser Gln<br>1560                   1565              1570               1575 | 5057 |
| ACC AAG CAG GCA GGA GAC AAC TTC CCC TAC CTG GTA GCA TAC CAA GCC<br>Thr Lys Gln Ala Gly Asp Asn Phe Pro Tyr Leu Val Ala Tyr Gln Ala<br>                1580              1585               1590 | 5105 |
| ACG GTG TGC GCC AGG GCT CAG GCC CCA CCT CCA TCA TGG GAT CAA ATG<br>Thr Val Cys Ala Arg Ala Gln Ala Pro Pro Pro Ser Trp Asp Gln Met<br>                1595              1600               1605 | 5153 |
| TGG AAG TGT CTC ATA CGG CTG AAA CCT ACG CTG CAC GGG CCA ACA CCC<br>Trp Lys Cys Leu Ile Arg Leu Lys Pro Thr Leu His Gly Pro Thr Pro<br>         1610               1615               1620 | 5201 |
| TTG CTG TAC AGG CTG GGA GCC GTC CAG AAT GAG GTC ACC CTC ACC CAC<br>Leu Leu Tyr Arg Leu Gly Ala Val Gln Asn Glu Val Thr Leu Thr His<br>         1625               1630               1635 | 5249 |

| | |
|---|---|
| CCC ATA ACC AAA TAC ATC ATG GCA TGC ATG TCG GCT GAC CTG GAG GTC<br>Pro Ile Thr Lys Tyr Ile Met Ala Cys Met Ser Ala Asp Leu Glu Val<br>1640                       1645                    1650                      1655 | 5297 |
| GTC ACT AGC ACC TGG GTG CTG GTG GGC GGA GTC CTT GCA GCT CTG GCC<br>Val Thr Ser Thr Trp Val Leu Val Gly Gly Val Leu Ala Ala Leu Ala<br>                    1660                    1665                    1670 | 5345 |
| GCG TAT TGC CTG ACA ACA GGC AGT GTG GTC ATT GTG GGT AGG ATT ATC<br>Ala Tyr Cys Leu Thr Thr Gly Ser Val Val Ile Val Gly Arg Ile Ile<br>             1675                    1680                    1685 | 5393 |
| TTG TCC GGG AGG CCG GCC ATT GTT CCC GAC AGG GAG CTT CTC TAC CAG<br>Leu Ser Gly Arg Pro Ala Ile Val Pro Asp Arg Glu Leu Leu Tyr Gln<br>             1690                    1695                    1700 | 5441 |
| GAG TTC GAT GAA ATG GAA GAG TGC GCC TCG CAC CTC CCT TAC ATC GAG<br>Glu Phe Asp Glu Met Glu Glu Cys Ala Ser His Leu Pro Tyr Ile Glu<br>1705                       1710                    1715 | 5489 |
| CAG GGA ATG CAG CTC GCC GAG CAA TTC AAG CAG AAA GCG CTC GGG TTA<br>Gln Gly Met Gln Leu Ala Glu Gln Phe Lys Gln Lys Ala Leu Gly Leu<br>1720                       1725                    1730                    1735 | 5537 |
| CTG CAA ACA GCC ACC AAA CAA GCG GAG GCT GCT GCT CCC GTG GTG GAG<br>Leu Gln Thr Ala Thr Lys Gln Ala Glu Ala Ala Ala Pro Val Val Glu<br>             1740                    1745                    1750 | 5585 |
| TCC AAG TGG CGA GCC CTT GAG ACA TTC TGG GCG AAG CAC ATG TGG AAT<br>Ser Lys Trp Arg Ala Leu Glu Thr Phe Trp Ala Lys His Met Trp Asn<br>                    1755                    1760                    1765 | 5633 |
| TTC ATC AGC GGG ATA CAG TAC TTA GCA GGC TTA TCC ACT CTG CCT GGG<br>Phe Ile Ser Gly Ile Gln Tyr Leu Ala Gly Leu Ser Thr Leu Pro Gly<br>             1770                    1775                    1780 | 5681 |
| AAC CCC GCA ATA GCA TCA TTG ATG GCA TTC ACA GCC TCT ATC ACC AGC<br>Asn Pro Ala Ile Ala Ser Leu Met Ala Phe Thr Ala Ser Ile Thr Ser<br>1785                       1790                    1795 | 5729 |
| CCG CTC ACC ACC CAA AGT ACC CTC CTG TTT AAC ATC TTG GGG GGG TGG<br>Pro Leu Thr Thr Gln Ser Thr Leu Leu Phe Asn Ile Leu Gly Gly Trp<br>1800                       1805                    1810                    1815 | 5777 |
| GTG GCT GCC CAA CTC GCC CCC CCC AGC GCC GCT TCG GCT TTC GTG GGC<br>Val Ala Ala Gln Leu Ala Pro Pro Ser Ala Ala Ser Ala Phe Val Gly<br>             1820                    1825                    1830 | 5825 |
| GCC GGC ATC GCC GGT GCG GCT GTT GGC AGC ATA GGC CTT GGG AAG GTG<br>Ala Gly Ile Ala Gly Ala Ala Val Gly Ser Ile Gly Leu Gly Lys Val<br>                    1835                    1840                    1845 | 5873 |
| CTT GTG GAC ATT CTG GCG GGT TAT GGA GCA GGA GTG GCC GGC GCG CTC<br>Leu Val Asp Ile Leu Ala Gly Tyr Gly Ala Gly Val Ala Gly Ala Leu<br>             1850                    1855                    1860 | 5921 |
| GTG GCC TTT AAG GTC ATG AGC GGC GAG ATG CCC TCC ACC GAG GAC CTG<br>Val Ala Phe Lys Val Met Ser Gly Glu Met Pro Ser Thr Glu Asp Leu<br>1865                       1870                    1875 | 5969 |
| GTC AAT CTA CTT CCT GCC ATC CTC TCT CCT GGC GCC CTG GTC GTC GGG<br>Val Asn Leu Leu Pro Ala Ile Leu Ser Pro Gly Ala Leu Val Val Gly<br>1880                       1885                    1890                    1895 | 6017 |
| GTC GTG TGT GCA GCA ATA CTG CGT CGA CAC GTG GGT CCG GGA GAG GGG<br>Val Val Cys Ala Ala Ile Leu Arg Arg His Val Gly Pro Gly Glu Gly<br>                    1900                    1905                    1910 | 6065 |
| GCT GTG CAG TGG ATG AAC CGG CTG ATA GCG TTC GCC TCG CGG GGT AAT<br>Ala Val Gln Trp Met Asn Arg Leu Ile Ala Phe Ala Ser Arg Gly Asn<br>             1915                    1920                    1925 | 6113 |
| CAT GTT TCC CCC ACG CAC TAT GTG CCT GAG AGC GAC GCC GCA GCG CGT<br>His Val Ser Pro Thr His Tyr Val Pro Glu Ser Asp Ala Ala Ala Arg<br>             1930                    1935                    1940 | 6161 |
| GTT ACT CAG ATC CTC TCC AGC CTT ACC ATC ACT CAG CTG CTG AAA AGG<br>Val Thr Gln Ile Leu Ser Ser Leu Thr Ile Thr Gln Leu Leu Lys Arg<br>1945                       1950                    1955 | 6209 |

```
CTC CAC CAG TGG ATT AAT GAA GAC TGC TCC ACA CCG TGT TCC GGC TCG        6257
Leu His Gln Trp Ile Asn Glu Asp Cys Ser Thr Pro Cys Ser Gly Ser
1960                1965                1970                1975

TGG CTA AGG GAT GTT TGG GAC TGG ATA TGC ACG GTG TTG ACT GAC TTC        6305
Trp Leu Arg Asp Val Trp Asp Trp Ile Cys Thr Val Leu Thr Asp Phe
                1980                1985                1990

AAG ACC TGG CTC CAG TCC AAG CTC CTG CCG CAG CTA CCT GGA GTC CCT        6353
Lys Thr Trp Leu Gln Ser Lys Leu Leu Pro Gln Leu Pro Gly Val Pro
            1995                2000                2005

TTT TTC TCG TGC CAA CGC GGG TAC AAG GGA GTC TGG CGG GGA GAC GGC        6401
Phe Phe Ser Cys Gln Arg Gly Tyr Lys Gly Val Trp Arg Gly Asp Gly
        2010                2015                2020

ATC ATG CAA ACC ACC TGC CCA TGT GGA GCA CAG ATC ACC GGA CAT GTC        6449
Ile Met Gln Thr Thr Cys Pro Cys Gly Ala Gln Ile Thr Gly His Val
    2025                2030                2035

AAA AAC GGT TCC ATG AGG ATC GTC GGG CCT AAG ACC TGC AGC AAC ACG        6497
Lys Asn Gly Ser Met Arg Ile Val Gly Pro Lys Thr Cys Ser Asn Thr
2040                2045                2050                2055

TGG CAT GGA ACA TTC CCC ATC AAC GCA TAC ACC ACG GGC CCC TGC ACA        6545
Trp His Gly Thr Phe Pro Ile Asn Ala Tyr Thr Thr Gly Pro Cys Thr
                2060                2065                2070

CCC TCT CCA GCG CCA AAC TAT TCT AGG GCG CTG TGG CGG GTG GCC GCT        6593
Pro Ser Pro Ala Pro Asn Tyr Ser Arg Ala Leu Trp Arg Val Ala Ala
            2075                2080                2085

GAG GAG TAC GTG GAG GTC ACG CGG GTG GGG GAT TTC CAC TAC GTG ACG        6641
Glu Glu Tyr Val Glu Val Thr Arg Val Gly Asp Phe His Tyr Val Thr
        2090                2095                2100

GGC ATG ACC ACT GAC AAC GTA AAG TGC CCA TGC CAG GTT CCG GCT CCT        6689
Gly Met Thr Thr Asp Asn Val Lys Cys Pro Cys Gln Val Pro Ala Pro
    2105                2110                2115

GAA TTC TTC TCG GAG GTG GAC GGA GTG CGG TTG CAC AGG TAC GCT CCG        6737
Glu Phe Phe Ser Glu Val Asp Gly Val Arg Leu His Arg Tyr Ala Pro
2120                2125                2130                2135

GCG TGC AGG CCT CTC CTA CGG GAG GAG GTT ACA TTC CAG GTC GGG CTC        6785
Ala Cys Arg Pro Leu Leu Arg Glu Glu Val Thr Phe Gln Val Gly Leu
                2140                2145                2150

AAC CAA TAC CTG GTT GGG TCA CAG CTA CCA TGC GAG CCC GAA CCG GAT        6833
Asn Gln Tyr Leu Val Gly Ser Gln Leu Pro Cys Glu Pro Glu Pro Asp
            2155                2160                2165

GTA GCA GTG CTC ACT TCC ATG CTC ACC GAC CCC TCC CAC ATC ACA GCA        6881
Val Ala Val Leu Thr Ser Met Leu Thr Asp Pro Ser His Ile Thr Ala
        2170                2175                2180

GAA ACG GCT AAG CGT AGG TTG GCC AGG GGG TCT CCC CCC TCC TTG GCC        6929
Glu Thr Ala Lys Arg Arg Leu Ala Arg Gly Ser Pro Pro Ser Leu Ala
    2185                2190                2195

AGC TCT TCA GCT AGC CAG TTG TCT GCG CCT TCC TTG AAG GCG ACA TGC        6977
Ser Ser Ser Ala Ser Gln Leu Ser Ala Pro Ser Leu Lys Ala Thr Cys
2200                2205                2210                2215

ACT ACC CAC CAT GTC TCT CCG GAC GCT GAC CTC ATC GAG GCC AAC CTC        7025
Thr Thr His His Val Ser Pro Asp Ala Asp Leu Ile Glu Ala Asn Leu
                2220                2225                2230

CTG TGG CGG CAG GAG ATG GGC GGG AAC ATC ACC CGC GTG GAG TCG AGG        7073
Leu Trp Arg Gln Glu Met Gly Gly Asn Ile Thr Arg Val Glu Ser Glu
            2235                2240                2245

AAC AAG GTG GTA GTC CTG GAC TCT TTC GAC CCG CTT CGA GCG GAG GAG        7121
Asn Lys Val Val Val Leu Asp Ser Phe Asp Pro Leu Arg Ala Glu Glu
        2250                2255                2260

GAT GAG AGG GAA GTA TCC GTT CCG GCG GAG ATC CTG CGG AAA TCC AAG        7169
Asp Glu Arg Glu Val Ser Val Pro Ala Glu Ile Leu Arg Lys Ser Lys
    2265                2270                2275
```

```
AAG TTC CCC GCA GCG ATG CCC ATC TGG GCG CGC CCG GAT TAC AAC CCT         7217
Lys Phe Pro Ala Ala Met Pro Ile Trp Ala Arg Pro Asp Tyr Asn Pro
2280            2285            2290            2295

CCA CTG TTA GAG TCC TGG AAG GAC CCG GAC TAC GTC CCT CCG GTG GTG         7265
Pro Leu Leu Glu Ser Trp Lys Asp Pro Asp Tyr Val Pro Pro Val Val
        2300            2305            2310

CAC GGG TGC CCG TTG CCA CCT ATC AAG GCC CCT CCA ATA CCA CCT CCA         7313
His Gly Cys Pro Leu Pro Pro Ile Lys Ala Pro Pro Ile Pro Pro Pro
            2315            2320            2325

CGG AGA AAG AGG ACG GTT GTC CTA ACA GAG TCC TCC GTG TCT TCT GCC         7361
Arg Arg Lys Arg Thr Val Val Leu Thr Glu Ser Ser Val Ser Ser Ala
2330            2335            2340

TTA GCG GAG CTC GCT ACT AAG ACC TTC GGC AGC TCC GAA TCA TCG GCC         7409
Leu Ala Glu Leu Ala Thr Lys Thr Phe Gly Ser Ser Glu Ser Ser Ala
    2345            2350            2355

GTC GAC AGC GGC ACG GCG ACC GCC CTT CCT GAC CAG GCC TCC GAC GAC         7457
Val Asp Ser Gly Thr Ala Thr Ala Leu Pro Asp Gln Ala Ser Asp Asp
2360            2365            2370            2375

GGT GAC AAA GGA TCC GAC GTT GAG TCG TAC TCC TCC ATG CCC CCC CTT         7505
Gly Asp Lys Gly Ser Asp Val Glu Ser Tyr Ser Ser Met Pro Pro Leu
        2380            2385            2390

GAG GGG GAA CCG GGG GAC CCC GAT CTC AGT GAC GGG TCT TGG TCT ACC         7553
Glu Gly Glu Pro Gly Asp Pro Asp Leu Ser Asp Gly Ser Trp Ser Thr
            2395            2400            2405

GTG AGC GAG GAA GCT AGT GAG GAT GTC GTC TGC TGC TCA ATG TCC TAC         7601
Val Ser Glu Glu Ala Ser Glu Asp Val Val Cys Cys Ser Met Ser Tyr
2410            2415            2420

ACA TGG ACA GGC GCC TTG ATC ACG CCA TGC GCT GCG GAG GAA AGC AAG         7649
Thr Trp Thr Gly Ala Leu Ile Thr Pro Cys Ala Ala Glu Glu Ser Lys
    2425            2430            2435

CTG CCC ATC AAC GCG TTG AGC AAC TCT TTG CTG CGC CAC CAT AAC ATG         7697
Leu Pro Ile Asn Ala Leu Ser Asn Ser Leu Leu Arg His His Asn Met
2440            2445            2450            2455

GTT TAT GCC ACA ACA TCT CGC AGC GCA GGC CTG CGG CAG AAG AAG GTC         7745
Val Tyr Ala Thr Thr Ser Arg Ser Ala Gly Leu Arg Gln Lys Lys Val
        2460            2465            2470

ACC TTT GAC AGA CTG CAA GTC CTG GAC GAC CAC TAC CGG GAC GTG CTC         7793
Thr Phe Asp Arg Leu Gln Val Leu Asp Asp His Tyr Arg Asp Val Leu
            2475            2480            2485

AAG GAG ATG AAG GCG AAG GCG TCC ACA GTT AAG GCT AAA CTC CTA TCC         7841
Lys Glu Met Lys Ala Lys Ala Ser Thr Val Lys Ala Lys Leu Leu Ser
2490            2495            2500

GTA GAG GAA GCC TGC AAG CTG ACG CCC CCA CAT TCG GCC AAA TCC AAG         7889
Val Glu Glu Ala Cys Lys Leu Thr Pro Pro His Ser Ala Lys Ser Lys
    2505            2510            2515

TTT GGC TAT GGG GCA AAG GAC GTC CGG AAC CTA TCC AGC AAG GCC GTT         7937
Phe Gly Tyr Gly Ala Lys Asp Val Arg Asn Leu Ser Ser Lys Ala Val
2520            2525            2530            2535

AAC CAC ATC CAC TCC GTG TGG AAG GAC TTG CTG GAA GAC ACT GTG ACA         7985
Asn His Ile His Ser Val Trp Lys Asp Leu Leu Glu Asp Thr Val Thr
        2540            2545            2550

CCA ATT GAC ACC ACC ATC ATG GCA AAA AAT GAG GTT TTC TGT GTC CAA         8033
Pro Ile Asp Thr Thr Ile Met Ala Lys Asn Glu Val Phe Cys Val Gln
            2555            2560            2565

CCA GAG AAA GGA GGC CGT AAG CCA GCC CGC CTT ATC GTA TTC CCA GAT         8081
Pro Glu Lys Gly Gly Arg Lys Pro Ala Arg Leu Ile Val Phe Pro Asp
2570            2575            2580

CTG GGA GTC CGT GTA TGC GAG AAG ATG GCC CTC TAT GAT GTG GTC TCC         8129
Leu Gly Val Arg Val Cys Glu Lys Met Ala Leu Tyr Asp Val Val Ser
    2585            2590            2595
```

| | | | | | | | | | | | | | | | | |
|---|---|---|---|---|---|---|---|---|---|---|---|---|---|---|---|---|
| ACC | CTT | CCT | CAG | GTC | GTG | ATG | GGC | TCC | TCA | TAC | GGA | TTC | CAG | TAC | TCT | 8177 |
| Thr | Leu | Pro | Gln | Val | Val | Met | Gly | Ser | Ser | Tyr | Gly | Phe | Gln | Tyr | Ser | |
| 2600 | | | | 2605 | | | | 2610 | | | | | | 2615 | | |
| CCT | GGG | CAG | CGA | GTC | GAG | TTC | CTG | GTG | AAT | ACC | TGG | AAA | TCA | AAG | AAA | 8225 |
| Pro | Gly | Gln | Arg | Val | Glu | Phe | Leu | Val | Asn | Thr | Trp | Lys | Ser | Lys | Lys | |
| | | | | 2620 | | | | 2625 | | | | | | 2630 | | |
| AAC | CCC | ATG | GGC | TTT | TCA | TAT | GAC | ACT | CGC | TGT | TTC | GAC | TCA | ACG | GTC | 8273 |
| Asn | Pro | Met | Gly | Phe | Ser | Tyr | Asp | Thr | Arg | Cys | Phe | Asp | Ser | Thr | Val | |
| | | 2635 | | | | 2640 | | | | 2645 | | | | | | |
| ACC | GAG | AAC | GAC | ATC | CGT | GTT | GAG | GAG | TCA | ATT | TAC | CAA | TGT | TGT | GAC | 8321 |
| Thr | Glu | Asn | Asp | Ile | Arg | Val | Glu | Glu | Ser | Ile | Tyr | Gln | Cys | Cys | Asp | |
| | | 2650 | | | | 2655 | | | | 2660 | | | | | | |
| TTG | GCC | CCC | GAA | GCC | AGA | CAG | GCC | ATA | AAA | TCG | CTC | ACA | GAG | CGG | CTT | 8369 |
| Leu | Ala | Pro | Glu | Ala | Arg | Gln | Ala | Ile | Lys | Ser | Leu | Thr | Glu | Arg | Leu | |
| | 2665 | | | | 2670 | | | | 2675 | | | | | | | |
| TAT | ATC | GGG | GGT | CCT | CTG | ACT | AAT | TCA | AAA | GGG | CAG | AAC | TGC | GGT | TAT | 8417 |
| Tyr | Ile | Gly | Gly | Pro | Leu | Thr | Asn | Ser | Lys | Gly | Gln | Asn | Cys | Gly | Tyr | |
| 2680 | | | | 2685 | | | | 2690 | | | | | | 2695 | | |
| CGC | CGG | TGC | CGC | GCG | AGC | GGC | GTG | CTG | ACG | ACT | AGC | TGC | GGT | AAC | ACC | 8465 |
| Arg | Arg | Cys | Arg | Ala | Ser | Gly | Val | Leu | Thr | Thr | Ser | Cys | Gly | Asn | Thr | |
| | | | | 2700 | | | | 2705 | | | | | | 2710 | | |
| CTC | ACA | TGT | TAC | TTG | AAG | GCC | TCT | GCA | GCC | TGT | CGA | GCT | GCG | AAG | CTC | 8513 |
| Leu | Thr | Cys | Tyr | Leu | Lys | Ala | Ser | Ala | Ala | Cys | Arg | Ala | Ala | Lys | Leu | |
| | | | 2715 | | | | 2720 | | | | 2725 | | | | | |
| CAG | GAC | TGC | ACG | ATG | CTC | GTG | AAC | GGA | GAC | GAC | CTC | GTC | GTT | ATC | TGT | 8561 |
| Gln | Asp | Cys | Thr | Met | Leu | Val | Asn | Gly | Asp | Asp | Leu | Val | Val | Ile | Cys | |
| | | | 2730 | | | | 2735 | | | | 2740 | | | | | |
| GAA | AGC | GCG | GGA | ACC | CAA | GAG | GAC | GCG | GCG | AGC | CTA | CGA | GTC | TTC | ACG | 8609 |
| Glu | Ser | Ala | Gly | Thr | Gln | Glu | Asp | Ala | Ala | Ser | Leu | Arg | Val | Phe | Thr | |
| 2745 | | | | 2750 | | | | | | 2755 | | | | | | |
| GAG | GCT | ATG | ACT | AGG | TAC | TCC | GCC | CCC | CCC | GGG | GAC | CCG | CCC | CAA | CCA | 8657 |
| Glu | Ala | Met | Thr | Arg | Tyr | Ser | Ala | Pro | Pro | Gly | Asp | Pro | Pro | Gln | Pro | |
| 2760 | | | | 2765 | | | | 2770 | | | | | | 2775 | | |
| GAA | TAC | GAC | TTG | GAG | CTG | ATA | ACA | TCA | TGT | TCC | TCC | AAT | GTG | TCG | GTC | 8705 |
| Glu | Tyr | Asp | Leu | Glu | Leu | Ile | Thr | Ser | Cys | Ser | Ser | Asn | Val | Ser | Val | |
| | | | | 2780 | | | | 2785 | | | | | | 2790 | | |
| GCC | CAC | GAT | GCA | TCA | GGC | AAA | AGG | GTG | TAC | TAC | CTC | ACC | CGT | GAT | CCC | 8753 |
| Ala | His | Asp | Ala | Ser | Gly | Lys | Arg | Val | Tyr | Tyr | Leu | Thr | Arg | Asp | Pro | |
| | | | 2795 | | | | 2800 | | | | | | 2805 | | | |
| ACC | ACC | CCC | CTA | GCA | CGG | GCT | GCG | TGG | GAG | ACA | GCT | AGA | CAC | ACT | CCA | 8801 |
| Thr | Thr | Pro | Leu | Ala | Arg | Ala | Ala | Trp | Glu | Thr | Ala | Arg | His | Thr | Pro | |
| | | 2810 | | | | 2815 | | | | | | 2820 | | | | |
| GTT | AAC | TCC | TGG | CTA | GGC | AAC | ATT | ATT | ATG | TAT | GCG | CCC | ACT | TTG | TGG | 8849 |
| Val | Asn | Ser | Trp | Leu | Gly | Asn | Ile | Ile | Met | Tyr | Ala | Pro | Thr | Leu | Trp | |
| | 2825 | | | | 2830 | | | | 2835 | | | | | | | |
| GCA | AGG | ATG | ATT | CTG | ATG | ACT | CAC | TTC | TTC | TCC | ATC | CTT | CTA | GCG | CAG | 8897 |
| Ala | Arg | Met | Ile | Leu | Met | Thr | His | Phe | Phe | Ser | Ile | Leu | Leu | Ala | Gln | |
| 2840 | | | | 2845 | | | | 2850 | | | | | | 2855 | | |
| GAG | CAA | CTT | GAA | AAA | GCC | CTG | GAC | TGC | CAG | ATC | TAC | GGG | GCC | TGT | TAC | 8945 |
| Glu | Gln | Leu | Glu | Lys | Ala | Leu | Asp | Cys | Gln | Ile | Tyr | Gly | Ala | Cys | Tyr | |
| | | | | 2860 | | | | 2865 | | | | | | 2870 | | |
| TCC | ATT | GAG | CCA | CTT | GAC | CTA | CCT | CAG | ATC | ATT | GAA | CGA | CTC | CAT | GGC | 8993 |
| Ser | Ile | Glu | Pro | Leu | Asp | Leu | Pro | Gln | Ile | Ile | Glu | Arg | Leu | His | Gly | |
| | | | | 2875 | | | | 2880 | | | | | | 2885 | | |
| CTT | AGC | GCA | TTT | TCA | CTC | CAT | AGT | TAC | TCT | CCA | GGT | GAG | ATC | AAT | AGG | 9041 |
| Leu | Ser | Ala | Phe | Ser | Leu | His | Ser | Tyr | Ser | Pro | Gly | Glu | Ile | Asn | Arg | |
| | | 2890 | | | | 2895 | | | | 2900 | | | | | | |
| GTG | GCT | TCA | TGC | CTC | AGG | AAA | CTT | GGG | GTA | CCA | CCC | TTG | CGA | GTC | TGG | 9089 |
| Val | Ala | Ser | Cys | Leu | Arg | Lys | Leu | Gly | Val | Pro | Pro | Leu | Arg | Val | Trp | |
| | 2905 | | | | 2910 | | | | 2915 | | | | | | | |

```
AGA CAT CGG GCC AGG AGC GTC CGC GCT AGG CTA CTG TCC CAG GGA GGG              9137
Arg His Arg Ala Arg Ser Val Arg Ala Arg Leu Leu Ser Gln Gly Gly
2920                2925                2930                2935

AGG GCC GCC ACT TGT GGC AAA TAC CTC TTC AAC TGG GCA GTA AAA ACC              9185
Arg Ala Ala Thr Cys Gly Lys Tyr Leu Phe Asn Trp Ala Val Lys Thr
                2940                2945                2950

AAA CTT AAA CTC ACT CCA ATC CCG GCT GCG TCC CGG CTG GAC TTG TCC              9233
Lys Leu Lys Leu Thr Pro Ile Pro Ala Ala Ser Arg Leu Asp Leu Ser
            2955                2960                2965

GGC TGG TTC GTT GCT GGT TAC AGC GGG GGA GAC ATA TAT CAC AGC CTG              9281
Gly Trp Phe Val Ala Gly Tyr Ser Gly Gly Asp Ile Tyr His Ser Leu
        2970                2975                2980

TCT CGT GCC CGA CCC CGT TGG TTC ATG CTG TGC CTA CTC CTA CTT TCT              9329
Ser Arg Ala Arg Pro Arg Trp Phe Met Leu Cys Leu Leu Leu Leu Ser
    2985                2990                2995

GTA GGG GTA GGC ATC TAC CTG CTC CCC AAC CGA TGAACGGGGA GATAAACACT            9382
Val Gly Val Gly Ile Tyr Leu Leu Pro Asn Arg
3000                3005                3010

CCAGGCCAAT AGGCCATCCC CCTTTTTTTT TTTT                                        9416
```

( 2 ) INFORMATION FOR SEQ ID NO:2:

( i ) SEQUENCE CHARACTERISTICS:
( A ) LENGTH: 3010 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Pro Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser Ala Tyr
            180                 185                 190

Glu Val His Asn Val Ser Gly Ile Tyr His Val Thr Asn Asp Cys Ser
        195                 200                 205

Asn Ala Ser Ile Val Tyr Glu Ala Ala Asp Leu Ile Met His Thr Pro
    210                 215                 220
```

| Gly 225 | Cys | Val | Pro | Cys 230 | Val | Arg | Glu | Gly | Asn 235 | Ser | Ser | Arg | Cys | Trp 240 | Val |
| Ala | Leu | Thr | Pro | Thr 245 | Leu | Ala | Ala | Arg | Asn 250 | Val | Thr | Ile | Pro | Thr 255 | Thr |
| Thr | Ile | Arg | Arg 260 | His | Val | Asp | Leu | Leu 265 | Val | Gly | Ala | Ala | Ala 270 | Phe | Cys |
| Ser | Ala | Met 275 | Tyr | Val | Gly | Asp | Leu 280 | Cys | Gly | Ser | Val | Phe 285 | Leu | Val | Ser |
| Gln | Leu 290 | Phe | Thr | Phe | Ser | Pro 295 | Arg | Arg | His | Val | Thr 300 | Leu | Gln | Asp | Cys |
| Asn 305 | Cys | Ser | Ile | Tyr | Pro 310 | Gly | His | Val | Ser | Gly 315 | His | Arg | Met | Ala | Trp 320 |
| Asp | Met | Met | Met | Asn 325 | Trp | Ser | Pro | Thr | Thr 330 | Ala | Leu | Val | Val | Ser 335 | Gln |
| Leu | Leu | Arg | Ile 340 | Pro | Gln | Ala | Val | Val 345 | Asp | Met | Val | Ala | Gly 350 | Ala | His |
| Trp | Gly | Val 355 | Leu | Ala | Gly | Leu | Ala 360 | Tyr | Tyr | Ser | Met | Ala 365 | Gly | Asn | Trp |
| Ala | Lys 370 | Val | Leu | Ile | Val | Met 375 | Leu | Leu | Phe | Ala | Gly 380 | Val | Asp | Gly | Asp |
| Thr 385 | His | Val | Thr | Gly | Gly 390 | Ala | Gln | Ala | Lys | Thr 395 | Thr | Asn | Arg | Leu | Val 400 |
| Ser | Met | Phe | Ala | Ser 405 | Gly | Pro | Ser | Gln | Lys 410 | Ile | Gln | Leu | Ile | Asn 415 | Thr |
| Asn | Gly | Ser | Trp 420 | His | Ile | Asn | Arg | Thr 425 | Ala | Leu | Asn | Cys | Asn 430 | Asp | Ser |
| Leu | Gln | Thr | Gly 435 | Phe | Leu | Ala | Ala 440 | Leu | Phe | Tyr | Thr | His 445 | Ser | Phe | Asn |
| Ser | Ser 450 | Gly | Cys | Pro | Glu | Arg 455 | Met | Ala | Gln | Cys | Arg 460 | Thr | Ile | Asp | Lys |
| Phe 465 | Asp | Gln | Gly | Trp | Gly 470 | Pro | Ile | Thr | Tyr | Ala 475 | Glu | Ser | Ser | Arg | Ser 480 |
| Asp | Gln | Arg | Pro | Tyr 485 | Cys | Trp | His | Tyr | Pro 490 | Pro | Pro | Gln | Cys | Thr 495 | Ile |
| Val | Pro | Ala | Ser 500 | Glu | Val | Cys | Gly | Pro 505 | Val | Tyr | Cys | Phe | Thr 510 | Pro | Ser |
| Pro | Val | Val 515 | Val | Gly | Thr | Thr | Asp 520 | Arg | Phe | Gly | Val | Pro 525 | Thr | Tyr | Arg |
| Trp | Gly 530 | Glu | Asn | Glu | Thr | Asp 535 | Val | Leu | Leu | Leu | Asn 540 | Asn | Thr | Arg | Pro |
| Pro 545 | Gln | Gly | Asn | Trp | Phe 550 | Gly | Cys | Thr | Trp | Met 555 | Asn | Ser | Thr | Gly | Phe 560 |
| Thr | Lys | Thr | Cys | Gly 565 | Gly | Pro | Pro | Cys | Asn 570 | Ile | Gly | Gly | Val | Gly 575 | Asn |
| Asn | Thr | Leu | Thr 580 | Cys | Pro | Thr | Asp 585 | Cys | Phe | Arg | Lys | His 590 | Pro | Glu | Ala |
| Thr | Tyr | Thr 595 | Lys | Cys | Gly | Ser 600 | Gly | Pro | Trp | Leu | Thr 605 | Pro | Arg | Cys | Met |
| Val | Asp 610 | Tyr | Pro | Tyr | Arg | Leu 615 | Trp | His | Tyr | Pro | Cys 620 | Thr | Val | Asn | Phe |
| Thr 625 | Ile | Phe | Lys | Val | Arg 630 | Met | Tyr | Val | Gly | Gly 635 | Val | Glu | His | Arg | Leu 640 |
| Asn | Ala | Ala | Cys | Asn | Trp | Thr | Arg | Gly | Glu | Arg | Cys | Asp | Leu | Glu | Asp |

-continued

|     |     |     | 645 |     |     |     | 650 |     |     |     |     | 655 |     |     |
|-----|-----|-----|-----|-----|-----|-----|-----|-----|-----|-----|-----|-----|-----|-----|
| Arg | Asp | Arg | Pro | Glu | Leu | Ser | Pro | Leu | Leu | Ser | Thr | Thr | Glu | Trp |
|     |     |     | 660 |     |     |     | 665 |     |     |     | 670 |     |     |     |
| Gln | Val | Leu | Pro | Cys | Ser | Phe | Thr | Thr | Leu | Pro | Ala | Leu | Ser | Thr | Gly |
|     |     | 675 |     |     |     | 680 |     |     |     |     | 685 |     |     |     |
| Leu | Ile | His | Leu | His | Gln | Asn | Ile | Val | Asp | Val | Gln | Tyr | Leu | Tyr | Gly |
|     | 690 |     |     |     | 695 |     |     |     |     | 700 |     |     |     |     |
| Ile | Gly | Ser | Ala | Val | Val | Ser | Phe | Ala | Ile | Lys | Trp | Glu | Tyr | Val | Leu |
| 705 |     |     |     |     | 710 |     |     |     | 715 |     |     |     |     | 720 |
| Leu | Leu | Phe | Leu | Leu | Leu | Ala | Asp | Ala | Arg | Val | Cys | Ala | Cys | Leu | Trp |
|     |     |     |     | 725 |     |     |     | 730 |     |     |     |     | 735 |     |
| Met | Met | Leu | Leu | Ile | Ala | Gln | Ala | Glu | Ala | Ala | Leu | Glu | Asn | Leu | Val |
|     |     |     | 740 |     |     |     | 745 |     |     |     | 750 |     |     |     |
| Val | Leu | Asn | Ser | Ala | Ser | Val | Ala | Gly | Ala | His | Gly | Ile | Leu | Ser | Phe |
|     |     | 755 |     |     |     | 760 |     |     |     |     | 765 |     |     |     |
| Leu | Val | Phe | Phe | Cys | Ala | Ala | Trp | Tyr | Ile | Lys | Gly | Arg | Leu | Val | Pro |
|     | 770 |     |     |     |     | 775 |     |     |     |     | 780 |     |     |     |
| Gly | Ala | Thr | Tyr | Ala | Leu | Tyr | Gly | Val | Trp | Pro | Leu | Leu | Leu | Leu | Leu |
| 785 |     |     |     |     | 790 |     |     |     | 795 |     |     |     |     | 800 |
| Leu | Ala | Leu | Pro | Pro | Arg | Ala | Tyr | Ala | Met | Asp | Arg | Glu | Met | Ala | Ala |
|     |     |     |     | 805 |     |     |     | 810 |     |     |     |     | 815 |     |
| Ser | Cys | Gly | Gly | Ala | Val | Phe | Val | Gly | Leu | Val | Leu | Leu | Thr | Leu | Ser |
|     |     |     | 820 |     |     |     |     | 825 |     |     |     |     | 830 |     |
| Pro | Tyr | Tyr | Lys | Val | Phe | Leu | Ala | Arg | Leu | Ile | Trp | Trp | Leu | Gln | Tyr |
|     |     | 835 |     |     |     |     | 840 |     |     |     |     | 845 |     |     |
| Phe | Thr | Thr | Arg | Ala | Glu | Ala | Asp | Leu | His | Val | Trp | Ile | Pro | Pro | Leu |
|     | 850 |     |     |     |     | 855 |     |     |     |     | 860 |     |     |     |
| Asn | Ala | Arg | Gly | Gly | Arg | Asp | Ala | Ile | Ile | Leu | Leu | Met | Cys | Ala | Val |
| 865 |     |     |     |     | 870 |     |     |     |     | 875 |     |     |     | 880 |
| His | Pro | Glu | Leu | Ile | Phe | Asp | Ile | Thr | Lys | Leu | Leu | Ile | Ala | Ile | Leu |
|     |     |     |     | 885 |     |     |     |     | 890 |     |     |     | 895 |     |
| Gly | Pro | Leu | Met | Val | Leu | Gln | Ala | Gly | Ile | Thr | Arg | Val | Pro | Tyr | Phe |
|     |     |     | 900 |     |     |     |     | 905 |     |     |     |     | 910 |     |
| Val | Arg | Ala | Gln | Gly | Leu | Ile | His | Ala | Cys | Met | Leu | Val | Arg | Lys | Val |
|     |     | 915 |     |     |     |     | 920 |     |     |     |     | 925 |     |     |
| Ala | Gly | Gly | His | Tyr | Val | Gln | Met | Ala | Phe | Met | Lys | Leu | Gly | Ala | Leu |
|     | 930 |     |     |     |     | 935 |     |     |     |     | 940 |     |     |     |
| Thr | Gly | Thr | Tyr | Ile | Tyr | Asn | His | Leu | Thr | Pro | Leu | Arg | Asp | Trp | Pro |
| 945 |     |     |     |     | 950 |     |     |     |     | 955 |     |     |     | 960 |
| Arg | Ala | Gly | Leu | Arg | Asp | Leu | Ala | Val | Ala | Val | Glu | Pro | Val | Val | Phe |
|     |     |     |     | 965 |     |     |     |     | 970 |     |     |     |     | 975 |
| Ser | Asp | Met | Glu | Thr | Lys | Ile | Ile | Thr | Trp | Gly | Ala | Asp | Thr | Ala | Ala |
|     |     |     | 980 |     |     |     |     | 985 |     |     |     |     | 990 |     |
| Cys | Gly | Asp | Ile | Ile | Leu | Gly | Leu | Pro | Val | Ser | Ala | Arg | Arg | Gly | Lys |
|     |     | 995 |     |     |     |     | 1000 |     |     |     |     | 1005 |     |     |
| Glu | Ile | Leu | Leu | Gly | Pro | Ala | Asp | Ser | Leu | Glu | Gly | Arg | Gly | Leu | Arg |
|     |     | 1010 |     |     |     |     | 1015 |     |     |     |     | 1020 |     |     |
| Leu | Leu | Ala | Pro | Ile | Thr | Ala | Tyr | Ser | Gln | Gln | Thr | Arg | Gly | Leu | Leu |
| 1025 |     |     |     |     | 1030 |     |     |     |     | 1035 |     |     |     | 1040 |
| Gly | Cys | Ile | Ile | Thr | Ser | Leu | Thr | Gly | Arg | Asp | Lys | Asn | Gln | Val | Glu |
|     |     |     |     | 1045 |     |     |     |     | 1050 |     |     |     |     | 1055 |
| Gly | Glu | Val | Gln | Val | Val | Ser | Thr | Ala | Thr | Gln | Ser | Phe | Leu | Ala | Thr |
|     |     |     | 1060 |     |     |     |     | 1065 |     |     |     |     | 1070 |     |

```
Cys Val Asn Gly Val Cys Trp Thr Val Tyr His Gly Ala Gly Ser Lys
            1075            1080                1085

Thr Leu Ala Ala Pro Lys Gly Pro Ile Thr Gln Met Tyr Thr Asn Val
    1090            1095            1100

Asp Gln Asp Leu Val Gly Trp Pro Lys Pro Gly Ala Arg Ser Leu
1105            1110            1115                    1120

Thr Pro Cys Thr Cys Gly Ser Ser Asp Leu Tyr Leu Val Thr Arg His
            1125            1130                1135

Ala Asp Val Ile Pro Val Arg Arg Arg Gly Asp Ser Arg Gly Ser Leu
            1140            1145                1150

Leu Ser Pro Arg Pro Val Ser Tyr Leu Lys Gly Ser Ser Gly Gly Pro
            1155            1160                1165

Leu Leu Cys Pro Phe Gly His Ala Val Gly Ile Phe Arg Ala Ala Val
            1170            1175                1180

Cys Thr Arg Gly Val Ala Lys Ala Val Asp Phe Val Pro Val Glu Ser
1185            1190            1195                    1200

Met Glu Thr Thr Met Arg Ser Pro Val Phe Thr Asp Asn Ser Ser Pro
            1205            1210                1215

Pro Ala Val Pro Gln Ser Phe Gln Val Ala His Leu His Ala Pro Thr
            1220            1225                1230

Gly Ser Gly Lys Ser Thr Lys Val Pro Ala Ala Tyr Ala Ala Gln Gly
            1235            1240                1245

Tyr Lys Val Leu Val Leu Asn Pro Ser Val Ala Ala Thr Leu Gly Phe
            1250            1255                1260

Gly Ala Tyr Met Ser Lys Ala His Gly Ile Asp Pro Asn Ile Arg Thr
1265            1270            1275                    1280

Gly Val Arg Thr Ile Thr Thr Gly Ala Pro Val Thr Tyr Ser Thr Tyr
            1285            1290                1295

Gly Lys Phe Leu Ala Asp Gly Gly Cys Ser Gly Gly Ala Tyr Asp Ile
            1300            1305                1310

Ile Ile Cys Asp Glu Cys His Ser Thr Asp Ser Thr Thr Ile Leu Gly
            1315            1320                1325

Ile Gly Thr Val Leu Asp Gln Ala Glu Thr Ala Gly Ala Arg Leu Val
            1330            1335                1340

Val Leu Ala Thr Ala Thr Pro Pro Gly Ser Val Thr Val Pro His Pro
1345            1350            1355                    1360

Asn Ile Glu Glu Val Ala Leu Ser Asn Thr Gly Glu Ile Pro Phe Tyr
            1365            1370                1375

Gly Lys Ala Ile Pro Ile Glu Ala Ile Arg Gly Gly Arg His Leu Ile
            1380            1385                1390

Phe Cys His Ser Lys Lys Lys Cys Asp Glu Leu Ala Ala Lys Leu Ser
            1395            1400                1405

Gly Leu Gly Ile Asn Ala Val Ala Tyr Tyr Arg Gly Leu Asp Val Ser
            1410            1415                1420

Val Ile Pro Thr Ile Gly Asp Val Val Val Ala Thr Asp Ala Leu
1425            1430            1435                    1440

Met Thr Gly Tyr Thr Gly Asp Phe Asp Ser Val Ile Asp Cys Asn Thr
            1445            1450                1455

Cys Val Thr Gln Thr Val Asp Phe Ser Leu Asp Pro Thr Phe Thr Ile
            1460            1465                1470

Glu Thr Thr Thr Val Pro Gln Asp Ala Val Ser Arg Ser Gln Arg Arg
            1475            1480                1485

Gly Arg Thr Gly Arg Gly Arg Arg Gly Ile Tyr Arg Phe Val Thr Pro
            1490            1495                1500
```

```
Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Ser
            1525                1530                1535

Val Arg Leu Arg Ala Tyr Leu Asn Thr Pro Gly Leu Pro Val Cys Gln
        1540                1545                1550

Asp His Leu Glu Phe Trp Glu Ser Val Phe Thr Gly Leu Thr His Ile
    1555                1560                1565

Asp Ala His Phe Leu Ser Gln Thr Lys Gln Ala Gly Asp Asn Phe Pro
1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
                1605                1610                1615

Thr Leu His Gly Pro Thr Pro Leu Leu Tyr Arg Leu Gly Ala Val Gln
            1620                1625                1630

Asn Glu Val Thr Leu Thr His Pro Ile Thr Lys Tyr Ile Met Ala Cys
        1635                1640                1645

Met Ser Ala Asp Leu Glu Val Val Thr Ser Thr Trp Val Leu Val Gly
    1650                1655                1660

Gly Val Leu Ala Ala Leu Ala Ala Tyr Cys Leu Thr Thr Gly Ser Val
1665                1670                1675                1680

Val Ile Val Gly Arg Ile Ile Leu Ser Gly Arg Pro Ala Ile Val Pro
                1685                1690                1695

Asp Arg Glu Leu Leu Tyr Gln Glu Phe Asp Glu Met Glu Glu Cys Ala
            1700                1705                1710

Ser His Leu Pro Tyr Ile Glu Gln Gly Met Gln Leu Ala Glu Gln Phe
        1715                1720                1725

Lys Gln Lys Ala Leu Gly Leu Leu Gln Thr Ala Thr Lys Gln Ala Glu
    1730                1735                1740

Ala Ala Ala Pro Val Val Glu Ser Lys Trp Arg Ala Leu Glu Thr Phe
1745                1750                1755                1760

Trp Ala Lys His Met Trp Asn Phe Ile Ser Gly Ile Gln Tyr Leu Ala
                1765                1770                1775

Gly Leu Ser Thr Leu Pro Gly Asn Pro Ala Ile Ala Ser Leu Met Ala
            1780                1785                1790

Phe Thr Ala Ser Ile Thr Ser Pro Leu Thr Thr Gln Ser Thr Leu Leu
        1795                1800                1805

Phe Asn Ile Leu Gly Gly Trp Val Ala Ala Gln Leu Ala Pro Pro Ser
    1810                1815                1820

Ala Ala Ser Ala Phe Val Gly Ala Gly Ile Ala Gly Ala Ala Val Gly
1825                1830                1835                1840

Ser Ile Gly Leu Gly Lys Val Leu Val Asp Ile Leu Ala Gly Tyr Gly
                1845                1850                1855

Ala Gly Val Ala Gly Ala Leu Val Ala Phe Lys Val Met Ser Gly Glu
            1860                1865                1870

Met Pro Ser Thr Glu Asp Leu Val Asn Leu Leu Pro Ala Ile Leu Ser
        1875                1880                1885

Pro Gly Ala Leu Val Val Gly Val Val Cys Ala Ala Ile Leu Arg Arg
    1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
```

-continued

```
              1925                    1930                   1935
Glu Ser Asp Ala Ala Ala Arg Val Thr Gln Ile Leu Ser Ser Leu Thr
              1940                   1945                   1950
Ile Thr Gln Leu Leu Lys Arg Leu His Gln Trp Ile Asn Glu Asp Cys
              1955                   1960                   1965
Ser Thr Pro Cys Ser Gly Ser Trp Leu Arg Asp Val Trp Asp Trp Ile
              1970                   1975                   1980
Cys Thr Val Leu Thr Asp Phe Lys Thr Trp Leu Gln Ser Lys Leu Leu
1985                   1990                   1995                   2000
Pro Gln Leu Pro Gly Val Pro Phe Phe Ser Cys Gln Arg Gly Tyr Lys
              2005                   2010                   2015
Gly Val Trp Arg Gly Asp Gly Ile Met Gln Thr Thr Cys Pro Cys Gly
              2020                   2025                   2030
Ala Gln Ile Thr Gly His Val Lys Asn Gly Ser Met Arg Ile Val Gly
              2035                   2040                   2045
Pro Lys Thr Cys Ser Asn Thr Trp His Gly Thr Phe Pro Ile Asn Ala
              2050                   2055                   2060
Tyr Thr Thr Gly Pro Cys Thr Pro Ser Pro Ala Pro Asn Tyr Ser Arg
2065                   2070                   2075                   2080
Ala Leu Trp Arg Val Ala Ala Glu Glu Tyr Val Glu Val Thr Arg Val
              2085                   2090                   2095
Gly Asp Phe His Tyr Val Thr Gly Met Thr Thr Asp Asn Val Lys Cys
              2100                   2105                   2110
Pro Cys Gln Val Pro Ala Pro Glu Phe Phe Ser Glu Val Asp Gly Val
              2115                   2120                   2125
Arg Leu His Arg Tyr Ala Pro Ala Cys Arg Pro Leu Leu Arg Glu Glu
              2130                   2135                   2140
Val Thr Phe Gln Val Gly Leu Asn Gln Tyr Leu Val Gly Ser Gln Leu
2145                   2150                   2155                   2160
Pro Cys Glu Pro Glu Pro Asp Val Ala Val Leu Thr Ser Met Leu Thr
              2165                   2170                   2175
Asp Pro Ser His Ile Thr Ala Glu Thr Ala Lys Arg Arg Leu Ala Arg
              2180                   2185                   2190
Gly Ser Pro Pro Ser Leu Ala Ser Ser Ser Ala Ser Gln Leu Ser Ala
              2195                   2200                   2205
Pro Ser Leu Lys Ala Thr Cys Thr Thr His His Val Ser Pro Asp Ala
              2210                   2215                   2220
Asp Leu Ile Glu Ala Asn Leu Leu Trp Arg Gln Glu Met Gly Gly Asn
2225                   2230                   2235                   2240
Ile Thr Arg Val Glu Ser Glu Asn Lys Val Val Val Leu Asp Ser Phe
              2245                   2250                   2255
Asp Pro Leu Arg Ala Glu Glu Asp Glu Arg Glu Val Ser Val Pro Ala
              2260                   2265                   2270
Glu Ile Leu Arg Lys Ser Lys Lys Phe Pro Ala Ala Met Pro Ile Trp
              2275                   2280                   2285
Ala Arg Pro Asp Tyr Asn Pro Pro Leu Leu Glu Ser Trp Lys Asp Pro
              2290                   2295                   2300
Asp Tyr Val Pro Pro Val Val His Gly Cys Pro Leu Pro Pro Ile Lys
2305                   2310                   2315                   2320
Ala Pro Pro Ile Pro Pro Pro Arg Arg Lys Arg Thr Val Val Leu Thr
              2325                   2330                   2335
Glu Ser Ser Val Ser Ser Ala Leu Ala Glu Leu Ala Thr Lys Thr Phe
              2340                   2345                   2350
```

```
Gly Ser Ser Glu Ser Ser Ala Val Asp Ser Gly Thr Ala Thr Ala Leu
        2355                2360                2365
Pro Asp Gln Ala Ser Asp Asp Gly Asp Lys Gly Ser Asp Val Glu Ser
    2370                2375                2380
Tyr Ser Ser Met Pro Pro Leu Glu Gly Glu Pro Gly Asp Pro Asp Leu
2385                2390                2395                2400
Ser Asp Gly Ser Trp Ser Thr Val Ser Glu Glu Ala Ser Glu Asp Val
                2405                2410                2415
Val Cys Cys Ser Met Ser Tyr Thr Trp Thr Gly Ala Leu Ile Thr Pro
            2420                2425                2430
Cys Ala Ala Glu Glu Ser Lys Leu Pro Ile Asn Ala Leu Ser Asn Ser
        2435                2440                2445
Leu Leu Arg His His Asn Met Val Tyr Ala Thr Thr Ser Arg Ser Ala
    2450                2455                2460
Gly Leu Arg Gln Lys Lys Val Thr Phe Asp Arg Leu Gln Val Leu Asp
2465                2470                2475                2480
Asp His Tyr Arg Asp Val Leu Lys Glu Met Lys Ala Lys Ala Ser Thr
                2485                2490                2495
Val Lys Ala Lys Leu Leu Ser Val Glu Glu Ala Cys Lys Leu Thr Pro
            2500                2505                2510
Pro His Ser Ala Lys Ser Lys Phe Gly Tyr Gly Ala Lys Asp Val Arg
        2515                2520                2525
Asn Leu Ser Ser Lys Ala Val Asn His Ile His Ser Val Trp Lys Asp
    2530                2535                2540
Leu Leu Glu Asp Thr Val Thr Pro Ile Asp Thr Thr Ile Met Ala Lys
2545                2550                2555                2560
Asn Glu Val Phe Cys Val Gln Pro Glu Lys Gly Gly Arg Lys Pro Ala
                2565                2570                2575
Arg Leu Ile Val Phe Pro Asp Leu Gly Val Arg Val Cys Glu Lys Met
            2580                2585                2590
Ala Leu Tyr Asp Val Val Ser Thr Leu Pro Gln Val Val Met Gly Ser
        2595                2600                2605
Ser Tyr Gly Phe Gln Tyr Ser Pro Gly Gln Arg Val Glu Phe Leu Val
    2610                2615                2620
Asn Thr Trp Lys Ser Lys Lys Asn Pro Met Gly Phe Ser Tyr Asp Thr
2625                2630                2635                2640
Arg Cys Phe Asp Ser Thr Val Thr Glu Asn Asp Ile Arg Val Glu Glu
                2645                2650                2655
Ser Ile Tyr Gln Cys Cys Asp Leu Ala Pro Glu Ala Arg Gln Ala Ile
            2660                2665                2670
Lys Ser Leu Thr Glu Arg Leu Tyr Ile Gly Gly Pro Leu Thr Asn Ser
        2675                2680                2685
Lys Gly Gln Asn Cys Gly Tyr Arg Arg Cys Arg Ala Ser Gly Val Leu
    2690                2695                2700
Thr Thr Ser Cys Gly Asn Thr Leu Thr Cys Tyr Leu Lys Ala Ser Ala
2705                2710                2715                2720
Ala Cys Arg Ala Ala Lys Leu Gln Asp Cys Thr Met Leu Val Asn Gly
                2725                2730                2735
Asp Asp Leu Val Val Ile Cys Glu Ser Ala Gly Thr Gln Glu Asp Ala
            2740                2745                2750
Ala Ser Leu Arg Val Phe Thr Glu Ala Met Thr Arg Tyr Ser Ala Pro
        2755                2760                2765
Pro Gly Asp Pro Pro Gln Pro Glu Tyr Asp Leu Glu Leu Ile Thr Ser
    2770                2775                2780
```

| | | | | | | | | | | | | | |
|---|---|---|---|---|---|---|---|---|---|---|---|---|---|
|Cys|Ser|Ser|Asn|Val|Ser|Val|Ala|His|Asp|Ala|Ser|Gly|Lys Arg Val|
|2785| | | |2790| | | |2795| | | |2800| |

Tyr Tyr Leu Thr Arg Asp Pro Thr Thr Pro Leu Ala Arg Ala Ala Trp
            2805                 2810             2815

Glu Thr Ala Arg His Thr Pro Val Asn Ser Trp Leu Gly Asn Ile Ile
          2820             2825               2830

Met Tyr Ala Pro Thr Leu Trp Ala Arg Met Ile Leu Met Thr His Phe
        2835             2840              2845

Phe Ser Ile Leu Leu Ala Gln Glu Gln Leu Glu Lys Ala Leu Asp Cys
    2850               2855              2860

Gln Ile Tyr Gly Ala Cys Tyr Ser Ile Glu Pro Leu Asp Leu Pro Gln
2865               2870             2875              2880

Ile Ile Glu Arg Leu His Gly Leu Ser Ala Phe Ser Leu His Ser Tyr
            2885             2890              2895

Ser Pro Gly Glu Ile Asn Arg Val Ala Ser Cys Leu Arg Lys Leu Gly
        2900             2905             2910

Val Pro Pro Leu Arg Val Trp Arg His Arg Ala Arg Ser Val Arg Ala
            2915             2920             2925

Arg Leu Leu Ser Gln Gly Gly Arg Ala Ala Thr Cys Gly Lys Tyr Leu
    2930               2935              2940

Phe Asn Trp Ala Val Lys Thr Lys Leu Lys Leu Thr Pro Ile Pro Ala
2945               2950             2955              2960

Ala Ser Arg Leu Asp Leu Ser Gly Trp Phe Val Ala Gly Tyr Ser Gly
            2965             2970              2975

Gly Asp Ile Tyr His Ser Leu Ser Arg Ala Arg Pro Arg Trp Phe Met
        2980             2985             2990

Leu Cys Leu Leu Leu Leu Ser Val Gly Val Gly Ile Tyr Leu Leu Pro
            2995             3000              3005

Asn Arg
3010

( 2 ) INFORMATION FOR SEQ ID NO:3:

( i ) SEQUENCE CHARACTERISTICS:
        ( A ) LENGTH: 1499 base pairs
        ( B ) TYPE: nucleic acid
        ( C ) STRANDEDNESS: single
        ( D ) TOPOLOGY: linear ( i i ) MOLECULE TYPE: cDNA from genomic RNA ( i x ) FEATURE:
        ( A ) NAME/KEY: CDS
        ( B ) LOCATION: 333..1499

( i x ) FEATURE:
        ( A ) NAME/KEY: misc_feature
        ( B ) LOCATION: 1..1499
        ( D ) OTHER INFORMATION: /note= "sequence = 1 - 1499 of SEQ
            ID NO: 1"

( x i ) SEQUENCE DESCRIPTION: SEQ ID NO:3:

| | | | | | |
|---|---|---|---|---|---|
|CGATTGGGGG|CGACACTCCA|CCATAGATCA|CTCCCCTGTG|AGGAACTACT|GTCTTCACGC|60|
|AGAAAGCGTC|TAGCCATGGC|GTTAGTATGA|GTGTCGTGCA|GCCTCCAGGA|CCCCCCCTCC|120|
|CGGGAGAGCC|ATAGTGGTCT|GCGGAACCGG|TGAGTACACC|GGAATTGCCA|GGACGACCGG|180|
|GTCCTTTCTT|GGATCAACCC|GCTCAATGCC|TGGAGATTTG|GGCGTGCCCC|CGCGAGACTG|240|
|CTAGCCGAGT|AGTGTTGGGT|CGCGAAAGGC|CTTGTGGTAC|TGCCTGATAG|GGTGCTTGCG|300|
|AGTGCCCCGG|GAGGTCTCGT|AGACCGTGCA|CC ATG AGC|ACG AAT CCT|AAA CCT|353|

|  |  |  |  |  |  |  |  |  |  |  |  |  |  |  | Met | Ser | Thr | Asn | Pro | Lys | Pro |  |
|---|---|---|---|---|---|---|---|---|---|---|---|---|---|---|---|---|---|---|---|---|---|---|
|  |  |  |  |  |  |  |  |  |  |  |  |  |  |  | 1 |  |  |  | 5 |  |  |  |

```
CAA AGA AAA ACC AAA CGT AAC ACC AAC CGC CGC CCA CAG GAC GTC AAG        401
Gln Arg Lys Thr Lys Arg Asn Thr Asn Arg Arg Pro Gln Asp Val Lys
         10              15              20

TTC CCG GGC GGT GGT CAG ATC GTT GGT GGA GTT TAC CTG TTG CCG CGC        449
Phe Pro Gly Gly Gly Gln Ile Val Gly Gly Val Tyr Leu Leu Pro Arg
     25              30              35

AGG GGC CCC AGG TTG GGT GTG CGC GCG CCC AGG AAG ACT TCC GAG CGG        497
Arg Gly Pro Arg Leu Gly Val Arg Ala Pro Arg Lys Thr Ser Glu Arg
 40              45              50              55

TCG CAA CCT CGT GGA AGG CGA CAA CCT ATC CCC AAG GCT CGC CGG CCC        545
Ser Gln Pro Arg Gly Arg Arg Gln Pro Ile Pro Lys Ala Arg Arg Pro
             60              65              70

GAG GGC AGG ACC TGG GCT CAG CCC GGG TAC CCT TGG CCT CTC TAT GGC        593
Glu Gly Arg Thr Trp Ala Gln Pro Gly Tyr Pro Trp Pro Leu Tyr Gly
             75              80              85

AAT GAG GGC TTA GGG TGG GCA GGA TGG CTC CTG TCA CCC CGC GGC TCC        641
Asn Glu Gly Leu Gly Trp Ala Gly Trp Leu Leu Ser Pro Arg Gly Ser
         90              95             100

CGG CCT AGT TGG GGC CCC ACG GAC CCC CGG CGT AGG TCG CGT AAT TTG        689
Arg Pro Ser Trp Gly Pro Thr Asp Pro Arg Arg Arg Ser Arg Asn Leu
    105             110             115

GGT AAG GTC ATC GAT ACC CTC ACA TGC GGC TTC GCC GAT CTC ATG GGG        737
Gly Lys Val Ile Asp Thr Leu Thr Cys Gly Phe Ala Asp Leu Met Gly
120             125             130             135

TAC ATT CCG CTC GTC GGC GCC CCC CTG GGG GGC GCT GCC AGG GCC CTG        785
Tyr Ile Pro Leu Val Gly Ala Pro Leu Gly Gly Ala Ala Arg Ala Leu
            140             145             150

GCA CAT GGT GTC CGG GTT CTG GAG GAC GGC GTG AAC TAT GCA ACA GGG        833
Ala His Gly Val Arg Val Leu Glu Asp Gly Val Asn Tyr Ala Thr Gly
            155             160             165

AAT CTG CCC GGT TGC TCT TTT TCT ATC TTC CTC TTG GCT CTG CTG TCC        881
Asn Leu Pro Gly Cys Ser Phe Ser Ile Phe Leu Leu Ala Leu Leu Ser
        170             175             180

TGC CTG ACC ACC CCA GCT TCC GCT TAC GAA GTG CAC AAC GTG TCC GGG        929
Cys Leu Thr Thr Pro Ala Ser Ala Tyr Glu Val His Asn Val Ser Gly
        185             190             195

ATA TAT CAT GTC ACG AAC GAC TGC TCC AAC GCA AGC ATT GTG TAT GAG        977
Ile Tyr His Val Thr Asn Asp Cys Ser Asn Ala Ser Ile Val Tyr Glu
200             205             210             215

GCA GCG GAC TTG ATC ATG CAT ACT CCT GGG TGC GTG CCC TGC GTT CGG       1025
Ala Ala Asp Leu Ile Met His Thr Pro Gly Cys Val Pro Cys Val Arg
            220             225             230

GAA GGC AAC TCC TCC CGC TGC TGG GTA GCG CTC ACT CCC ACG CTC GCA       1073
Glu Gly Asn Ser Ser Arg Cys Trp Val Ala Leu Thr Pro Thr Leu Ala
        235             240             245

GCC AGG AAC GTC ACC ATC CCC ACC ACG ACG ATA CGA CGC CAC GTC GAT       1121
Ala Arg Asn Val Thr Ile Pro Thr Thr Thr Ile Arg Arg His Val Asp
        250             255             260

CTG CTC GTT GGG GCG GCT GCT TTC TGT TCC GCT ATG TAC GTG GGG GAC       1169
Leu Leu Val Gly Ala Ala Ala Phe Cys Ser Ala Met Tyr Val Gly Asp
    265             270             275

CTC TGC GGA TCT GTT TTC CTC GTC TCT CAG CTG TTC ACC TTC TCG CCT       1217
Leu Cys Gly Ser Val Phe Leu Val Ser Gln Leu Phe Thr Phe Ser Pro
280             285             290             295

CGC CGG CAT GTG ACA TTA CAG GAC TGT AAC TGC TCA ATT TAT CCC GGC       1265
Arg Arg His Val Thr Leu Gln Asp Cys Asn Cys Ser Ile Tyr Pro Gly
            300             305             310

CAT GTG TCG GGT CAC CGT ATG GCT TGG GAC ATG ATG ATG AAC TGG TCG       1313
```

|  |  |  |  |  |  |  |  |  |  |  |  |  |  |  |
|---|---|---|---|---|---|---|---|---|---|---|---|---|---|---|
| His | Val | Ser | Gly<br>315 | His | Arg | Met | Ala | Trp<br>320 | Asp | Met | Met | Met<br>325 | Asn | Trp | Ser |

```
CCC  ACA  ACA  GCC  CTA  GTG  GTG  TCG  CAG  TTA  CTC  CGG  ATC  CCA  CAA  GCC      1361
Pro  Thr  Thr  Ala  Leu  Val  Val  Ser  Gln  Leu  Leu  Arg  Ile  Pro  Gln  Ala
          330                     335                     340

GTC  GTG  GAC  ATG  GTG  GCG  GGG  GCC  CAC  TGG  GGA  GTC  CTG  GCG  GGC  CTT      1409
Val  Val  Asp  Met  Val  Ala  Gly  Ala  His  Trp  Gly  Val  Leu  Ala  Gly  Leu
          345                     350                     355

GCC  TAC  TAT  TCC  ATG  GCG  GGG  AAC  TGG  GCT  AAG  GTT  CTG  ATT  GTG  ATG      1457
Ala  Tyr  Tyr  Ser  Met  Ala  Gly  Asn  Trp  Ala  Lys  Val  Leu  Ile  Val  Met
360            365                     370                          375

CTA  CTT  TTT  GCT  GGC  GTT  GAC  GGG  GAT  ACC  CAC  GTG  ACA  GGG                1499
Leu  Leu  Phe  Ala  Gly  Val  Asp  Gly  Asp  Thr  His  Val  Thr  Gly
               380                     385
```

( 2 ) INFORMATION FOR SEQ ID NO:4:

( i ) SEQUENCE CHARACTERISTICS:
        ( A ) LENGTH: 389 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ser  Thr  Asn  Pro  Lys  Pro  Gln  Arg  Lys  Thr  Lys  Arg  Asn  Thr  Asn
1               5                    10                       15

Arg  Arg  Pro  Gln  Asp  Val  Lys  Phe  Pro  Gly  Gly  Gly  Gln  Ile  Val  Gly
          20                     25                      30

Gly  Val  Tyr  Leu  Leu  Pro  Arg  Arg  Gly  Pro  Arg  Leu  Gly  Val  Arg  Ala
               35                  40                       45

Pro  Arg  Lys  Thr  Ser  Glu  Arg  Ser  Gln  Pro  Arg  Gly  Arg  Arg  Gln  Pro
     50                     55                      60

Ile  Pro  Lys  Ala  Arg  Arg  Pro  Glu  Gly  Arg  Thr  Trp  Ala  Gln  Pro  Gly
65                       70                     75                            80

Tyr  Pro  Trp  Pro  Leu  Tyr  Gly  Asn  Glu  Gly  Leu  Gly  Trp  Ala  Gly  Trp
                    85                      90                          95

Leu  Leu  Ser  Pro  Arg  Gly  Ser  Arg  Pro  Ser  Trp  Gly  Pro  Thr  Asp  Pro
               100                     105                      110

Arg  Arg  Arg  Ser  Arg  Asn  Leu  Gly  Lys  Val  Ile  Asp  Thr  Leu  Thr  Cys
          115                     120                      125

Gly  Phe  Ala  Asp  Leu  Met  Gly  Tyr  Ile  Pro  Leu  Val  Gly  Ala  Pro  Leu
     130                     135                      140

Gly  Gly  Ala  Ala  Arg  Ala  Leu  Ala  His  Gly  Val  Arg  Val  Leu  Glu  Asp
145                      150                     155                           160

Gly  Val  Asn  Tyr  Ala  Thr  Gly  Asn  Leu  Pro  Gly  Cys  Ser  Phe  Ser  Ile
                    165                     170                      175

Phe  Leu  Leu  Ala  Leu  Leu  Ser  Cys  Leu  Thr  Thr  Pro  Ala  Ser  Ala  Tyr
               180                     185                      190

Glu  Val  His  Asn  Val  Ser  Gly  Ile  Tyr  His  Val  Thr  Asn  Asp  Cys  Ser
          195                     200                      205

Asn  Ala  Ser  Ile  Val  Tyr  Glu  Ala  Ala  Asp  Leu  Ile  Met  His  Thr  Pro
     210                     215                      220

Gly  Cys  Val  Pro  Cys  Val  Arg  Glu  Gly  Asn  Ser  Ser  Arg  Cys  Trp  Val
225                      230                     235                           240

Ala  Leu  Thr  Pro  Thr  Leu  Ala  Ala  Arg  Asn  Val  Thr  Ile  Pro  Thr  Thr
               245                     250                      255

Thr  Ile  Arg  Arg  His  Val  Asp  Leu  Leu  Val  Gly  Ala  Ala  Ala  Phe  Cys
```

|  | 260 |  |  |  |  | 265 |  |  |  |  | 270 |  |  |
|---|---|---|---|---|---|---|---|---|---|---|---|---|---|
| Ser | Ala | Met<br>275 | Tyr | Val | Gly | Asp | Leu<br>280 | Cys | Gly | Ser | Val | Phe<br>285 | Leu | Val | Ser |

Gln Leu Phe Thr Phe Ser Pro Arg Arg His Val Thr Leu Gln Asp Cys
    290                     295                 300

Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Ala Gly Asn Trp
        355                 360                 365

Ala Lys Val Leu Ile Val Met Leu Leu Phe Ala Gly Val Asp Gly Asp
    370                 375                 380

Thr His Val Thr Gly
385

(2) INFORMATION FOR SEQ ID NO:5:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: cDNA from genomic RNA (ix) FEATURE:
        (A) NAME/KEY: misc_feature
        (B) LOCATION: 1..90
        (D) OTHER INFORMATION: /note="sequence = 333 - 422 of
            SEQ ID NO: 1"

(ix) FEATURE:
        (A) NAME/KEY: CDS
        (B) LOCATION: 1..90

(xi) SEQUENCE DESCRIPTION: SEQ ID NO:5:

ATG AGC ACG AAT CCT AAA CCT CAA AGA AAA ACC AAA CGT AAC ACC AAC    48
Met Ser Thr Asn Pro Lys Pro Gln Arg Lys Thr Lys Arg Asn Thr Asn
1                 5                   10                  15

CGC CGC CCA CAG GAC GTC AAG TTC CCG GGC GGT GGT CAG ATC    90
Arg Arg Pro Gln Asp Val Lys Phe Pro Gly Gly Gly Gln Ile
            20                  25                  30

(2) INFORMATION FOR SEQ ID NO:6:

(i) SEQUENCE CHARACTERISTICS:
        (A) LENGTH: 30 amino acids
        (B) TYPE: amino acid
        (D) TOPOLOGY: linear (ii) MOLECULE TYPE: protein (xi) SEQUENCE DESCRIPTION: SEQ ID NO:6:

Met Ser Thr Asn Pro Lys Pro Gln Arg Lys Thr Lys Arg Asn Thr Asn
1                 5                   10                  15

Arg Arg Pro Gln Asp Val Lys Phe Pro Gly Gly Gly Gln Ile
            20                  25                  30

(2) INFORMATION FOR SEQ ID NO:7:

(i) SEQUENCE CHARACTERISTICS:
        (A) LENGTH: 345 base pairs (B) TYPE: nucleic acid
(C) STRANDEDNESS: single
(D) TOPOLOGY: linear (ii) MOLECULE TYPE: cDNA from genomic RNA (ix) FEATURE:
(A) NAME/KEY: misc_feature
(B) LOCATION: 1..345
(D) OTHER INFORMATION: /note: "sequence = 333 - 677 of SEQ ID NO: 1"

(ix) FEATURE:
(A) NAME/KEY: CDS
(B) LOCATION: 1..345

(xi) SEQUENCE DESCRIPTION: SEQ ID NO:7:

| ATG | AGC | ACG | AAT | CCT | AAA | CCT | CAA | AGA | AAA | ACC | AAA | CGT | AAC | ACC | AAC | 48 |
| Met | Ser | Thr | Asn | Pro | Lys | Pro | Gln | Arg | Lys | Thr | Lys | Arg | Asn | Thr | Asn | |
| 1 | | | | 5 | | | | | 10 | | | | | 15 | | |

| CGC | CGC | CCA | CAG | GAC | GTC | AAG | TTC | CCG | GGC | GGT | GGT | CAG | ATC | GTT | GGT | 96 |
| Arg | Arg | Pro | Gln | Asp | Val | Lys | Phe | Pro | Gly | Gly | Gly | Gln | Ile | Val | Gly | |
| | | | 20 | | | | | 25 | | | | | 30 | | | |

| GGA | GTT | TAC | CTG | TTG | CCG | CGC | AGG | GGC | CCC | AGG | TTG | GGT | GTG | CGC | GCG | 144 |
| Gly | Val | Tyr | Leu | Leu | Pro | Arg | Arg | Gly | Pro | Arg | Leu | Gly | Val | Arg | Ala | |
| | | 35 | | | | | 40 | | | | | 45 | | | | |

| CCC | AGG | AAG | ACT | TCC | GAG | CGG | TCG | CAA | CCT | CGT | GGA | AGG | CGA | CAA | CCT | 192 |
| Pro | Arg | Lys | Thr | Ser | Glu | Arg | Ser | Gln | Pro | Arg | Gly | Arg | Arg | Gln | Pro | |
| | 50 | | | | | 55 | | | | | 60 | | | | | |

| ATC | CCC | AAG | GCT | CGC | CGG | CCC | GAG | GGC | AGG | ACC | TGG | GCT | CAG | CCC | GGG | 240 |
| Ile | Pro | Lys | Ala | Arg | Arg | Pro | Glu | Gly | Arg | Thr | Trp | Ala | Gln | Pro | Gly | |
| 65 | | | | | 70 | | | | | 75 | | | | | 80 | |

| TAC | CCT | TGG | CCT | CTC | TAT | GGC | AAT | GAG | GGC | TTA | GGG | TGG | GCA | GGA | TGG | 288 |
| Tyr | Pro | Trp | Pro | Leu | Tyr | Gly | Asn | Glu | Gly | Leu | Gly | Trp | Ala | Gly | Trp | |
| | | | | 85 | | | | | 90 | | | | | 95 | | |

| CTC | CTG | TCA | CCC | CGC | GGC | TCC | CGG | CCT | AGT | TGG | GGC | CCC | ACG | GAC | CCC | 336 |
| Leu | Leu | Ser | Pro | Arg | Gly | Ser | Arg | Pro | Ser | Trp | Gly | Pro | Thr | Asp | Pro | |
| | | | 100 | | | | | 105 | | | | | 110 | | | |

| CGG | CGT | AGG | | | | | | | | | | | | | | 345 |
| Arg | Arg | Arg | | | | | | | | | | | | | | |
| | | 115 | | | | | | | | | | | | | | |

(2) INFORMATION FOR SEQ ID NO:8:

(i) SEQUENCE CHARACTERISTICS:
(A) LENGTH: 115 amino acids
(B) TYPE: amino acid
(D) TOPOLOGY: linear (ii) MOLECULE TYPE: protein (xi) SEQUENCE DESCRIPTION: SEQ ID NO:8:

| Met | Ser | Thr | Asn | Pro | Lys | Pro | Gln | Arg | Lys | Thr | Lys | Arg | Asn | Thr | Asn |
| 1 | | | | 5 | | | | | 10 | | | | | 15 | |

| Arg | Arg | Pro | Gln | Asp | Val | Lys | Phe | Pro | Gly | Gly | Gly | Gln | Ile | Val | Gly |
| | | | 20 | | | | | 25 | | | | | 30 | | |

| Gly | Val | Tyr | Leu | Leu | Pro | Arg | Arg | Gly | Pro | Arg | Leu | Gly | Val | Arg | Ala |
| | | 35 | | | | | 40 | | | | | 45 | | | |

| Pro | Arg | Lys | Thr | Ser | Glu | Arg | Ser | Gln | Pro | Arg | Gly | Arg | Arg | Gln | Pro |
| | 50 | | | | | 55 | | | | | 60 | | | | |

| Ile | Pro | Lys | Ala | Arg | Arg | Pro | Glu | Gly | Arg | Thr | Trp | Ala | Gln | Pro | Gly |
| 65 | | | | | 70 | | | | | 75 | | | | | 80 |

| Tyr | Pro | Trp | Pro | Leu | Tyr | Gly | Asn | Glu | Gly | Leu | Gly | Trp | Ala | Gly | Trp |
| | | | | 85 | | | | | 90 | | | | | 95 | |

```
Leu Leu Ser Pro Arg Gly Ser Arg Pro Ser Trp Gly Pro Thr Asp Pro
        100                 105                 110

Arg Arg Arg
    115
```

( 2 ) INFORMATION FOR SEQ ID NO:9:

( i ) SEQUENCE CHARACTERISTICS:
      ( A ) LENGTH: 1167 base pairs
      ( B ) TYPE: nucleic acid
      ( C ) STRANDEDNESS: single
      ( D ) TOPOLOGY: linear ( i i ) MOLECULE TYPE: cDNA from genomic RNA ( i x ) FEATURE:
      ( A ) NAME/KEY: misc_feature
      ( B ) LOCATION: 1..1167
      ( D ) OTHER INFORMATION: /note: "sequence = 333 - 1499 of
            SEQ ID NO: 1"

( i x ) FEATURE:
      ( A ) NAME/KEY: CDS
      ( B ) LOCATION: 1..1167

( x i ) SEQUENCE DESCRIPTION: SEQ ID NO:9:

```
ATG AGC ACG AAT CCT AAA CCT CAA AGA AAA ACC AAA CGT AAC ACC AAC    48
Met Ser Thr Asn Pro Lys Pro Gln Arg Lys Thr Lys Arg Asn Thr Asn
 1               5                  10                  15

CGC CGC CCA CAG GAC GTC AAG TTC CCG GGC GGT GGT CAG ATC GTT GGT    96
Arg Arg Pro Gln Asp Val Lys Phe Pro Gly Gly Gly Gln Ile Val Gly
             20                  25                  30

GGA GTT TAC CTG TTG CCG CGC AGG GGC CCC AGG TTG GGT GTG CGC GCG   144
Gly Val Tyr Leu Leu Pro Arg Arg Gly Pro Arg Leu Gly Val Arg Ala
         35                  40                  45

CCC AGG AAG ACT TCC GAG CGG TCG CAA CCT CGT GGA AGG CGA CAA CCT   192
Pro Arg Lys Thr Ser Glu Arg Ser Gln Pro Arg Gly Arg Arg Gln Pro
     50                  55                  60

ATC CCC AAG GCT CGC CGG CCC GAG GGC AGG ACC TGG GCT CAG CCC GGG   240
Ile Pro Lys Ala Arg Arg Pro Glu Gly Arg Thr Trp Ala Gln Pro Gly
 65                  70                  75                  80

TAC CCT TGG CCT CTC TAT GGC AAT GAG GGC TTA GGG TGG GCA GGA TGG   288
Tyr Pro Trp Pro Leu Tyr Gly Asn Glu Gly Leu Gly Trp Ala Gly Trp
                 85                  90                  95

CTC CTG TCA CCC CGC GGC TCC CGG CCT AGT TGG GGC CCC ACG GAC CCC   336
Leu Leu Ser Pro Arg Gly Ser Arg Pro Ser Trp Gly Pro Thr Asp Pro
            100                 105                 110

CGG CGT AGG TCG CGT AAT TTG GGT AAG GTC ATC GAT ACC CTC ACA TGC   384
Arg Arg Arg Ser Arg Asn Leu Gly Lys Val Ile Asp Thr Leu Thr Cys
        115                 120                 125

GGC TTC GCC GAT CTC ATG GGG TAC ATT CCG CTC GTC GGC GCC CCC CTG   432
Gly Phe Ala Asp Leu Met Gly Tyr Ile Pro Leu Val Gly Ala Pro Leu
    130                 135                 140

GGG GGC GCT GCC AGG GCC CTG GCA CAT GGT GTC CGG GTT CTG GAG GAC   480
Gly Gly Ala Ala Arg Ala Leu Ala His Gly Val Arg Val Leu Glu Asp
145                 150                 155                 160

GGC GTG AAC TAT GCA ACA GGG AAT CTG CCC GGT TGC TCT TTT TCT ATC   528
Gly Val Asn Tyr Ala Thr Gly Asn Leu Pro Gly Cys Ser Phe Ser Ile
                165                 170                 175

TTC CTC TTG GCT CTG CTG TCC TGC CTG ACC ACC CCA GCT TCC GCT TAC   576
Phe Leu Leu Ala Leu Leu Ser Cys Leu Thr Thr Pro Ala Ser Ala Tyr
            180                 185                 190

GAA GTG CAC AAC GTG TCC GGG ATA TAT CAT GTC ACG AAC GAC TGC TCC   624
Glu Val His Asn Val Ser Gly Ile Tyr His Val Thr Asn Asp Cys Ser
        195                 200                 205
```

```
AAC  GCA  AGC  ATT  GTG  TAT  GAG  GCA  GCG  GAC  TTG  ATC  ATG  CAT  ACT  CCT         672
Asn  Ala  Ser  Ile  Val  Tyr  Glu  Ala  Ala  Asp  Leu  Ile  Met  His  Thr  Pro
210                           215                           220

GGG  TGC  GTG  CCC  TGC  GTT  CGG  GAA  GGC  AAC  TCC  TCC  CGC  TGC  TGG  GTA         720
Gly  Cys  Val  Pro  Cys  Val  Arg  Glu  Gly  Asn  Ser  Ser  Arg  Cys  Trp  Val
225                           230                           235                 240

GCG  CTC  ACT  CCC  ACG  CTC  GCA  GCC  AGG  AAC  GTC  ACC  ATC  CCC  ACC  ACG         768
Ala  Leu  Thr  Pro  Thr  Leu  Ala  Ala  Arg  Asn  Val  Thr  Ile  Pro  Thr  Thr
                    245                           250                      255

ACG  ATA  CGA  CGC  CAC  GTC  GAT  CTG  CTC  GTT  GGG  GCG  GCT  GCT  TTC  TGT         816
Thr  Ile  Arg  Arg  His  Val  Asp  Leu  Leu  Val  Gly  Ala  Ala  Ala  Phe  Cys
               260                           265                      270

TCC  GCT  ATG  TAC  GTG  GGG  GAC  CTC  TGC  GGA  TCT  GTT  TTC  CTC  GTC  TCT         864
Ser  Ala  Met  Tyr  Val  Gly  Asp  Leu  Cys  Gly  Ser  Val  Phe  Leu  Val  Ser
          275                           280                      285

CAG  CTG  TTC  ACC  TTC  TCG  CCT  CGC  CGG  CAT  GTG  ACA  TTA  CAG  GAC  TGT         912
Gln  Leu  Phe  Thr  Phe  Ser  Pro  Arg  Arg  His  Val  Thr  Leu  Gln  Asp  Cys
290                           295                           300

AAC  TGC  TCA  ATT  TAT  CCC  GGC  CAT  GTG  TCG  GGT  CAC  CGT  ATG  GCT  TGG         960
Asn  Cys  Ser  Ile  Tyr  Pro  Gly  His  Val  Ser  Gly  His  Arg  Met  Ala  Trp
305                           310                           315                 320

GAC  ATG  ATG  ATG  AAC  TGG  TCG  CCC  ACA  ACA  GCC  CTA  GTG  GTG  TCG  CAG        1008
Asp  Met  Met  Met  Asn  Trp  Ser  Pro  Thr  Thr  Ala  Leu  Val  Val  Ser  Gln
                    325                           330                      335

TTA  CTC  CGG  ATC  CCA  CAA  GCC  GTC  GTG  GAC  ATG  GTG  GCG  GGG  GCC  CAC        1056
Leu  Leu  Arg  Ile  Pro  Gln  Ala  Val  Val  Asp  Met  Val  Ala  Gly  Ala  His
               340                           345                      350

TGG  GGA  GTC  CTG  GCG  GGC  CTT  GCC  TAC  TAT  TCC  ATG  GCG  GGG  AAC  TGG        1104
Trp  Gly  Val  Leu  Ala  Gly  Leu  Ala  Tyr  Tyr  Ser  Met  Ala  Gly  Asn  Trp
          355                           360                      365

GCT  AAG  GTT  CTG  ATT  GTG  ATG  CTA  CTT  TTT  GCT  GGC  GTT  GAC  GGG  GAT        1152
Ala  Lys  Val  Leu  Ile  Val  Met  Leu  Leu  Phe  Ala  Gly  Val  Asp  Gly  Asp
370                           375                           380

ACC  CAC  GTG  ACA  GGG                                                              1167
Thr  His  Val  Thr  Gly
385
```

( 2 ) INFORMATION FOR SEQ ID NO:10:

( i ) SEQUENCE CHARACTERISTICS:
        ( A ) LENGTH: 389 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met  Ser  Thr  Asn  Pro  Lys  Pro  Gln  Arg  Lys  Thr  Lys  Arg  Asn  Thr  Asn
1                   5                        10                       15

Arg  Arg  Pro  Gln  Asp  Val  Lys  Phe  Pro  Gly  Gly  Gly  Gln  Ile  Val  Gly
               20                       25                       30

Gly  Val  Tyr  Leu  Leu  Pro  Arg  Arg  Gly  Pro  Arg  Leu  Gly  Val  Arg  Ala
          35                        40                       45

Pro  Arg  Lys  Thr  Ser  Glu  Arg  Ser  Gln  Pro  Arg  Gly  Arg  Arg  Gln  Pro
     50                       55                       60

Ile  Pro  Lys  Ala  Arg  Arg  Pro  Glu  Gly  Arg  Thr  Trp  Ala  Gln  Pro  Gly
65                       70                       75                       80

Tyr  Pro  Trp  Pro  Leu  Tyr  Gly  Asn  Glu  Gly  Leu  Gly  Trp  Ala  Gly  Trp
                    85                       90                       95

Leu  Leu  Ser  Pro  Arg  Gly  Ser  Arg  Pro  Ser  Trp  Gly  Pro  Thr  Asp  Pro
```

```
                    100                       105                          110
Arg  Arg  Arg  Ser  Arg  Asn  Leu  Gly  Lys  Val  Ile  Asp  Thr  Leu  Thr  Cys
          115                      120                      125

Gly  Phe  Ala  Asp  Leu  Met  Gly  Tyr  Ile  Pro  Leu  Val  Gly  Ala  Pro  Leu
     130                      135                 140

Gly  Gly  Ala  Ala  Arg  Ala  Leu  Ala  His  Gly  Val  Arg  Val  Leu  Glu  Asp
145                      150                      155                      160

Gly  Val  Asn  Tyr  Ala  Thr  Gly  Asn  Leu  Pro  Gly  Cys  Ser  Phe  Ser  Ile
               165                      170                      175

Phe  Leu  Leu  Ala  Leu  Leu  Ser  Cys  Leu  Thr  Thr  Pro  Ala  Ser  Ala  Tyr
               180                      185                      190

Glu  Val  His  Asn  Val  Ser  Gly  Ile  Tyr  His  Val  Thr  Asn  Asp  Cys  Ser
          195                      200                      205

Asn  Ala  Ser  Ile  Val  Tyr  Glu  Ala  Ala  Asp  Leu  Ile  Met  His  Thr  Pro
     210                      215                      220

Gly  Cys  Val  Pro  Cys  Val  Arg  Glu  Gly  Asn  Ser  Ser  Arg  Cys  Trp  Val
225                      230                      235                      240

Ala  Leu  Thr  Pro  Thr  Leu  Ala  Ala  Arg  Asn  Val  Thr  Ile  Pro  Thr  Thr
               245                      250                      255

Thr  Ile  Arg  Arg  His  Val  Asp  Leu  Leu  Val  Gly  Ala  Ala  Ala  Phe  Cys
               260                      265                      270

Ser  Ala  Met  Tyr  Val  Gly  Asp  Leu  Cys  Gly  Ser  Val  Phe  Leu  Val  Ser
          275                      280                      285

Gln  Leu  Phe  Thr  Phe  Ser  Pro  Arg  Arg  His  Val  Thr  Leu  Gln  Asp  Cys
     290                      295                      300

Asn  Cys  Ser  Ile  Tyr  Pro  Gly  His  Val  Ser  Gly  His  Arg  Met  Ala  Trp
305                      310                      315                      320

Asp  Met  Met  Met  Asn  Trp  Ser  Pro  Thr  Thr  Ala  Leu  Val  Val  Ser  Gln
               325                      330                      335

Leu  Leu  Arg  Ile  Pro  Gln  Ala  Val  Val  Asp  Met  Val  Ala  Gly  Ala  His
               340                      345                      350

Trp  Gly  Val  Leu  Ala  Gly  Leu  Ala  Tyr  Tyr  Ser  Met  Ala  Gly  Asn  Trp
          355                      360                      365

Ala  Lys  Val  Leu  Ile  Val  Met  Leu  Leu  Phe  Ala  Gly  Val  Asp  Gly  Asp
     370                      375                      380

Thr  His  Val  Thr  Gly
385
```

( 2 ) INFORMATION FOR SEQ ID NO:11:

( i ) SEQUENCE CHARACTERISTICS:
    ( A ) LENGTH: 6039 base pairs
    ( B ) TYPE: nucleic acid
    ( C ) STRANDEDNESS: single
    ( D ) TOPOLOGY: linear ( i i ) MOLECULE TYPE: cDNA from genomic RNA ( i x ) FEATURE:
    ( A ) NAME/KEY: misc_feature
    ( B ) LOCATION: 1..6039
    ( D ) OTHER INFORMATION: /note= "sequence = 333 - 6371 of
      SEQ ID NO: 1"

( i x ) FEATURE:
    ( A ) NAME/KEY: CDS
    ( B ) LOCATION: 1..6039

( x i ) SEQUENCE DESCRIPTION: SEQ ID NO:11:

ATG  AGC  ACG  AAT  CCT  AAA  CCT  CAA  AGA  AAA  ACC  AAA  CGT  AAC  ACC  AAC    48

|  |  |  |  |  |  |  |  |  |  |  |  |  |  |  |  |
|---|---|---|---|---|---|---|---|---|---|---|---|---|---|---|---|
| Met | Ser | Thr | Asn | Pro | Lys | Pro | Gln | Arg | Lys | Thr | Lys | Arg | Asn | Thr | Asn |
| 1 |  |  |  | 5 |  |  |  |  | 10 |  |  |  |  | 15 |  |

| CGC | CGC | CCA | CAG | GAC | GTC | AAG | TTC | CCG | GGC | GGT | GGT | CAG | ATC | GTT | GGT | 96 |
|---|---|---|---|---|---|---|---|---|---|---|---|---|---|---|---|---|
| Arg | Arg | Pro | Gln | Asp | Val | Lys | Phe | Pro | Gly | Gly | Gly | Gln | Ile | Val | Gly |  |
|  |  |  | 20 |  |  |  |  | 25 |  |  |  |  | 30 |  |  |  |

| GGA | GTT | TAC | CTG | TTG | CCG | CGC | AGG | GGC | CCC | AGG | TTG | GGT | GTG | CGC | GCG | 144 |
|---|---|---|---|---|---|---|---|---|---|---|---|---|---|---|---|---|
| Gly | Val | Tyr | Leu | Leu | Pro | Arg | Arg | Gly | Pro | Arg | Leu | Gly | Val | Arg | Ala |  |
|  |  | 35 |  |  |  |  | 40 |  |  |  |  | 45 |  |  |  |  |

| CCC | AGG | AAG | ACT | TCC | GAG | CGG | TCG | CAA | CCT | CGT | GGA | AGG | CGA | CAA | CCT | 192 |
|---|---|---|---|---|---|---|---|---|---|---|---|---|---|---|---|---|
| Pro | Arg | Lys | Thr | Ser | Glu | Arg | Ser | Gln | Pro | Arg | Gly | Arg | Arg | Gln | Pro |  |
|  | 50 |  |  |  | 55 |  |  |  |  | 60 |  |  |  |  |  |  |

| ATC | CCC | AAG | GCT | CGC | CGG | CCC | GAG | GGC | AGG | ACC | TGG | GCT | CAG | CCC | GGG | 240 |
|---|---|---|---|---|---|---|---|---|---|---|---|---|---|---|---|---|
| Ile | Pro | Lys | Ala | Arg | Arg | Pro | Glu | Gly | Arg | Thr | Trp | Ala | Gln | Pro | Gly |  |
| 65 |  |  |  | 70 |  |  |  |  | 75 |  |  |  |  |  | 80 |  |

| TAC | CCT | TGG | CCT | CTC | TAT | GGC | AAT | GAG | GGC | TTA | GGG | TGG | GCA | GGA | TGG | 288 |
|---|---|---|---|---|---|---|---|---|---|---|---|---|---|---|---|---|
| Tyr | Pro | Trp | Pro | Leu | Tyr | Gly | Asn | Glu | Gly | Leu | Gly | Trp | Ala | Gly | Trp |  |
|  |  |  |  | 85 |  |  |  |  | 90 |  |  |  |  | 95 |  |  |

| CTC | CTG | TCA | CCC | CGC | GGC | TCC | CGG | CCT | AGT | TGG | GGC | CCC | ACG | GAC | CCC | 336 |
|---|---|---|---|---|---|---|---|---|---|---|---|---|---|---|---|---|
| Leu | Leu | Ser | Pro | Arg | Gly | Ser | Arg | Pro | Ser | Trp | Gly | Pro | Thr | Asp | Pro |  |
|  |  |  | 100 |  |  |  |  | 105 |  |  |  |  | 110 |  |  |  |

| CGG | CGT | AGG | TCG | CGT | AAT | TTG | GGT | AAG | GTC | ATC | GAT | ACC | CTC | ACA | TGC | 384 |
|---|---|---|---|---|---|---|---|---|---|---|---|---|---|---|---|---|
| Arg | Arg | Arg | Ser | Arg | Asn | Leu | Gly | Lys | Val | Ile | Asp | Thr | Leu | Thr | Cys |  |
|  |  | 115 |  |  |  |  | 120 |  |  |  |  | 125 |  |  |  |  |

| GGC | TTC | GCC | GAT | CTC | ATG | GGG | TAC | ATT | CCG | CTC | GTC | GGC | GCC | CCC | CTG | 432 |
|---|---|---|---|---|---|---|---|---|---|---|---|---|---|---|---|---|
| Gly | Phe | Ala | Asp | Leu | Met | Gly | Tyr | Ile | Pro | Leu | Val | Gly | Ala | Pro | Leu |  |
|  |  | 130 |  |  |  | 135 |  |  |  |  | 140 |  |  |  |  |  |

| GGG | GGC | GCT | GCC | AGG | GCC | CTG | GCA | CAT | GGT | GTC | CGG | GTT | CTG | GAG | GAC | 480 |
|---|---|---|---|---|---|---|---|---|---|---|---|---|---|---|---|---|
| Gly | Gly | Ala | Ala | Arg | Ala | Leu | Ala | His | Gly | Val | Arg | Val | Leu | Glu | Asp |  |
| 145 |  |  |  |  | 150 |  |  |  |  | 155 |  |  |  |  | 160 |  |

| GGC | GTG | AAC | TAT | GCA | ACA | GGG | AAT | CTG | CCC | GGT | TGC | TCT | TTT | TCT | ATC | 528 |
|---|---|---|---|---|---|---|---|---|---|---|---|---|---|---|---|---|
| Gly | Val | Asn | Tyr | Ala | Thr | Gly | Asn | Leu | Pro | Gly | Cys | Ser | Phe | Ser | Ile |  |
|  |  |  |  | 165 |  |  |  |  | 170 |  |  |  |  | 175 |  |  |

| TTC | CTC | TTG | GCT | CTG | CTG | TCC | TGC | CTG | ACC | ACC | CCA | GCT | TCC | GCT | TAC | 576 |
|---|---|---|---|---|---|---|---|---|---|---|---|---|---|---|---|---|
| Phe | Leu | Leu | Ala | Leu | Leu | Ser | Cys | Leu | Thr | Thr | Pro | Ala | Ser | Ala | Tyr |  |
|  |  |  | 180 |  |  |  |  | 185 |  |  |  |  | 190 |  |  |  |

| GAA | GTG | CAC | AAC | GTG | TCC | GGG | ATA | TAT | CAT | GTC | ACG | AAC | GAC | TGC | TCC | 624 |
|---|---|---|---|---|---|---|---|---|---|---|---|---|---|---|---|---|
| Glu | Val | His | Asn | Val | Ser | Gly | Ile | Tyr | His | Val | Thr | Asn | Asp | Cys | Ser |  |
|  |  | 195 |  |  |  |  | 200 |  |  |  |  | 205 |  |  |  |  |

| AAC | GCA | AGC | ATT | GTG | TAT | GAG | GCA | GCG | GAC | TTG | ATC | ATG | CAT | ACT | CCT | 672 |
|---|---|---|---|---|---|---|---|---|---|---|---|---|---|---|---|---|
| Asn | Ala | Ser | Ile | Val | Tyr | Glu | Ala | Ala | Asp | Leu | Ile | Met | His | Thr | Pro |  |
| 210 |  |  |  |  | 215 |  |  |  |  | 220 |  |  |  |  |  |  |

| GGG | TGC | GTG | CCC | TGC | GTT | CGG | GAA | GGC | AAC | TCC | TCC | CGC | TGC | TGG | GTA | 720 |
|---|---|---|---|---|---|---|---|---|---|---|---|---|---|---|---|---|
| Gly | Cys | Val | Pro | Cys | Val | Arg | Glu | Gly | Asn | Ser | Ser | Arg | Cys | Trp | Val |  |
| 225 |  |  |  |  | 230 |  |  |  |  | 235 |  |  |  |  | 240 |  |

| GCG | CTC | ACT | CCC | ACG | CTC | GCA | GCC | AGG | AAC | GTC | ACC | ATC | CCC | ACC | ACG | 768 |
|---|---|---|---|---|---|---|---|---|---|---|---|---|---|---|---|---|
| Ala | Leu | Thr | Pro | Thr | Leu | Ala | Ala | Arg | Asn | Val | Thr | Ile | Pro | Thr | Thr |  |
|  |  |  | 245 |  |  |  |  | 250 |  |  |  |  | 255 |  |  |  |

| ACG | ATA | CGA | CGC | CAC | GTC | GAT | CTG | CTC | GTT | GGG | GCG | GCT | GCT | TTC | TGT | 816 |
|---|---|---|---|---|---|---|---|---|---|---|---|---|---|---|---|---|
| Thr | Ile | Arg | Arg | His | Val | Asp | Leu | Leu | Val | Gly | Ala | Ala | Ala | Phe | Cys |  |
|  |  |  | 260 |  |  |  |  | 265 |  |  |  |  | 270 |  |  |  |

| TCC | GCT | ATG | TAC | GTG | GGG | GAC | CTC | TGC | GGA | TCT | GTT | TTC | CTC | GTC | TCT | 864 |
|---|---|---|---|---|---|---|---|---|---|---|---|---|---|---|---|---|
| Ser | Ala | Met | Tyr | Val | Gly | Asp | Leu | Cys | Gly | Ser | Val | Phe | Leu | Val | Ser |  |
|  |  | 275 |  |  |  |  | 280 |  |  |  |  | 285 |  |  |  |  |

| CAG | CTG | TTC | ACC | TTC | TCG | CCT | CGC | CGG | CAT | GTG | ACA | TTA | CAG | GAC | TGT | 912 |
|---|---|---|---|---|---|---|---|---|---|---|---|---|---|---|---|---|
| Gln | Leu | Phe | Thr | Phe | Ser | Pro | Arg | Arg | His | Val | Thr | Leu | Gln | Asp | Cys |  |
|  | 290 |  |  |  |  | 295 |  |  |  |  | 300 |  |  |  |  |  |

| AAC | TGC | TCA | ATT | TAT | CCC | GGC | CAT | GTG | TCG | GGT | CAC | CGT | ATG | GCT | TGG | 960 |
|---|---|---|---|---|---|---|---|---|---|---|---|---|---|---|---|---|
| Asn | Cys | Ser | Ile | Tyr | Pro | Gly | His | Val | Ser | Gly | His | Arg | Met | Ala | Trp |  |
| 305 |  |  |  |  | 310 |  |  |  |  | 315 |  |  |  |  | 320 |  |

| GAC | ATG | ATG | ATG | AAC | TGG | TCG | CCC | ACA | ACA | GCC | CTA | GTG | GTG | TCG | CAG | 1008 |

-continued

| | | | | Asp | Met | Met | Met | Asn | Trp | Ser | Pro | Thr | Thr | Ala | Leu | Val | Val | Ser | Gln | |
| | | | | | | | | 325 | | | | | 330 | | | | | | 335 | |

| TTA | CTC | CGG | ATC | CCA | CAA | GCC | GTC | GTG | GAC | ATG | GTG | GCG | GGG | GCC | CAC | 1056 |
| Leu | Leu | Arg | Ile | Pro | Gln | Ala | Val | Val | Asp | Met | Val | Ala | Gly | Ala | His | |
| | | | 340 | | | | | 345 | | | | | | 350 | | |

| TGG | GGA | GTC | CTG | GCG | GGC | CTT | GCC | TAC | TAT | TCC | ATG | GCG | GGG | AAC | TGG | 1104 |
| Trp | Gly | Val | Leu | Ala | Gly | Leu | Ala | Tyr | Tyr | Ser | Met | Ala | Gly | Asn | Trp | |
| | | 355 | | | | | 360 | | | | | 365 | | | | |

| GCT | AAG | GTT | CTG | ATT | GTG | ATG | CTA | CTT | TTT | GCT | GGC | GTT | GAC | GGG | GAT | 1152 |
| Ala | Lys | Val | Leu | Ile | Val | Met | Leu | Leu | Phe | Ala | Gly | Val | Asp | Gly | Asp | |
| | 370 | | | | | 375 | | | | | 380 | | | | | |

| ACC | CAC | GTG | ACA | GGG | GGG | GCG | CAA | GCC | AAA | ACC | ACC | AAC | AGG | CTC | GTG | 1200 |
| Thr | His | Val | Thr | Gly | Gly | Ala | Gln | Ala | Lys | Thr | Thr | Asn | Arg | Leu | Val | |
| 385 | | | | | 390 | | | | | 395 | | | | | 400 | |

| TCC | ATG | TTC | GCA | AGT | GGG | CCG | TCT | CAG | AAA | ATC | CAG | CTT | ATA | AAC | ACC | 1248 |
| Ser | Met | Phe | Ala | Ser | Gly | Pro | Ser | Gln | Lys | Ile | Gln | Leu | Ile | Asn | Thr | |
| | | | | 405 | | | | | 410 | | | | | 415 | | |

| AAT | GGG | AGT | TGG | CAC | ATC | AAC | AGG | ACT | GCC | CTG | AAC | TGC | AAT | GAC | TCT | 1296 |
| Asn | Gly | Ser | Trp | His | Ile | Asn | Arg | Thr | Ala | Leu | Asn | Cys | Asn | Asp | Ser | |
| | | | 420 | | | | | 425 | | | | | 430 | | | |

| CTC | CAG | ACT | GGG | TTT | CTT | GCC | GCG | CTG | TTC | TAC | ACA | CAT | AGT | TTC | AAC | 1344 |
| Leu | Gln | Thr | Gly | Phe | Leu | Ala | Ala | Leu | Phe | Tyr | Thr | His | Ser | Phe | Asn | |
| | | 435 | | | | | 440 | | | | | 445 | | | | |

| TCG | TCC | GGG | TGC | CCA | GAG | CGC | ATG | GCC | CAG | TGC | CGC | ACC | ATT | GAC | AAG | 1392 |
| Ser | Ser | Gly | Cys | Pro | Glu | Arg | Met | Ala | Gln | Cys | Arg | Thr | Ile | Asp | Lys | |
| | 450 | | | | | 455 | | | | | 460 | | | | | |

| TTC | GAC | CAG | GGA | TGG | GGT | CCC | ATT | ACT | TAT | GCT | GAG | TCT | AGC | AGA | TCA | 1440 |
| Phe | Asp | Gln | Gly | Trp | Gly | Pro | Ile | Thr | Tyr | Ala | Glu | Ser | Ser | Arg | Ser | |
| 465 | | | | | 470 | | | | | 475 | | | | | 480 | |

| GAC | CAG | AGG | CCA | TAT | TGC | TGG | CAC | TAC | CCA | CCT | CCA | CAA | TGT | ACC | ATC | 1488 |
| Asp | Gln | Arg | Pro | Tyr | Cys | Trp | His | Tyr | Pro | Pro | Pro | Gln | Cys | Thr | Ile | |
| | | | | 485 | | | | | 490 | | | | | 495 | | |

| GTA | CCT | GCG | TCG | GAG | GTG | TGC | GGC | CCA | GTG | TAC | TGC | TTC | ACC | CCA | AGC | 1536 |
| Val | Pro | Ala | Ser | Glu | Val | Cys | Gly | Pro | Val | Tyr | Cys | Phe | Thr | Pro | Ser | |
| | | | 500 | | | | | 505 | | | | | 510 | | | |

| CCT | GTC | GTC | GTG | GGG | ACG | ACC | GAT | CGT | TTC | GGT | GTC | CCT | ACG | TAT | AGA | 1584 |
| Pro | Val | Val | Val | Gly | Thr | Thr | Asp | Arg | Phe | Gly | Val | Pro | Thr | Tyr | Arg | |
| | | 515 | | | | | 520 | | | | | 525 | | | | |

| TGG | GGG | GAG | AAC | GAG | ACT | GAC | GTG | CTG | CTG | CTC | AAC | AAC | ACG | CGG | CCG | 1632 |
| Trp | Gly | Glu | Asn | Glu | Thr | Asp | Val | Leu | Leu | Leu | Asn | Asn | Thr | Arg | Pro | |
| | 530 | | | | | 535 | | | | | 540 | | | | | |

| CCG | CAA | GGC | AAC | TGG | TTC | GGC | TGC | ACA | TGG | ATG | AAT | AGC | ACC | GGG | TTC | 1680 |
| Pro | Gln | Gly | Asn | Trp | Phe | Gly | Cys | Thr | Trp | Met | Asn | Ser | Thr | Gly | Phe | |
| 545 | | | | | 550 | | | | | 555 | | | | | 560 | |

| ACC | AAG | ACA | TGT | GGG | GGG | CCC | CCG | TGT | AAC | ATC | GGG | GGG | GTC | GGC | AAC | 1728 |
| Thr | Lys | Thr | Cys | Gly | Gly | Pro | Pro | Cys | Asn | Ile | Gly | Gly | Val | Gly | Asn | |
| | | | | 565 | | | | | 570 | | | | | 575 | | |

| AAC | ACC | CTG | ACC | TGC | CCC | ACG | GAC | TGC | TTC | CGG | AAG | CAC | CCC | GAG | GCT | 1776 |
| Asn | Thr | Leu | Thr | Cys | Pro | Thr | Asp | Cys | Phe | Arg | Lys | His | Pro | Glu | Ala | |
| | | | 580 | | | | | 585 | | | | | 590 | | | |

| ACC | TAC | ACA | AAA | TGT | GGT | TCG | GGG | CCT | TGG | CTG | ACA | CCT | AGG | TGC | ATG | 1824 |
| Thr | Tyr | Thr | Lys | Cys | Gly | Ser | Gly | Pro | Trp | Leu | Thr | Pro | Arg | Cys | Met | |
| | | 595 | | | | | 600 | | | | | 605 | | | | |

| GTT | GAC | TAT | CCA | TAC | AGG | CTC | TGG | CAT | TAC | CCC | TGC | ACT | GTT | AAC | TTT | 1872 |
| Val | Asp | Tyr | Pro | Tyr | Arg | Leu | Trp | His | Tyr | Pro | Cys | Thr | Val | Asn | Phe | |
| | 610 | | | | | 615 | | | | | 620 | | | | | |

| ACC | ATC | TTC | AAG | GTT | AGG | ATG | TAT | GTG | GGG | GGG | GTG | GAG | CAC | AGG | CTC | 1920 |
| Thr | Ile | Phe | Lys | Val | Arg | Met | Tyr | Val | Gly | Gly | Val | Glu | His | Arg | Leu | |
| 625 | | | | | 630 | | | | | 635 | | | | | 640 | |

| AAT | GCT | GCA | TGC | AAT | TGG | ACC | CGA | GGA | GAG | CGT | TGT | GAC | TTG | GAG | GAC | 1968 |

```
        Asn Ala Ala Cys Asn Trp Thr Arg Gly Glu Arg Cys Asp Leu Glu Asp
                        645             650             655

AGG GAT AGG CCG GAG CTC AGC CCG CTG CTG CTG TCT ACA ACA GAG TGG         2016
Arg Asp Arg Pro Glu Leu Ser Pro Leu Leu Leu Ser Thr Thr Glu Trp
            660             665             670

CAG GTA CTG CCC TGT TCC TTC ACC ACC CTA CCA GCT CTG TCC ACT GGC         2064
Gln Val Leu Pro Cys Ser Phe Thr Thr Leu Pro Ala Leu Ser Thr Gly
            675             680             685

TTG ATT CAC CTC CAT CAG AAC ATC GTG GAC GTG CAA TAC CTA TAC GGT         2112
Leu Ile His Leu His Gln Asn Ile Val Asp Val Gln Tyr Leu Tyr Gly
            690             695             700

ATA GGG TCA GCG GTT GTC TCC TTT GCA ATC AAA TGG GAG TAT GTC CTG         2160
Ile Gly Ser Ala Val Val Ser Phe Ala Ile Lys Trp Glu Tyr Val Leu
705             710             715             720

TTG CTT TTC CTT CTC CTA GCG GAC GCA CGT GTC TGT GCC TGC TTG TGG         2208
Leu Leu Phe Leu Leu Leu Ala Asp Ala Arg Val Cys Ala Cys Leu Trp
                725             730             735

ATG ATG CTG CTG ATA GCC CAG GCC GAG GCC GCC TTG GAG AAC CTG GTG         2256
Met Met Leu Leu Ile Ala Gln Ala Glu Ala Ala Leu Glu Asn Leu Val
            740             745             750

GTC CTC AAT TCG GCG TCT GTG GCC GGC GCA CAT GGC ATC CTC TCC TTC         2304
Val Leu Asn Ser Ala Ser Val Ala Gly Ala His Gly Ile Leu Ser Phe
            755             760             765

CTT GTG TTC TTC TGT GCC GCC TGG TAC ATC AAA GGC AGG CTG GTC CCT         2352
Leu Val Phe Phe Cys Ala Ala Trp Tyr Ile Lys Gly Arg Leu Val Pro
            770             775             780

GGG GCG ACA TAT GCT CTT TAT GGC GTG TGG CCG CTG CTC CTG CTC TTG         2400
Gly Ala Thr Tyr Ala Leu Tyr Gly Val Trp Pro Leu Leu Leu Leu Leu
785             790             795             800

CTG GCA TTA CCA CCG CGA GCT TAC GCC ATG GAC CGG GAG ATG GCT GCA         2448
Leu Ala Leu Pro Pro Arg Ala Tyr Ala Met Asp Arg Glu Met Ala Ala
                805             810             815

TCG TGC GGA GGC GCG GTT TTT GTG GGT CTG GTA CTC CTG ACT TTG TCA         2496
Ser Cys Gly Gly Ala Val Phe Val Gly Leu Val Leu Leu Thr Leu Ser
            820             825             830

CCA TAC TAC AAG GTG TTC CTC GCT AGG CTC ATA TGG TGG TTA CAA TAT         2544
Pro Tyr Tyr Lys Val Phe Leu Ala Arg Leu Ile Trp Trp Leu Gln Tyr
            835             840             845

TTT ACC ACC AGA GCC GAG GCG GAC TTA CAT GTG TGG ATC CCC CCC CTC         2592
Phe Thr Thr Arg Ala Glu Ala Asp Leu His Val Trp Ile Pro Pro Leu
850             855             860

AAC GCT CGG GGA GGC CGC GAT GCC ATC ATC CTC CTC ATG TGC GCA GTC         2640
Asn Ala Arg Gly Gly Arg Asp Ala Ile Ile Leu Leu Met Cys Ala Val
865             870             875             880

CAT CCA GAG CTA ATC TTT GAC ATC ACC AAA CTT CTA ATT GCC ATA CTC         2688
His Pro Glu Leu Ile Phe Asp Ile Thr Lys Leu Leu Ile Ala Ile Leu
                885             890             895

GGT CCG CTC ATG GTG CTC CAA GCT GGC ATA ACC AGA GTG CCG TAC TTC         2736
Gly Pro Leu Met Val Leu Gln Ala Gly Ile Thr Arg Val Pro Tyr Phe
            900             905             910

GTG CGC GCT CAA GGG CTC ATT CAT GCA TGC ATG TTA GTG CGG AAG GTC         2784
Val Arg Ala Gln Gly Leu Ile His Ala Cys Met Leu Val Arg Lys Val
            915             920             925

GCT GGG GGT CAT TAT GTC CAA ATG GCC TTC ATG AAG CTG GGC GCG CTG         2832
Ala Gly Gly His Tyr Val Gln Met Ala Phe Met Lys Leu Gly Ala Leu
            930             935             940

ACA GGC ACG TAC ATT TAC AAC CAT CTT ACC CCG CTA CGG GAT TGG CCA         2880
Thr Gly Thr Tyr Ile Tyr Asn His Leu Thr Pro Leu Arg Asp Trp Pro
945             950             955             960

CGC GCG GGC CTA CGA GAC CTT GCG GTG GCA GTG GAG CCC GTC GTC TTC         2928
```

|     |     |     |     |     |     |     |     |     |     |     |     |     |     |     |     |
| --- | --- | --- | --- | --- | --- | --- | --- | --- | --- | --- | --- | --- | --- | --- | --- |
| Arg | Ala | Gly | Leu | Arg | Asp | Leu | Ala | Val | Ala | Val | Glu | Pro | Val | Val | Phe |
|     |     |     |     | 965 |     |     |     |     | 970 |     |     |     |     | 975 |     |

| TCC | GAC | ATG | GAG | ACC | AAG | ATC | ATC | ACC | TGG | GGA | GCA | GAC | ACC | GCG | GCG | 2976 |
| --- | --- | --- | --- | --- | --- | --- | --- | --- | --- | --- | --- | --- | --- | --- | --- | --- |
| Ser | Asp | Met | Glu | Thr | Lys | Ile | Ile | Thr | Trp | Gly | Ala | Asp | Thr | Ala | Ala |     |
|     |     |     | 980 |     |     |     |     | 985 |     |     |     |     | 990 |     |     |     |

| TGT | GGG | GAC | ATC | ATC | TTG | GGT | CTG | CCC | GTC | TCC | GCC | CGA | AGG | GGA | AAG | 3024 |
| --- | --- | --- | --- | --- | --- | --- | --- | --- | --- | --- | --- | --- | --- | --- | --- | --- |
| Cys | Gly | Asp | Ile | Ile | Leu | Gly | Leu | Pro | Val | Ser | Ala | Arg | Arg | Gly | Lys |     |
|     |     |     | 995 |     |     |     |     | 1000 |     |     |     |     | 1005 |     |     |     |

| GAG | ATA | CTC | CTG | GGC | CCG | GCC | GAT | AGT | CTT | GAA | GGG | CGG | GGG | TTG | CGA | 3072 |
| --- | --- | --- | --- | --- | --- | --- | --- | --- | --- | --- | --- | --- | --- | --- | --- | --- |
| Glu | Ile | Leu | Leu | Gly | Pro | Ala | Asp | Ser | Leu | Glu | Gly | Arg | Gly | Leu | Arg |     |
|     | 1010 |     |     |     |     | 1015 |     |     |     |     | 1020 |     |     |     |     |     |

| CTC | CTC | GCG | CCC | ATC | ACG | GCC | TAC | TCC | CAA | CAG | ACG | CGG | GGC | CTA | CTT | 3120 |
| --- | --- | --- | --- | --- | --- | --- | --- | --- | --- | --- | --- | --- | --- | --- | --- | --- |
| Leu | Leu | Ala | Pro | Ile | Thr | Ala | Tyr | Ser | Gln | Gln | Thr | Arg | Gly | Leu | Leu |     |
| 1025 |     |     |     |     | 1030 |     |     |     |     | 1035 |     |     |     |     | 1040 |     |

| GGT | TGC | ATC | ATC | ACT | AGC | CTT | ACA | GGC | CGG | GAC | AAG | AAC | CAG | GTC | GAG | 3168 |
| --- | --- | --- | --- | --- | --- | --- | --- | --- | --- | --- | --- | --- | --- | --- | --- | --- |
| Gly | Cys | Ile | Ile | Thr | Ser | Leu | Thr | Gly | Arg | Asp | Lys | Asn | Gln | Val | Glu |     |
|     |     |     |     | 1045 |     |     |     |     | 1050 |     |     |     |     | 1055 |     |     |

| GGA | GAG | GTT | CAG | GTG | GTT | TCC | ACC | GCA | ACA | CAA | TCC | TTC | CTG | GCG | ACC | 3216 |
| --- | --- | --- | --- | --- | --- | --- | --- | --- | --- | --- | --- | --- | --- | --- | --- | --- |
| Gly | Glu | Val | Gln | Val | Val | Ser | Thr | Ala | Thr | Gln | Ser | Phe | Leu | Ala | Thr |     |
|     |     |     | 1060 |     |     |     |     | 1065 |     |     |     |     | 1070 |     |     |     |

| TGC | GTC | AAC | GGC | GTG | TGT | TGG | ACC | GTT | TAC | CAT | GGT | GCT | GGC | TCA | AAG | 3264 |
| --- | --- | --- | --- | --- | --- | --- | --- | --- | --- | --- | --- | --- | --- | --- | --- | --- |
| Cys | Val | Asn | Gly | Val | Cys | Trp | Thr | Val | Tyr | His | Gly | Ala | Gly | Ser | Lys |     |
|     |     | 1075 |     |     |     |     | 1080 |     |     |     |     | 1085 |     |     |     |     |

| ACC | TTA | GCC | GCG | CCA | AAG | GGG | CCA | ATC | ACC | CAG | ATG | TAC | ACT | AAT | GTG | 3312 |
| --- | --- | --- | --- | --- | --- | --- | --- | --- | --- | --- | --- | --- | --- | --- | --- | --- |
| Thr | Leu | Ala | Ala | Pro | Lys | Gly | Pro | Ile | Thr | Gln | Met | Tyr | Thr | Asn | Val |     |
|     | 1090 |     |     |     |     | 1095 |     |     |     |     | 1100 |     |     |     |     |     |

| GAC | CAG | GAC | CTC | GTC | GGC | TGG | CCC | AAG | CCC | CCC | GGG | GCG | CGT | TCC | TTG | 3360 |
| --- | --- | --- | --- | --- | --- | --- | --- | --- | --- | --- | --- | --- | --- | --- | --- | --- |
| Asp | Gln | Asp | Leu | Val | Gly | Trp | Pro | Lys | Pro | Pro | Gly | Ala | Arg | Ser | Leu |     |
| 1105 |     |     |     |     | 1110 |     |     |     |     | 1115 |     |     |     |     | 1120 |     |

| ACA | CCA | TGC | ACC | TGT | GGC | AGC | TCA | GAC | CTT | TAC | TTG | GTC | ACG | AGA | CAT | 3408 |
| --- | --- | --- | --- | --- | --- | --- | --- | --- | --- | --- | --- | --- | --- | --- | --- | --- |
| Thr | Pro | Cys | Thr | Cys | Gly | Ser | Ser | Asp | Leu | Tyr | Leu | Val | Thr | Arg | His |     |
|     |     |     | 1125 |     |     |     |     | 1130 |     |     |     |     | 1135 |     |     |     |

| GCT | GAC | GTC | ATT | CCG | GTG | CGC | CGG | CGG | GGC | GAC | AGT | AGG | GGG | AGC | CTG | 3456 |
| --- | --- | --- | --- | --- | --- | --- | --- | --- | --- | --- | --- | --- | --- | --- | --- | --- |
| Ala | Asp | Val | Ile | Pro | Val | Arg | Arg | Arg | Gly | Asp | Ser | Arg | Gly | Ser | Leu |     |
|     |     |     | 1140 |     |     |     |     | 1145 |     |     |     |     | 1150 |     |     |     |

| CTC | TCC | CCC | AGG | CCT | GTC | TCC | TAC | TTG | AAG | GGC | TCT | TCG | GGT | GGT | CCA | 3504 |
| --- | --- | --- | --- | --- | --- | --- | --- | --- | --- | --- | --- | --- | --- | --- | --- | --- |
| Leu | Ser | Pro | Arg | Pro | Val | Ser | Tyr | Leu | Lys | Gly | Ser | Ser | Gly | Gly | Pro |     |
|     | 1155 |     |     |     |     | 1160 |     |     |     |     | 1165 |     |     |     |     |     |

| CTG | CTC | TGC | CCC | TTC | GGG | CAC | GCT | GTG | GGC | ATC | TTC | CGG | GCT | GCC | GTA | 3552 |
| --- | --- | --- | --- | --- | --- | --- | --- | --- | --- | --- | --- | --- | --- | --- | --- | --- |
| Leu | Leu | Cys | Pro | Phe | Gly | His | Ala | Val | Gly | Ile | Phe | Arg | Ala | Ala | Val |     |
| 1170 |     |     |     |     | 1175 |     |     |     |     | 1180 |     |     |     |     |     |     |

| TGC | ACC | CGG | GGG | GTT | GCG | AAG | GCG | GTG | GAC | TTT | GTG | CCC | GTA | GAG | TCC | 3600 |
| --- | --- | --- | --- | --- | --- | --- | --- | --- | --- | --- | --- | --- | --- | --- | --- | --- |
| Cys | Thr | Arg | Gly | Val | Ala | Lys | Ala | Val | Asp | Phe | Val | Pro | Val | Glu | Ser |     |
| 1185 |     |     |     |     | 1190 |     |     |     |     | 1195 |     |     |     |     | 1200 |     |

| ATG | GAA | ACT | ACT | ATG | CGG | TCT | CCG | GTC | TTC | ACG | GAC | AAC | TCA | TCC | CCC | 3648 |
| --- | --- | --- | --- | --- | --- | --- | --- | --- | --- | --- | --- | --- | --- | --- | --- | --- |
| Met | Glu | Thr | Thr | Met | Arg | Ser | Pro | Val | Phe | Thr | Asp | Asn | Ser | Ser | Pro |     |
|     |     |     |     | 1205 |     |     |     |     | 1210 |     |     |     |     | 1215 |     |     |

| CCG | GCC | GTA | CCG | CAG | TCA | TTT | CAA | GTG | GCC | CAC | CTA | CAC | GCT | CCC | ACT | 3696 |
| --- | --- | --- | --- | --- | --- | --- | --- | --- | --- | --- | --- | --- | --- | --- | --- | --- |
| Pro | Ala | Val | Pro | Gln | Ser | Phe | Gln | Val | Ala | His | Leu | His | Ala | Pro | Thr |     |
|     |     | 1220 |     |     |     |     | 1225 |     |     |     |     | 1230 |     |     |     |     |

| GGC | AGC | GGC | AAG | AGT | ACT | AAA | GTG | CCG | GCT | GCA | TAT | GCA | GCC | CAA | GGG | 3744 |
| --- | --- | --- | --- | --- | --- | --- | --- | --- | --- | --- | --- | --- | --- | --- | --- | --- |
| Gly | Ser | Gly | Lys | Ser | Thr | Lys | Val | Pro | Ala | Ala | Tyr | Ala | Ala | Gln | Gly |     |
|     |     | 1235 |     |     |     |     | 1240 |     |     |     |     | 1245 |     |     |     |     |

| TAC | AAG | GTG | CTC | GTC | CTC | AAT | CCG | TCC | GTT | GCC | GCT | ACC | TTA | GGG | TTT | 3792 |
| --- | --- | --- | --- | --- | --- | --- | --- | --- | --- | --- | --- | --- | --- | --- | --- | --- |
| Tyr | Lys | Val | Leu | Val | Leu | Asn | Pro | Ser | Val | Ala | Ala | Thr | Leu | Gly | Phe |     |
|     | 1250 |     |     |     |     | 1255 |     |     |     |     | 1260 |     |     |     |     |     |

| GGG | GCG | TAT | ATG | TCT | AAG | GCA | CAC | GGT | ATT | GAC | CCC | AAC | ATC | AGA | ACT | 3840 |
| --- | --- | --- | --- | --- | --- | --- | --- | --- | --- | --- | --- | --- | --- | --- | --- | --- |
| Gly | Ala | Tyr | Met | Ser | Lys | Ala | His | Gly | Ile | Asp | Pro | Asn | Ile | Arg | Thr |     |
| 1265 |     |     |     |     | 1270 |     |     |     |     | 1275 |     |     |     |     | 1280 |     |

| GGG | GTA | AGG | ACC | ATT | ACC | ACA | GGC | GCC | CCC | GTC | ACA | TAC | TCT | ACC | TAT | 3888 |
| --- | --- | --- | --- | --- | --- | --- | --- | --- | --- | --- | --- | --- | --- | --- | --- | --- |

| | | | | | | | | | | | | | | | |
|---|---|---|---|---|---|---|---|---|---|---|---|---|---|---|---|
| Gly | Val | Arg | Thr | Ile<br>1285 | Thr | Thr | Gly | Ala | Pro<br>1290 | Val | Thr | Tyr | Ser | Thr<br>1295 | Tyr |

| | | | | | | | | | | | | | | | | |
|---|---|---|---|---|---|---|---|---|---|---|---|---|---|---|---|---|
| GGC | AAG | TTT | CTT | GCC | GAT | GGT | GGT | TGC | TCT | GGG | GGC | GCT | TAT | GAC | ATC | 3936 |
| Gly | Lys | Phe | Leu<br>1300 | Ala | Asp | Gly | Gly | Cys<br>1305 | Ser | Gly | Gly | Ala | Tyr<br>1310 | Asp | Ile | |
| ATA | ATA | TGT | GAT | GAG | TGC | CAT | TCA | ACT | GAC | TCG | ACT | ACA | ATC | TTG | GGC | 3984 |
| Ile | Ile<br>1315 | Cys | Asp | Glu | Cys | His<br>1320 | Ser | Thr | Asp | Ser | Thr<br>1325 | Thr | Ile | Leu | Gly | |
| ATC | GGC | ACA | GTC | CTG | GAC | CAA | GCG | GAG | ACG | GCT | GGA | GCG | CGG | CTT | GTC | 4032 |
| Ile | Gly<br>1330 | Thr | Val | Leu | Asp | Gln<br>1335 | Ala | Glu | Thr | Ala | Gly<br>1340 | Ala | Arg | Leu | Val | |
| GTG | CTC | GCC | ACC | GCT | ACG | CCT | CCG | GGA | TCG | GTC | ACC | GTG | CCA | CAC | CCA | 4080 |
| Val | Leu | Ala | Thr | Ala | Thr | Pro | Pro | Gly | Ser | Val | Thr | Val | Pro | His | Pro | |
| 1345 | | | | 1350 | | | | | 1355 | | | | | 1360 | | |
| AAC | ATC | GAG | GAG | GTG | GCC | CTG | TCT | AAT | ACT | GGA | GAG | ATC | CCC | TTC | TAT | 4128 |
| Asn | Ile | Glu | Glu | Val | Ala | Leu | Ser | Asn | Thr | Gly | Glu | Ile | Pro | Phe | Tyr | |
| | | | | 1365 | | | | | 1370 | | | | | 1375 | | |
| GGC | AAA | GCC | ATC | CCC | ATT | GAA | GCC | ATC | AGG | GGG | GGA | AGG | CAT | CTC | ATT | 4176 |
| Gly | Lys | Ala | Ile<br>1380 | Pro | Ile | Glu | Ala | Ile<br>1385 | Arg | Gly | Gly | Arg | His<br>1390 | Leu | Ile | |
| TTC | TGT | CAT | TCC | AAG | AAG | AAG | TGC | GAC | GAG | CTC | GCC | GCA | AAG | CTG | TCA | 4224 |
| Phe | Cys | His<br>1395 | Ser | Lys | Lys | Lys | Cys<br>1400 | Asp | Glu | Leu | Ala | Ala<br>1405 | Lys | Leu | Ser | |
| GGC | CTC | GGA | ATC | AAC | GCT | GTG | GCG | TAT | TAC | CGG | GGG | CTC | GAT | GTG | TCC | 4272 |
| Gly | Leu | Gly<br>1410 | Ile | Asn | Ala | Val | Ala<br>1415 | Tyr | Tyr | Arg | Gly | Leu<br>1420 | Asp | Val | Ser | |
| GTC | ATA | CCA | ACT | ATC | GGA | GAC | GTC | GTT | GTC | GTG | GCA | ACA | GAC | GCT | CTG | 4320 |
| Val | Ile | Pro | Thr | Ile | Gly | Asp | Val | Val | Val | Val | Ala | Thr | Asp | Ala | Leu | |
| 1425 | | | | | 1430 | | | | | 1435 | | | | | 1440 | |
| ATG | ACG | GGC | TAT | ACG | GGC | GAC | TTT | GAC | TCA | GTG | ATC | GAC | TGT | AAC | ACA | 4368 |
| Met | Thr | Gly | Tyr | Thr<br>1445 | Gly | Asp | Phe | Asp | Ser<br>1450 | Val | Ile | Asp | Cys | Asn<br>1455 | Thr | |
| TGT | GTC | ACC | CAG | ACA | GTC | GAC | TTC | AGC | TTG | GAT | CCC | ACC | TTC | ACC | ATT | 4416 |
| Cys | Val | Thr | Gln<br>1460 | Thr | Val | Asp | Phe | Ser<br>1465 | Leu | Asp | Pro | Thr | Phe<br>1470 | Thr | Ile | |
| GAG | ACG | ACG | ACC | GTG | CCT | CAA | GAC | GCA | GTG | TCG | CGC | TCG | CAG | CGG | CGG | 4464 |
| Glu | Thr | Thr<br>1475 | Thr | Val | Pro | Gln | Asp<br>1480 | Ala | Val | Ser | Arg | Ser<br>1485 | Gln | Arg | Arg | |
| GGT | AGG | ACT | GGC | AGG | GGT | AGG | AGA | GGC | ATC | TAC | AGG | TTT | GTG | ACT | CCG | 4512 |
| Gly | Arg<br>1490 | Thr | Gly | Arg | Gly<br>1495 | Arg | Arg | Gly | Ile | Tyr<br>1500 | Arg | Phe | Val | Thr | Pro | |
| GGA | GAA | CGG | CCC | TCG | GGC | ATG | TTC | GAT | TCC | TCG | GTC | CTG | TGT | GAG | TGC | 4560 |
| Gly | Glu | Arg | Pro | Ser<br>1510 | Gly | Met | Phe | Asp | Ser<br>1515 | Ser | Val | Leu | Cys | Glu<br>1520 | Cys | |
| 1505 | | | | | | | | | | | | | | | | |
| TAT | GAC | GCG | GGC | TGT | GCT | TGG | TAC | GAG | CTC | ACC | CCG | GCC | GAG | ACC | TCG | 4608 |
| Tyr | Asp | Ala | Gly | Cys<br>1525 | Ala | Trp | Tyr | Glu | Leu<br>1530 | Thr | Pro | Ala | Glu | Thr<br>1535 | Ser | |
| GTT | AGG | TTG | CGG | GCC | TAC | CTG | AAC | ACA | CCA | GGG | TTG | CCC | GTT | TGC | CAG | 4656 |
| Val | Arg | Leu | Arg | Ala<br>1540 | Tyr | Leu | Asn | Thr | Pro<br>1545 | Gly | Leu | Pro | Val | Cys<br>1550 | Gln | |
| GAC | CAC | CTG | GAG | TTC | TGG | GAG | AGT | GTC | TTC | ACA | GGC | CTC | ACC | CAT | ATA | 4704 |
| Asp | His | Leu | Glu | Phe | Trp | Glu | Ser | Val | Phe | Thr | Gly | Leu | Thr | His | Ile | |
| | | | 1555 | | | | | 1560 | | | | | 1565 | | | |
| GAT | GCA | CAC | TTC | TTG | TCC | CAG | ACC | AAG | CAG | GCA | GGA | GAC | AAC | TTC | CCC | 4752 |
| Asp | Ala | His<br>1570 | Phe | Leu | Ser | Gln | Thr<br>1575 | Lys | Gln | Ala | Gly | Asp<br>1580 | Asn | Phe | Pro | |
| TAC | CTG | GTA | GCA | TAC | CAA | GCC | ACG | GTG | TGC | GCC | AGG | GCT | CAG | GCC | CCA | 4800 |
| Tyr | Leu | Val | Ala | Tyr | Gln | Ala | Thr | Val | Cys | Ala | Arg | Ala | Gln | Ala | Pro | |
| 1585 | | | | | 1590 | | | | | 1595 | | | | | 1600 | |
| CCT | CCA | TCA | TGG | GAT | CAA | ATG | TGG | AAG | TGT | CTC | ATA | CGG | CTG | AAA | CCT | 4848 |

-continued

| | | | | | | | | | | | | | | | | |
|---|---|---|---|---|---|---|---|---|---|---|---|---|---|---|---|---|
| Pro | Pro | Ser | Trp | Asp | Gln | Met | Trp | Lys | Cys | Leu | Ile | Arg | Leu | Lys | Pro | |
| | | | | 1605 | | | | 1610 | | | | | | 1615 | | |
| ACG | CTG | CAC | GGG | CCA | ACA | CCC | TTG | CTG | TAC | AGG | CTG | GGA | GCC | GTC | CAG | 4896 |
| Thr | Leu | His | Gly | Pro | Thr | Pro | Leu | Leu | Tyr | Arg | Leu | Gly | Ala | Val | Gln | |
| | | | 1620 | | | | | 1625 | | | | | 1630 | | | |
| AAT | GAG | GTC | ACC | CTC | ACC | CAC | CCC | ATA | ACC | AAA | TAC | ATC | ATG | GCA | TGC | 4944 |
| Asn | Glu | Val | Thr | Leu | Thr | His | Pro | Ile | Thr | Lys | Tyr | Ile | Met | Ala | Cys | |
| | | | 1635 | | | | 1640 | | | | | 1645 | | | | |
| ATG | TCG | GCT | GAC | CTG | GAG | GTC | GTC | ACT | AGC | ACC | TGG | GTG | CTG | GTG | GGC | 4992 |
| Met | Ser | Ala | Asp | Leu | Glu | Val | Val | Thr | Ser | Thr | Trp | Val | Leu | Val | Gly | |
| | 1650 | | | | 1655 | | | | | | 1660 | | | | | |
| GGA | GTC | CTT | GCA | GCT | CTG | GCC | GCG | TAT | TGC | CTG | ACA | ACA | GGC | AGT | GTG | 5040 |
| Gly | Val | Leu | Ala | Ala | Leu | Ala | Ala | Tyr | Cys | Leu | Thr | Thr | Gly | Ser | Val | |
| 1665 | | | | 1670 | | | | | 1675 | | | | | 1680 | | |
| GTC | ATT | GTG | GGT | AGG | ATT | ATC | TTG | TCC | GGG | AGG | CCG | GCC | ATT | GTT | CCC | 5088 |
| Val | Ile | Val | Gly | Arg | Ile | Ile | Leu | Ser | Gly | Arg | Pro | Ala | Ile | Val | Pro | |
| | | | 1685 | | | | | 1690 | | | | | 1695 | | | |
| GAC | AGG | GAG | CTT | CTC | TAC | CAG | GAG | TTC | GAT | GAA | ATG | GAA | GAG | TGC | GCC | 5136 |
| Asp | Arg | Glu | Leu | Leu | Tyr | Gln | Glu | Phe | Asp | Glu | Met | Glu | Glu | Cys | Ala | |
| | | 1700 | | | | | 1705 | | | | | 1710 | | | | |
| TCG | CAC | CTC | CCT | TAC | ATC | GAG | CAG | GGA | ATG | CAG | CTC | GCC | GAG | CAA | TTC | 5184 |
| Ser | His | Leu | Pro | Tyr | Ile | Glu | Gln | Gly | Met | Gln | Leu | Ala | Glu | Gln | Phe | |
| | | 1715 | | | | | 1720 | | | | | 1725 | | | | |
| AAG | CAG | AAA | GCG | CTC | GGG | TTA | CTG | CAA | ACA | GCC | ACC | AAA | CAA | GCG | GAG | 5232 |
| Lys | Gln | Lys | Ala | Leu | Gly | Leu | Leu | Gln | Thr | Ala | Thr | Lys | Gln | Ala | Glu | |
| | 1730 | | | | 1735 | | | | | | 1740 | | | | | |
| GCT | GCT | GCT | CCC | GTG | GTG | GAG | TCC | AAG | TGG | CGA | GCC | CTT | GAG | ACA | TTC | 5280 |
| Ala | Ala | Ala | Pro | Val | Val | Glu | Ser | Lys | Trp | Arg | Ala | Leu | Glu | Thr | Phe | |
| 1745 | | | | 1750 | | | | | 1755 | | | | | 1760 | | |
| TGG | GCG | AAG | CAC | ATG | TGG | AAT | TTC | ATC | AGC | GGG | ATA | CAG | TAC | TTA | GCA | 5328 |
| Trp | Ala | Lys | His | Met | Trp | Asn | Phe | Ile | Ser | Gly | Ile | Gln | Tyr | Leu | Ala | |
| | | | 1765 | | | | | 1770 | | | | | 1775 | | | |
| GGC | TTA | TCC | ACT | CTG | CCT | GGG | AAC | CCC | GCA | ATA | GCA | TCA | TTG | ATG | GCA | 5376 |
| Gly | Leu | Ser | Thr | Leu | Pro | Gly | Asn | Pro | Ala | Ile | Ala | Ser | Leu | Met | Ala | |
| | | | 1780 | | | | 1785 | | | | | | 1790 | | | |
| TTC | ACA | GCC | TCT | ATC | ACC | AGC | CCG | CTC | ACC | ACC | CAA | AGT | ACC | CTC | CTG | 5424 |
| Phe | Thr | Ala | Ser | Ile | Thr | Ser | Pro | Leu | Thr | Thr | Gln | Ser | Thr | Leu | Leu | |
| | | | 1795 | | | | 1800 | | | | | 1805 | | | | |
| TTT | AAC | ATC | TTG | GGG | GGG | TGG | GTG | GCT | GCC | CAA | CTC | GCC | CCC | CCC | AGC | 5472 |
| Phe | Asn | Ile | Leu | Gly | Gly | Trp | Val | Ala | Ala | Gln | Leu | Ala | Pro | Pro | Ser | |
| | | 1810 | | | | 1815 | | | | | 1820 | | | | | |
| GCC | GCT | TCG | GCT | TTC | GTG | GGC | GCC | GGC | ATC | GCC | GGT | GCG | GCT | GTT | GGC | 5520 |
| Ala | Ala | Ser | Ala | Phe | Val | Gly | Ala | Gly | Ile | Ala | Gly | Ala | Ala | Val | Gly | |
| 1825 | | | | 1830 | | | | | 1835 | | | | | 1840 | | |
| AGC | ATA | GGC | CTT | GGG | AAG | GTG | CTT | GTG | GAC | ATT | CTG | GCG | GGT | TAT | GGA | 5568 |
| Ser | Ile | Gly | Leu | Gly | Lys | Val | Leu | Val | Asp | Ile | Leu | Ala | Gly | Tyr | Gly | |
| | | | 1845 | | | | | 1850 | | | | | 1855 | | | |
| GCA | GGA | GTG | GCC | GGC | GCG | CTC | GTG | GCC | TTT | AAG | GTC | ATG | AGC | GGC | GAG | 5616 |
| Ala | Gly | Val | Ala | Gly | Ala | Leu | Val | Ala | Phe | Lys | Val | Met | Ser | Gly | Glu | |
| | | | 1860 | | | | | 1865 | | | | | 1870 | | | |
| ATG | CCC | TCC | ACC | GAG | GAC | CTG | GTC | AAT | CTA | CTT | CCT | GCC | ATC | CTC | TCT | 5664 |
| Met | Pro | Ser | Thr | Glu | Asp | Leu | Val | Asn | Leu | Leu | Pro | Ala | Ile | Leu | Ser | |
| | | | 1875 | | | | 1880 | | | | | 1885 | | | | |
| CCT | GGC | GCC | CTG | GTC | GTC | GGG | GTC | GTG | TGT | GCA | GCA | ATA | CTG | CGT | CGA | 5712 |
| Pro | Gly | Ala | Leu | Val | Val | Gly | Val | Val | Cys | Ala | Ala | Ile | Leu | Arg | Arg | |
| | 1890 | | | | 1895 | | | | | | 1900 | | | | | |
| CAC | GTG | GGT | CCG | GGA | GAG | GGG | GCT | GTG | CAG | TGG | ATG | AAC | CGG | CTG | ATA | 5760 |
| His | Val | Gly | Pro | Gly | Glu | Gly | Ala | Val | Gln | Trp | Met | Asn | Arg | Leu | Ile | |
| 1905 | | | | 1910 | | | | | 1915 | | | | | 1920 | | |
| GCG | TTC | GCC | TCG | CGG | GGT | AAT | CAT | GTT | TCC | CCC | ACG | CAC | TAT | GTG | CCT | 5808 |

```
Ala  Phe  Ala  Ser  Arg  Gly  Asn  His  Val  Ser  Pro  Thr  His  Tyr  Val  Pro
               1925                     1930                     1935

GAG  AGC  GAC  GCC  GCA  GCG  CGT  GTT  ACT  CAG  ATC  CTC  TCC  AGC  CTT  ACC    5856
Glu  Ser  Asp  Ala  Ala  Ala  Arg  Val  Thr  Gln  Ile  Leu  Ser  Ser  Leu  Thr
               1940                     1945                     1950

ATC  ACT  CAG  CTG  CTG  AAA  AGG  CTC  CAC  CAG  TGG  ATT  AAT  GAA  GAC  TGC    5904
Ile  Thr  Gln  Leu  Leu  Lys  Arg  Leu  His  Gln  Trp  Ile  Asn  Glu  Asp  Cys
               1955                     1960                     1965

TCC  ACA  CCG  TGT  TCC  GGC  TCG  TGG  CTA  AGG  GAT  GTT  TGG  GAC  TGG  ATA    5952
Ser  Thr  Pro  Cys  Ser  Gly  Ser  Trp  Leu  Arg  Asp  Val  Trp  Asp  Trp  Ile
               1970                     1975                     1980

TGC  ACG  GTG  TTG  ACT  GAC  TTC  AAG  ACC  TGG  CTC  CAG  TCC  AAG  CTC  CTG    6000
Cys  Thr  Val  Leu  Thr  Asp  Phe  Lys  Thr  Trp  Leu  Gln  Ser  Lys  Leu  Leu
1985                1990                     1995                     2000

CCG  CAG  CTA  CCT  GGA  GTC  CCT  TTT  TTC  TCG  TGC  CAA  CGC                   6039
Pro  Gln  Leu  Pro  Gly  Val  Pro  Phe  Phe  Ser  Cys  Gln  Arg
               2005                     2010
```

( 2 ) INFORMATION FOR SEQ ID NO:12:

( i ) SEQUENCE CHARACTERISTICS:
        ( A ) LENGTH: 2013 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met  Ser  Thr  Asn  Pro  Lys  Pro  Gln  Arg  Lys  Thr  Lys  Arg  Asn  Thr  Asn
1                   5                   10                      15

Arg  Arg  Pro  Gln  Asp  Val  Lys  Phe  Pro  Gly  Gly  Gly  Gln  Ile  Val  Gly
               20                  25                      30

Gly  Val  Tyr  Leu  Leu  Pro  Arg  Arg  Gly  Pro  Arg  Leu  Gly  Val  Arg  Ala
               35                  40                      45

Pro  Arg  Lys  Thr  Ser  Glu  Arg  Ser  Gln  Pro  Arg  Gly  Arg  Arg  Gln  Pro
     50                  55                      60

Ile  Pro  Lys  Ala  Arg  Arg  Pro  Glu  Gly  Arg  Thr  Trp  Ala  Gln  Pro  Gly
65                       70                  75                           80

Tyr  Pro  Trp  Pro  Leu  Tyr  Gly  Asn  Glu  Gly  Leu  Gly  Trp  Ala  Gly  Trp
                    85                  90                       95

Leu  Leu  Ser  Pro  Arg  Gly  Ser  Arg  Pro  Ser  Trp  Gly  Pro  Thr  Asp  Pro
                    100                 105                      110

Arg  Arg  Arg  Ser  Arg  Asn  Leu  Gly  Lys  Val  Ile  Asp  Thr  Leu  Thr  Cys
               115                 120                      125

Gly  Phe  Ala  Asp  Leu  Met  Gly  Tyr  Ile  Pro  Leu  Val  Gly  Ala  Pro  Leu
     130                 135                      140

Gly  Gly  Ala  Ala  Arg  Ala  Leu  Ala  His  Gly  Val  Arg  Val  Leu  Glu  Asp
145                      150                 155                          160

Gly  Val  Asn  Tyr  Ala  Thr  Gly  Asn  Leu  Pro  Gly  Cys  Ser  Phe  Ser  Ile
                    165                 170                      175

Phe  Leu  Leu  Ala  Leu  Leu  Ser  Cys  Leu  Thr  Thr  Pro  Ala  Ser  Ala  Tyr
                    180                 185                      190

Glu  Val  His  Asn  Val  Ser  Gly  Ile  Tyr  His  Val  Thr  Asn  Asp  Cys  Ser
               195                 200                      205

Asn  Ala  Ser  Ile  Val  Tyr  Glu  Ala  Ala  Asp  Leu  Ile  Met  His  Thr  Pro
     210                 215                      220

Gly  Cys  Val  Pro  Cys  Val  Arg  Glu  Gly  Asn  Ser  Ser  Arg  Cys  Trp  Val
225                      230                 235                          240
```

| | | | | | | | | | | | | | | |
|---|---|---|---|---|---|---|---|---|---|---|---|---|---|---|
| Ala | Leu | Thr | Pro | Thr 245 | Leu | Ala | Ala | Arg 250 | Asn | Val | Thr | Ile | Pro 255 | Thr |
| Thr | Ile | Arg | Arg 260 | His | Val | Asp | Leu 265 | Val | Gly | Ala | Ala | Ala 270 | Phe | Cys |
| Ser | Ala | Met 275 | Tyr | Val | Gly | Asp | Leu 280 | Cys | Gly | Ser | Val | Phe 285 | Leu | Val | Ser |
| Gln | Leu 290 | Phe | Thr | Phe | Ser | Pro 295 | Arg | Arg | His | Val | Thr 300 | Leu | Gln | Asp | Cys |
| Asn 305 | Cys | Ser | Ile | Tyr | Pro 310 | Gly | His | Val | Ser | Gly 315 | His | Arg | Met | Ala | Trp 320 |
| Asp | Met | Met | Met | Asn 325 | Trp | Ser | Pro | Thr | Thr 330 | Ala | Leu | Val | Val | Ser 335 | Gln |
| Leu | Leu | Arg | Ile 340 | Pro | Gln | Ala | Val | Val 345 | Asp | Met | Val | Ala 350 | Gly | Ala | His |
| Trp | Gly | Val 355 | Leu | Ala | Gly | Leu | Ala 360 | Tyr | Tyr | Ser | Met 365 | Ala | Gly | Asn | Trp |
| Ala | Lys 370 | Val | Leu | Ile | Val | Met 375 | Leu | Leu | Phe | Ala | Gly 380 | Val | Asp | Gly | Asp |
| Thr 385 | His | Val | Thr | Gly | Gly 390 | Ala | Gln | Ala | Lys | Thr 395 | Thr | Asn | Arg | Leu | Val 400 |
| Ser | Met | Phe | Ala | Ser 405 | Gly | Pro | Ser | Gln | Lys 410 | Ile | Gln | Leu | Ile | Asn 415 | Thr |
| Asn | Gly | Ser | Trp 420 | His | Ile | Asn | Arg | Thr 425 | Ala | Leu | Asn | Cys | Asn 430 | Asp | Ser |
| Leu | Gln | Thr 435 | Gly | Phe | Leu | Ala | Ala 440 | Leu | Phe | Tyr | Thr | His 445 | Ser | Phe | Asn |
| Ser | Ser 450 | Gly | Cys | Pro | Glu | Arg 455 | Met | Ala | Gln | Cys | Arg 460 | Thr | Ile | Asp | Lys |
| Phe 465 | Asp | Gln | Gly | Trp | Gly 470 | Pro | Ile | Thr | Tyr | Ala 475 | Glu | Ser | Ser | Arg | Ser 480 |
| Asp | Gln | Arg | Pro | Tyr 485 | Cys | Trp | His | Tyr | Pro 490 | Pro | Pro | Gln | Cys | Thr 495 | Ile |
| Val | Pro | Ala | Ser 500 | Glu | Val | Cys | Gly | Pro 505 | Val | Tyr | Cys | Phe | Thr 510 | Pro | Ser |
| Pro | Val | Val 515 | Val | Gly | Thr | Thr | Asp 520 | Arg | Phe | Gly | Val | Pro 525 | Thr | Tyr | Arg |
| Trp | Gly 530 | Glu | Asn | Glu | Thr | Asp 535 | Val | Leu | Leu | Leu | Asn 540 | Asn | Thr | Arg | Pro |
| Pro 545 | Gln | Gly | Asn | Trp | Phe 550 | Gly | Cys | Thr | Trp | Met 555 | Asn | Ser | Thr | Gly | Phe 560 |
| Thr | Lys | Thr | Cys | Gly 565 | Gly | Pro | Pro | Cys | Asn 570 | Ile | Gly | Gly | Val | Gly 575 | Asn |
| Asn | Thr | Leu | Thr 580 | Cys | Pro | Thr | Asp | Cys 585 | Phe | Arg | Lys | His | Pro 590 | Glu | Ala |
| Thr | Tyr | Thr 595 | Lys | Cys | Gly | Ser | Gly 600 | Pro | Trp | Leu | Thr | Pro 605 | Arg | Cys | Met |
| Val | Asp | Tyr 610 | Pro | Tyr | Arg | Leu | Trp 615 | His | Tyr | Pro | Cys 620 | Thr | Val | Asn | Phe |
| Thr 625 | Ile | Phe | Lys | Val | Arg 630 | Met | Tyr | Val | Gly | Gly 635 | Val | Glu | His | Arg | Leu 640 |
| Asn | Ala | Ala | Cys | Asn 645 | Trp | Thr | Arg | Gly | Glu 650 | Arg | Cys | Asp | Leu | Glu 655 | Asp |
| Arg | Asp | Arg | Pro | Glu 660 | Leu | Ser | Pro | Leu | Leu 665 | Leu | Ser | Thr | Thr 670 | Glu | Trp |

```
Gln  Val  Leu  Pro  Cys  Ser  Phe  Thr  Thr  Leu  Pro  Ala  Leu  Ser  Thr  Gly
          675                 680                 685

Leu  Ile  His  Leu  His  Gln  Asn  Ile  Val  Asp  Val  Gln  Tyr  Leu  Tyr  Gly
          690                 695                 700

Ile  Gly  Ser  Ala  Val  Val  Ser  Phe  Ala  Ile  Lys  Trp  Glu  Tyr  Val  Leu
705                      710                 715                           720

Leu  Leu  Phe  Leu  Leu  Leu  Ala  Asp  Ala  Arg  Val  Cys  Ala  Cys  Leu  Trp
               725                 730                      735

Met  Met  Leu  Leu  Ile  Ala  Gln  Ala  Glu  Ala  Ala  Leu  Glu  Asn  Leu  Val
          740                 745                 750

Val  Leu  Asn  Ser  Ala  Ser  Val  Ala  Gly  Ala  His  Gly  Ile  Leu  Ser  Phe
          755                 760                 765

Leu  Val  Phe  Phe  Cys  Ala  Ala  Trp  Tyr  Ile  Lys  Gly  Arg  Leu  Val  Pro
          770                 775                 780

Gly  Ala  Thr  Tyr  Ala  Leu  Tyr  Gly  Val  Trp  Pro  Leu  Leu  Leu  Leu  Leu
785                      790                 795                           800

Leu  Ala  Leu  Pro  Pro  Arg  Ala  Tyr  Ala  Met  Asp  Arg  Glu  Met  Ala  Ala
               805                 810                      815

Ser  Cys  Gly  Gly  Ala  Val  Phe  Val  Gly  Leu  Val  Leu  Leu  Thr  Leu  Ser
          820                 825                 830

Pro  Tyr  Tyr  Lys  Val  Phe  Leu  Ala  Arg  Leu  Ile  Trp  Trp  Leu  Gln  Tyr
          835                 840                 845

Phe  Thr  Thr  Arg  Ala  Glu  Ala  Asp  Leu  His  Val  Trp  Ile  Pro  Pro  Leu
     850                 855                 860

Asn  Ala  Arg  Gly  Gly  Arg  Asp  Ala  Ile  Ile  Leu  Leu  Met  Cys  Ala  Val
865                      870                 875                           880

His  Pro  Glu  Leu  Ile  Phe  Asp  Ile  Thr  Lys  Leu  Leu  Ile  Ala  Ile  Leu
               885                 890                      895

Gly  Pro  Leu  Met  Val  Leu  Gln  Ala  Gly  Ile  Thr  Arg  Val  Pro  Tyr  Phe
          900                 905                 910

Val  Arg  Ala  Gln  Gly  Leu  Ile  His  Ala  Cys  Met  Leu  Val  Arg  Lys  Val
          915                 920                 925

Ala  Gly  Gly  His  Tyr  Val  Gln  Met  Ala  Phe  Met  Lys  Leu  Gly  Ala  Leu
          930                 935                 940

Thr  Gly  Thr  Tyr  Ile  Tyr  Asn  His  Leu  Thr  Pro  Leu  Arg  Asp  Trp  Pro
945                      950                 955                           960

Arg  Ala  Gly  Leu  Arg  Asp  Leu  Ala  Val  Ala  Val  Glu  Pro  Val  Val  Phe
               965                 970                      975

Ser  Asp  Met  Glu  Thr  Lys  Ile  Ile  Thr  Trp  Gly  Ala  Asp  Thr  Ala  Ala
          980                 985                 990

Cys  Gly  Asp  Ile  Ile  Leu  Gly  Leu  Pro  Val  Ser  Ala  Arg  Arg  Gly  Lys
          995                 1000                1005

Glu  Ile  Leu  Leu  Gly  Pro  Ala  Asp  Ser  Leu  Glu  Gly  Arg  Gly  Leu  Arg
     1010                1015                1020

Leu  Leu  Ala  Pro  Ile  Thr  Ala  Tyr  Ser  Gln  Gln  Thr  Arg  Gly  Leu  Leu
1025                     1030                1035                          1040

Gly  Cys  Ile  Ile  Thr  Ser  Leu  Thr  Gly  Arg  Asp  Lys  Asn  Gln  Val  Glu
               1045                1050                     1055

Gly  Glu  Val  Gln  Val  Val  Ser  Thr  Ala  Thr  Gln  Ser  Phe  Leu  Ala  Thr
          1060                1065                1070

Cys  Val  Asn  Gly  Val  Cys  Trp  Thr  Val  Tyr  His  Gly  Ala  Gly  Ser  Lys
          1075                1080                1085

Thr  Leu  Ala  Ala  Pro  Lys  Gly  Pro  Ile  Thr  Gln  Met  Tyr  Thr  Asn  Val
```

-continued

|   |   |   |   |   |   |   |   |   |   |   |   |   |   |
|---|---|---|---|---|---|---|---|---|---|---|---|---|---|
|   | 1090 |   |   |   | 1095 |   |   |   | 1100 |   |   |   |   |
| Asp | Gln | Asp | Leu | Val | Gly | Trp | Pro | Lys | Pro | Pro | Gly | Ala | Arg | Ser | Leu |
| 1105 |   |   |   | 1110 |   |   |   | 1115 |   |   |   |   | 1120 |
| Thr | Pro | Cys | Thr | Cys | Gly | Ser | Ser | Asp | Leu | Tyr | Leu | Val | Thr | Arg | His |
|   |   |   | 1125 |   |   |   | 1130 |   |   |   | 1135 |
| Ala | Asp | Val | Ile | Pro | Val | Arg | Arg | Arg | Gly | Asp | Ser | Arg | Gly | Ser | Leu |
|   |   |   | 1140 |   |   |   | 1145 |   |   |   | 1150 |
| Leu | Ser | Pro | Arg | Pro | Val | Ser | Tyr | Leu | Lys | Gly | Ser | Ser | Gly | Gly | Pro |
|   |   | 1155 |   |   |   | 1160 |   |   |   | 1165 |
| Leu | Leu | Cys | Pro | Phe | Gly | His | Ala | Val | Gly | Ile | Phe | Arg | Ala | Ala | Val |
|   | 1170 |   |   |   | 1175 |   |   |   | 1180 |
| Cys | Thr | Arg | Gly | Val | Ala | Lys | Ala | Val | Asp | Phe | Val | Pro | Val | Glu | Ser |
| 1185 |   |   |   | 1190 |   |   |   | 1195 |   |   |   |   | 1200 |
| Met | Glu | Thr | Thr | Met | Arg | Ser | Pro | Val | Phe | Thr | Asp | Asn | Ser | Ser | Pro |
|   |   |   | 1205 |   |   |   | 1210 |   |   |   | 1215 |
| Pro | Ala | Val | Pro | Gln | Ser | Phe | Gln | Val | Ala | His | Leu | His | Ala | Pro | Thr |
|   |   |   | 1220 |   |   |   | 1225 |   |   |   | 1230 |
| Gly | Ser | Gly | Lys | Ser | Thr | Lys | Val | Pro | Ala | Ala | Tyr | Ala | Ala | Gln | Gly |
|   |   | 1235 |   |   |   | 1240 |   |   |   | 1245 |
| Tyr | Lys | Val | Leu | Val | Leu | Asn | Pro | Ser | Val | Ala | Ala | Thr | Leu | Gly | Phe |
|   | 1250 |   |   |   | 1255 |   |   |   | 1260 |
| Gly | Ala | Tyr | Met | Ser | Lys | Ala | His | Gly | Ile | Asp | Pro | Asn | Ile | Arg | Thr |
| 1265 |   |   |   | 1270 |   |   |   | 1275 |   |   |   |   | 1280 |
| Gly | Val | Arg | Thr | Ile | Thr | Thr | Gly | Ala | Pro | Val | Thr | Tyr | Ser | Thr | Tyr |
|   |   |   | 1285 |   |   |   | 1290 |   |   |   | 1295 |
| Gly | Lys | Phe | Leu | Ala | Asp | Gly | Gly | Cys | Ser | Gly | Gly | Ala | Tyr | Asp | Ile |
|   |   | 1300 |   |   |   | 1305 |   |   |   | 1310 |
| Ile | Ile | Cys | Asp | Glu | Cys | His | Ser | Thr | Asp | Ser | Thr | Thr | Ile | Leu | Gly |
|   |   | 1315 |   |   |   | 1320 |   |   |   | 1325 |
| Ile | Gly | Thr | Val | Leu | Asp | Gln | Ala | Glu | Thr | Ala | Gly | Ala | Arg | Leu | Val |
|   |   | 1330 |   |   |   | 1335 |   |   |   | 1340 |
| Val | Leu | Ala | Thr | Ala | Thr | Pro | Pro | Gly | Ser | Val | Thr | Val | Pro | His | Pro |
| 1345 |   |   |   | 1350 |   |   |   | 1355 |   |   |   |   | 1360 |
| Asn | Ile | Glu | Glu | Val | Ala | Leu | Ser | Asn | Thr | Gly | Glu | Ile | Pro | Phe | Tyr |
|   |   |   | 1365 |   |   |   | 1370 |   |   |   | 1375 |
| Gly | Lys | Ala | Ile | Pro | Ile | Glu | Ala | Ile | Arg | Gly | Gly | Arg | His | Leu | Ile |
|   |   |   | 1380 |   |   |   | 1385 |   |   |   | 1390 |
| Phe | Cys | His | Ser | Lys | Lys | Lys | Cys | Asp | Glu | Leu | Ala | Ala | Lys | Leu | Ser |
|   |   |   | 1395 |   |   |   | 1400 |   |   |   | 1405 |
| Gly | Leu | Gly | Ile | Asn | Ala | Val | Ala | Tyr | Tyr | Arg | Gly | Leu | Asp | Val | Ser |
|   | 1410 |   |   |   | 1415 |   |   |   | 1420 |
| Val | Ile | Pro | Thr | Ile | Gly | Asp | Val | Val | Val | Ala | Thr | Asp | Ala | Leu |
| 1425 |   |   |   | 1430 |   |   |   | 1435 |   |   |   |   | 1440 |
| Met | Thr | Gly | Tyr | Thr | Gly | Asp | Phe | Asp | Ser | Val | Ile | Asp | Cys | Asn | Thr |
|   |   |   | 1445 |   |   |   | 1450 |   |   |   | 1455 |
| Cys | Val | Thr | Gln | Thr | Val | Asp | Phe | Ser | Leu | Asp | Pro | Thr | Phe | Thr | Ile |
|   |   |   | 1460 |   |   |   | 1465 |   |   |   | 1470 |
| Glu | Thr | Thr | Thr | Val | Pro | Gln | Asp | Ala | Val | Ser | Arg | Ser | Gln | Arg | Arg |
|   |   | 1475 |   |   |   | 1480 |   |   |   | 1485 |
| Gly | Arg | Thr | Gly | Arg | Gly | Arg | Arg | Gly | Ile | Tyr | Arg | Phe | Val | Thr | Pro |
|   | 1490 |   |   |   | 1495 |   |   |   | 1500 |
| Gly | Glu | Arg | Pro | Ser | Gly | Met | Phe | Asp | Ser | Ser | Val | Leu | Cys | Glu | Cys |
| 1505 |   |   |   | 1510 |   |   |   | 1515 |   |   |   |   | 1520 |

Tyr Asp Ala Gly Cys Ala Trp Tyr Glu Leu Thr Pro Ala Glu Thr Ser
                1525                    1530                    1535

Val Arg Leu Arg Ala Tyr Leu Asn Thr Pro Gly Leu Pro Val Cys Gln
                1540                    1545                    1550

Asp His Leu Glu Phe Trp Glu Ser Val Phe Thr Gly Leu Thr His Ile
            1555                    1560                    1565

Asp Ala His Phe Leu Ser Gln Thr Lys Gln Ala Gly Asp Asn Phe Pro
            1570                    1575                    1580

Tyr Leu Val Ala Tyr Gln Ala Thr Val Cys Ala Arg Ala Gln Ala Pro
1585                    1590                    1595                    1600

Pro Pro Ser Trp Asp Gln Met Trp Lys Cys Leu Ile Arg Leu Lys Pro
                1605                    1610                    1615

Thr Leu His Gly Pro Thr Pro Leu Leu Tyr Arg Leu Gly Ala Val Gln
                1620                    1625                    1630

Asn Glu Val Thr Leu Thr His Pro Ile Thr Lys Tyr Ile Met Ala Cys
                1635                    1640                    1645

Met Ser Ala Asp Leu Glu Val Val Thr Ser Thr Trp Val Leu Val Gly
                1650                    1655                    1660

Gly Val Leu Ala Ala Leu Ala Ala Tyr Cys Leu Thr Thr Gly Ser Val
1665                    1670                    1675                    1680

Val Ile Val Gly Arg Ile Ile Leu Ser Gly Arg Pro Ala Ile Val Pro
                1685                    1690                    1695

Asp Arg Glu Leu Leu Tyr Gln Glu Phe Asp Glu Met Glu Glu Cys Ala
                1700                    1705                    1710

Ser His Leu Pro Tyr Ile Glu Gln Gly Met Gln Leu Ala Glu Gln Phe
            1715                    1720                    1725

Lys Gln Lys Ala Leu Gly Leu Leu Gln Thr Ala Thr Lys Gln Ala Glu
            1730                    1735                    1740

Ala Ala Ala Pro Val Val Glu Ser Lys Trp Arg Ala Leu Glu Thr Phe
1745                    1750                    1755                    1760

Trp Ala Lys His Met Trp Asn Phe Ile Ser Gly Ile Gln Tyr Leu Ala
                1765                    1770                    1775

Gly Leu Ser Thr Leu Pro Gly Asn Pro Ala Ile Ala Ser Leu Met Ala
            1780                    1785                    1790

Phe Thr Ala Ser Ile Thr Ser Pro Leu Thr Thr Gln Ser Thr Leu Leu
            1795                    1800                    1805

Phe Asn Ile Leu Gly Gly Trp Val Ala Ala Gln Leu Ala Pro Pro Ser
            1810                    1815                    1820

Ala Ala Ser Ala Phe Val Gly Ala Gly Ile Ala Gly Ala Ala Val Gly
1825                    1830                    1835                    1840

Ser Ile Gly Leu Gly Lys Val Leu Val Asp Ile Leu Ala Gly Tyr Gly
                1845                    1850                    1855

Ala Gly Val Ala Gly Ala Leu Val Ala Phe Lys Val Met Ser Gly Glu
            1860                    1865                    1870

Met Pro Ser Thr Glu Asp Leu Val Asn Leu Leu Pro Ala Ile Leu Ser
            1875                    1880                    1885

Pro Gly Ala Leu Val Val Gly Val Val Cys Ala Ala Ile Leu Arg Arg
            1890                    1895                    1900

His Val Gly Pro Gly Glu Gly Ala Val Gln Trp Met Asn Arg Leu Ile
1905                    1910                    1915                    1920

Ala Phe Ala Ser Arg Gly Asn His Val Ser Pro Thr His Tyr Val Pro
                1925                    1930                    1935

Glu Ser Asp Ala Ala Ala Arg Val Thr Gln Ile Leu Ser Ser Leu Thr
                1940                    1945                    1950

```
Ile Thr Gln Leu Leu Lys Arg Leu His Gln Trp Ile Asn Glu Asp Cys
         1955                1960                1965

Ser Thr Pro Cys Ser Gly Ser Trp Leu Arg Asp Val Trp Asp Trp Ile
         1970                1975                1980

Cys Thr Val Leu Thr Asp Phe Lys Thr Trp Leu Gln Ser Lys Leu Leu
1985                1990                1995                2000

Pro Gln Leu Pro Gly Val Pro Phe Phe Ser Cys Gln Arg
              2005                2010
```

(2) INFORMATION FOR SEQ ID NO:13:

(i) SEQUENCE CHARACTERISTICS:
        (A) LENGTH: 9030 base pairs
        (B) TYPE: nucleic acid
        (C) STRANDEDNESS: single
        (D) TOPOLOGY: linear (ii) MOLECULE TYPE: cDNA from genomic RNA (ix) FEATURE:
        (A) NAME/KEY: misc_feature
        (B) LOCATION: 1..9030
        (D) OTHER INFORMATION: /note: "sequence = 333 - 9362 of
            SEQ ID NO: 1"

(ix) FEATURE:
        (A) NAME/KEY: CDS
        (B) LOCATION: 1..9030

(xi) SEQUENCE DESCRIPTION: SEQ ID NO:13:

```
ATG AGC ACG AAT CCT AAA CCT CAA AGA AAA ACC AAA CGT AAC ACC AAC        48
Met Ser Thr Asn Pro Lys Pro Gln Arg Lys Thr Lys Arg Asn Thr Asn
 1               5                  10                  15

CGC CGC CCA CAG GAC GTC AAG TTC CCG GGC GGT GGT CAG ATC GTT GGT        96
Arg Arg Pro Gln Asp Val Lys Phe Pro Gly Gly Gly Gln Ile Val Gly
             20                  25                  30

GGA GTT TAC CTG TTG CCG CGC AGG GGC CCC AGG TTG GGT GTG CGC GCG       144
Gly Val Tyr Leu Leu Pro Arg Arg Gly Pro Arg Leu Gly Val Arg Ala
         35                  40                  45

CCC AGG AAG ACT TCC GAG CGG TCG CAA CCT CGT GGA AGG CGA CAA CCT       192
Pro Arg Lys Thr Ser Glu Arg Ser Gln Pro Arg Gly Arg Arg Gln Pro
     50                  55                  60

ATC CCC AAG GCT CGC CGG CCC GAG GGC AGG ACC TGG GCT CAG CCC GGG       240
Ile Pro Lys Ala Arg Arg Pro Glu Gly Arg Thr Trp Ala Gln Pro Gly
 65                  70                  75                  80

TAC CCT TGG CCT CTC TAT GGC AAT GAG GGC TTA GGG TGG GCA GGA TGG       288
Tyr Pro Trp Pro Leu Tyr Gly Asn Glu Gly Leu Gly Trp Ala Gly Trp
                 85                  90                  95

CTC CTG TCA CCC CGC GGC TCC CGG CCT AGT TGG GGC CCC ACG GAC CCC       336
Leu Leu Ser Pro Arg Gly Ser Arg Pro Ser Trp Gly Pro Thr Asp Pro
            100                 105                 110

CGG CGT AGG TCG CGT AAT TTG GGT AAG GTC ATC GAT ACC CTC ACA TGC       384
Arg Arg Arg Ser Arg Asn Leu Gly Lys Val Ile Asp Thr Leu Thr Cys
        115                 120                 125

GGC TTC GCC GAT CTC ATG GGG TAC ATT CCG CTC GTC GGC GCC CCC CTG       432
Gly Phe Ala Asp Leu Met Gly Tyr Ile Pro Leu Val Gly Ala Pro Leu
    130                 135                 140

GGG GGC GCT GCC AGG GCC CTG GCA CAT GGT GTC CGG GTT CTG GAG GAC       480
Gly Gly Ala Ala Arg Ala Leu Ala His Gly Val Arg Val Leu Glu Asp
145                 150                 155                 160

GGC GTG AAC TAT GCA ACA GGG AAT CTG CCC GGT TGC TCT TTT TCT ATC       528
Gly Val Asn Tyr Ala Thr Gly Asn Leu Pro Gly Cys Ser Phe Ser Ile
                165                 170                 175
```

| | | | | | | | | | | | | | | | | |
|---|---|---|---|---|---|---|---|---|---|---|---|---|---|---|---|---|
| TTC | CTC | TTG | GCT | CTG | CTG | TCC | TGC | CTG | ACC | ACC | CCA | GCT | TCC | GCT | TAC | 576 |
| Phe | Leu | Leu | Ala | Leu | Leu | Ser | Cys | Leu | Thr | Thr | Pro | Ala | Ser | Ala | Tyr | |
| | | 180 | | | | | 185 | | | | | | 190 | | | |
| GAA | GTG | CAC | AAC | GTG | TCC | GGG | ATA | TAT | CAT | GTC | ACG | AAC | GAC | TGC | TCC | 624 |
| Glu | Val | His | Asn | Val | Ser | Gly | Ile | Tyr | His | Val | Thr | Asn | Asp | Cys | Ser | |
| | | 195 | | | | | 200 | | | | | 205 | | | | |
| AAC | GCA | AGC | ATT | GTG | TAT | GAG | GCA | GCG | GAC | TTG | ATC | ATG | CAT | ACT | CCT | 672 |
| Asn | Ala | Ser | Ile | Val | Tyr | Glu | Ala | Ala | Asp | Leu | Ile | Met | His | Thr | Pro | |
| | 210 | | | | | 215 | | | | | 220 | | | | | |
| GGG | TGC | GTG | CCC | TGC | GTT | CGG | GAA | GGC | AAC | TCC | TCC | CGC | TGC | TGG | GTA | 720 |
| Gly | Cys | Val | Pro | Cys | Val | Arg | Glu | Gly | Asn | Ser | Ser | Arg | Cys | Trp | Val | |
| 225 | | | | | 230 | | | | | 235 | | | | | 240 | |
| GCG | CTC | ACT | CCC | ACG | CTC | GCA | GCC | AGG | AAC | GTC | ACC | ATC | CCC | ACC | ACG | 768 |
| Ala | Leu | Thr | Pro | Thr | Leu | Ala | Ala | Arg | Asn | Val | Thr | Ile | Pro | Thr | Thr | |
| | | | | 245 | | | | | 250 | | | | | 255 | | |
| ACG | ATA | CGA | CGC | CAC | GTC | GAT | CTG | CTC | GTT | GGG | GCG | GCT | GCT | TTC | TGT | 816 |
| Thr | Ile | Arg | Arg | His | Val | Asp | Leu | Leu | Val | Gly | Ala | Ala | Ala | Phe | Cys | |
| | | | 260 | | | | | 265 | | | | | 270 | | | |
| TCC | GCT | ATG | TAC | GTG | GGG | GAC | CTC | TGC | GGA | TCT | GTT | TTC | CTC | GTC | TCT | 864 |
| Ser | Ala | Met | Tyr | Val | Gly | Asp | Leu | Cys | Gly | Ser | Val | Phe | Leu | Val | Ser | |
| | | 275 | | | | | 280 | | | | | 285 | | | | |
| CAG | CTG | TTC | ACC | TTC | TCG | CCT | CGC | CGG | CAT | GTG | ACA | TTA | CAG | GAC | TGT | 912 |
| Gln | Leu | Phe | Thr | Phe | Ser | Pro | Arg | Arg | His | Val | Thr | Leu | Gln | Asp | Cys | |
| | 290 | | | | | 295 | | | | | 300 | | | | | |
| AAC | TGC | TCA | ATT | TAT | CCC | GGC | CAT | GTG | TCG | GGT | CAC | CGT | ATG | GCT | TGG | 960 |
| Asn | Cys | Ser | Ile | Tyr | Pro | Gly | His | Val | Ser | Gly | His | Arg | Met | Ala | Trp | |
| 305 | | | | | 310 | | | | | 315 | | | | | 320 | |
| GAC | ATG | ATG | ATG | AAC | TGG | TCG | CCC | ACA | ACA | GCC | CTA | GTG | GTG | TCG | CAG | 1008 |
| Asp | Met | Met | Met | Asn | Trp | Ser | Pro | Thr | Thr | Ala | Leu | Val | Val | Ser | Gln | |
| | | | | 325 | | | | | 330 | | | | | 335 | | |
| TTA | CTC | CGG | ATC | CCA | CAA | GCC | GTC | GTG | GAC | ATG | GTG | GCG | GGG | GCC | CAC | 1056 |
| Leu | Leu | Arg | Ile | Pro | Gln | Ala | Val | Val | Asp | Met | Val | Ala | Gly | Ala | His | |
| | | | 340 | | | | | 345 | | | | | 350 | | | |
| TGG | GGA | GTC | CTG | GCG | GGC | CTT | GCC | TAC | TAT | TCC | ATG | GCG | GGG | AAC | TGG | 1104 |
| Trp | Gly | Val | Leu | Ala | Gly | Leu | Ala | Tyr | Tyr | Ser | Met | Ala | Gly | Asn | Trp | |
| | | 355 | | | | | 360 | | | | | 365 | | | | |
| GCT | AAG | GTT | CTG | ATT | GTG | ATG | CTA | CTT | TTT | GCT | GGC | GTT | GAC | GGG | GAT | 1152 |
| Ala | Lys | Val | Leu | Ile | Val | Met | Leu | Leu | Phe | Ala | Gly | Val | Asp | Gly | Asp | |
| | 370 | | | | | 375 | | | | | 380 | | | | | |
| ACC | CAC | GTG | ACA | GGG | GGG | GCG | CAA | GCC | AAA | ACC | ACC | AAC | AGG | CTC | GTG | 1200 |
| Thr | His | Val | Thr | Gly | Gly | Ala | Gln | Ala | Lys | Thr | Thr | Asn | Arg | Leu | Val | |
| 385 | | | | | 390 | | | | | 395 | | | | | 400 | |
| TCC | ATG | TTC | GCA | AGT | GGG | CCG | TCT | CAG | AAA | ATC | CAG | CTT | ATA | AAC | ACC | 1248 |
| Ser | Met | Phe | Ala | Ser | Gly | Pro | Ser | Gln | Lys | Ile | Gln | Leu | Ile | Asn | Thr | |
| | | | | 405 | | | | | 410 | | | | | 415 | | |
| AAT | GGG | AGT | TGG | CAC | ATC | AAC | AGG | ACT | GCC | CTG | AAC | TGC | AAT | GAC | TCT | 1296 |
| Asn | Gly | Ser | Trp | His | Ile | Asn | Arg | Thr | Ala | Leu | Asn | Cys | Asn | Asp | Ser | |
| | | | 420 | | | | | 425 | | | | | 430 | | | |
| CTC | CAG | ACT | GGG | TTT | CTT | GCC | GCG | CTG | TTC | TAC | ACA | CAT | AGT | TTC | AAC | 1344 |
| Leu | Gln | Thr | Gly | Phe | Leu | Ala | Ala | Leu | Phe | Tyr | Thr | His | Ser | Phe | Asn | |
| | | 435 | | | | | 440 | | | | | 445 | | | | |
| TCG | TCC | GGG | TGC | CCA | GAG | CGC | ATG | GCC | CAG | TGC | CGC | ACC | ATT | GAC | AAG | 1392 |
| Ser | Ser | Gly | Cys | Pro | Glu | Arg | Met | Ala | Gln | Cys | Arg | Thr | Ile | Asp | Lys | |
| | 450 | | | | | 455 | | | | | 460 | | | | | |
| TTC | GAC | CAG | GGA | TGG | GGT | CCC | ATT | ACT | TAT | GCT | GAG | TCT | AGC | AGA | TCA | 1440 |
| Phe | Asp | Gln | Gly | Trp | Gly | Pro | Ile | Thr | Tyr | Ala | Glu | Ser | Ser | Arg | Ser | |
| 465 | | | | | 470 | | | | | 475 | | | | | 480 | |
| GAC | CAG | AGG | CCA | TAT | TGC | TGG | CAC | TAC | CCA | CCT | CCA | CAA | TGT | ACC | ATC | 1488 |
| Asp | Gln | Arg | Pro | Tyr | Cys | Trp | His | Tyr | Pro | Pro | Pro | Gln | Cys | Thr | Ile | |
| | | | | 485 | | | | | 490 | | | | | 495 | | |

| | | | | | | | | | | | | | | | | |
|---|---|---|---|---|---|---|---|---|---|---|---|---|---|---|---|---|
| GTA | CCT | GCG | TCG | GAG | GTG | TGC | GGC | CCA | GTG | TAC | TGC | TTC | ACC | CCA | AGC | 1536 |
| Val | Pro | Ala | Ser | Glu | Val | Cys | Gly | Pro | Val | Tyr | Cys | Phe | Thr | Pro | Ser | |
| | | | 500 | | | | 505 | | | | | 510 | | | | |
| CCT | GTC | GTC | GTG | GGG | ACG | ACC | GAT | CGT | TTC | GGT | GTC | CCT | ACG | TAT | AGA | 1584 |
| Pro | Val | Val | Val | Gly | Thr | Thr | Asp | Arg | Phe | Gly | Val | Pro | Thr | Tyr | Arg | |
| | | 515 | | | | 520 | | | | | 525 | | | | | |
| TGG | GGG | GAG | AAC | GAG | ACT | GAC | GTG | CTG | CTG | CTC | AAC | AAC | ACG | CGG | CCG | 1632 |
| Trp | Gly | Glu | Asn | Glu | Thr | Asp | Val | Leu | Leu | Leu | Asn | Asn | Thr | Arg | Pro | |
| | 530 | | | | | 535 | | | | | 540 | | | | | |
| CCG | CAA | GGC | AAC | TGG | TTC | GGC | TGC | ACA | TGG | ATG | AAT | AGC | ACC | GGG | TTC | 1680 |
| Pro | Gln | Gly | Asn | Trp | Phe | Gly | Cys | Thr | Trp | Met | Asn | Ser | Thr | Gly | Phe | |
| 545 | | | | | 550 | | | | | 555 | | | | | 560 | |
| ACC | AAG | ACA | TGT | GGG | GGG | CCC | CCG | TGT | AAC | ATC | GGG | GGG | GTC | GGC | AAC | 1728 |
| Thr | Lys | Thr | Cys | Gly | Gly | Pro | Pro | Cys | Asn | Ile | Gly | Gly | Val | Gly | Asn | |
| | | | | 565 | | | | | 570 | | | | | 575 | | |
| AAC | ACC | CTG | ACC | TGC | CCC | ACG | GAC | TGC | TTC | CGG | AAG | CAC | CCC | GAG | GCT | 1776 |
| Asn | Thr | Leu | Thr | Cys | Pro | Thr | Asp | Cys | Phe | Arg | Lys | His | Pro | Glu | Ala | |
| | | | 580 | | | | | 585 | | | | | 590 | | | |
| ACC | TAC | ACA | AAA | TGT | GGT | TCG | GGG | CCT | TGG | CTG | ACA | CCT | AGG | TGC | ATG | 1824 |
| Thr | Tyr | Thr | Lys | Cys | Gly | Ser | Gly | Pro | Trp | Leu | Thr | Pro | Arg | Cys | Met | |
| | | 595 | | | | | 600 | | | | | 605 | | | | |
| GTT | GAC | TAT | CCA | TAC | AGG | CTC | TGG | CAT | TAC | CCC | TGC | ACT | GTT | AAC | TTT | 1872 |
| Val | Asp | Tyr | Pro | Tyr | Arg | Leu | Trp | His | Tyr | Pro | Cys | Thr | Val | Asn | Phe | |
| | 610 | | | | | 615 | | | | | 620 | | | | | |
| ACC | ATC | TTC | AAG | GTT | AGG | ATG | TAT | GTG | GGG | GGG | GTG | GAG | CAC | AGG | CTC | 1920 |
| Thr | Ile | Phe | Lys | Val | Arg | Met | Tyr | Val | Gly | Gly | Val | Glu | His | Arg | Leu | |
| 625 | | | | | 630 | | | | | 635 | | | | | 640 | |
| AAT | GCT | GCA | TGC | AAT | TGG | ACC | CGA | GGA | GAG | CGT | TGT | GAC | TTG | GAG | GAC | 1968 |
| Asn | Ala | Ala | Cys | Asn | Trp | Thr | Arg | Gly | Glu | Arg | Cys | Asp | Leu | Glu | Asp | |
| | | | | 645 | | | | | 650 | | | | | 655 | | |
| AGG | GAT | AGG | CCG | GAG | CTC | AGC | CCG | CTG | CTG | CTG | TCT | ACA | ACA | GAG | TGG | 2016 |
| Arg | Asp | Arg | Pro | Glu | Leu | Ser | Pro | Leu | Leu | Leu | Ser | Thr | Thr | Glu | Trp | |
| | | | 660 | | | | | 665 | | | | | 670 | | | |
| CAG | GTA | CTG | CCC | TGT | TCC | TTC | ACC | ACC | CTA | CCA | GCT | CTG | TCC | ACT | GGC | 2064 |
| Gln | Val | Leu | Pro | Cys | Ser | Phe | Thr | Thr | Leu | Pro | Ala | Leu | Ser | Thr | Gly | |
| | | 675 | | | | | 680 | | | | | 685 | | | | |
| TTG | ATT | CAC | CTC | CAT | CAG | AAC | ATC | GTG | GAC | GTG | CAA | TAC | CTA | TAC | GGT | 2112 |
| Leu | Ile | His | Leu | His | Gln | Asn | Ile | Val | Asp | Val | Gln | Tyr | Leu | Tyr | Gly | |
| | 690 | | | | | 695 | | | | | 700 | | | | | |
| ATA | GGG | TCA | GCG | GTT | GTC | TCC | TTT | GCA | ATC | AAA | TGG | GAG | TAT | GTC | CTG | 2160 |
| Ile | Gly | Ser | Ala | Val | Val | Ser | Phe | Ala | Ile | Lys | Trp | Glu | Tyr | Val | Leu | |
| 705 | | | | | 710 | | | | | 715 | | | | | 720 | |
| TTG | CTT | TTC | CTT | CTC | CTA | GCG | GAC | GCA | CGT | GTC | TGT | GCC | TGC | TTG | TGG | 2208 |
| Leu | Leu | Phe | Leu | Leu | Leu | Ala | Asp | Ala | Arg | Val | Cys | Ala | Cys | Leu | Trp | |
| | | | | 725 | | | | | 730 | | | | | 735 | | |
| ATG | ATG | CTG | CTG | ATA | GCC | CAG | GCC | GAG | GCC | GCC | TTG | GAG | AAC | CTG | GTG | 2256 |
| Met | Met | Leu | Leu | Ile | Ala | Gln | Ala | Glu | Ala | Ala | Leu | Glu | Asn | Leu | Val | |
| | | | 740 | | | | | 745 | | | | | 750 | | | |
| GTC | CTC | AAT | TCG | GCG | TCT | GTG | GCC | GGC | GCA | CAT | GGC | ATC | CTC | TCC | TTC | 2304 |
| Val | Leu | Asn | Ser | Ala | Ser | Val | Ala | Gly | Ala | His | Gly | Ile | Leu | Ser | Phe | |
| | | 755 | | | | | 760 | | | | | 765 | | | | |
| CTT | GTG | TTC | TTC | TGT | GCC | GCC | TGG | TAC | ATC | AAA | GGC | AGG | CTG | GTC | CCT | 2352 |
| Leu | Val | Phe | Phe | Cys | Ala | Ala | Trp | Tyr | Ile | Lys | Gly | Arg | Leu | Val | Pro | |
| | 770 | | | | | 775 | | | | | 780 | | | | | |
| GGG | GCG | ACA | TAT | GCT | CTT | TAT | GGC | GTG | TGG | CCG | CTC | CTC | CTG | CTC | TTG | 2400 |
| Gly | Ala | Thr | Tyr | Ala | Leu | Tyr | Gly | Val | Trp | Pro | Leu | Leu | Leu | Leu | Leu | |
| 785 | | | | | 790 | | | | | 795 | | | | | 800 | |
| CTG | GCA | TTA | CCA | CCG | CGA | GCT | TAC | GCC | ATG | GAC | CGG | GAG | ATG | GCT | GCA | 2448 |
| Leu | Ala | Leu | Pro | Pro | Arg | Ala | Tyr | Ala | Met | Asp | Arg | Glu | Met | Ala | Ala | |
| | | | | 805 | | | | | 810 | | | | | 815 | | |

-continued

| | | | | | | | | | | | | | | | | |
|---|---|---|---|---|---|---|---|---|---|---|---|---|---|---|---|---|
| TCG | TGC | GGA | GGC | GCG | GTT | TTT | GTG | GGT | CTG | GTA | CTC | CTG | ACT | TTG | TCA | 2496 |
| Ser | Cys | Gly | Gly | Ala | Val | Phe | Val | Gly | Leu | Val | Leu | Leu | Thr | Leu | Ser | |
| | | 820 | | | | | 825 | | | | | 830 | | | | |
| CCA | TAC | TAC | AAG | GTG | TTC | CTC | GCT | AGG | CTC | ATA | TGG | TGG | TTA | CAA | TAT | 2544 |
| Pro | Tyr | Tyr | Lys | Val | Phe | Leu | Ala | Arg | Leu | Ile | Trp | Trp | Leu | Gln | Tyr | |
| | | 835 | | | | 840 | | | | | 845 | | | | | |
| TTT | ACC | ACC | AGA | GCC | GAG | GCG | GAC | TTA | CAT | GTG | TGG | ATC | CCC | CCC | CTC | 2592 |
| Phe | Thr | Thr | Arg | Ala | Glu | Ala | Asp | Leu | His | Val | Trp | Ile | Pro | Pro | Leu | |
| | 850 | | | | | 855 | | | | 860 | | | | | | |
| AAC | GCT | CGG | GGA | GGC | CGC | GAT | GCC | ATC | ATC | CTC | CTC | ATG | TGC | GCA | GTC | 2640 |
| Asn | Ala | Arg | Gly | Gly | Arg | Asp | Ala | Ile | Ile | Leu | Leu | Met | Cys | Ala | Val | |
| 865 | | | | 870 | | | | | 875 | | | | | | 880 | |
| CAT | CCA | GAG | CTA | ATC | TTT | GAC | ATC | ACC | AAA | CTT | CTA | ATT | GCC | ATA | CTC | 2688 |
| His | Pro | Glu | Leu | Ile | Phe | Asp | Ile | Thr | Lys | Leu | Leu | Ile | Ala | Ile | Leu | |
| | | | | 885 | | | | 890 | | | | | | 895 | | |
| GGT | CCG | CTC | ATG | GTG | CTC | CAA | GCT | GGC | ATA | ACC | AGA | GTG | CCG | TAC | TTC | 2736 |
| Gly | Pro | Leu | Met | Val | Leu | Gln | Ala | Gly | Ile | Thr | Arg | Val | Pro | Tyr | Phe | |
| | | | 900 | | | | | 905 | | | | | 910 | | | |
| GTG | CGC | GCT | CAA | GGG | CTC | ATT | CAT | GCA | TGC | ATG | TTA | GTG | CGG | AAG | GTC | 2784 |
| Val | Arg | Ala | Gln | Gly | Leu | Ile | His | Ala | Cys | Met | Leu | Val | Arg | Lys | Val | |
| | | 915 | | | | | 920 | | | | | 925 | | | | |
| GCT | GGG | GGT | CAT | TAT | GTC | CAA | ATG | GCC | TTC | ATG | AAG | CTG | GGC | GCG | CTG | 2832 |
| Ala | Gly | Gly | His | Tyr | Val | Gln | Met | Ala | Phe | Met | Lys | Leu | Gly | Ala | Leu | |
| | 930 | | | | | 935 | | | | | 940 | | | | | |
| ACA | GGC | ACG | TAC | ATT | TAC | AAC | CAT | CTT | ACC | CCG | CTA | CGG | GAT | TGG | CCA | 2880 |
| Thr | Gly | Thr | Tyr | Ile | Tyr | Asn | His | Leu | Thr | Pro | Leu | Arg | Asp | Trp | Pro | |
| 945 | | | | | 950 | | | | 955 | | | | | | 960 | |
| CGC | GCG | GGC | CTA | CGA | GAC | CTT | GCG | GTG | GCA | GTG | GAG | CCC | GTC | GTC | TTC | 2928 |
| Arg | Ala | Gly | Leu | Arg | Asp | Leu | Ala | Val | Ala | Val | Glu | Pro | Val | Val | Phe | |
| | | | | 965 | | | | | 970 | | | | | 975 | | |
| TCC | GAC | ATG | GAG | ACC | AAG | ATC | ATC | ACC | TGG | GGA | GCA | GAC | ACC | GCG | GCG | 2976 |
| Ser | Asp | Met | Glu | Thr | Lys | Ile | Ile | Thr | Trp | Gly | Ala | Asp | Thr | Ala | Ala | |
| | | | 980 | | | | | 985 | | | | | 990 | | | |
| TGT | GGG | GAC | ATC | ATC | TTG | GGT | CTG | CCC | GTC | TCC | GCC | CGA | AGG | GGA | AAG | 3024 |
| Cys | Gly | Asp | Ile | Ile | Leu | Gly | Leu | Pro | Val | Ser | Ala | Arg | Arg | Gly | Lys | |
| | | 995 | | | | 1000 | | | | | 1005 | | | | | |
| GAG | ATA | CTC | CTG | GGC | CCG | GCC | GAT | AGT | CTT | GAA | GGG | CGG | GGG | TTG | CGA | 3072 |
| Glu | Ile | Leu | Leu | Gly | Pro | Ala | Asp | Ser | Leu | Glu | Gly | Arg | Gly | Leu | Arg | |
| | 1010 | | | | 1015 | | | | | 1020 | | | | | | |
| CTC | CTC | GCG | CCC | ATC | ACG | GCC | TAC | TCC | CAA | CAG | ACG | CGG | GGC | CTA | CTT | 3120 |
| Leu | Leu | Ala | Pro | Ile | Thr | Ala | Tyr | Ser | Gln | Gln | Thr | Arg | Gly | Leu | Leu | |
| 1025 | | | | 1030 | | | | | 1035 | | | | | 1040 | | |
| GGT | TGC | ATC | ATC | ACT | AGC | CTT | ACA | GGC | CGG | GAC | AAG | AAC | CAG | GTC | GAG | 3168 |
| Gly | Cys | Ile | Ile | Thr | Ser | Leu | Thr | Gly | Arg | Asp | Lys | Asn | Gln | Val | Glu | |
| | | | | 1045 | | | | | 1050 | | | | | 1055 | | |
| GGA | GAG | GTT | CAG | GTG | GTT | TCC | ACC | GCA | ACA | CAA | TCC | TTC | CTG | GCG | ACC | 3216 |
| Gly | Glu | Val | Gln | Val | Val | Ser | Thr | Ala | Thr | Gln | Ser | Phe | Leu | Ala | Thr | |
| | | | 1060 | | | | | 1065 | | | | | 1070 | | | |
| TGC | GTC | AAC | GGC | GTG | TGT | TGG | ACC | GTT | TAC | CAT | GGT | GCT | GGC | TCA | AAG | 3264 |
| Cys | Val | Asn | Gly | Val | Cys | Trp | Thr | Val | Tyr | His | Gly | Ala | Gly | Ser | Lys | |
| | | 1075 | | | | 1080 | | | | | 1085 | | | | | |
| ACC | TTA | GCC | GCG | CCA | AAG | GGG | CCA | ATC | ACC | CAG | ATG | TAC | ACT | AAT | GTG | 3312 |
| Thr | Leu | Ala | Ala | Pro | Lys | Gly | Pro | Ile | Thr | Gln | Met | Tyr | Thr | Asn | Val | |
| | 1090 | | | | 1095 | | | | | 1100 | | | | | | |
| GAC | CAG | GAC | CTC | GTC | GGC | TGG | CCC | AAG | CCC | CCC | GGG | GCG | CGT | TCC | TTG | 3360 |
| Asp | Gln | Asp | Leu | Val | Gly | Trp | Pro | Lys | Pro | Pro | Gly | Ala | Arg | Ser | Leu | |
| 1105 | | | | 1110 | | | | | 1115 | | | | | 1120 | | |
| ACA | CCA | TGC | ACC | TGT | GGC | AGC | TCA | GAC | CTT | TAC | TTG | GTC | ACG | AGA | CAT | 3408 |
| Thr | Pro | Cys | Thr | Cys | Gly | Ser | Ser | Asp | Leu | Tyr | Leu | Val | Thr | Arg | His | |
| | | | | 1125 | | | | | 1130 | | | | | 1135 | | |

```
GCT GAC GTC ATT CCG GTG CGC CGG CGG GGC GAC AGT AGG GGG AGC CTG           3456
Ala Asp Val Ile Pro Val Arg Arg Arg Gly Asp Ser Arg Gly Ser Leu
        1140             1145                 1150

CTC TCC CCC AGG CCT GTC TCC TAC TTG AAG GGC TCT TCG GGT GGT CCA           3504
Leu Ser Pro Arg Pro Val Ser Tyr Leu Lys Gly Ser Ser Gly Gly Pro
        1155             1160                 1165

CTG CTC TGC CCC TTC GGG CAC GCT GTG GGC ATC TTC CGG GCT GCC GTA           3552
Leu Leu Cys Pro Phe Gly His Ala Val Gly Ile Phe Arg Ala Ala Val
        1170             1175                 1180

TGC ACC CGG GGG GTT GCG AAG GCG GTG GAC TTT GTG CCC GTA GAG TCC           3600
Cys Thr Arg Gly Val Ala Lys Ala Val Asp Phe Val Pro Val Glu Ser
1185             1190             1195                 1200

ATG GAA ACT ACT ATG CGG TCT CCG GTC TTC ACG GAC AAC TCA TCC CCC           3648
Met Glu Thr Thr Met Arg Ser Pro Val Phe Thr Asp Asn Ser Ser Pro
                1205             1210                 1215

CCG GCC GTA CCG CAG TCA TTT CAA GTG GCC CAC CTA CAC GCT CCC ACT           3696
Pro Ala Val Pro Gln Ser Phe Gln Val Ala His Leu His Ala Pro Thr
        1220             1225                 1230

GGC AGC GGC AAG AGT ACT AAA GTG CCG GCT GCA TAT GCA GCC CAA GGG           3744
Gly Ser Gly Lys Ser Thr Lys Val Pro Ala Ala Tyr Ala Ala Gln Gly
        1235             1240                 1245

TAC AAG GTG CTC GTC CTC AAT CCG TCC GTT GCC GCT ACC TTA GGG TTT           3792
Tyr Lys Val Leu Val Leu Asn Pro Ser Val Ala Ala Thr Leu Gly Phe
        1250             1255                 1260

GGG GCG TAT ATG TCT AAG GCA CAC GGT ATT GAC CCC AAC ATC AGA ACT           3840
Gly Ala Tyr Met Ser Lys Ala His Gly Ile Asp Pro Asn Ile Arg Thr
1265             1270             1275                 1280

GGG GTA AGG ACC ATT ACC ACA GGC GCC CCC GTC ACA TAC TCT ACC TAT           3888
Gly Val Arg Thr Ile Thr Thr Gly Ala Pro Val Thr Tyr Ser Thr Tyr
                1285             1290                 1295

GGC AAG TTT CTT GCC GAT GGT GGT TGC TCT GGG GGC GCT TAT GAC ATC           3936
Gly Lys Phe Leu Ala Asp Gly Gly Cys Ser Gly Gly Ala Tyr Asp Ile
        1300             1305                 1310

ATA ATA TGT GAT GAG TGC CAT TCA ACT GAC TCG ACT ACA ATC TTG GGC           3984
Ile Ile Cys Asp Glu Cys His Ser Thr Asp Ser Thr Thr Ile Leu Gly
        1315             1320                 1325

ATC GGC ACA GTC CTG GAC CAA GCG GAG ACG GCT GGA GCG CGG CTT GTC           4032
Ile Gly Thr Val Leu Asp Gln Ala Glu Thr Ala Gly Ala Arg Leu Val
        1330             1335                 1340

GTG CTC GCC ACC GCT ACG CCT CCG GGA TCG GTC ACC GTG CCA CAC CCA           4080
Val Leu Ala Thr Ala Thr Pro Pro Gly Ser Val Thr Val Pro His Pro
1345             1350             1355                 1360

AAC ATC GAG GAG GTG GCC CTG TCT AAT ACT GGA GAG ATC CCC TTC TAT           4128
Asn Ile Glu Glu Val Ala Leu Ser Asn Thr Gly Glu Ile Pro Phe Tyr
                1365             1370                 1375

GGC AAA GCC ATC CCC ATT GAA GCC ATC AGG GGG GGA AGG CAT CTC ATT           4176
Gly Lys Ala Ile Pro Ile Glu Ala Ile Arg Gly Gly Arg His Leu Ile
        1380             1385                 1390

TTC TGT CAT TCC AAG AAG AAG TGC GAC GAG CTC GCC GCA AAG CTG TCA           4224
Phe Cys His Ser Lys Lys Lys Cys Asp Glu Leu Ala Ala Lys Leu Ser
        1395             1400                 1405

GGC CTC GGA ATC AAC GCT GTG GCG TAT TAC CGG GGG CTC GAT GTG TCC           4272
Gly Leu Gly Ile Asn Ala Val Ala Tyr Tyr Arg Gly Leu Asp Val Ser
        1410             1415                 1420

GTC ATA CCA ACT ATC GGA GAC GTC GTT GTC GTG GCA ACA GAC GCT CTG           4320
Val Ile Pro Thr Ile Gly Asp Val Val Val Val Ala Thr Asp Ala Leu
1425             1430             1435                 1440

ATG ACG GGC TAT ACG GGC GAC TTT GAC TCA GTG ATC GAC TGT AAC ACA           4368
Met Thr Gly Tyr Thr Gly Asp Phe Asp Ser Val Ile Asp Cys Asn Thr
                1445             1450                 1455
```

| | | | | | | | | | | | | | | | | |
|---|---|---|---|---|---|---|---|---|---|---|---|---|---|---|---|---|
| TGT | GTC | ACC | CAG | ACA | GTC | GAC | TTC | AGC | TTG | GAT | CCC | ACC | TTC | ACC | ATT | 4416 |
| Cys | Val | Thr | Gln | Thr | Val | Asp | Phe | Ser | Leu | Asp | Pro | Thr | Phe | Thr | Ile | |
| | | | 1460 | | | | 1465 | | | | | 1470 | | | | |
| GAG | ACG | ACG | ACC | GTG | CCT | CAA | GAC | GCA | GTG | TCG | CGC | TCG | CAG | CGG | CGG | 4464 |
| Glu | Thr | Thr | Thr | Val | Pro | Gln | Asp | Ala | Val | Ser | Arg | Ser | Gln | Arg | Arg | |
| | | 1475 | | | | | 1480 | | | | | 1485 | | | | |
| GGT | AGG | ACT | GGC | AGG | GGT | AGG | AGA | GGC | ATC | TAC | AGG | TTT | GTG | ACT | CCG | 4512 |
| Gly | Arg | Thr | Gly | Arg | Gly | Arg | Arg | Gly | Ile | Tyr | Arg | Phe | Val | Thr | Pro | |
| | 1490 | | | | | 1495 | | | | | 1500 | | | | | |
| GGA | GAA | CGG | CCC | TCG | GGC | ATG | TTC | GAT | TCC | TCG | GTC | CTG | TGT | GAG | TGC | 4560 |
| Gly | Glu | Arg | Pro | Ser | Gly | Met | Phe | Asp | Ser | Ser | Val | Leu | Cys | Glu | Cys | |
| 1505 | | | | | 1510 | | | | | 1515 | | | | | 1520 | |
| TAT | GAC | GCG | GGC | TGT | GCT | TGG | TAC | GAG | CTC | ACC | CCG | GCC | GAG | ACC | TCG | 4608 |
| Tyr | Asp | Ala | Gly | Cys | Ala | Trp | Tyr | Glu | Leu | Thr | Pro | Ala | Glu | Thr | Ser | |
| | | | | 1525 | | | | | 1530 | | | | | 1535 | | |
| GTT | AGG | TTG | CGG | GCC | TAC | CTG | AAC | ACA | CCA | GGG | TTG | CCC | GTT | TGC | CAG | 4656 |
| Val | Arg | Leu | Arg | Ala | Tyr | Leu | Asn | Thr | Pro | Gly | Leu | Pro | Val | Cys | Gln | |
| | | | 1540 | | | | | 1545 | | | | | 1550 | | | |
| GAC | CAC | CTG | GAG | TTC | TGG | GAG | AGT | GTC | TTC | ACA | GGC | CTC | ACC | CAT | ATA | 4704 |
| Asp | His | Leu | Glu | Phe | Trp | Glu | Ser | Val | Phe | Thr | Gly | Leu | Thr | His | Ile | |
| | | | 1555 | | | | | 1560 | | | | | 1565 | | | |
| GAT | GCA | CAC | TTC | TTG | TCC | CAG | ACC | AAG | CAG | GCA | GGA | GAC | AAC | TTC | CCC | 4752 |
| Asp | Ala | His | Phe | Leu | Ser | Gln | Thr | Lys | Gln | Ala | Gly | Asp | Asn | Phe | Pro | |
| | 1570 | | | | | 1575 | | | | | 1580 | | | | | |
| TAC | CTG | GTA | GCA | TAC | CAA | GCC | ACG | GTG | TGC | GCC | AGG | GCT | CAG | GCC | CCA | 4800 |
| Tyr | Leu | Val | Ala | Tyr | Gln | Ala | Thr | Val | Cys | Ala | Arg | Ala | Gln | Ala | Pro | |
| 1585 | | | | | 1590 | | | | | 1595 | | | | | 1600 | |
| CCT | CCA | TCA | TGG | GAT | CAA | ATG | TGG | AAG | TGT | CTC | ATA | CGG | CTG | AAA | CCT | 4848 |
| Pro | Pro | Ser | Trp | Asp | Gln | Met | Trp | Lys | Cys | Leu | Ile | Arg | Leu | Lys | Pro | |
| | | | | 1605 | | | | | 1610 | | | | | 1615 | | |
| ACG | CTG | CAC | GGG | CCA | ACA | CCC | TTG | CTG | TAC | AGG | CTG | GGA | GCC | GTC | CAG | 4896 |
| Thr | Leu | His | Gly | Pro | Thr | Pro | Leu | Leu | Tyr | Arg | Leu | Gly | Ala | Val | Gln | |
| | | | 1620 | | | | | 1625 | | | | | 1630 | | | |
| AAT | GAG | GTC | ACC | CTC | ACC | CAC | CCC | ATA | ACC | AAA | TAC | ATC | ATG | GCA | TGC | 4944 |
| Asn | Glu | Val | Thr | Leu | Thr | His | Pro | Ile | Thr | Lys | Tyr | Ile | Met | Ala | Cys | |
| | | | 1635 | | | | | 1640 | | | | | 1645 | | | |
| ATG | TCG | GCT | GAC | CTG | GAG | GTC | GTC | ACT | AGC | ACC | TGG | GTG | CTG | GTG | GGC | 4992 |
| Met | Ser | Ala | Asp | Leu | Glu | Val | Val | Thr | Ser | Thr | Trp | Val | Leu | Val | Gly | |
| | 1650 | | | | | 1655 | | | | | 1660 | | | | | |
| GGA | GTC | CTT | GCA | GCT | CTG | GCC | GCG | TAT | TGC | CTG | ACA | ACA | GGC | AGT | GTG | 5040 |
| Gly | Val | Leu | Ala | Ala | Leu | Ala | Ala | Tyr | Cys | Leu | Thr | Thr | Gly | Ser | Val | |
| 1665 | | | | | 1670 | | | | | 1675 | | | | | 1680 | |
| GTC | ATT | GTG | GGT | AGG | ATT | ATC | TTG | TCC | GGG | AGG | CCG | GCC | ATT | GTT | CCC | 5088 |
| Val | Ile | Val | Gly | Arg | Ile | Ile | Leu | Ser | Gly | Arg | Pro | Ala | Ile | Val | Pro | |
| | | | | 1685 | | | | | 1690 | | | | | 1695 | | |
| GAC | AGG | GAG | CTT | CTC | TAC | CAG | GAG | TTC | GAT | GAA | ATG | GAA | GAG | TGC | GCC | 5136 |
| Asp | Arg | Glu | Leu | Leu | Tyr | Gln | Glu | Phe | Asp | Glu | Met | Glu | Glu | Cys | Ala | |
| | | | 1700 | | | | | 1705 | | | | | 1710 | | | |
| TCG | CAC | CTC | CCT | TAC | ATC | GAG | CAG | GGA | ATG | CAG | CTC | GCC | GAG | CAA | TTC | 5184 |
| Ser | His | Leu | Pro | Tyr | Ile | Glu | Gln | Gly | Met | Gln | Leu | Ala | Glu | Gln | Phe | |
| | | 1715 | | | | | 1720 | | | | | 1725 | | | | |
| AAG | CAG | AAA | GCG | CTC | GGG | TTA | CTG | CAA | ACA | GCC | ACC | AAA | CAA | GCG | GAG | 5232 |
| Lys | Gln | Lys | Ala | Leu | Gly | Leu | Leu | Gln | Thr | Ala | Thr | Lys | Gln | Ala | Glu | |
| | 1730 | | | | | 1735 | | | | | 1740 | | | | | |
| GCT | GCT | GCT | CCC | GTG | GTG | GAG | TCC | AAG | TGG | CGA | GCC | CTT | GAG | ACA | TTC | 5280 |
| Ala | Ala | Ala | Pro | Val | Val | Glu | Ser | Lys | Trp | Arg | Ala | Leu | Glu | Thr | Phe | |
| 1745 | | | | | 1750 | | | | | 1755 | | | | | 1760 | |
| TGG | GCG | AAG | CAC | ATG | TGG | AAT | TTC | ATC | AGC | GGG | ATA | CAG | TAC | TTA | GCA | 5328 |
| Trp | Ala | Lys | His | Met | Trp | Asn | Phe | Ile | Ser | Gly | Ile | Gln | Tyr | Leu | Ala | |
| | | | | 1765 | | | | | 1770 | | | | | 1775 | | |

| | | | | | | | | | | | | | | | | |
|---|---|---|---|---|---|---|---|---|---|---|---|---|---|---|---|---|
| GGC | TTA | TCC | ACT | CTG | CCT | GGG | AAC | CCC | GCA | ATA | GCA | TCA | TTG | ATG | GCA | 5376 |
| Gly | Leu | Ser | Thr | Leu | Pro | Gly | Asn | Pro | Ala | Ile | Ala | Ser | Leu | Met | Ala | |
| | | | 1780 | | | | 1785 | | | | | 1790 | | | | |
| TTC | ACA | GCC | TCT | ATC | ACC | AGC | CCG | CTC | ACC | ACC | CAA | AGT | ACC | CTC | CTG | 5424 |
| Phe | Thr | Ala | Ser | Ile | Thr | Ser | Pro | Leu | Thr | Thr | Gln | Ser | Thr | Leu | Leu | |
| | | 1795 | | | | 1800 | | | | | 1805 | | | | | |
| TTT | AAC | ATC | TTG | GGG | GGG | TGG | GTG | GCT | GCC | CAA | CTC | GCC | CCC | CCC | AGC | 5472 |
| Phe | Asn | Ile | Leu | Gly | Gly | Trp | Val | Ala | Ala | Gln | Leu | Ala | Pro | Pro | Ser | |
| | 1810 | | | | 1815 | | | | | 1820 | | | | | | |
| GCC | GCT | TCG | GCT | TTC | GTG | GGC | GCC | GGC | ATC | GCC | GGT | GCG | GCT | GTT | GGC | 5520 |
| Ala | Ala | Ser | Ala | Phe | Val | Gly | Ala | Gly | Ile | Ala | Gly | Ala | Ala | Val | Gly | |
| 1825 | | | | 1830 | | | | | 1835 | | | | | 1840 | | |
| AGC | ATA | GGC | CTT | GGG | AAG | GTG | CTT | GTG | GAC | ATT | CTG | GCG | GGT | TAT | GGA | 5568 |
| Ser | Ile | Gly | Leu | Gly | Lys | Val | Leu | Val | Asp | Ile | Leu | Ala | Gly | Tyr | Gly | |
| | | | | 1845 | | | | | 1850 | | | | | 1855 | | |
| GCA | GGA | GTG | GCC | GGC | GCG | CTC | GTG | GCC | TTT | AAG | GTC | ATG | AGC | GGC | GAG | 5616 |
| Ala | Gly | Val | Ala | Gly | Ala | Leu | Val | Ala | Phe | Lys | Val | Met | Ser | Gly | Glu | |
| | | | 1860 | | | | | 1865 | | | | | 1870 | | | |
| ATG | CCC | TCC | ACC | GAG | GAC | CTG | GTC | AAT | CTA | CTT | CCT | GCC | ATC | CTC | TCT | 5664 |
| Met | Pro | Ser | Thr | Glu | Asp | Leu | Val | Asn | Leu | Leu | Pro | Ala | Ile | Leu | Ser | |
| | | 1875 | | | | | 1880 | | | | | 1885 | | | | |
| CCT | GGC | GCC | CTG | GTC | GTC | GGG | GTC | GTG | TGT | GCA | GCA | ATA | CTG | CGT | CGA | 5712 |
| Pro | Gly | Ala | Leu | Val | Val | Gly | Val | Val | Cys | Ala | Ala | Ile | Leu | Arg | Arg | |
| | 1890 | | | | | 1895 | | | | | 1900 | | | | | |
| CAC | GTG | GGT | CCG | GGA | GAG | GGG | GCT | GTG | CAG | TGG | ATG | AAC | CGG | CTG | ATA | 5760 |
| His | Val | Gly | Pro | Gly | Glu | Gly | Ala | Val | Gln | Trp | Met | Asn | Arg | Leu | Ile | |
| 1905 | | | | 1910 | | | | | 1915 | | | | | 1920 | | |
| GCG | TTC | GCC | TCG | CGG | GGT | AAT | CAT | GTT | TCC | CCC | ACG | CAC | TAT | GTG | CCT | 5808 |
| Ala | Phe | Ala | Ser | Arg | Gly | Asn | His | Val | Ser | Pro | Thr | His | Tyr | Val | Pro | |
| | | | 1925 | | | | | 1930 | | | | | 1935 | | | |
| GAG | AGC | GAC | GCC | GCA | GCG | CGT | GTT | ACT | CAG | ATC | CTC | TCC | AGC | CTT | ACC | 5856 |
| Glu | Ser | Asp | Ala | Ala | Ala | Arg | Val | Thr | Gln | Ile | Leu | Ser | Ser | Leu | Thr | |
| | | | 1940 | | | | | 1945 | | | | | 1950 | | | |
| ATC | ACT | CAG | CTG | CTG | AAA | AGG | CTC | CAC | CAG | TGG | ATT | AAT | GAA | GAC | TGC | 5904 |
| Ile | Thr | Gln | Leu | Leu | Lys | Arg | Leu | His | Gln | Trp | Ile | Asn | Glu | Asp | Cys | |
| | | | | 1955 | | | | | 1960 | | | | | 1965 | | |
| TCC | ACA | CCG | TGT | TCC | GGC | TCG | TGG | CTA | AGG | GAT | GTT | TGG | GAC | TGG | ATA | 5952 |
| Ser | Thr | Pro | Cys | Ser | Gly | Ser | Trp | Leu | Arg | Asp | Val | Trp | Asp | Trp | Ile | |
| | 1970 | | | | | 1975 | | | | | 1980 | | | | | |
| TGC | ACG | GTG | TTG | ACT | GAC | TTC | AAG | ACC | TGG | CTC | CAG | TCC | AAG | CTC | CTG | 6000 |
| Cys | Thr | Val | Leu | Thr | Asp | Phe | Lys | Thr | Trp | Leu | Gln | Ser | Lys | Leu | Leu | |
| 1985 | | | | 1990 | | | | | 1995 | | | | | 2000 | | |
| CCG | CAG | CTA | CCT | GGA | GTC | CCT | TTT | TTC | TCG | TGC | CAA | CGC | GGG | TAC | AAG | 6048 |
| Pro | Gln | Leu | Pro | Gly | Val | Pro | Phe | Phe | Ser | Cys | Gln | Arg | Gly | Tyr | Lys | |
| | | | | 2005 | | | | | 2010 | | | | | 2015 | | |
| GGA | GTC | TGG | CGG | GGA | GAC | GGC | ATC | ATG | CAA | ACC | ACC | TGC | CCA | TGT | GGA | 6096 |
| Gly | Val | Trp | Arg | Gly | Asp | Gly | Ile | Met | Gln | Thr | Thr | Cys | Pro | Cys | Gly | |
| | | | 2020 | | | | | 2025 | | | | | 2030 | | | |
| GCA | CAG | ATC | ACC | GGA | CAT | GTC | AAA | AAC | GGT | TCC | ATG | AGG | ATC | GTC | GGG | 6144 |
| Ala | Gln | Ile | Thr | Gly | His | Val | Lys | Asn | Gly | Ser | Met | Arg | Ile | Val | Gly | |
| | | | 2035 | | | | | 2040 | | | | | 2045 | | | |
| CCT | AAG | ACC | TGC | AGC | AAC | ACG | TGG | CAT | GGA | ACA | TTC | CCC | ATC | AAC | GCA | 6192 |
| Pro | Lys | Thr | Cys | Ser | Asn | Thr | Trp | His | Gly | Thr | Phe | Pro | Ile | Asn | Ala | |
| | 2050 | | | | | 2055 | | | | | 2060 | | | | | |
| TAC | ACC | ACG | GGC | CCC | TGC | ACA | CCC | TCT | CCA | GCG | CCA | AAC | TAT | TCT | AGG | 6240 |
| Tyr | Thr | Thr | Gly | Pro | Cys | Thr | Pro | Ser | Pro | Ala | Pro | Asn | Tyr | Ser | Arg | |
| 2065 | | | | 2070 | | | | | 2075 | | | | | 2080 | | |
| GCG | CTG | TGG | CGG | GTG | GCC | GCT | GAG | GAG | TAC | GTG | GAG | GTC | ACG | CGG | GTG | 6288 |
| Ala | Leu | Trp | Arg | Val | Ala | Ala | Glu | Glu | Tyr | Val | Glu | Val | Thr | Arg | Val | |
| | | | | 2085 | | | | | 2090 | | | | | 2095 | | |

```
GGG GAT TTC CAC TAC GTG ACG GGC ATG ACC ACT GAC AAC GTA AAG TGC       6336
Gly Asp Phe His Tyr Val Thr Gly Met Thr Thr Asp Asn Val Lys Cys
            2100            2105            2110

CCA TGC CAG GTT CCG GCT CCT GAA TTC TTC TCG GAG GTG GAC GGA GTG       6384
Pro Cys Gln Val Pro Ala Pro Glu Phe Phe Ser Glu Val Asp Gly Val
        2115            2120            2125

CGG TTG CAC AGG TAC GCT CCG GCG TGC AGG CCT CTC CTA CGG GAG GAG       6432
Arg Leu His Arg Tyr Ala Pro Ala Cys Arg Pro Leu Leu Arg Glu Glu
        2130            2135            2140

GTT ACA TTC CAG GTC GGG CTC AAC CAA TAC CTG GTT GGG TCA CAG CTA       6480
Val Thr Phe Gln Val Gly Leu Asn Gln Tyr Leu Val Gly Ser Gln Leu
        2145            2150            2155            2160

CCA TGC GAG CCC GAA CCG GAT GTA GCA GTG CTC ACT TCC ATG CTC ACC       6528
Pro Cys Glu Pro Glu Pro Asp Val Ala Val Leu Thr Ser Met Leu Thr
        2165            2170            2175

GAC CCC TCC CAC ATC ACA GCA GAA ACG GCT AAG CGT AGG TTG GCC AGG       6576
Asp Pro Ser His Ile Thr Ala Glu Thr Ala Lys Arg Arg Leu Ala Arg
        2180            2185            2190

GGG TCT CCC CCC TCC TTG GCC AGC TCT TCA GCT AGC CAG TTG TCT GCG       6624
Gly Ser Pro Pro Ser Leu Ala Ser Ser Ser Ala Ser Gln Leu Ser Ala
        2195            2200            2205

CCT TCC TTG AAG GCG ACA TGC ACT ACC CAC CAT GTC TCT CCG GAC GCT       6672
Pro Ser Leu Lys Ala Thr Cys Thr Thr His His Val Ser Pro Asp Ala
        2210            2215            2220

GAC CTC ATC GAG GCC AAC CTC CTG TGG CGG CAG GAG ATG GGC GGG AAC       6720
Asp Leu Ile Glu Ala Asn Leu Leu Trp Arg Gln Glu Met Gly Gly Asn
2225            2230            2235            2240

ATC ACC CGC GTG GAG TCG GAG AAC AAG GTG GTA GTC CTG GAC TCT TTC       6768
Ile Thr Arg Val Glu Ser Glu Asn Lys Val Val Val Leu Asp Ser Phe
            2245            2250            2255

GAC CCG CTT CGA GCG GAG GAG GAT GAG AGG GAA GTA TCC GTT CCG GCG       6816
Asp Pro Leu Arg Ala Glu Glu Asp Glu Arg Glu Val Ser Val Pro Ala
        2260            2265            2270

GAG ATC CTG CGG AAA TCC AAG AAG TTC CCC GCA GCG ATG CCC ATC TGG       6864
Glu Ile Leu Arg Lys Ser Lys Lys Phe Pro Ala Ala Met Pro Ile Trp
        2275            2280            2285

GCG CGC CCG GAT TAC AAC CCT CCA CTG TTA GAG TCC TGG AAG GAC CCG       6912
Ala Arg Pro Asp Tyr Asn Pro Pro Leu Leu Glu Ser Trp Lys Asp Pro
        2290            2295            2300

GAC TAC GTC CCT CCG GTG GTG CAC GGG TGC CCG TTG CCA CCT ATC AAG       6960
Asp Tyr Val Pro Pro Val Val His Gly Cys Pro Leu Pro Pro Ile Lys
2305            2310            2315            2320

GCC CCT CCA ATA CCA CCT CCA CGG AGA AAG AGG ACG GTT GTC CTA ACA       7008
Ala Pro Pro Ile Pro Pro Pro Arg Arg Lys Arg Thr Val Val Leu Thr
            2325            2330            2335

GAG TCC TCC GTG TCT TCT GCC TTA GCG GAG CTC GCT ACT AAG ACC TTC       7056
Glu Ser Ser Val Ser Ser Ala Leu Ala Glu Leu Ala Thr Lys Thr Phe
        2340            2345            2350

GGC AGC TCC GAA TCA TCG GCC GTC GAC AGC GGC ACG GCG ACC GCC CTT       7104
Gly Ser Ser Glu Ser Ser Ala Val Asp Ser Gly Thr Ala Thr Ala Leu
        2355            2360            2365

CCT GAC CAG GCC TCC GAC GAC GGT GAC AAA GGA TCC GAC GTT GAG TCG       7152
Pro Asp Gln Ala Ser Asp Asp Gly Asp Lys Gly Ser Asp Val Glu Ser
        2370            2375            2380

TAC TCC TCC ATG CCC CCC CTT GAG GGG GAA CCG GGG GAC CCC GAT CTC       7200
Tyr Ser Ser Met Pro Pro Leu Glu Gly Glu Pro Gly Asp Pro Asp Leu
2385            2390            2395            2400

AGT GAC GGG TCT TGG TCT ACC GTG AGC GAG GAA GCT AGT GAG GAT GTC       7248
Ser Asp Gly Ser Trp Ser Thr Val Ser Glu Glu Ala Ser Glu Asp Val
            2405            2410            2415
```

| | |
|---|---|
| GTC TGC TGC TCA ATG TCC TAC ACA TGG ACA GGC GCC TTG ATC ACG CCA<br>Val Cys Cys Ser Met Ser Tyr Thr Trp Thr Gly Ala Leu Ile Thr Pro<br>                    2420                               2425                             2430 | 7296 |
| TGC GCT GCG GAG GAA AGC AAG CTG CCC ATC AAC GCG TTG AGC AAC TCT<br>Cys Ala Ala Glu Glu Ser Lys Leu Pro Ile Asn Ala Leu Ser Asn Ser<br>                    2435                               2440                             2445 | 7344 |
| TTG CTG CGC CAC CAT AAC ATG GTT TAT GCC ACA ACA TCT CGC AGC GCA<br>Leu Leu Arg His His Asn Met Val Tyr Ala Thr Thr Ser Arg Ser Ala<br>2450                               2455                             2460 | 7392 |
| GGC CTG CGG CAG AAG AAG GTC ACC TTT GAC AGA CTG CAA GTC CTG GAC<br>Gly Leu Arg Gln Lys Lys Val Thr Phe Asp Arg Leu Gln Val Leu Asp<br>2465                               2470                             2475                           2480 | 7440 |
| GAC CAC TAC CGG GAC GTG CTC AAG GAG ATG AAG GCG AAG GCG TCC ACA<br>Asp His Tyr Arg Asp Val Leu Lys Glu Met Lys Ala Lys Ala Ser Thr<br>                    2485                               2490                             2495 | 7488 |
| GTT AAG GCT AAA CTC CTA TCC GTA GAG GAA GCC TGC AAG CTG ACG CCC<br>Val Lys Ala Lys Leu Leu Ser Val Glu Glu Ala Cys Lys Leu Thr Pro<br>                    2500                               2505                             2510 | 7536 |
| CCA CAT TCG GCC AAA TCC AAG TTT GGC TAT GGG GCA AAG GAC GTC CGG<br>Pro His Ser Ala Lys Ser Lys Phe Gly Tyr Gly Ala Lys Asp Val Arg<br>                    2515                               2520                             2525 | 7584 |
| AAC CTA TCC AGC AAG GCC GTT AAC CAC ATC CAC TCC GTG TGG AAG GAC<br>Asn Leu Ser Ser Lys Ala Val Asn His Ile His Ser Val Trp Lys Asp<br>                    2530                               2535                             2540 | 7632 |
| TTG CTG GAA GAC ACT GTG ACA CCA ATT GAC ACC ACC ATC ATG GCA AAA<br>Leu Leu Glu Asp Thr Val Thr Pro Ile Asp Thr Thr Ile Met Ala Lys<br>2545                               2550                             2555                           2560 | 7680 |
| AAT GAG GTT TTC TGT GTC CAA CCA GAG AAA GGA GGC CGT AAG CCA GCC<br>Asn Glu Val Phe Cys Val Gln Pro Glu Lys Gly Gly Arg Lys Pro Ala<br>                    2565                               2570                             2575 | 7728 |
| CGC CTT ATC GTA TTC CCA GAT CTG GGA GTC CGT GTA TGC GAG AAG ATG<br>Arg Leu Ile Val Phe Pro Asp Leu Gly Val Arg Val Cys Glu Lys Met<br>                    2580                               2585                             2590 | 7776 |
| GCC CTC TAT GAT GTG GTC TCC ACC CTT CCT CAG GTC GTG ATG GGC TCC<br>Ala Leu Tyr Asp Val Val Ser Thr Leu Pro Gln Val Val Met Gly Ser<br>                    2595                               2600                             2605 | 7824 |
| TCA TAC GGA TTC CAG TAC TCT CCT GGG CAG CGA GTC GAG TTC CTG GTG<br>Ser Tyr Gly Phe Gln Tyr Ser Pro Gly Gln Arg Val Glu Phe Leu Val<br>                    2610                               2615                             2620 | 7872 |
| AAT ACC TGG AAA TCA AAG AAA AAC CCC ATG GGC TTT TCA TAT GAC ACT<br>Asn Thr Trp Lys Ser Lys Lys Asn Pro Met Gly Phe Ser Tyr Asp Thr<br>2625                               2630                             2635                           2640 | 7920 |
| CGC TGT TTC GAC TCA ACG GTC ACC GAG AAC GAC ATC CGT GTT GAG GAG<br>Arg Cys Phe Asp Ser Thr Val Thr Glu Asn Asp Ile Arg Val Glu Glu<br>                    2645                               2650                             2655 | 7968 |
| TCA ATT TAC CAA TGT TGT GAC TTG GCC CCC GAA GCC AGA CAG GCC ATA<br>Ser Ile Tyr Gln Cys Cys Asp Leu Ala Pro Glu Ala Arg Gln Ala Ile<br>                    2660                               2665                             2670 | 8016 |
| AAA TCG CTC ACA GAG CGG CTT TAT ATC GGG GGT CCT CTG ACT AAT TCA<br>Lys Ser Leu Thr Glu Arg Leu Tyr Ile Gly Gly Pro Leu Thr Asn Ser<br>                    2675                               2680                             2685 | 8064 |
| AAA GGG CAG AAC TGC GGT TAT CGC CGG TGC CGC GCG AGC GGC GTG CTG<br>Lys Gly Gln Asn Cys Gly Tyr Arg Arg Cys Arg Ala Ser Gly Val Leu<br>                    2690                               2695                             2700 | 8112 |
| ACG ACT AGC TGC GGT AAC ACC CTC ACA TGT TAC TTG AAG GCC TCT GCA<br>Thr Thr Ser Cys Gly Asn Thr Leu Thr Cys Tyr Leu Lys Ala Ser Ala<br>2705                               2710                             2715                           2720 | 8160 |
| GCC TGT CGA GCT GCG AAG CTC CAG GAC TGC ACG ATG CTC GTG AAC GGA<br>Ala Cys Arg Ala Ala Lys Leu Gln Asp Cys Thr Met Leu Val Asn Gly<br>                    2725                               2730                             2735 | 8208 |

| | | | | | | | | | | | | | | | | |
|---|---|---|---|---|---|---|---|---|---|---|---|---|---|---|---|---|
| GAC | GAC | CTC | GTC | GTT | ATC | TGT | GAA | AGC | GCG | GGA | ACC | CAA | GAG | GAC | GCG | 8256 |
| Asp | Asp | Leu | Val | Val | Ile | Cys | Glu | Ser | Ala | Gly | Thr | Gln | Glu | Asp | Ala | |
| | | | 2740 | | | | 2745 | | | | | | 2750 | | | |
| GCG | AGC | CTA | CGA | GTC | TTC | ACG | GAG | GCT | ATG | ACT | AGG | TAC | TCC | GCC | CCC | 8304 |
| Ala | Ser | Leu | Arg | Val | Phe | Thr | Glu | Ala | Met | Thr | Arg | Tyr | Ser | Ala | Pro | |
| | | 2755 | | | | | 2760 | | | | | 2765 | | | | |
| CCC | GGG | GAC | CCG | CCC | CAA | CCA | GAA | TAC | GAC | TTG | GAG | CTG | ATA | ACA | TCA | 8352 |
| Pro | Gly | Asp | Pro | Pro | Gln | Pro | Glu | Tyr | Asp | Leu | Glu | Leu | Ile | Thr | Ser | |
| | | 2770 | | | | 2775 | | | | | 2780 | | | | | |
| TGT | TCC | TCC | AAT | GTG | TCG | GTC | GCC | CAC | GAT | GCA | TCA | GGC | AAA | AGG | GTG | 8400 |
| Cys | Ser | Ser | Asn | Val | Ser | Val | Ala | His | Asp | Ala | Ser | Gly | Lys | Arg | Val | |
| 2785 | | | | | 2790 | | | | 2795 | | | | | | 2800 | |
| TAC | TAC | CTC | ACC | CGT | GAT | CCC | ACC | ACC | CCC | CTA | GCA | CGG | GCT | GCG | TGG | 8448 |
| Tyr | Tyr | Leu | Thr | Arg | Asp | Pro | Thr | Thr | Pro | Leu | Ala | Arg | Ala | Ala | Trp | |
| | | | | 2805 | | | | | 2810 | | | | | 2815 | | |
| GAG | ACA | GCT | AGA | CAC | ACT | CCA | GTT | AAC | TCC | TGG | CTA | GGC | AAC | ATT | ATT | 8496 |
| Glu | Thr | Ala | Arg | His | Thr | Pro | Val | Asn | Ser | Trp | Leu | Gly | Asn | Ile | Ile | |
| | | | 2820 | | | | | 2825 | | | | | 2830 | | | |
| ATG | TAT | GCG | CCC | ACT | TTG | TGG | GCA | AGG | ATG | ATT | CTG | ATG | ACT | CAC | TTC | 8544 |
| Met | Tyr | Ala | Pro | Thr | Leu | Trp | Ala | Arg | Met | Ile | Leu | Met | Thr | His | Phe | |
| | | 2835 | | | | | 2840 | | | | | 2845 | | | | |
| TTC | TCC | ATC | CTT | CTA | GCG | CAG | GAG | CAA | CTT | GAA | AAA | GCC | CTG | GAC | TGC | 8592 |
| Phe | Ser | Ile | Leu | Leu | Ala | Gln | Glu | Gln | Leu | Glu | Lys | Ala | Leu | Asp | Cys | |
| | | 2850 | | | | | 2855 | | | | | 2860 | | | | |
| CAG | ATC | TAC | GGG | GCC | TGT | TAC | TCC | ATT | GAG | CCA | CTT | GAC | CTA | CCT | CAG | 8640 |
| Gln | Ile | Tyr | Gly | Ala | Cys | Tyr | Ser | Ile | Glu | Pro | Leu | Asp | Leu | Pro | Gln | |
| 2865 | | | | | 2870 | | | | | 2875 | | | | | 2880 | |
| ATC | ATT | GAA | CGA | CTC | CAT | GGC | CTT | AGC | GCA | TTT | TCA | CTC | CAT | AGT | TAC | 8688 |
| Ile | Ile | Glu | Arg | Leu | His | Gly | Leu | Ser | Ala | Phe | Ser | Leu | His | Ser | Tyr | |
| | | | | 2885 | | | | | 2890 | | | | | 2895 | | |
| TCT | CCA | GGT | GAG | ATC | AAT | AGG | GTG | GCT | TCA | TGC | CTC | AGG | AAA | CTT | GGG | 8736 |
| Ser | Pro | Gly | Glu | Ile | Asn | Arg | Val | Ala | Ser | Cys | Leu | Arg | Lys | Leu | Gly | |
| | | | 2900 | | | | | 2905 | | | | | 2910 | | | |
| GTA | CCA | CCC | TTG | CGA | GTC | TGG | AGA | CAT | CGG | GCC | AGG | AGC | GTC | CGC | GCT | 8784 |
| Val | Pro | Pro | Leu | Arg | Val | Trp | Arg | His | Arg | Ala | Arg | Ser | Val | Arg | Ala | |
| | | | 2915 | | | | | 2920 | | | | | 2925 | | | |
| AGG | CTA | CTG | TCC | CAG | GGA | GGG | AGG | GCC | GCC | ACT | TGT | GGC | AAA | TAC | CTC | 8832 |
| Arg | Leu | Leu | Ser | Gln | Gly | Gly | Arg | Ala | Ala | Thr | Cys | Gly | Lys | Tyr | Leu | |
| | | 2930 | | | | | 2935 | | | | | 2940 | | | | |
| TTC | AAC | TGG | GCA | GTA | AAA | ACC | AAA | CTT | AAA | CTC | ACT | CCA | ATC | CCG | GCT | 8880 |
| Phe | Asn | Trp | Ala | Val | Lys | Thr | Lys | Leu | Lys | Leu | Thr | Pro | Ile | Pro | Ala | |
| 2945 | | | | | 2950 | | | | | 2955 | | | | | 2960 | |
| GCG | TCC | CGG | CTG | GAC | TTG | TCC | GGC | TGG | TTC | GTT | GCT | GGT | TAC | AGC | GGG | 8928 |
| Ala | Ser | Arg | Leu | Asp | Leu | Ser | Gly | Trp | Phe | Val | Ala | Gly | Tyr | Ser | Gly | |
| | | | | 2965 | | | | | 2970 | | | | | 2975 | | |
| GGA | GAC | ATA | TAT | CAC | AGC | CTG | TCT | CGT | GCC | CGA | CCC | CGT | TGG | TTC | ATG | 8976 |
| Gly | Asp | Ile | Tyr | His | Ser | Leu | Ser | Arg | Ala | Arg | Pro | Arg | Trp | Phe | Met | |
| | | | 2980 | | | | | 2985 | | | | | 2990 | | | |
| CTG | TGC | CTA | CTC | CTA | CTT | TCT | GTA | GGG | GTA | GGC | ATC | TAC | CTG | CTC | CCC | 9024 |
| Leu | Cys | Leu | Leu | Leu | Leu | Ser | Val | Gly | Val | Gly | Ile | Tyr | Leu | Leu | Pro | |
| | | 2995 | | | | | 3000 | | | | | 3005 | | | | |
| AAC | CGA | | | | | | | | | | | | | | | 9030 |
| Asn | Arg | | | | | | | | | | | | | | | |
| 3010 | | | | | | | | | | | | | | | | |

( 2 ) INFORMATION FOR SEQ ID NO:14:

( i ) SEQUENCE CHARACTERISTICS:
        ( A ) LENGTH: 3010 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| Met | Ser | Thr | Asn | Pro | Lys | Pro | Gln | Arg | Lys | Thr | Lys | Arg | Asn | Thr | Asn |
|---|---|---|---|---|---|---|---|---|---|---|---|---|---|---|---|
| 1 | | | | 5 | | | | | 10 | | | | | | 15 |
| Arg | Arg | Pro | Gln | Asp | Val | Lys | Phe | Pro | Gly | Gly | Gly | Gln | Ile | Val | Gly |
| | | | 20 | | | | | 25 | | | | | 30 | | |
| Gly | Val | Tyr | Leu | Leu | Pro | Arg | Arg | Gly | Pro | Arg | Leu | Gly | Val | Arg | Ala |
| | | 35 | | | | | 40 | | | | | 45 | | | |
| Pro | Arg | Lys | Thr | Ser | Glu | Arg | Ser | Gln | Pro | Arg | Gly | Arg | Arg | Gln | Pro |
| | 50 | | | | | 55 | | | | | 60 | | | | |
| Ile | Pro | Lys | Ala | Arg | Arg | Pro | Glu | Gly | Arg | Thr | Trp | Ala | Gln | Pro | Gly |
| 65 | | | | | 70 | | | | | 75 | | | | | 80 |
| Tyr | Pro | Trp | Pro | Leu | Tyr | Gly | Asn | Glu | Gly | Leu | Gly | Trp | Ala | Gly | Trp |
| | | | | 85 | | | | | 90 | | | | | 95 | |
| Leu | Leu | Ser | Pro | Arg | Gly | Ser | Arg | Pro | Ser | Trp | Gly | Pro | Thr | Asp | Pro |
| | | | 100 | | | | | 105 | | | | | 110 | | |
| Arg | Arg | Arg | Ser | Arg | Asn | Leu | Gly | Lys | Val | Ile | Asp | Thr | Leu | Thr | Cys |
| | | | 115 | | | | | 120 | | | | | 125 | | |
| Gly | Phe | Ala | Asp | Leu | Met | Gly | Tyr | Ile | Pro | Leu | Val | Gly | Ala | Pro | Leu |
| | | 130 | | | | | 135 | | | | | 140 | | | |
| Gly | Gly | Ala | Ala | Arg | Ala | Leu | Ala | His | Gly | Val | Arg | Val | Leu | Glu | Asp |
| 145 | | | | | 150 | | | | | 155 | | | | | 160 |
| Gly | Val | Asn | Tyr | Ala | Thr | Gly | Asn | Leu | Pro | Gly | Cys | Ser | Phe | Ser | Ile |
| | | | | 165 | | | | | 170 | | | | | 175 | |
| Phe | Leu | Leu | Ala | Leu | Leu | Ser | Cys | Leu | Thr | Thr | Pro | Ala | Ser | Ala | Tyr |
| | | | | 180 | | | | | 185 | | | | | 190 | |
| Glu | Val | His | Asn | Val | Ser | Gly | Ile | Tyr | His | Val | Thr | Asn | Asp | Cys | Ser |
| | | | 195 | | | | | 200 | | | | | 205 | | |
| Asn | Ala | Ser | Ile | Val | Tyr | Glu | Ala | Ala | Asp | Leu | Ile | Met | His | Thr | Pro |
| | 210 | | | | | 215 | | | | | 220 | | | | |
| Gly | Cys | Val | Pro | Cys | Val | Arg | Glu | Gly | Asn | Ser | Ser | Arg | Cys | Trp | Val |
| 225 | | | | | 230 | | | | | 235 | | | | | 240 |
| Ala | Leu | Thr | Pro | Thr | Leu | Ala | Ala | Arg | Asn | Val | Thr | Ile | Pro | Thr | Thr |
| | | | | 245 | | | | | 250 | | | | | 255 | |
| Thr | Ile | Arg | Arg | His | Val | Asp | Leu | Leu | Val | Gly | Ala | Ala | Ala | Phe | Cys |
| | | | 260 | | | | | 265 | | | | | 270 | | |
| Ser | Ala | Met | Tyr | Val | Gly | Asp | Leu | Cys | Gly | Ser | Val | Phe | Leu | Val | Ser |
| | | | 275 | | | | | 280 | | | | | 285 | | |
| Gln | Leu | Phe | Thr | Phe | Ser | Pro | Arg | Arg | His | Val | Thr | Leu | Gln | Asp | Cys |
| | 290 | | | | | 295 | | | | | 300 | | | | |
| Asn | Cys | Ser | Ile | Tyr | Pro | Gly | His | Val | Ser | Gly | His | Arg | Met | Ala | Trp |
| 305 | | | | | 310 | | | | | 315 | | | | | 320 |
| Asp | Met | Met | Met | Asn | Trp | Ser | Pro | Thr | Thr | Ala | Leu | Val | Val | Ser | Gln |
| | | | | 325 | | | | | 330 | | | | | 335 | |
| Leu | Leu | Arg | Ile | Pro | Gln | Ala | Val | Val | Asp | Met | Val | Ala | Gly | Ala | His |
| | | | 340 | | | | | 345 | | | | | 350 | | |
| Trp | Gly | Val | Leu | Ala | Gly | Leu | Ala | Tyr | Tyr | Ser | Met | Ala | Gly | Asn | Trp |
| | | 355 | | | | | 360 | | | | | 365 | | | |
| Ala | Lys | Val | Leu | Ile | Val | Met | Leu | Leu | Phe | Ala | Gly | Val | Asp | Gly | Asp |
| | 370 | | | | | 375 | | | | | 380 | | | | |
| Thr | His | Val | Thr | Gly | Gly | Ala | Gln | Ala | Lys | Thr | Thr | Asn | Arg | Leu | Val |
| 385 | | | | | 390 | | | | | 395 | | | | | 400 |
| Ser | Met | Phe | Ala | Ser | Gly | Pro | Ser | Gln | Lys | Ile | Gln | Leu | Ile | Asn | Thr |

|     |     |     | 405 |     |     |     | 410 |     |     |     | 415 |     |     |
|-----|-----|-----|-----|-----|-----|-----|-----|-----|-----|-----|-----|-----|-----|

Asn Gly Ser Trp His Ile Asn Arg Thr Ala Leu Asn Cys Asn Asp Ser
            420                 425             430

Leu Gln Thr Gly Phe Leu Ala Ala Leu Phe Tyr Thr His Ser Phe Asn
            435                 440             445

Ser Ser Gly Cys Pro Glu Arg Met Ala Gln Cys Arg Thr Ile Asp Lys
        450         455             460

Phe Asp Gln Gly Trp Gly Pro Ile Thr Tyr Ala Glu Ser Ser Arg Ser
465             470             475                         480

Asp Gln Arg Pro Tyr Cys Trp His Tyr Pro Pro Gln Cys Thr Ile
            485                 490             495

Val Pro Ala Ser Glu Val Cys Gly Pro Val Tyr Cys Phe Thr Pro Ser
            500             505             510

Pro Val Val Val Gly Thr Thr Asp Arg Phe Gly Val Pro Thr Tyr Arg
        515             520             525

Trp Gly Glu Asn Glu Thr Asp Val Leu Leu Leu Asn Asn Thr Arg Pro
    530             535             540

Pro Gln Gly Asn Trp Phe Gly Cys Thr Trp Met Asn Ser Thr Gly Phe
545             550             555                         560

Thr Lys Thr Cys Gly Gly Pro Pro Cys Asn Ile Gly Gly Val Gly Asn
            565             570             575

Asn Thr Leu Thr Cys Pro Thr Asp Cys Phe Arg Lys His Pro Glu Ala
            580             585             590

Thr Tyr Thr Lys Cys Gly Ser Gly Pro Trp Leu Thr Pro Arg Cys Met
            595             600             605

Val Asp Tyr Pro Tyr Arg Leu Trp His Tyr Pro Cys Thr Val Asn Phe
    610             615             620

Thr Ile Phe Lys Val Arg Met Tyr Val Gly Gly Val Glu His Arg Leu
625             630             635                         640

Asn Ala Ala Cys Asn Trp Thr Arg Gly Glu Arg Cys Asp Leu Glu Asp
            645             650             655

Arg Asp Arg Pro Glu Leu Ser Pro Leu Leu Leu Ser Thr Thr Glu Trp
            660             665             670

Gln Val Leu Pro Cys Ser Phe Thr Thr Leu Pro Ala Leu Ser Thr Gly
            675             680             685

Leu Ile His Leu His Gln Asn Ile Val Asp Val Gln Tyr Leu Tyr Gly
            690             695             700

Ile Gly Ser Ala Val Val Ser Phe Ala Ile Lys Trp Glu Tyr Val Leu
705                 710             715                     720

Leu Leu Phe Leu Leu Leu Ala Asp Ala Arg Val Cys Ala Cys Leu Trp
                725             730             735

Met Met Leu Leu Ile Ala Gln Ala Glu Ala Ala Leu Glu Asn Leu Val
        740             745             750

Val Leu Asn Ser Ala Ser Val Ala Gly Ala His Gly Ile Leu Ser Phe
        755             760             765

Leu Val Phe Phe Cys Ala Ala Trp Tyr Ile Lys Gly Arg Leu Val Pro
    770             775             780

Gly Ala Thr Tyr Ala Leu Tyr Gly Val Trp Pro Leu Leu Leu Leu Leu
785                 790             795                     800

Leu Ala Leu Pro Pro Arg Ala Tyr Ala Met Asp Arg Glu Met Ala Ala
            805             810             815

Ser Cys Gly Gly Ala Val Phe Val Gly Leu Val Leu Leu Thr Leu Ser
            820             825             830

```
Pro Tyr Tyr Lys Val Phe Leu Ala Arg Leu Ile Trp Trp Leu Gln Tyr
        835                 840                 845
Phe Thr Thr Arg Ala Glu Ala Asp Leu His Val Trp Ile Pro Pro Leu
    850                 855                 860
Asn Ala Arg Gly Gly Arg Asp Ala Ile Ile Leu Leu Met Cys Ala Val
865                 870                 875                 880
His Pro Glu Leu Ile Phe Asp Ile Thr Lys Leu Leu Ile Ala Ile Leu
                885                 890                 895
Gly Pro Leu Met Val Leu Gln Ala Gly Ile Thr Arg Val Pro Tyr Phe
                900                 905                 910
Val Arg Ala Gln Gly Leu Ile His Ala Cys Met Leu Val Arg Lys Val
        915                 920                 925
Ala Gly Gly His Tyr Val Gln Met Ala Phe Met Lys Leu Gly Ala Leu
930                 935                 940
Thr Gly Thr Tyr Ile Tyr Asn His Leu Thr Pro Leu Arg Asp Trp Pro
945                 950                 955                 960
Arg Ala Gly Leu Arg Asp Leu Ala Val Ala Val Glu Pro Val Val Phe
                965                 970                 975
Ser Asp Met Glu Thr Lys Ile Ile Thr Trp Gly Ala Asp Thr Ala Ala
            980                 985                 990
Cys Gly Asp Ile Ile Leu Gly Leu Pro Val Ser Ala Arg Arg Gly Lys
        995                 1000                1005
Glu Ile Leu Leu Gly Pro Ala Asp Ser Leu Glu Gly Arg Gly Leu Arg
    1010                1015                1020
Leu Leu Ala Pro Ile Thr Ala Tyr Ser Gln Gln Thr Arg Gly Leu Leu
1025                1030                1035                1040
Gly Cys Ile Ile Thr Ser Leu Thr Gly Arg Asp Lys Asn Gln Val Glu
                1045                1050                1055
Gly Glu Val Gln Val Val Ser Thr Ala Thr Gln Ser Phe Leu Ala Thr
                1060                1065                1070
Cys Val Asn Gly Val Cys Trp Thr Val Tyr His Gly Ala Gly Ser Lys
            1075                1080                1085
Thr Leu Ala Ala Pro Lys Gly Pro Ile Thr Gln Met Tyr Thr Asn Val
    1090                1095                1100
Asp Gln Asp Leu Val Gly Trp Pro Lys Pro Pro Gly Ala Arg Ser Leu
1105                1110                1115                1120
Thr Pro Cys Thr Cys Gly Ser Ser Asp Leu Tyr Leu Val Thr Arg His
            1125                1130                1135
Ala Asp Val Ile Pro Val Arg Arg Arg Gly Asp Ser Arg Gly Ser Leu
                1140                1145                1150
Leu Ser Pro Arg Pro Val Ser Tyr Leu Lys Gly Ser Ser Gly Gly Pro
        1155                1160                1165
Leu Leu Cys Pro Phe Gly His Ala Val Gly Ile Phe Arg Ala Ala Val
    1170                1175                1180
Cys Thr Arg Gly Val Ala Lys Ala Val Asp Phe Val Pro Val Glu Ser
1185                1190                1195                1200
Met Glu Thr Thr Met Arg Ser Pro Val Phe Thr Asp Asn Ser Ser Pro
                1205                1210                1215
Pro Ala Val Pro Gln Ser Phe Gln Val Ala His Leu His Ala Pro Thr
                1220                1225                1230
Gly Ser Gly Lys Ser Thr Lys Val Pro Ala Ala Tyr Ala Ala Gln Gly
            1235                1240                1245
Tyr Lys Val Leu Val Leu Asn Pro Ser Val Ala Ala Thr Leu Gly Phe
    1250                1255                1260
```

```
Gly Ala Tyr Met Ser Lys Ala His Gly Ile Asp Pro Asn Ile Arg Thr
1265                 1270                1275                1280

Gly Val Arg Thr Ile Thr Thr Gly Ala Pro Val Thr Tyr Ser Thr Tyr
                1285                1290                1295

Gly Lys Phe Leu Ala Asp Gly Gly Cys Ser Gly Gly Ala Tyr Asp Ile
            1300                1305                1310

Ile Ile Cys Asp Glu Cys His Ser Thr Asp Ser Thr Thr Ile Leu Gly
        1315                1320                1325

Ile Gly Thr Val Leu Asp Gln Ala Glu Thr Ala Gly Ala Arg Leu Val
    1330                1335                1340

Val Leu Ala Thr Ala Thr Pro Pro Gly Ser Val Thr Val Pro His Pro
1345                1350                1355                1360

Asn Ile Glu Glu Val Ala Leu Ser Asn Thr Gly Glu Ile Pro Phe Tyr
                1365                1370                1375

Gly Lys Ala Ile Pro Ile Glu Ala Ile Arg Gly Gly Arg His Leu Ile
            1380                1385                1390

Phe Cys His Ser Lys Lys Lys Cys Asp Glu Leu Ala Ala Lys Leu Ser
        1395                1400                1405

Gly Leu Gly Ile Asn Ala Val Ala Tyr Tyr Arg Gly Leu Asp Val Ser
    1410                1415                1420

Val Ile Pro Thr Ile Gly Asp Val Val Val Val Ala Thr Asp Ala Leu
1425                1430                1435                1440

Met Thr Gly Tyr Thr Gly Asp Phe Asp Ser Val Ile Asp Cys Asn Thr
                1445                1450                1455

Cys Val Thr Gln Thr Val Asp Phe Ser Leu Asp Pro Thr Phe Thr Ile
            1460                1465                1470

Glu Thr Thr Thr Val Pro Gln Asp Ala Val Ser Arg Ser Gln Arg Arg
        1475                1480                1485

Gly Arg Thr Gly Arg Gly Arg Arg Gly Ile Tyr Arg Phe Val Thr Pro
    1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Ser
                1525                1530                1535

Val Arg Leu Arg Ala Tyr Leu Asn Thr Pro Gly Leu Pro Val Cys Gln
            1540                1545                1550

Asp His Leu Glu Phe Trp Glu Ser Val Phe Thr Gly Leu Thr His Ile
        1555                1560                1565

Asp Ala His Phe Leu Ser Gln Thr Lys Gln Ala Gly Asp Asn Phe Pro
    1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
                1605                1610                1615

Thr Leu His Gly Pro Thr Pro Leu Leu Tyr Arg Leu Gly Ala Val Gln
            1620                1625                1630

Asn Glu Val Thr Leu Thr His Pro Ile Thr Lys Tyr Ile Met Ala Cys
        1635                1640                1645

Met Ser Ala Asp Leu Glu Val Val Thr Ser Thr Trp Val Leu Val Gly
    1650                1655                1660

Gly Val Leu Ala Ala Leu Ala Ala Tyr Cys Leu Thr Thr Gly Ser Val
1665                1670                1675                1680

Val Ile Val Gly Arg Ile Ile Leu Ser Gly Arg Pro Ala Ile Val Pro
```

|  |  |  |
|---|---|---|
| 1685 | 1690 | 1695 |

Asp Arg Glu Leu Leu Tyr Gln Glu Phe Asp Glu Met Glu Cys Ala
          1700                    1705               1710

Ser His Leu Pro Tyr Ile Glu Gln Gly Met Gln Leu Ala Glu Gln Phe
        1715                 1720               1725

Lys Gln Lys Ala Leu Gly Leu Leu Gln Thr Ala Thr Lys Gln Ala Glu
   1730                 1735               1740

Ala Ala Ala Pro Val Val Glu Ser Lys Trp Arg Ala Leu Glu Thr Phe
1745               1750               1755             1760

Trp Ala Lys His Met Trp Asn Phe Ile Ser Gly Ile Gln Tyr Leu Ala
             1765               1770               1775

Gly Leu Ser Thr Leu Pro Gly Asn Pro Ala Ile Ala Ser Leu Met Ala
         1780               1785               1790

Phe Thr Ala Ser Ile Thr Ser Pro Leu Thr Thr Gln Ser Thr Leu Leu
        1795               1800               1805

Phe Asn Ile Leu Gly Gly Trp Val Ala Ala Gln Leu Ala Pro Pro Ser
    1810               1815               1820

Ala Ala Ser Ala Phe Val Gly Ala Gly Ile Ala Gly Ala Ala Val Gly
1825               1830               1835             1840

Ser Ile Gly Leu Gly Lys Val Leu Val Asp Ile Leu Ala Gly Tyr Gly
         1845               1850               1855

Ala Gly Val Ala Gly Ala Leu Val Ala Phe Lys Val Met Ser Gly Glu
             1860               1865               1870

Met Pro Ser Thr Glu Asp Leu Val Asn Leu Leu Pro Ala Ile Leu Ser
        1875               1880               1885

Pro Gly Ala Leu Val Val Gly Val Val Cys Ala Ala Ile Leu Arg Arg
   1890                 1895               1900

His Val Gly Pro Gly Glu Gly Ala Val Gln Trp Met Asn Arg Leu Ile
1905               1910               1915             1920

Ala Phe Ala Ser Arg Gly Asn His Val Ser Pro Thr His Tyr Val Pro
             1925               1930               1935

Glu Ser Asp Ala Ala Ala Arg Val Thr Gln Ile Leu Ser Ser Leu Thr
          1940               1945               1950

Ile Thr Gln Leu Leu Lys Arg Leu His Gln Trp Ile Asn Glu Asp Cys
      1955               1960               1965

Ser Thr Pro Cys Ser Gly Ser Trp Leu Arg Asp Val Trp Asp Trp Ile
1970               1975               1980

Cys Thr Val Leu Thr Asp Phe Lys Thr Trp Leu Gln Ser Lys Leu Leu
1985               1990               1995             2000

Pro Gln Leu Pro Gly Val Pro Phe Phe Ser Cys Gln Arg Gly Tyr Lys
             2005               2010               2015

Gly Val Trp Arg Gly Asp Gly Ile Met Gln Thr Thr Cys Pro Cys Gly
        2020               2025               2030

Ala Gln Ile Thr Gly His Val Lys Asn Gly Ser Met Arg Ile Val Gly
    2035               2040               2045

Pro Lys Thr Cys Ser Asn Thr Trp His Gly Thr Phe Pro Ile Asn Ala
   2050                 2055               2060

Tyr Thr Thr Gly Pro Cys Thr Pro Ser Pro Ala Pro Asn Tyr Ser Arg
2065               2070               2075             2080

Ala Leu Trp Arg Val Ala Ala Glu Glu Tyr Val Glu Val Thr Arg Val
             2085               2090               2095

Gly Asp Phe His Tyr Val Thr Gly Met Thr Thr Asp Asn Val Lys Cys
         2100               2105               2110

```
Pro Cys Gln Val Pro Ala Pro Glu Phe Phe Ser Glu Val Asp Gly Val
        2115                2120                2125

Arg Leu His Arg Tyr Ala Pro Ala Cys Arg Pro Leu Leu Arg Glu Glu
        2130                2135                2140

Val Thr Phe Gln Val Gly Leu Asn Gln Tyr Leu Val Gly Ser Gln Leu
2145                2150                2155                2160

Pro Cys Glu Pro Glu Pro Asp Val Ala Val Leu Thr Ser Met Leu Thr
        2165                2170                2175

Asp Pro Ser His Ile Thr Ala Glu Thr Ala Lys Arg Arg Leu Ala Arg
        2180                2185                2190

Gly Ser Pro Pro Ser Leu Ala Ser Ser Ser Ala Ser Gln Leu Ser Ala
        2195                2200                2205

Pro Ser Leu Lys Ala Thr Cys Thr Thr His His Val Ser Pro Asp Ala
        2210                2215                2220

Asp Leu Ile Glu Ala Asn Leu Leu Trp Arg Gln Glu Met Gly Gly Asn
2225                2230                2235                2240

Ile Thr Arg Val Glu Ser Glu Asn Lys Val Val Val Leu Asp Ser Phe
        2245                2250                2255

Asp Pro Leu Arg Ala Glu Glu Asp Glu Arg Glu Val Ser Val Pro Ala
        2260                2265                2270

Glu Ile Leu Arg Lys Ser Lys Lys Phe Pro Ala Ala Met Pro Ile Trp
        2275                2280                2285

Ala Arg Pro Asp Tyr Asn Pro Pro Leu Leu Glu Ser Trp Lys Asp Pro
        2290                2295                2300

Asp Tyr Val Pro Pro Val Val His Gly Cys Pro Leu Pro Pro Ile Lys
2305                2310                2315                2320

Ala Pro Pro Ile Pro Pro Pro Arg Arg Lys Arg Thr Val Val Leu Thr
        2325                2330                2335

Glu Ser Ser Val Ser Ser Ala Leu Ala Glu Leu Ala Thr Lys Thr Phe
        2340                2345                2350

Gly Ser Ser Glu Ser Ser Ala Val Asp Ser Gly Thr Ala Thr Ala Leu
        2355                2360                2365

Pro Asp Gln Ala Ser Asp Asp Gly Asp Lys Gly Ser Asp Val Glu Ser
        2370                2375                2380

Tyr Ser Ser Met Pro Pro Leu Glu Gly Glu Pro Gly Asp Pro Asp Leu
2385                2390                2395                2400

Ser Asp Gly Ser Trp Ser Thr Val Ser Glu Glu Ala Ser Glu Asp Val
        2405                2410                2415

Val Cys Cys Ser Met Ser Tyr Thr Trp Thr Gly Ala Leu Ile Thr Pro
        2420                2425                2430

Cys Ala Ala Glu Glu Ser Lys Leu Pro Ile Asn Ala Leu Ser Asn Ser
        2435                2440                2445

Leu Leu Arg His His Asn Met Val Tyr Ala Thr Thr Ser Arg Ser Ala
        2450                2455                2460

Gly Leu Arg Gln Lys Lys Val Thr Phe Asp Arg Leu Gln Val Leu Asp
2465                2470                2475                2480

Asp His Tyr Arg Asp Val Leu Lys Glu Met Lys Ala Lys Ala Ser Thr
        2485                2490                2495

Val Lys Ala Lys Leu Leu Ser Val Glu Glu Ala Cys Lys Leu Thr Pro
        2500                2505                2510

Pro His Ser Ala Lys Ser Lys Phe Gly Tyr Gly Ala Lys Asp Val Arg
        2515                2520                2525

Asn Leu Ser Ser Lys Ala Val Asn His Ile His Ser Val Trp Lys Asp
2530                2535                2540
```

```
Leu  Leu  Glu  Asp  Thr  Val  Thr  Pro  Ile  Asp  Thr  Thr  Ile  Met  Ala  Lys
2545                2550                2555                          2560

Asn  Glu  Val  Phe  Cys  Val  Gln  Pro  Glu  Lys  Gly  Gly  Arg  Lys  Pro  Ala
                    2565                2570                          2575

Arg  Leu  Ile  Val  Phe  Pro  Asp  Leu  Gly  Val  Arg  Val  Cys  Glu  Lys  Met
                2580                2585                2590

Ala  Leu  Tyr  Asp  Val  Val  Ser  Thr  Leu  Pro  Gln  Val  Val  Met  Gly  Ser
           2595                2600                          2605

Ser  Tyr  Gly  Phe  Gln  Tyr  Ser  Pro  Gly  Gln  Arg  Val  Glu  Phe  Leu  Val
           2610                2615                2620

Asn  Thr  Trp  Lys  Ser  Lys  Lys  Asn  Pro  Met  Gly  Phe  Ser  Tyr  Asp  Thr
2625                2630                2635                          2640

Arg  Cys  Phe  Asp  Ser  Thr  Val  Thr  Glu  Asn  Asp  Ile  Arg  Val  Glu  Glu
                    2645                2650                          2655

Ser  Ile  Tyr  Gln  Cys  Cys  Asp  Leu  Ala  Pro  Glu  Ala  Arg  Gln  Ala  Ile
                2660                2665                2670

Lys  Ser  Leu  Thr  Glu  Arg  Leu  Tyr  Ile  Gly  Gly  Pro  Leu  Thr  Asn  Ser
           2675                2680                          2685

Lys  Gly  Gln  Asn  Cys  Gly  Tyr  Arg  Arg  Cys  Arg  Ala  Ser  Gly  Val  Leu
           2690                2695                2700

Thr  Thr  Ser  Cys  Gly  Asn  Thr  Leu  Thr  Cys  Tyr  Leu  Lys  Ala  Ser  Ala
2705                2710                2715                          2720

Ala  Cys  Arg  Ala  Ala  Lys  Leu  Gln  Asp  Cys  Thr  Met  Leu  Val  Asn  Gly
                    2725                2730                          2735

Asp  Asp  Leu  Val  Val  Ile  Cys  Glu  Ser  Ala  Gly  Thr  Gln  Glu  Asp  Ala
                2740                2745                2750

Ala  Ser  Leu  Arg  Val  Phe  Thr  Glu  Ala  Met  Thr  Arg  Tyr  Ser  Ala  Pro
           2755                2760                          2765

Pro  Gly  Asp  Pro  Pro  Gln  Pro  Glu  Tyr  Asp  Leu  Glu  Leu  Ile  Thr  Ser
      2770                2775                          2780

Cys  Ser  Ser  Asn  Val  Ser  Val  Ala  His  Asp  Ala  Ser  Gly  Lys  Arg  Val
2785                2790                2795                          2800

Tyr  Tyr  Leu  Thr  Arg  Asp  Pro  Thr  Thr  Pro  Leu  Ala  Arg  Ala  Ala  Trp
                2805                2810                          2815

Glu  Thr  Ala  Arg  His  Thr  Pro  Val  Asn  Ser  Trp  Leu  Gly  Asn  Ile  Ile
                2820                2825                          2830

Met  Tyr  Ala  Pro  Thr  Leu  Trp  Ala  Arg  Met  Ile  Leu  Met  Thr  His  Phe
           2835                2840                          2845

Phe  Ser  Ile  Leu  Leu  Ala  Gln  Glu  Gln  Leu  Glu  Lys  Ala  Leu  Asp  Cys
      2850                2855                2860

Gln  Ile  Tyr  Gly  Ala  Cys  Tyr  Ser  Ile  Glu  Pro  Leu  Asp  Leu  Pro  Gln
2865                2870                2875                          2880

Ile  Ile  Glu  Arg  Leu  His  Gly  Leu  Ser  Ala  Phe  Ser  Leu  His  Ser  Tyr
                2885                2890                2895

Ser  Pro  Gly  Glu  Ile  Asn  Arg  Val  Ala  Ser  Cys  Leu  Arg  Lys  Leu  Gly
           2900                2905                          2910

Val  Pro  Pro  Leu  Arg  Val  Trp  Arg  His  Arg  Ala  Arg  Ser  Val  Arg  Ala
           2915                2920                          2925

Arg  Leu  Leu  Ser  Gln  Gly  Gly  Arg  Ala  Ala  Thr  Cys  Gly  Lys  Tyr  Leu
      2930                2935                          2940

Phe  Asn  Trp  Ala  Val  Lys  Thr  Lys  Leu  Lys  Leu  Thr  Pro  Ile  Pro  Ala
2945                2950                2955                          2960

Ala  Ser  Arg  Leu  Asp  Leu  Ser  Gly  Trp  Phe  Val  Ala  Gly  Tyr  Ser  Gly
```

-continued

```
                            2965                        2970                        2975
Gly Asp Ile Tyr His Ser Leu Ser Arg Ala Arg Pro Arg Trp Phe Met
                2980                        2985                        2990
Leu Cys Leu Leu Leu Leu Ser Val Gly Val Gly Ile Tyr Leu Leu Pro
                2995                        3000                        3005
Asn Arg
    3010
```

( 2 ) INFORMATION FOR SEQ ID NO:15:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( i i ) MOLECULE TYPE: cDNA from genomic RNA ( i x ) FEATURE:
        ( A ) NAME/KEY: misc_feature
        ( B ) LOCATION: 1..90
        ( D ) OTHER INFORMATION: /note: "sequence = 474 - 563 of SEQ ID NO: 1"

( i x ) FEATURE:
        ( A ) NAME/KEY: CDS
        ( B ) LOCATION: 1..90

( x i ) SEQUENCE DESCRIPTION: SEQ ID NO:15:

```
GCG CCC AGG AAG ACT TCC GAG CGG TCG CAA CCT CGT GGA AGG CGA CAA    48
Ala Pro Arg Lys Thr Ser Glu Arg Ser Gln Pro Arg Gly Arg Arg Gln
 1               5                   10                  15

CCT ATC CCC AAG GCT CGC CGG CCC GAG GGC AGG ACC TGG GCT            90
Pro Ile Pro Lys Ala Arg Arg Pro Glu Gly Arg Thr Trp Ala
                20                  25                  30
```

( 2 ) INFORMATION FOR SEQ ID NO:16:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Ala Pro Arg Lys Thr Ser Glu Arg Ser Gln Pro Arg Gly Arg Arg Gln
 1               5                   10                  15
Pro Ile Pro Lys Ala Arg Arg Pro Glu Gly Arg Thr Trp Ala
                20                  25                  30
```

( 2 ) INFORMATION FOR SEQ ID NO:17:

( i ) SEQUENCE CHARACTERISTICS:
        ( A ) LENGTH: 228 base pairs
        ( B ) TYPE: nucleic acid
        ( C ) STRANDEDNESS: single
        ( D ) TOPOLOGY: linear ( i i ) MOLECULE TYPE: cDNA from genomic RNA ( i x ) FEATURE:
        ( A ) NAME/KEY: misc_feature
        ( B ) LOCATION: 1..228
        ( D ) OTHER INFORMATION: /note: "sequence = 678 - 905 of SEQ ID NO: 1"

( i x ) FEATURE:
        ( A ) NAME/KEY: CDS
        ( B ) LOCATION: 1..228

( x i ) SEQUENCE DESCRIPTION: SEQ ID NO:17:

| TCG | CGT | AAT | TTG | GGT | AAG | GTC | ATC | GAT | ACC | CTC | ACA | TGC | GGC | TTC | GCC | 48 |
|---|---|---|---|---|---|---|---|---|---|---|---|---|---|---|---|---|
| Ser | Arg | Asn | Leu | Gly | Lys | Val | Ile | Asp | Thr | Leu | Thr | Cys | Gly | Phe | Ala | |
| 1 | | | | 5 | | | | | 10 | | | | | 15 | | |

| GAT | CTC | ATG | GGG | TAC | ATT | CCG | CTC | GTC | GGC | GCC | CCC | CTG | GGG | GGC | GCT | 96 |
|---|---|---|---|---|---|---|---|---|---|---|---|---|---|---|---|---|
| Asp | Leu | Met | Gly | Tyr | Ile | Pro | Leu | Val | Gly | Ala | Pro | Leu | Gly | Gly | Ala | |
| | | | 20 | | | | | 25 | | | | | 30 | | | |

| GCC | AGG | GCC | CTG | GCA | CAT | GGT | GTC | CGG | GTT | CTG | GAG | GAC | GGC | GTG | AAC | 144 |
|---|---|---|---|---|---|---|---|---|---|---|---|---|---|---|---|---|
| Ala | Arg | Ala | Leu | Ala | His | Gly | Val | Arg | Val | Leu | Glu | Asp | Gly | Val | Asn | |
| | | 35 | | | | | 40 | | | | | 45 | | | | |

| TAT | GCA | ACA | GGG | AAT | CTG | CCC | GGT | TGC | TCT | TTT | TCT | ATC | TTC | CTC | TTG | 192 |
|---|---|---|---|---|---|---|---|---|---|---|---|---|---|---|---|---|
| Tyr | Ala | Thr | Gly | Asn | Leu | Pro | Gly | Cys | Ser | Phe | Ser | Ile | Phe | Leu | Leu | |
| | 50 | | | | | 55 | | | | | 60 | | | | | |

| GCT | CTG | CTG | TCC | TGC | CTG | ACC | ACC | CCA | GCT | TCC | GCT | | | | | 228 |
|---|---|---|---|---|---|---|---|---|---|---|---|---|---|---|---|---|
| Ala | Leu | Leu | Ser | Cys | Leu | Thr | Thr | Pro | Ala | Ser | Ala | | | | | |
| 65 | | | | 70 | | | | | 75 | | | | | | | |

( 2 ) INFORMATION FOR SEQ ID NO:18:

( i ) SEQUENCE CHARACTERISTICS:
        ( A ) LENGTH: 76 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

| Ser | Arg | Asn | Leu | Gly | Lys | Val | Ile | Asp | Thr | Leu | Thr | Cys | Gly | Phe | Ala |
|---|---|---|---|---|---|---|---|---|---|---|---|---|---|---|---|
| 1 | | | | 5 | | | | | 10 | | | | | 15 | |

| Asp | Leu | Met | Gly | Tyr | Ile | Pro | Leu | Val | Gly | Ala | Pro | Leu | Gly | Gly | Ala |
|---|---|---|---|---|---|---|---|---|---|---|---|---|---|---|---|
| | | | 20 | | | | | 25 | | | | | 30 | | |

| Ala | Arg | Ala | Leu | Ala | His | Gly | Val | Arg | Val | Leu | Glu | Asp | Gly | Val | Asn |
|---|---|---|---|---|---|---|---|---|---|---|---|---|---|---|---|
| | | 35 | | | | | 40 | | | | | 45 | | | |

| Tyr | Ala | Thr | Gly | Asn | Leu | Pro | Gly | Cys | Ser | Phe | Ser | Ile | Phe | Leu | Leu |
|---|---|---|---|---|---|---|---|---|---|---|---|---|---|---|---|
| | 50 | | | | | 55 | | | | | 60 | | | | |

| Ala | Leu | Leu | Ser | Cys | Leu | Thr | Thr | Pro | Ala | Ser | Ala |
|---|---|---|---|---|---|---|---|---|---|---|---|
| 65 | | | | | 70 | | | | | 75 | |

( 2 ) INFORMATION FOR SEQ ID NO:19:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: cDNA from genomic RNA ( i x ) FEATURE:
        ( A ) NAME/KEY: misc_feature
        ( B ) LOCATION: 1..48
        ( D ) OTHER INFORMATION: /note: "sequence = 906 - 953 of
           SEQ ID NO: 1"

( i x ) FEATURE:
        ( A ) NAME/KEY: CDS
        ( B ) LOCATION: 1..48

( x i ) SEQUENCE DESCRIPTION: SEQ ID NO:19:

| TAC | GAA | GTG | CAC | AAC | GTG | TCC | GGG | ATA | TAT | CAT | GTC | ACG | AAC | GAC | TGC | 48 |
|---|---|---|---|---|---|---|---|---|---|---|---|---|---|---|---|---|
| Tyr | Glu | Val | His | Asn | Val | Ser | Gly | Ile | Tyr | His | Val | Thr | Asn | Asp | Cys | |
| 1 | | | | 5 | | | | | 10 | | | | | 15 | | |

( 2 ) INFORMATION FOR SEQ ID NO:20:

( i ) SEQUENCE CHARACTERISTICS:
  ( A ) LENGTH: 16 amino acids
  ( B ) TYPE: amino acid
  ( D ) TOPOLOGY: linear ( i i ) MOLECULE TYPE: protein ( x i ) SEQUENCE DESCRIPTION: SEQ ID NO:20:

Tyr Glu Val His Asn Val Ser Gly Ile Tyr His Val Thr Asn Asp Cys
 1               5                  10                  15

( 2 ) INFORMATION FOR SEQ ID NO:21:

( i ) SEQUENCE CHARACTERISTICS:
    ( A ) LENGTH: 594 base pairs
    ( B ) TYPE: nucleic acid
    ( C ) STRANDEDNESS: single
    ( D ) TOPOLOGY: linear ( i i ) MOLECULE TYPE: cDNA from genomic RNA ( i x ) FEATURE:
    ( A ) NAME/KEY: misc_feature
    ( B ) LOCATION: 1..594
    ( D ) OTHER INFORMATION: /note: "sequence = 906 - 1499 of SEQ ID NO: 1"

( i x ) FEATURE:
    ( A ) NAME/KEY: CDS
    ( B ) LOCATION: 1..594

( x i ) SEQUENCE DESCRIPTION: SEQ ID NO:21:

```
TAC GAA GTG CAC AAC GTG TCC GGG ATA TAT CAT GTC ACG AAC GAC TGC        48
Tyr Glu Val His Asn Val Ser Gly Ile Tyr His Val Thr Asn Asp Cys
 1               5                  10                  15

TCC AAC GCA AGC ATT GTG TAT GAG GCA GCG GAC TTG ATC ATG CAT ACT        96
Ser Asn Ala Ser Ile Val Tyr Glu Ala Ala Asp Leu Ile Met His Thr
                20                  25                  30

CCT GGG TGC GTG CCC TGC GTT CGG GAA GGC AAC TCC TCC CGC TGC TGG       144
Pro Gly Cys Val Pro Cys Val Arg Glu Gly Asn Ser Ser Arg Cys Trp
            35                  40                  45

GTA GCG CTC ACT CCC ACG CTC GCA GCC AGG AAC GTC ACC ATC CCC ACC       192
Val Ala Leu Thr Pro Thr Leu Ala Ala Arg Asn Val Thr Ile Pro Thr
        50                  55                  60

ACG ACG ATA CGA CGC CAC GTC GAT CTG CTC GTT GGG GCG GCT GCT TTC       240
Thr Thr Ile Arg Arg His Val Asp Leu Leu Val Gly Ala Ala Ala Phe
 65                 70                  75                  80

TGT TCC GCT ATG TAC GTG GGG GAC CTC TGC GGA TCT GTT TTC CTC GTC       288
Cys Ser Ala Met Tyr Val Gly Asp Leu Cys Gly Ser Val Phe Leu Val
                85                  90                  95

TCT CAG CTG TTC ACC TTC TCG CCT CGC CGG CAT GTG ACA TTA CAG GAC       336
Ser Gln Leu Phe Thr Phe Ser Pro Arg Arg His Val Thr Leu Gln Asp
            100                 105                 110

TGT AAC TGC TCA ATT TAT CCC GGC CAT GTG TCG GGT CAC CGT ATG GCT       384
Cys Asn Cys Ser Ile Tyr Pro Gly His Val Ser Gly His Arg Met Ala
        115                 120                 125

TGG GAC ATG ATG ATG AAC TGG TCG CCC ACA ACA GCC CTA GTG GTG TCG       432
Trp Asp Met Met Met Asn Trp Ser Pro Thr Thr Ala Leu Val Val Ser
 130                 135                 140

CAG TTA CTC CGG ATC CCA CAA GCC GTC GTG GAC ATG GTG GCG GGG GCC       480
Gln Leu Leu Arg Ile Pro Gln Ala Val Val Asp Met Val Ala Gly Ala
145                 150                 155                 160

CAC TGG GGA GTC CTG GCG GGC CTT GCC TAC TAT TCC ATG GCG GGG AAC       528
His Trp Gly Val Leu Ala Gly Leu Ala Tyr Tyr Ser Met Ala Gly Asn
                165                 170                 175

TGG GCT AAG GTT CTG ATT GTG ATG CTA CTT TTT GCT GGC GTT GAC GGG       576
```

5,747,339

147                                                                                  148
-continued

```
Trp Ala Lys Val Leu Ile Val Met Leu Leu Phe Ala Gly Val Asp Gly
            180                 185                 190

GAT ACC CAC GTG ACA GGG                                                        594
Asp Thr His Val Thr Gly
        195
```

(2) INFORMATION FOR SEQ ID NO:22:

(i) SEQUENCE CHARACTERISTICS:
        (A) LENGTH: 198 amino acids
        (B) TYPE: amino acid
        (D) TOPOLOGY: linear (ii) MOLECULE TYPE: protein (xi) SEQUENCE DESCRIPTION: SEQ ID NO:22:

```
Tyr Glu Val His Asn Val Ser Gly Ile Tyr His Val Thr Asn Asp Cys
 1               5                  10                  15

Ser Asn Ala Ser Ile Val Tyr Glu Ala Ala Asp Leu Ile Met His Thr
            20                  25                  30

Pro Gly Cys Val Pro Cys Val Arg Glu Gly Asn Ser Ser Arg Cys Trp
            35                  40                  45

Val Ala Leu Thr Pro Thr Leu Ala Ala Arg Asn Val Thr Ile Pro Thr
    50                  55                  60

Thr Thr Ile Arg Arg His Val Asp Leu Leu Val Gly Ala Ala Ala Phe
65                  70                  75                  80

Cys Ser Ala Met Tyr Val Gly Asp Leu Cys Gly Ser Val Phe Leu Val
                85                  90                  95

Ser Gln Leu Phe Thr Phe Ser Pro Arg Arg His Val Thr Leu Gln Asp
            100                 105                 110

Cys Asn Cys Ser Ile Tyr Pro Gly His Val Ser Gly His Arg Met Ala
            115                 120                 125

Trp Asp Met Met Met Asn Trp Ser Pro Thr Thr Ala Leu Val Val Ser
    130                 135                 140

Gln Leu Leu Arg Ile Pro Gln Ala Val Val Asp Met Val Ala Gly Ala
145                 150                 155                 160

His Trp Gly Val Leu Ala Gly Leu Ala Tyr Tyr Ser Met Ala Gly Asn
                165                 170                 175

Trp Ala Lys Val Leu Ile Val Met Leu Leu Phe Ala Gly Val Asp Gly
            180                 185                 190

Asp Thr His Val Thr Gly
        195
```

(2) INFORMATION FOR SEQ ID NO:23:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA from genomic RNA (ix) FEATURE:
        (A) NAME/KEY: misc_feature
        (B) LOCATION: 1..27
        (D) OTHER INFORMATION: /note: "sequence = 1020 - 1046 of
            SEQ ID NO: 1"

(ix) FEATURE:
        (A) NAME/KEY: CDS
        (B) LOCATION: 1..27

(xi) SEQUENCE DESCRIPTION: SEQ ID NO:23:

```
GTT CGG GAA GGC AAC TCC TCC CGC TGC                                                        27
Val Arg Glu Gly Asn Ser Ser Arg Cys
 1           5
```

( 2 ) INFORMATION FOR SEQ ID NO:24:

( i ) SEQUENCE CHARACTERISTICS:
       ( A ) LENGTH: 9 amino acids
       ( B ) TYPE: amino acid
       ( D ) TOPOLOGY: linear ( i i ) MOLECULE TYPE: protein ( x i ) SEQUENCE DESCRIPTION: SEQ ID NO:24:

```
Val Arg Glu Gly Asn Ser Ser Arg Cys
 1           5
```

( 2 ) INFORMATION FOR SEQ ID NO:25:

( i ) SEQUENCE CHARACTERISTICS:
       ( A ) LENGTH: 102 base pairs
       ( B ) TYPE: nucleic acid
       ( C ) STRANDEDNESS: single
       ( D ) TOPOLOGY: linear ( i i ) MOLECULE TYPE: cDNA from genomic RNA ( i x ) FEATURE:
       ( A ) NAME/KEY: misc_feature
       ( B ) LOCATION: 1..102
       ( D ) OTHER INFORMATION: /note= "sequence = 1020 - 1121 of
             SEQ ID NO: 1"

( i x ) FEATURE:
       ( A ) NAME/KEY: CDS
       ( B ) LOCATION: 1..102

( x i ) SEQUENCE DESCRIPTION: SEQ ID NO:25:

```
GTT CGG GAA GGC AAC TCC TCC CGC TGC TGG GTA GCG CTC ACT CCC ACG        48
Val Arg Glu Gly Asn Ser Ser Arg Cys Trp Val Ala Leu Thr Pro Thr
 1           5                   10                  15

CTC GCA GCC AGG AAC GTC ACC ATC CCC ACC ACG ACG ATA CGA CGC CAC        96
Leu Ala Ala Arg Asn Val Thr Ile Pro Thr Thr Thr Ile Arg Arg His
             20                  25                  30

GTC GAT                                                               102
Val Asp
```

( 2 ) INFORMATION FOR SEQ ID NO:26:

( i ) SEQUENCE CHARACTERISTICS:
       ( A ) LENGTH: 34 amino acids
       ( B ) TYPE: amino acid
       ( D ) TOPOLOGY: linear ( i i ) MOLECULE TYPE: protein ( x i ) SEQUENCE DESCRIPTION: SEQ ID NO:26:

```
Val Arg Glu Gly Asn Ser Ser Arg Cys Trp Val Ala Leu Thr Pro Thr
 1           5                   10                  15

Leu Ala Ala Arg Asn Val Thr Ile Pro Thr Thr Thr Ile Arg Arg His
             20                  25                  30

Val Asp
```

( 2 ) INFORMATION FOR SEQ ID NO:27:

( i ) SEQUENCE CHARACTERISTICS:
       ( A ) LENGTH: 39 base pairs
       ( B ) TYPE: nucleic acid ( C ) STRANDEDNESS: single
( D ) TOPOLOGY: linear ( i i ) MOLECULE TYPE: cDNA from genomic RNA ( i x ) FEATURE:
( A ) NAME/KEY: misc_feature
( B ) LOCATION: 1..39
( D ) OTHER INFORMATION: /note: "sequence = 1194 - 1232 of SEQ ID NO: 1"

( i x ) FEATURE:
( A ) NAME/KEY: CDS
( B ) LOCATION: 1..39

( x i ) SEQUENCE DESCRIPTION: SEQ ID NO:27:

| TCT | CAG | CTG | TTC | ACC | TTC | TCG | CCT | CGC | CGG | CAT | GTG | ACA | 39 |
|---|---|---|---|---|---|---|---|---|---|---|---|---|---|
| Ser | Gln | Leu | Phe | Thr | Phe | Ser | Pro | Arg | Arg | His | Val | Thr | |
| 1 | | | | 5 | | | | | | 10 | | | |

( 2 ) INFORMATION FOR SEQ ID NO:28:

( i ) SEQUENCE CHARACTERISTICS:
( A ) LENGTH: 13 amino acids
( B ) TYPE: amino acid
( D ) TOPOLOGY: linear ( i i ) MOLECULE TYPE: protein ( x i ) SEQUENCE DESCRIPTION: SEQ ID NO:28:

Ser Gln Leu Phe Thr Phe Ser Pro Arg Arg His Val Thr
1               5                       10

( 2 ) INFORMATION FOR SEQ ID NO:29:

( i ) SEQUENCE CHARACTERISTICS:
( A ) LENGTH: 114 base pairs
( B ) TYPE: nucleic acid
( C ) STRANDEDNESS: single
( D ) TOPOLOGY: linear ( i i ) MOLECULE TYPE: cDNA from genomic RNA ( i x ) FEATURE:
( A ) NAME/KEY: misc_feature
( B ) LOCATION: 1..114
( D ) OTHER INFORMATION: /note: "sequence = 1209 - 1322 of SEQ ID NO: 1"

( i x ) FEATURE:
( A ) NAME/KEY: CDS
( B ) LOCATION: 1..114

( x i ) SEQUENCE DESCRIPTION: SEQ ID NO:29:

| TTC | TCG | CCT | CGC | CGG | CAT | GTG | ACA | TTA | CAG | GAC | TGT | AAC | TGC | TCA | ATT | 48 |
|---|---|---|---|---|---|---|---|---|---|---|---|---|---|---|---|---|
| Phe | Ser | Pro | Arg | Arg | His | Val | Thr | Leu | Gln | Asp | Cys | Asn | Cys | Ser | Ile | |
| 1 | | | | 5 | | | | | 10 | | | | | 15 | | |

| TAT | CCC | GGC | CAT | GTG | TCG | GGT | CAC | CGT | ATG | GCT | TGG | GAC | ATG | ATG | ATG | 96 |
|---|---|---|---|---|---|---|---|---|---|---|---|---|---|---|---|---|
| Tyr | Pro | Gly | His | Val | Ser | Gly | His | Arg | Met | Ala | Trp | Asp | Met | Met | Met | |
| | | | | 20 | | | | | 25 | | | | | 30 | | |

| AAC | TGG | TCG | CCC | ACA | ACA | 114 |
|---|---|---|---|---|---|---|
| Asn | Trp | Ser | Pro | Thr | Thr | |
| | | 35 | | | | |

( 2 ) INFORMATION FOR SEQ ID NO:30:

( i ) SEQUENCE CHARACTERISTICS:
( A ) LENGTH: 38 amino acids
( B ) TYPE: amino acid
( D ) TOPOLOGY: linear ( i i ) MOLECULE TYPE: protein (xi) SEQUENCE DESCRIPTION: SEQ ID NO:30:

| Phe | Ser | Pro | Arg | Arg | His | Val | Thr | Leu | Gln | Asp | Cys | Asn | Cys | Ser | Ile |
|---|---|---|---|---|---|---|---|---|---|---|---|---|---|---|---|
| 1 | | | | 5 | | | | | 10 | | | | | 15 | |

| Tyr | Pro | Gly | His | Val | Ser | Gly | His | Arg | Met | Ala | Trp | Asp | Met | Met | Met |
|---|---|---|---|---|---|---|---|---|---|---|---|---|---|---|---|
| | | | 20 | | | | | 25 | | | | | 30 | | |

| Asn | Trp | Ser | Pro | Thr | Thr |
|---|---|---|---|---|---|
| | | 35 | | | |

(2) INFORMATION FOR SEQ ID NO:31:

(i) SEQUENCE CHARACTERISTICS:
(A) LENGTH: 7917 base pairs
(B) TYPE: nucleic acid
(C) STRANDEDNESS: single
(D) TOPOLOGY: linear (ii) MOLECULE TYPE: cDNA from genomic RNA (ix) FEATURE:
(A) NAME/KEY: CDS
(B) LOCATION: 1..7862

(ix) FEATURE:
(A) NAME/KEY: misc_feature
(B) LOCATION: 1..7916
(D) OTHER INFORMATION: /note= "sequence = 1500 - 9416 of SEQ ID NO: 1"

(xi) SEQUENCE DESCRIPTION: SEQ ID NO:31:

| GGG | GCG | CAA | GCC | AAA | ACC | ACC | AAC | AGG | CTC | GTG | TCC | ATG | TTC | GCA | AGT | 48 |
|---|---|---|---|---|---|---|---|---|---|---|---|---|---|---|---|---|
| Gly | Ala | Gln | Ala | Lys | Thr | Thr | Asn | Arg | Leu | Val | Ser | Met | Phe | Ala | Ser | |
| 1 | | | | 5 | | | | | 10 | | | | | 15 | | |

| GGG | CCG | TCT | CAG | AAA | ATC | CAG | CTT | ATA | AAC | ACC | AAT | GGG | AGT | TGG | CAC | 96 |
|---|---|---|---|---|---|---|---|---|---|---|---|---|---|---|---|---|
| Gly | Pro | Ser | Gln | Lys | Ile | Gln | Leu | Ile | Asn | Thr | Asn | Gly | Ser | Trp | His | |
| | | | 20 | | | | | 25 | | | | | 30 | | | |

| ATC | AAC | AGG | ACT | GCC | CTG | AAC | TGC | AAT | GAC | TCT | CTC | CAG | ACT | GGG | TTT | 144 |
|---|---|---|---|---|---|---|---|---|---|---|---|---|---|---|---|---|
| Ile | Asn | Arg | Thr | Ala | Leu | Asn | Cys | Asn | Asp | Ser | Leu | Gln | Thr | Gly | Phe | |
| | | 35 | | | | | 40 | | | | | 45 | | | | |

| CTT | GCC | GCG | CTG | TTC | TAC | ACA | CAT | AGT | TTC | AAC | TCG | TCC | GGG | TGC | CCA | 192 |
|---|---|---|---|---|---|---|---|---|---|---|---|---|---|---|---|---|
| Leu | Ala | Ala | Leu | Phe | Tyr | Thr | His | Ser | Phe | Asn | Ser | Ser | Gly | Cys | Pro | |
| | 50 | | | | | 55 | | | | | 60 | | | | | |

| GAG | CGC | ATG | GCC | CAG | TGC | CGC | ACC | ATT | GAC | AAG | TTC | GAC | CAG | GGA | TGG | 240 |
|---|---|---|---|---|---|---|---|---|---|---|---|---|---|---|---|---|
| Glu | Arg | Met | Ala | Gln | Cys | Arg | Thr | Ile | Asp | Lys | Phe | Asp | Gln | Gly | Trp | |
| 65 | | | | | 70 | | | | | 75 | | | | | 80 | |

| GGT | CCC | ATT | ACT | TAT | GCT | GAG | TCT | AGC | AGA | TCA | GAC | CAG | AGG | CCA | TAT | 288 |
|---|---|---|---|---|---|---|---|---|---|---|---|---|---|---|---|---|
| Gly | Pro | Ile | Thr | Tyr | Ala | Glu | Ser | Ser | Arg | Ser | Asp | Gln | Arg | Pro | Tyr | |
| | | | | 85 | | | | | 90 | | | | | 95 | | |

| TGC | TGG | CAC | TAC | CCA | CCT | CCA | CAA | TGT | ACC | ATC | GTA | CCT | GCG | TCG | GAG | 336 |
|---|---|---|---|---|---|---|---|---|---|---|---|---|---|---|---|---|
| Cys | Trp | His | Tyr | Pro | Pro | Pro | Gln | Cys | Thr | Ile | Val | Pro | Ala | Ser | Glu | |
| | | | 100 | | | | | 105 | | | | | 110 | | | |

| GTG | TGC | GGC | CCA | GTG | TAC | TGC | TTC | ACC | CCA | AGC | CCT | GTC | GTC | GTG | GGG | 384 |
|---|---|---|---|---|---|---|---|---|---|---|---|---|---|---|---|---|
| Val | Cys | Gly | Pro | Val | Tyr | Cys | Phe | Thr | Pro | Ser | Pro | Val | Val | Val | Gly | |
| | | 115 | | | | | 120 | | | | | 125 | | | | |

| ACG | ACC | GAT | CGT | TTC | GGT | GTC | CCT | ACG | TAT | AGA | TGG | GGG | GAG | AAC | GAG | 432 |
|---|---|---|---|---|---|---|---|---|---|---|---|---|---|---|---|---|
| Thr | Thr | Asp | Arg | Phe | Gly | Val | Pro | Thr | Tyr | Arg | Trp | Gly | Glu | Asn | Glu | |
| | 130 | | | | | 135 | | | | | 140 | | | | | |

| ACT | GAC | GTG | CTG | CTG | CTC | AAC | AAC | ACG | CGG | CCG | CCG | CAA | GGC | AAC | TGG | 480 |
|---|---|---|---|---|---|---|---|---|---|---|---|---|---|---|---|---|
| Thr | Asp | Val | Leu | Leu | Leu | Asn | Asn | Thr | Arg | Pro | Pro | Gln | Gly | Asn | Trp | |
| 145 | | | | | 150 | | | | | 155 | | | | | 160 | |

| TTC | GGC | TGC | ACA | TGG | ATG | AAT | AGC | ACC | GGG | TTC | ACC | AAG | ACA | TGT | GGG | 528 |
|---|---|---|---|---|---|---|---|---|---|---|---|---|---|---|---|---|
| Phe | Gly | Cys | Thr | Trp | Met | Asn | Ser | Thr | Gly | Phe | Thr | Lys | Thr | Cys | Gly | |
| | | | | 165 | | | | | 170 | | | | | 175 | | |

| GGG | CCC | CCG | TGT | AAC | ATC | GGG | GGG | GTC | GGC | AAC | AAC | ACC | CTG | ACC | TGC | 576 |

```
Gly Pro Pro Cys Asn Ile Gly Gly Val Gly Asn Asn Thr Leu Thr Cys
            180                 185                 190

CCC ACG GAC TGC TTC CGG AAG CAC CCC GAG GCT ACC TAC ACA AAA TGT        624
Pro Thr Asp Cys Phe Arg Lys His Pro Glu Ala Thr Tyr Thr Lys Cys
            195                 200                 205

GGT TCG GGG CCT TGG CTG ACA CCT AGG TGC ATG GTT GAC TAT CCA TAC        672
Gly Ser Gly Pro Trp Leu Thr Pro Arg Cys Met Val Asp Tyr Pro Tyr
            210                 215                 220

AGG CTC TGG CAT TAC CCC TGC ACT GTT AAC TTT ACC ATC TTC AAG GTT        720
Arg Leu Trp His Tyr Pro Cys Thr Val Asn Phe Thr Ile Phe Lys Val
225                 230                 235                 240

AGG ATG TAT GTG GGG GGG GTG GAG CAC AGG CTC AAT GCT GCA TGC AAT        768
Arg Met Tyr Val Gly Gly Val Glu His Arg Leu Asn Ala Ala Cys Asn
                    245                 250                 255

TGG ACC CGA GGA GAG CGT TGT GAC TTG GAG GAC AGG GAT AGG CCG GAG        816
Trp Thr Arg Gly Glu Arg Cys Asp Leu Glu Asp Arg Asp Arg Pro Glu
            260                 265                 270

CTC AGC CCG CTG CTG CTG TCT ACA ACA GAG TGG CAG GTA CTG CCC TGT        864
Leu Ser Pro Leu Leu Leu Ser Thr Thr Glu Trp Gln Val Leu Pro Cys
            275                 280                 285

TCC TTC ACC ACC CTA CCA GCT CTG TCC ACT GGC TTG ATT CAC CTC CAT        912
Ser Phe Thr Thr Leu Pro Ala Leu Ser Thr Gly Leu Ile His Leu His
            290                 295                 300

CAG AAC ATC GTG GAC GTG CAA TAC CTA TAC GGT ATA GGG TCA GCG GTT        960
Gln Asn Ile Val Asp Val Gln Tyr Leu Tyr Gly Ile Gly Ser Ala Val
305                 310                 315                 320

GTC TCC TTT GCA ATC AAA TGG GAG TAT GTC CTG TTG CTT TTC CTT CTC       1008
Val Ser Phe Ala Ile Lys Trp Glu Tyr Val Leu Leu Leu Phe Leu Leu
                325                 330                 335

CTA GCG GAC GCA CGT GTC TGT GCC TGC TTG TGG ATG ATG CTG CTG ATA       1056
Leu Ala Asp Ala Arg Val Cys Ala Cys Leu Trp Met Met Leu Leu Ile
            340                 345                 350

GCC CAG GCC GAG GCC GCC TTG GAG AAC CTG GTG GTC CTC AAT GCG GCG       1104
Ala Gln Ala Glu Ala Ala Leu Glu Asn Leu Val Val Leu Asn Ser Ala
            355                 360                 365

TCT GTG GCC GGC GCA CAT GGC ATC CTC TCC TTC CTT GTG TTC TTC TGT       1152
Ser Val Ala Gly Ala His Gly Ile Leu Ser Phe Leu Val Phe Phe Cys
            370                 375                 380

GCC GCC TGG TAC ATC AAA GGC AGG CTG GTC CCT GGG GCG ACA TAT GCT       1200
Ala Ala Trp Tyr Ile Lys Gly Arg Leu Val Pro Gly Ala Thr Tyr Ala
385                 390                 395                 400

CTT TAT GGC GTG TGG CCG CTG CTC CTG CTC TTG CTG GCA TTA CCA CCG       1248
Leu Tyr Gly Val Trp Pro Leu Leu Leu Leu Leu Ala Leu Pro Pro
                405                 410                 415

CGA GCT TAC GCC ATG GAC CGG GAG ATG GCT GCA TCG TGC GGA GGC GCG       1296
Arg Ala Tyr Ala Met Asp Arg Glu Met Ala Ala Ser Cys Gly Gly Ala
            420                 425                 430

GTT TTT GTG GGT CTG GTA CTC CTG ACT TTG TCA CCA TAC TAC AAG GTG       1344
Val Phe Val Gly Leu Val Leu Leu Thr Leu Ser Pro Tyr Tyr Lys Val
            435                 440                 445

TTC CTC GCT AGG CTC ATA TGG TGG TTA CAA TAT TTT ACC ACC AGA GCC       1392
Phe Leu Ala Arg Leu Ile Trp Trp Leu Gln Tyr Phe Thr Thr Arg Ala
            450                 455                 460

GAG GCG GAC TTA CAT GTG TGG ATC CCC CCC CTC AAC GCT CGG GGA GGC       1440
Glu Ala Asp Leu His Val Trp Ile Pro Pro Leu Asn Ala Arg Gly Gly
465                 470                 475                 480

CGC GAT GCC ATC ATC CTC CTC ATG TGC GCA GTC CAT CCA GAG CTA ATC       1488
Arg Asp Ala Ile Ile Leu Leu Met Cys Ala Val His Pro Glu Leu Ile
                485                 490                 495

TTT GAC ATC ACC AAA CTT CTA ATT GCC ATA CTC GGT CCG CTC ATG GTG       1536
```

| | | | | | | | | | | | | | | | | |
|---|---|---|---|---|---|---|---|---|---|---|---|---|---|---|---|---|
| Phe | Asp | Ile | Thr 500 | Lys | Leu | Leu | Ile 505 | Ala | Ile | Leu | Gly | Pro 510 | Leu | Met | Val | |
| CTC | CAA | GCT | GGC | ATA | ACC | AGA | GTG | CCG | TAC | TTC | GTG | CGC | GCT | CAA | GGG | 1584 |
| Leu | Gln | Ala 515 | Gly | Ile | Thr | Arg | Val 520 | Pro | Tyr | Phe | Val | Arg 525 | Ala | Gln | Gly | |
| CTC | ATT | CAT | GCA | TGC | ATG | TTA | GTG | CGG | AAG | GTC | GCT | GGG | GGT | CAT | TAT | 1632 |
| Leu | Ile 530 | His | Ala | Cys | Met | Leu 535 | Val | Arg | Lys | Val | Ala 540 | Gly | Gly | His | Tyr | |
| GTC | CAA | ATG | GCC | TTC | ATG | AAG | CTG | GGC | GCG | CTG | ACA | GGC | ACG | TAC | ATT | 1680 |
| Val 545 | Gln | Met | Ala | Phe | Met 550 | Lys | Leu | Gly | Ala | Leu 555 | Thr | Gly | Thr | Tyr | Ile 560 | |
| TAC | AAC | CAT | CTT | ACC | CCG | CTA | CGG | GAT | TGG | CCA | CGC | GCG | GGC | CTA | CGA | 1728 |
| Tyr | Asn | His | Leu | Thr 565 | Pro | Leu | Arg | Asp | Trp 570 | Pro | Arg | Ala | Gly | Leu 575 | Arg | |
| GAC | CTT | GCG | GTG | GCA | GTG | GAG | CCC | GTC | GTC | TTC | TCC | GAC | ATG | GAG | ACC | 1776 |
| Asp | Leu | Ala | Val 580 | Ala | Val | Glu | Pro | Val 585 | Val | Phe | Ser | Asp | Met 590 | Glu | Thr | |
| AAG | ATC | ATC | ACC | TGG | GGA | GCA | GAC | ACC | GCG | GCG | TGT | GGG | GAC | ATC | ATC | 1824 |
| Lys | Ile | Ile 595 | Thr | Trp | Gly | Ala | Asp 600 | Thr | Ala | Ala | Cys | Gly 605 | Asp | Ile | Ile | |
| TTG | GGT | CTG | CCC | GTC | TCC | GCC | CGA | AGG | GGA | AAG | GAG | ATA | CTC | CTG | GGC | 1872 |
| Leu | Gly 610 | Leu | Pro | Val | Ser 615 | Ala | Arg | Arg | Gly | Lys 620 | Glu | Ile | Leu | Leu | Gly | |
| CCG | GCC | GAT | AGT | CTT | GAA | GGG | CGG | GGG | TTG | CGA | CTC | CTC | GCG | CCC | ATC | 1920 |
| Pro 625 | Ala | Asp | Ser | Leu | Glu 630 | Gly | Arg | Gly | Leu | Arg 635 | Leu | Leu | Ala | Pro | Ile 640 | |
| ACG | GCC | TAC | TCC | CAA | CAG | ACG | CGG | GGC | CTA | CTT | GGT | TGC | ATC | ATC | ACT | 1968 |
| Thr | Ala | Tyr | Ser | Gln 645 | Gln | Thr | Arg | Gly | Leu 650 | Leu | Gly | Cys | Ile | Ile 655 | Thr | |
| AGC | CTT | ACA | GGC | CGG | GAC | AAG | AAC | CAG | GTC | GAG | GGA | GAG | GTT | CAG | GTG | 2016 |
| Ser | Leu | Thr | Gly 660 | Arg | Asp | Lys | Asn | Gln 665 | Val | Glu | Gly | Glu | Val 670 | Gln | Val | |
| GTT | TCC | ACC | GCA | ACA | CAA | TCC | TTC | CTG | GCG | ACC | TGC | GTC | AAC | GGC | GTG | 2064 |
| Val | Ser | Thr | Ala | Thr 675 | Gln | Ser | Phe | Leu 680 | Ala | Thr | Cys | Val | Asn 685 | Gly | Val | |
| TGT | TGG | ACC | GTT | TAC | CAT | GGT | GCT | GGC | TCA | AAG | ACC | TTA | GCC | GCG | CCA | 2112 |
| Cys | Trp 690 | Thr | Val | Tyr | His | Gly 695 | Ala | Gly | Ser | Lys | Thr 700 | Leu | Ala | Ala | Pro | |
| AAG | GGG | CCA | ATC | ACC | CAG | ATG | TAC | ACT | AAT | GTG | GAC | CAG | GAC | CTC | GTC | 2160 |
| Lys | Gly 705 | Pro | Ile | Thr | Gln | Met 710 | Tyr | Thr | Asn | Val | Asp 715 | Gln | Asp | Leu | Val 720 | |
| GGC | TGG | CCC | AAG | CCC | CCC | GGG | GCG | CGT | TCC | TTG | ACA | CCA | TGC | ACC | TGT | 2208 |
| Gly | Trp | Pro | Lys | Pro 725 | Pro | Gly | Ala | Arg | Ser 730 | Leu | Thr | Pro | Cys | Thr 735 | Cys | |
| GGC | AGC | TCA | GAC | CTT | TAC | TTG | GTC | ACG | AGA | CAT | GCT | GAC | GTC | ATT | CCG | 2256 |
| Gly | Ser | Ser | Asp 740 | Leu | Tyr | Leu | Val | Thr 745 | Arg | His | Ala | Asp | Val 750 | Ile | Pro | |
| GTG | CGC | CGG | CGG | GGC | GAC | AGT | AGG | GGG | AGC | CTG | CTC | TCC | CCC | AGG | CCT | 2304 |
| Val | Arg | Arg 755 | Arg | Gly | Asp | Ser | Arg 760 | Gly | Ser | Leu | Leu | Ser 765 | Pro | Arg | Pro | |
| GTC | TCC | TAC | TTG | AAG | GGC | TCT | TCG | GGT | GGT | CCA | CTG | CTC | TGC | CCC | TTC | 2352 |
| Val | Ser | Tyr 770 | Leu | Lys | Gly | Ser | Ser 775 | Gly | Gly | Pro | Leu | Leu 780 | Cys | Pro | Phe | |
| GGG | CAC | GCT | GTG | GGC | ATC | TTC | CGG | GCT | GCC | GTA | TGC | ACC | CGG | GGG | GTT | 2400 |
| Gly | His | Ala | Val | Gly 785 | Ile | Phe | Arg | Ala 790 | Ala | Val | Cys | Thr | Arg 795 | Gly | Val 800 | |
| GCG | AAG | GCG | GTG | GAC | TTT | GTG | CCC | GTA | GAG | TCC | ATG | GAA | ACT | ACT | ATG | 2448 |
| Ala | Lys | Ala | Val | Asp 805 | Phe | Val | Pro | Val | Glu 810 | Ser | Met | Glu | Thr | Thr 815 | Met | |
| CGG | TCT | CCG | GTC | TTC | ACG | GAC | AAC | TCA | TCC | CCC | CCG | GCC | GTA | CCG | CAG | 2496 |

-continued

| | | | | | | | | | | | | | | |
|---|---|---|---|---|---|---|---|---|---|---|---|---|---|---|
| Arg | Ser | Pro | Val 820 | Phe | Thr | Asp | Asn | Ser 825 | Ser | Pro | Pro | Ala | Val 830 | Pro | Gln |

| | | | | | | | | | | | | | | | | |
|---|---|---|---|---|---|---|---|---|---|---|---|---|---|---|---|---|
| TCA | TTT | CAA | GTG | GCC | CAC | CTA | CAC | GCT | CCC | ACT | GGC | AGC | GGC | AAG | AGT | 2544 |
| Ser | Phe | Gln 835 | Val | Ala | His | Leu | His 840 | Ala | Pro | Thr | Gly | Ser 845 | Gly | Lys | Ser | |
| ACT | AAA | GTG | CCG | GCT | GCA | TAT | GCA | GCC | CAA | GGG | TAC | AAG | GTG | CTC | GTC | 2592 |
| Thr | Lys | Val 850 | Pro | Ala | Ala | Tyr | Ala 855 | Ala | Gln | Gly | Tyr | Lys 860 | Val | Leu | Val | |
| CTC | AAT | CCG | TCC | GTT | GCC | GCT | ACC | TTA | GGG | TTT | GGG | GCG | TAT | ATG | TCT | 2640 |
| Leu 865 | Asn | Pro | Ser | Val | Ala 870 | Ala | Thr | Leu | Gly | Phe 875 | Gly | Ala | Tyr | Met | Ser 880 | |
| AAG | GCA | CAC | GGT | ATT | GAC | CCC | AAC | ATC | AGA | ACT | GGG | GTA | AGG | ACC | ATT | 2688 |
| Lys | Ala | His | Gly | Ile 885 | Asp | Pro | Asn | Ile | Arg 890 | Thr | Gly | Val | Arg | Thr 895 | Ile | |
| ACC | ACA | GGC | GCC | CCC | GTC | ACA | TAC | TCT | ACC | TAT | GGC | AAG | TTT | CTT | GCC | 2736 |
| Thr | Thr | Gly | Ala 900 | Pro | Val | Thr | Tyr | Ser 905 | Thr | Tyr | Gly | Lys | Phe 910 | Leu | Ala | |
| GAT | GGT | GGT | TGC | TCT | GGG | GGC | GCT | TAT | GAC | ATC | ATA | ATA | TGT | GAT | GAG | 2784 |
| Asp | Gly | Gly 915 | Cys | Ser | Gly | Gly | Ala 920 | Tyr | Asp | Ile | Ile | Ile 925 | Cys | Asp | Glu | |
| TGC | CAT | TCA | ACT | GAC | TCG | ACT | ACA | ATC | TTG | GGC | ATC | GGC | ACA | GTC | CTG | 2832 |
| Cys | His | Ser 930 | Thr | Asp | Ser | Thr | Thr 935 | Ile | Leu | Gly | Ile | Gly 940 | Thr | Val | Leu | |
| GAC | CAA | GCG | GAG | ACG | GCT | GGA | GCG | CGG | CTT | GTC | GTG | CTC | GCC | ACC | GCT | 2880 |
| Asp 945 | Gln | Ala | Glu | Thr | Ala 950 | Gly | Ala | Arg | Leu | Val 955 | Val | Leu | Ala | Thr | Ala 960 | |
| ACG | CCT | CCG | GGA | TCG | GTC | ACC | GTG | CCA | CAC | CCA | AAC | ATC | GAG | GAG | GTG | 2928 |
| Thr | Pro | Pro | Gly | Ser 965 | Val | Thr | Val | Pro | His 970 | Pro | Asn | Ile | Glu | Glu 975 | Val | |
| GCC | CTG | TCT | AAT | ACT | GGA | GAG | ATC | CCC | TTC | TAT | GGC | AAA | GCC | ATC | CCC | 2976 |
| Ala | Leu | Ser | Asn 980 | Thr | Gly | Glu | Ile | Pro 985 | Phe | Tyr | Gly | Lys | Ala 990 | Ile | Pro | |
| ATT | GAA | GCC | ATC | AGG | GGG | GGA | AGG | CAT | CTC | ATT | TTC | TGT | CAT | TCC | AAG | 3024 |
| Ile | Glu | Ala 995 | Ile | Arg | Gly | Gly | Arg 1000 | His | Leu | Ile | Phe | Cys 1005 | His | Ser | Lys | |
| AAG | AAG | TGC | GAC | GAG | CTC | GCC | GCA | AAG | CTG | TCA | GGC | CTC | GGA | ATC | AAC | 3072 |
| Lys | Lys | Cys 1010 | Asp | Glu | Leu | Ala | Ala 1015 | Lys | Leu | Ser | Gly | Leu 1020 | Gly | Ile | Asn | |
| GCT | GTG | GCG | TAT | TAC | CGG | GGG | CTC | GAT | GTG | TCC | GTC | ATA | CCA | ACT | ATC | 3120 |
| Ala | Val | Ala 1025 | Tyr | Tyr | Arg | Gly | Leu 1030 | Asp | Val | Ser | Val | Ile 1035 | Pro | Thr | Ile 1040 | |
| GGA | GAC | GTC | GTT | GTC | GTG | GCA | ACA | GAC | GCT | CTG | ATG | ACG | GGC | TAT | ACG | 3168 |
| Gly | Asp | Val | Val 1045 | Val | Val | Ala | Thr | Asp 1050 | Ala | Leu | Met | Thr | Gly 1055 | Tyr | Thr | |
| GGC | GAC | TTT | GAC | TCA | GTG | ATC | GAC | TGT | AAC | ACA | TGT | GTC | ACC | CAG | ACA | 3216 |
| Gly | Asp | Phe | Asp | Ser 1060 | Val | Ile | Asp | Cys 1065 | Asn | Thr | Cys | Val | Thr 1070 | Gln | Thr | |
| GTC | GAC | TTC | AGC | TTG | GAT | CCC | ACC | TTC | ACC | ATT | GAG | ACG | ACG | ACC | GTG | 3264 |
| Val | Asp | Phe | Ser 1075 | Leu | Asp | Pro | Thr 1080 | Phe | Thr | Ile | Glu | Thr 1085 | Thr | Thr | Val | |
| CCT | CAA | GAC | GCA | GTG | TCG | CGC | TCG | CAG | CGG | CGG | GGT | AGG | ACT | GGC | AGG | 3312 |
| Pro | Gln | Asp 1090 | Ala | Val | Ser | Arg | Ser 1095 | Gln | Arg | Arg | Gly | Arg 1100 | Thr | Gly | Arg | |
| GGT | AGG | AGA | GGC | ATC | TAC | AGG | TTT | GTG | ACT | CCG | GGA | GAA | CGG | CCC | TCG | 3360 |
| Gly 1105 | Arg | Arg | Gly | Ile | Tyr 1110 | Arg | Phe | Val | Thr 1115 | Pro | Gly | Glu | Arg | Pro 1120 | Ser | |
| GGC | ATG | TTC | GAT | TCC | TCG | GTC | CTG | TGT | GAG | TGC | TAT | GAC | GCG | GGC | TGT | 3408 |
| Gly | Met | Phe | Asp | Ser 1125 | Ser | Val | Leu | Cys 1130 | Glu | Cys | Tyr | Asp | Ala 1135 | Gly | Cys | |
| GCT | TGG | TAC | GAG | CTC | ACC | CCG | GCC | GAG | ACC | TCG | GTT | AGG | TTG | CGG | GCC | 3456 |

-continued

```
Ala Trp Tyr Glu Leu Thr Pro Ala Glu Thr Ser Val Arg Leu Arg Ala
        1140                1145                1150

TAC CTG AAC ACA CCA GGG TTG CCC GTT TGC CAG GAC CAC CTG GAG TTC    3504
Tyr Leu Asn Thr Pro Gly Leu Pro Val Cys Gln Asp His Leu Glu Phe
        1155                1160                1165

TGG GAG AGT GTC TTC ACA GGC CTC ACC CAT ATA GAT GCA CAC TTC TTG    3552
Trp Glu Ser Val Phe Thr Gly Leu Thr His Ile Asp Ala His Phe Leu
        1170                1175                1180

TCC CAG ACC AAG CAG GCA GGA GAC AAC TTC CCC TAC CTG GTA GCA TAC    3600
Ser Gln Thr Lys Gln Ala Gly Asp Asn Phe Pro Tyr Leu Val Ala Tyr
1185                1190                1195                1200

CAA GCC ACG GTG TGC GCC AGG GCT CAG GCC CCA CCT CCA TCA TGG GAT    3648
Gln Ala Thr Val Cys Ala Arg Ala Gln Ala Pro Pro Pro Ser Trp Asp
                1205                1210                1215

CAA ATG TGG AAG TGT CTC ATA CGG CTG AAA CCT ACG CTG CAC GGG CCA    3696
Gln Met Trp Lys Cys Leu Ile Arg Leu Lys Pro Thr Leu His Gly Pro
        1220                1225                1230

ACA CCC TTG CTG TAC AGG CTG GGA GCC GTC CAG AAT GAG GTC ACC CTC    3744
Thr Pro Leu Leu Tyr Arg Leu Gly Ala Val Gln Asn Glu Val Thr Leu
        1235                1240                1245

ACC CAC CCC ATA ACC AAA TAC ATC ATG GCA TGC ATG TCG GCT GAC CTG    3792
Thr His Pro Ile Thr Lys Tyr Ile Met Ala Cys Met Ser Ala Asp Leu
        1250                1255                1260

GAG GTC GTC ACT AGC ACC TGG GTG CTG GTG GGC GGA GTC CTT GCA GCT    3840
Glu Val Val Thr Ser Thr Trp Val Leu Val Gly Gly Val Leu Ala Ala
1265                1270                1275                1280

CTG GCC GCG TAT TGC CTG ACA ACA GGC AGT GTG GTC ATT GTG GGT AGG    3888
Leu Ala Ala Tyr Cys Leu Thr Thr Gly Ser Val Val Ile Val Gly Arg
                1285                1290                1295

ATT ATC TTG TCC GGG AGG CCG GCC ATT GTT CCC GAC AGG GAG CTT CTC    3936
Ile Ile Leu Ser Gly Arg Pro Ala Ile Val Pro Asp Arg Glu Leu Leu
        1300                1305                1310

TAC CAG GAG TTC GAT GAA ATG GAA GAG TGC GCC TCG CAC CTC CCT TAC    3984
Tyr Gln Glu Phe Asp Glu Met Glu Glu Cys Ala Ser His Leu Pro Tyr
        1315                1320                1325

ATC GAG CAG GGA ATG CAG CTC GCC GAG CAA TTC AAG CAG AAA GCG CTC    4032
Ile Glu Gln Gly Met Gln Leu Ala Glu Gln Phe Lys Gln Lys Ala Leu
        1330                1335                1340

GGG TTA CTG CAA ACA GCC ACC AAA CAA GCG GAG GCT GCT GCT CCC GTG    4080
Gly Leu Leu Gln Thr Ala Thr Lys Gln Ala Glu Ala Ala Ala Pro Val
1345                1350                1355                1360

GTG GAG TCC AAG TGG CGA GCC CTT GAG ACA TTC TGG GCG AAG CAC ATG    4128
Val Glu Ser Lys Trp Arg Ala Leu Glu Thr Phe Trp Ala Lys His Met
                1365                1370                1375

TGG AAT TTC ATC AGC GGG ATA CAG TAC TTA GCA GGC TTA TCC ACT CTG    4176
Trp Asn Phe Ile Ser Gly Ile Gln Tyr Leu Ala Gly Leu Ser Thr Leu
        1380                1385                1390

CCT GGG AAC CCC GCA ATA GCA TCA TTG ATG GCA TTC ACA GCC TCT ATC    4224
Pro Gly Asn Pro Ala Ile Ala Ser Leu Met Ala Phe Thr Ala Ser Ile
        1395                1400                1405

ACC AGC CCG CTC ACC ACC CAA AGT ACC CTC CTG TTT AAC ATC TTG GGG    4272
Thr Ser Pro Leu Thr Thr Gln Ser Thr Leu Leu Phe Asn Ile Leu Gly
        1410                1415                1420

GGG TGG GTG GCT GCC CAA CTC GCC CCC CCC AGC GCC GCT TCG GCT TTC    4320
Gly Trp Val Ala Ala Gln Leu Ala Pro Pro Ser Ala Ala Ser Ala Phe
1425                1430                1435                1440

GTG GGC GCC GGC ATC GCC GGT GCG GCT GTT GGC AGC ATA GGC CTT GGG    4368
Val Gly Ala Gly Ile Ala Gly Ala Ala Val Gly Ser Ile Gly Leu Gly
                1445                1450                1455

AAG GTG CTT GTG GAC ATT CTG GCG GGT TAT GGA GCA GGA GTG GCC GGC    4416
```

|  |  |
|---|---|
| Lys Val Leu Val Asp Ile Leu Ala Gly Tyr Gly Ala Gly Val Ala Gly<br>1460 1465 1470 | |
| GCG CTC GTG GCC TTT AAG GTC ATG AGC GGC GAG ATG CCC TCC ACC GAG<br>Ala Leu Val Ala Phe Lys Val Met Ser Gly Glu Met Pro Ser Thr Glu<br>1475 1480 1485 | 4464 |
| GAC CTG GTC AAT CTA CTT CCT GCC ATC CTC TCT CCT GGC GCC CTG GTC<br>Asp Leu Val Asn Leu Leu Pro Ala Ile Leu Ser Pro Gly Ala Leu Val<br>1490 1495 1500 | 4512 |
| GTC GGG GTC GTG TGT GCA GCA ATA CTG CGT CGA CAC GTG GGT CCG GGA<br>Val Gly Val Val Cys Ala Ala Ile Leu Arg Arg His Val Gly Pro Gly<br>1505 1510 1515 1520 | 4560 |
| GAG GGG GCT GTG CAG TGG ATG AAC CGG CTG ATA GCG TTC GCC TCG CGG<br>Glu Gly Ala Val Gln Trp Met Asn Arg Leu Ile Ala Phe Ala Ser Arg<br>1525 1530 1535 | 4608 |
| GGT AAT CAT GTT TCC CCC ACG CAC TAT GTG CCT GAG AGC GAC GCC GCA<br>Gly Asn His Val Ser Pro Thr His Tyr Val Pro Glu Ser Asp Ala Ala<br>1540 1545 1550 | 4656 |
| GCG CGT GTT ACT CAG ATC CTC TCC AGC CTT ACC ATC ACT CAG CTG CTG<br>Ala Arg Val Thr Gln Ile Leu Ser Ser Leu Thr Ile Thr Gln Leu Leu<br>1555 1560 1565 | 4704 |
| AAA AGG CTC CAC CAG TGG ATT AAT GAA GAC TGC TCC ACA CCG TGT TCC<br>Lys Arg Leu His Gln Trp Ile Asn Glu Asp Cys Ser Thr Pro Cys Ser<br>1570 1575 1580 | 4752 |
| GGC TCG TGG CTA AGG GAT GTT TGG GAC TGG ATA TGC ACG GTG TTG ACT<br>Gly Ser Trp Leu Arg Asp Val Trp Asp Trp Ile Cys Thr Val Leu Thr<br>1585 1590 1595 1600 | 4800 |
| GAC TTC AAG ACC TGG CTC CAG TCC AAG CTC CTG CCG CAG CTA CCT GGA<br>Asp Phe Lys Thr Trp Leu Gln Ser Lys Leu Leu Pro Gln Leu Pro Gly<br>1605 1610 1615 | 4848 |
| GTC CCT TTT TTC TCG TGC CAA CGC GGG TAC AAG GGA GTC TGG CGG GGA<br>Val Pro Phe Phe Ser Cys Gln Arg Gly Tyr Lys Gly Val Trp Arg Gly<br>1620 1625 1630 | 4896 |
| GAC GGC ATC ATG CAA ACC ACC TGC CCA TGT GGA GCA CAG ATC ACC GGA<br>Asp Gly Ile Met Gln Thr Thr Cys Pro Cys Gly Ala Gln Ile Thr Gly<br>1635 1640 1645 | 4944 |
| CAT GTC AAA AAC GGT TCC ATG AGG ATC GTC GGG CCT AAG ACC TGC AGC<br>His Val Lys Asn Gly Ser Met Arg Ile Val Gly Pro Lys Thr Cys Ser<br>1650 1655 1660 | 4992 |
| AAC ACG TGG CAT GGA ACA TTC CCC ATC AAC GCA TAC ACC ACG GGC CCC<br>Asn Thr Trp His Gly Thr Phe Pro Ile Asn Ala Tyr Thr Thr Gly Pro<br>1665 1670 1675 1680 | 5040 |
| TGC ACA CCC TCT CCA GCG CCA AAC TAT TCT AGG GCG CTG TGG CGG GTG<br>Cys Thr Pro Ser Pro Ala Pro Asn Tyr Ser Arg Ala Leu Trp Arg Val<br>1685 1690 1695 | 5088 |
| GCC GCT GAG GAG TAC GTG GAG GTC ACG CGG GTG GGG GAT TTC CAC TAC<br>Ala Ala Glu Glu Tyr Val Glu Val Thr Arg Val Gly Asp Phe His Tyr<br>1700 1705 1710 | 5136 |
| GTG ACG GGC ATG ACC ACT GAC AAC GTA AAG TGC CCA TGC CAG GTT CCG<br>Val Thr Gly Met Thr Thr Asp Asn Val Lys Cys Pro Cys Gln Val Pro<br>1715 1720 1725 | 5184 |
| GCT CCT GAA TTC TTC TCG GAG GTG GAC GGA GTG CGG TTG CAC AGG TAC<br>Ala Pro Glu Phe Phe Ser Glu Val Asp Gly Val Arg Leu His Arg Tyr<br>1730 1735 1740 | 5232 |
| GCT CCG GCG TGC AGG CCT CTC CTA CGG GAG GAG GTT ACA TTC CAG GTC<br>Ala Pro Ala Cys Arg Pro Leu Leu Arg Glu Glu Val Thr Phe Gln Val<br>1745 1750 1755 1760 | 5280 |
| GGG CTC AAC CAA TAC CTG GTT GGG TCA CAG CTA CCA TGC GAG CCC GAA<br>Gly Leu Asn Gln Tyr Leu Val Gly Ser Gln Leu Pro Cys Glu Pro Glu<br>1765 1770 1775 | 5328 |
| CCG GAT GTA GCA GTG CTC ACT TCC ATG CTC ACC GAC CCC TCC CAC ATC | 5376 |

```
Pro Asp Val Ala Val Leu Thr Ser Met Leu Thr Asp Pro Ser His Ile
        1780            1785            1790

ACA GCA GAA ACG GCT AAG CGT AGG TTG GCC AGG GGG TCT CCC CCC TCC      5424
Thr Ala Glu Thr Ala Lys Arg Arg Leu Ala Arg Gly Ser Pro Pro Ser
        1795            1800            1805

TTG GCC AGC TCT TCA GCT AGC CAG TTG TCT GCG CCT TCC TTG AAG GCG      5472
Leu Ala Ser Ser Ser Ala Ser Gln Leu Ser Ala Pro Ser Leu Lys Ala
        1810            1815            1820

ACA TGC ACT ACC CAC CAT GTC TCT CCG GAC GCT GAC CTC ATC GAG GCC      5520
Thr Cys Thr Thr His His Val Ser Pro Asp Ala Asp Leu Ile Glu Ala
1825            1830            1835            1840

AAC CTC CTG TGG CGG CAG GAG ATG GGC GGG AAC ATC ACC CGC GTG GAG      5568
Asn Leu Leu Trp Arg Gln Glu Met Gly Gly Asn Ile Thr Arg Val Glu
            1845            1850            1855

TCG GAG AAC AAG GTG GTA GTC CTG GAC TCT TTC GAC CCG CTT CGA GCG      5616
Ser Glu Asn Lys Val Val Val Leu Asp Ser Phe Asp Pro Leu Arg Ala
        1860            1865            1870

GAG GAG GAT GAG AGG GAA GTA TCC GTT CCG GCG GAG ATC CTG CGG AAA      5664
Glu Glu Asp Glu Arg Glu Val Ser Val Pro Ala Glu Ile Leu Arg Lys
        1875            1880            1885

TCC AAG AAG TTC CCC GCA GCG ATG CCC ATC TGG GCG CGC CCG GAT TAC      5712
Ser Lys Lys Phe Pro Ala Ala Met Pro Ile Trp Ala Arg Pro Asp Tyr
    1890            1895            1900

AAC CCT CCA CTG TTA GAG TCC TGG AAG GAC CCG GAC TAC GTC CCT CCG      5760
Asn Pro Pro Leu Leu Glu Ser Trp Lys Asp Pro Asp Tyr Val Pro Pro
1905            1910            1915            1920

GTG GTG CAC GGG TGC CCG TTG CCA CCT ATC AAG GCC CCT CCA ATA CCA      5808
Val Val His Gly Cys Pro Leu Pro Pro Ile Lys Ala Pro Pro Ile Pro
            1925            1930            1935

CCT CCA CGG AGA AAG AGG ACG GTT GTC CTA ACA GAG TCC TCC GTG TCT      5856
Pro Pro Arg Arg Lys Arg Thr Val Val Leu Thr Glu Ser Ser Val Ser
        1940            1945            1950

TCT GCC TTA GCG GAG CTC GCT ACT AAG ACC TTC GGC AGC TCC GAA TCA      5904
Ser Ala Leu Ala Glu Leu Ala Thr Lys Thr Phe Gly Ser Ser Glu Ser
        1955            1960            1965

TCG GCC GTC GAC AGC GGC ACG GCG ACC GCC CTT CCT GAC CAG GCC TCC      5952
Ser Ala Val Asp Ser Gly Thr Ala Thr Ala Leu Pro Asp Gln Ala Ser
    1970            1975            1980

GAC GAC GGT GAC AAA GGA TCC GAC GTT GAG TCG TAC TCC TCC ATG CCC      6000
Asp Asp Gly Asp Lys Gly Ser Asp Val Glu Ser Tyr Ser Ser Met Pro
1985            1990            1995            2000

CCC CTT GAG GGG GAA CCG GGG GAC CCC GAT CTC AGT GAC GGG TCT TGG      6048
Pro Leu Glu Gly Glu Pro Gly Asp Pro Asp Leu Ser Asp Gly Ser Trp
            2005            2010            2015

TCT ACC GTG AGC GAG GAA GCT AGT GAG GAT GTC GTC TGC TGC TCA ATG      6096
Ser Thr Val Ser Glu Glu Ala Ser Glu Asp Val Val Cys Cys Ser Met
        2020            2025            2030

TCC TAC ACA TGG ACA GGC GCC TTG ATC ACG CCA TGC GCT GCG GAG GAA      6144
Ser Tyr Thr Trp Thr Gly Ala Leu Ile Thr Pro Cys Ala Ala Glu Glu
        2035            2040            2045

AGC AAG CTG CCC ATC AAC GCG TTG AGC AAC TCT TTG CTG CGC CAC CAT      6192
Ser Lys Leu Pro Ile Asn Ala Leu Ser Asn Ser Leu Leu Arg His His
    2050            2055            2060

AAC ATG GTT TAT GCC ACA ACA TCT CGC AGC GCA GGC CTG CGG CAG AAG      6240
Asn Met Val Tyr Ala Thr Thr Ser Arg Ser Ala Gly Leu Arg Gln Lys
2065            2070            2075            2080

AAG GTC ACC TTT GAC AGA CTG CAA GTC CTG GAC GAC CAC TAC CGG GAC      6288
Lys Val Thr Phe Asp Arg Leu Gln Val Leu Asp Asp His Tyr Arg Asp
            2085            2090            2095

GTG CTC AAG GAG ATG AAG GCG AAG GCG TCC ACA GTT AAG GCT AAA CTC      6336
```

```
Val Leu Lys Glu Met Lys Ala Lys Ala Ser Thr Val Lys Ala Lys Leu
         2100            2105                 2110

CTA TCC GTA GAG GAA GCC TGC AAG CTG ACG CCC CCA CAT TCG GCC AAA        6384
Leu Ser Val Glu Glu Ala Cys Lys Leu Thr Pro Pro His Ser Ala Lys
         2115            2120                 2125

TCC AAG TTT GGC TAT GGG GCA AAG GAC GTC CGG AAC CTA TCC AGC AAG        6432
Ser Lys Phe Gly Tyr Gly Ala Lys Asp Val Arg Asn Leu Ser Ser Lys
         2130            2135                 2140

GCC GTT AAC CAC ATC CAC TCC GTG TGG AAG GAC TTG CTG GAA GAC ACT        6480
Ala Val Asn His Ile His Ser Val Trp Lys Asp Leu Leu Glu Asp Thr
2145            2150            2155                 2160

GTG ACA CCA ATT GAC ACC ACC ATC ATG GCA AAA AAT GAG GTT TTC TGT        6528
Val Thr Pro Ile Asp Thr Thr Ile Met Ala Lys Asn Glu Val Phe Cys
         2165            2170                 2175

GTC CAA CCA GAG AAA GGA GGC CGT AAG CCA GCC CGC CTT ATC GTA TTC        6576
Val Gln Pro Glu Lys Gly Gly Arg Lys Pro Ala Arg Leu Ile Val Phe
         2180            2185                 2190

CCA GAT CTG GGA GTC CGT GTA TGC GAG AAG ATG GCC CTC TAT GAT GTG        6624
Pro Asp Leu Gly Val Arg Val Cys Glu Lys Met Ala Leu Tyr Asp Val
         2195            2200                 2205

GTC TCC ACC CTT CCT CAG GTC GTG ATG GGC TCC TCA TAC GGA TTC CAG        6672
Val Ser Thr Leu Pro Gln Val Val Met Gly Ser Ser Tyr Gly Phe Gln
         2210            2215                 2220

TAC TCT CCT GGG CAG CGA GTC GAG TTC CTG GTG AAT ACC TGG AAA TCA        6720
Tyr Ser Pro Gly Gln Arg Val Glu Phe Leu Val Asn Thr Trp Lys Ser
2225            2230            2235                 2240

AAG AAA AAC CCC ATG GGC TTT TCA TAT GAC ACT CGC TGT TTC GAC TCA        6768
Lys Lys Asn Pro Met Gly Phe Ser Tyr Asp Thr Arg Cys Phe Asp Ser
         2245            2250                 2255

ACG GTC ACC GAG AAC GAC ATC CGT GTT GAG GAG TCA ATT TAC CAA TGT        6816
Thr Val Thr Glu Asn Asp Ile Arg Val Glu Glu Ser Ile Tyr Gln Cys
         2260            2265                 2270

TGT GAC TTG GCC CCC GAA GCC AGA CAG GCC ATA AAA TCG CTC ACA GAG        6864
Cys Asp Leu Ala Pro Glu Ala Arg Gln Ala Ile Lys Ser Leu Thr Glu
         2275            2280                 2285

CGG CTT TAT ATC GGG GGT CCT CTG ACT AAT TCA AAA GGG CAG AAC TGC        6912
Arg Leu Tyr Ile Gly Gly Pro Leu Thr Asn Ser Lys Gly Gln Asn Cys
         2290            2295                 2300

GGT TAT CGC CGG TGC CGC GCG AGC GGC GTG CTG ACG ACT AGC TGC GGT        6960
Gly Tyr Arg Arg Cys Arg Ala Ser Gly Val Leu Thr Thr Ser Cys Gly
2305            2310            2315                 2320

AAC ACC CTC ACA TGT TAC TTG AAG GCC TCT GCA GCC TGT CGA GCT GCG        7008
Asn Thr Leu Thr Cys Tyr Leu Lys Ala Ser Ala Ala Cys Arg Ala Ala
         2325            2330                 2335

AAG CTC CAG GAC TGC ACG ATG CTC GTG AAC GGA GAC GAC CTC GTC GTT        7056
Lys Leu Gln Asp Cys Thr Met Leu Val Asn Gly Asp Asp Leu Val Val
         2340            2345                 2350

ATC TGT GAA AGC GCG GGA ACC CAA GAG GAC GCG GCG AGC CTA CGA GTC        7104
Ile Cys Glu Ser Ala Gly Thr Gln Glu Asp Ala Ala Ser Leu Arg Val
         2355            2360                 2365

TTC ACG GAG GCT ATG ACT AGG TAC TCC GCC CCC CCC GGG GAC CCG CCC        7152
Phe Thr Glu Ala Met Thr Arg Tyr Ser Ala Pro Pro Gly Asp Pro Pro
         2370            2375                 2380

CAA CCA GAA TAC GAC TTG GAG CTG ATA ACA TCA TGT TCC TCC AAT GTG        7200
Gln Pro Glu Tyr Asp Leu Glu Leu Ile Thr Ser Cys Ser Ser Asn Val
2385            2390            2395                 2400

TCG GTC GCC CAC GAT GCA TCA GGC AAA AGG GTG TAC TAC CTC ACC CGT        7248
Ser Val Ala His Asp Ala Ser Gly Lys Arg Val Tyr Tyr Leu Thr Arg
         2405            2410                 2415

GAT CCC ACC ACC CCC CTA GCA CGG GCT GCG TGG GAG ACA GCT AGA CAC        7296
```

| | | | | | | | | | | | | | | | | |
|---|---|---|---|---|---|---|---|---|---|---|---|---|---|---|---|---|
| Asp | Pro | Thr | Thr | Pro | Leu | Ala | Arg | Ala | Ala | Trp | Glu | Thr | Ala | Arg | His | |
| | | | 2420 | | | | 2425 | | | | | 2430 | | | | |

```
ACT   CCA   GTT   AAC   TCC   TGG   CTA   GGC   AAC   ATT   ATT   ATG   TAT   GCG   CCC   ACT    7344
Thr   Pro   Val   Asn   Ser   Trp   Leu   Gly   Asn   Ile   Ile   Met   Tyr   Ala   Pro   Thr
            2435                    2440                          2445

TTG   TGG   GCA   AGG   ATG   ATT   CTG   ATG   ACT   CAC   TTC   TTC   TCC   ATC   CTT   CTA    7392
Leu   Trp   Ala   Arg   Met   Ile   Leu   Met   Thr   His   Phe   Phe   Ser   Ile   Leu   Leu
      2450                          2455                          2460

GCG   CAG   GAG   CAA   CTT   GAA   AAA   GCC   CTG   GAC   TGC   CAG   ATC   TAC   GGG   GCC    7440
Ala   Gln   Glu   Gln   Leu   Glu   Lys   Ala   Leu   Asp   Cys   Gln   Ile   Tyr   Gly   Ala
2465                    2470                          2475                          2480

TGT   TAC   TCC   ATT   GAG   CCA   CTT   GAC   CTA   CCT   CAG   ATC   ATT   GAA   CGA   CTC    7488
Cys   Tyr   Ser   Ile   Glu   Pro   Leu   Asp   Leu   Pro   Gln   Ile   Ile   Glu   Arg   Leu
                        2485                          2490                          2495

CAT   GGC   CTT   AGC   GCA   TTT   TCA   CTC   CAT   AGT   TAC   TCT   CCA   GGT   GAG   ATC    7536
His   Gly   Leu   Ser   Ala   Phe   Ser   Leu   His   Ser   Tyr   Ser   Pro   Gly   Glu   Ile
                  2500                          2505                          2510

AAT   AGG   GTG   GCT   TCA   TGC   CTC   AGG   AAA   CTT   GGG   GTA   CCA   CCC   TTG   CGA    7584
Asn   Arg   Val   Ala   Ser   Cys   Leu   Arg   Lys   Leu   Gly   Val   Pro   Pro   Leu   Arg
            2515                          2520                          2525

GTC   TGG   AGA   CAT   CGG   GCC   AGG   AGC   GTC   CGC   GCT   AGG   CTA   CTG   TCC   CAG    7632
Val   Trp   Arg   His   Arg   Ala   Arg   Ser   Val   Arg   Ala   Arg   Leu   Leu   Ser   Gln
      2530                          2535                          2540

GGA   GGG   AGG   GCC   GCC   ACT   TGT   GGC   AAA   TAC   CTC   TTC   AAC   TGG   GCA   GTA    7680
Gly   Gly   Arg   Ala   Ala   Thr   Cys   Gly   Lys   Tyr   Leu   Phe   Asn   Trp   Ala   Val
2545                    2550                          2555                          2560

AAA   ACC   AAA   CTT   AAA   CTC   ACT   CCA   ATC   CCG   GCT   GCG   TCC   CGG   CTG   GAC    7728
Lys   Thr   Lys   Leu   Lys   Leu   Thr   Pro   Ile   Pro   Ala   Ala   Ser   Arg   Leu   Asp
                        2565                          2570                          2575

TTG   TCC   GGC   TGG   TTC   GTT   GCT   GGT   TAC   AGC   GGG   GGA   GAC   ATA   TAT   CAC    7776
Leu   Ser   Gly   Trp   Phe   Val   Ala   Gly   Tyr   Ser   Gly   Gly   Asp   Ile   Tyr   His
                  2580                          2585                          2590

AGC   CTG   TCT   CGT   GCC   CGA   CCC   CGT   TGG   TTC   ATG   CTG   TGC   CTA   CTC   CTA    7824
Ser   Leu   Ser   Arg   Ala   Arg   Pro   Arg   Trp   Phe   Met   Leu   Cys   Leu   Leu   Leu
            2595                          2600                          2605

CTT   TCT   GTA   GGG   GTA   GGC   ATC   TAC   CTG   CTC   CCC   AAC   CG ATGAACGGGG              7872
Leu   Ser   Val   Gly   Val   Gly   Ile   Tyr   Leu   Leu   Pro   Asn
2610                          2615                    262

AGATAAACAC  TCCAGGCCAA  TAGGCCATCC  CCCTTTTTTT  TTTTT                                              7917
```

( 2 ) INFORMATION FOR SEQ ID NO:32:

( i ) SEQUENCE CHARACTERISTICS:
        ( A ) LENGTH: 2620 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

```
Gly   Ala   Gln   Ala   Lys   Thr   Thr   Asn   Arg   Leu   Val   Ser   Met   Phe   Ala   Ser
  1                 5                           10                          15

Gly   Pro   Ser   Gln   Lys   Ile   Gln   Leu   Ile   Asn   Thr   Asn   Gly   Ser   Trp   His
                  20                          25                          30

Ile   Asn   Arg   Thr   Ala   Leu   Asn   Cys   Asn   Asp   Ser   Leu   Gln   Thr   Gly   Phe
            35                          40                          45

Leu   Ala   Ala   Leu   Phe   Tyr   Thr   His   Ser   Phe   Asn   Ser   Ser   Gly   Cys   Pro
      50                          55                          60

Glu   Arg   Met   Ala   Gln   Cys   Arg   Thr   Ile   Asp   Lys   Phe   Asp   Gln   Gly   Trp
65                          70                          75                          80
```

```
Gly  Pro  Ile  Thr  Tyr  Ala  Glu  Ser  Ser  Arg  Ser  Asp  Gln  Arg  Pro  Tyr
                         85                  90                       95

Cys  Trp  His  Tyr  Pro  Pro  Pro  Gln  Cys  Thr  Ile  Val  Pro  Ala  Ser  Glu
               100                      105                      110

Val  Cys  Gly  Pro  Val  Tyr  Cys  Phe  Thr  Pro  Ser  Pro  Val  Val  Val  Gly
               115                      120                      125

Thr  Thr  Asp  Arg  Phe  Gly  Val  Pro  Thr  Tyr  Arg  Trp  Gly  Glu  Asn  Glu
     130                      135                      140

Thr  Asp  Val  Leu  Leu  Leu  Asn  Asn  Thr  Arg  Pro  Pro  Gln  Gly  Asn  Trp
145                           150                      155                 160

Phe  Gly  Cys  Thr  Trp  Met  Asn  Ser  Thr  Gly  Phe  Thr  Lys  Thr  Cys  Gly
                    165                      170                      175

Gly  Pro  Pro  Cys  Asn  Ile  Gly  Gly  Val  Gly  Asn  Asn  Thr  Leu  Thr  Cys
                    180                      185                      190

Pro  Thr  Asp  Cys  Phe  Arg  Lys  His  Pro  Glu  Ala  Thr  Tyr  Thr  Lys  Cys
               195                      200                      205

Gly  Ser  Gly  Pro  Trp  Leu  Thr  Pro  Arg  Cys  Met  Val  Asp  Tyr  Pro  Tyr
     210                      215                      220

Arg  Leu  Trp  His  Tyr  Pro  Cys  Thr  Val  Asn  Phe  Thr  Ile  Phe  Lys  Val
225                           230                      235                 240

Arg  Met  Tyr  Val  Gly  Gly  Val  Glu  His  Arg  Leu  Asn  Ala  Ala  Cys  Asn
                         245                      250                      255

Trp  Thr  Arg  Gly  Glu  Arg  Cys  Asp  Leu  Glu  Asp  Arg  Asp  Arg  Pro  Glu
               260                      265                      270

Leu  Ser  Pro  Leu  Leu  Leu  Ser  Thr  Thr  Glu  Trp  Gln  Val  Leu  Pro  Cys
               275                      280                      285

Ser  Phe  Thr  Thr  Leu  Pro  Ala  Leu  Ser  Thr  Gly  Leu  Ile  His  Leu  His
     290                      295                      300

Gln  Asn  Ile  Val  Asp  Val  Gln  Tyr  Leu  Tyr  Gly  Ile  Gly  Ser  Ala  Val
305                           310                      315                 320

Val  Ser  Phe  Ala  Ile  Lys  Trp  Glu  Tyr  Val  Leu  Leu  Leu  Phe  Leu  Leu
                    325                      330                      335

Leu  Ala  Asp  Ala  Arg  Val  Cys  Ala  Cys  Leu  Trp  Met  Met  Leu  Leu  Ile
                    340                      345                      350

Ala  Gln  Ala  Glu  Ala  Ala  Leu  Glu  Asn  Leu  Val  Val  Leu  Asn  Ser  Ala
          355                      360                      365

Ser  Val  Ala  Gly  Ala  His  Gly  Ile  Leu  Ser  Phe  Leu  Val  Phe  Phe  Cys
     370                      375                      380

Ala  Ala  Trp  Tyr  Ile  Lys  Gly  Arg  Leu  Val  Pro  Gly  Ala  Thr  Tyr  Ala
385                           390                      395                 400

Leu  Tyr  Gly  Val  Trp  Pro  Leu  Leu  Leu  Leu  Leu  Ala  Leu  Pro  Pro
                    405                      410                      415

Arg  Ala  Tyr  Ala  Met  Asp  Arg  Glu  Met  Ala  Ala  Ser  Cys  Gly  Gly  Ala
               420                      425                      430

Val  Phe  Val  Gly  Leu  Val  Leu  Leu  Thr  Leu  Ser  Pro  Tyr  Tyr  Lys  Val
          435                      440                      445

Phe  Leu  Ala  Arg  Leu  Ile  Trp  Trp  Leu  Gln  Tyr  Phe  Thr  Thr  Arg  Ala
     450                      455                      460

Glu  Ala  Asp  Leu  His  Val  Trp  Ile  Pro  Pro  Leu  Asn  Ala  Arg  Gly  Gly
465                      470                      475                      480

Arg  Asp  Ala  Ile  Ile  Leu  Leu  Met  Cys  Ala  Val  His  Pro  Glu  Leu  Ile
               485                      490                      495

Phe  Asp  Ile  Thr  Lys  Leu  Leu  Ile  Ala  Ile  Leu  Gly  Pro  Leu  Met  Val
               500                      505                      510
```

-continued

| | | | | | | | | | | | | | | |
|---|---|---|---|---|---|---|---|---|---|---|---|---|---|---|
| Leu | Gln | Ala | Gly | Ile | Thr | Arg | Val | Pro | Tyr | Phe | Val | Arg | Ala | Gln | Gly |
| | | 515 | | | | 520 | | | | | 525 | | | | |
| Leu | Ile | His | Ala | Cys | Met | Leu | Val | Arg | Lys | Val | Ala | Gly | Gly | His | Tyr |
| | | 530 | | | | 535 | | | | | 540 | | | | |
| Val | Gln | Met | Ala | Phe | Met | Lys | Leu | Gly | Ala | Leu | Thr | Gly | Thr | Tyr | Ile |
| 545 | | | | | 550 | | | | | 555 | | | | | 560 |
| Tyr | Asn | His | Leu | Thr | Pro | Leu | Arg | Asp | Trp | Pro | Arg | Ala | Gly | Leu | Arg |
| | | | | 565 | | | | | 570 | | | | | 575 | |
| Asp | Leu | Ala | Val | Ala | Val | Glu | Pro | Val | Val | Phe | Ser | Asp | Met | Glu | Thr |
| | | | 580 | | | | | 585 | | | | | 590 | | |
| Lys | Ile | Ile | Thr | Trp | Gly | Ala | Asp | Thr | Ala | Ala | Cys | Gly | Asp | Ile | Ile |
| | | | 595 | | | | 600 | | | | | 605 | | | |
| Leu | Gly | Leu | Pro | Val | Ser | Ala | Arg | Arg | Gly | Lys | Glu | Ile | Leu | Leu | Gly |
| | 610 | | | | | 615 | | | | | 620 | | | | |
| Pro | Ala | Asp | Ser | Leu | Glu | Gly | Arg | Gly | Leu | Arg | Leu | Leu | Ala | Pro | Ile |
| 625 | | | | | 630 | | | | | 635 | | | | | 640 |
| Thr | Ala | Tyr | Ser | Gln | Gln | Thr | Arg | Gly | Leu | Leu | Gly | Cys | Ile | Ile | Thr |
| | | | | 645 | | | | | 650 | | | | | 655 | |
| Ser | Leu | Thr | Gly | Arg | Asp | Lys | Asn | Gln | Val | Glu | Gly | Glu | Val | Gln | Val |
| | | | 660 | | | | | 665 | | | | | 670 | | |
| Val | Ser | Thr | Ala | Thr | Gln | Ser | Phe | Leu | Ala | Thr | Cys | Val | Asn | Gly | Val |
| | | 675 | | | | | 680 | | | | | 685 | | | |
| Cys | Trp | Thr | Val | Tyr | His | Gly | Ala | Gly | Ser | Lys | Thr | Leu | Ala | Ala | Pro |
| | 690 | | | | | 695 | | | | | 700 | | | | |
| Lys | Gly | Pro | Ile | Thr | Gln | Met | Tyr | Thr | Asn | Val | Asp | Gln | Asp | Leu | Val |
| 705 | | | | 710 | | | | | 715 | | | | | | 720 |
| Gly | Trp | Pro | Lys | Pro | Pro | Gly | Ala | Arg | Ser | Leu | Thr | Pro | Cys | Thr | Cys |
| | | | | 725 | | | | | 730 | | | | | 735 | |
| Gly | Ser | Ser | Asp | Leu | Tyr | Leu | Val | Thr | Arg | His | Ala | Asp | Val | Ile | Pro |
| | | | 740 | | | | | 745 | | | | | 750 | | |
| Val | Arg | Arg | Arg | Gly | Asp | Ser | Arg | Gly | Ser | Leu | Leu | Ser | Pro | Arg | Pro |
| | | 755 | | | | | 760 | | | | | 765 | | | |
| Val | Ser | Tyr | Leu | Lys | Gly | Ser | Ser | Gly | Gly | Pro | Leu | Leu | Cys | Pro | Phe |
| | 770 | | | | | 775 | | | | | 780 | | | | |
| Gly | His | Ala | Val | Gly | Ile | Phe | Arg | Ala | Ala | Val | Cys | Thr | Arg | Gly | Val |
| 785 | | | | | 790 | | | | | 795 | | | | | 800 |
| Ala | Lys | Ala | Val | Asp | Phe | Val | Pro | Val | Glu | Ser | Met | Glu | Thr | Thr | Met |
| | | | | 805 | | | | | 810 | | | | | 815 | |
| Arg | Ser | Pro | Val | Phe | Thr | Asp | Asn | Ser | Ser | Pro | Pro | Ala | Val | Pro | Gln |
| | | | 820 | | | | | 825 | | | | | 830 | | |
| Ser | Phe | Gln | Val | Ala | His | Leu | His | Ala | Pro | Thr | Gly | Ser | Gly | Lys | Ser |
| | | 835 | | | | | 840 | | | | | 845 | | | |
| Thr | Lys | Val | Pro | Ala | Ala | Tyr | Ala | Ala | Gln | Gly | Tyr | Lys | Val | Leu | Val |
| | 850 | | | | | 855 | | | | | 860 | | | | |
| Leu | Asn | Pro | Ser | Val | Ala | Ala | Thr | Leu | Gly | Phe | Gly | Ala | Tyr | Met | Ser |
| 865 | | | | | 870 | | | | | 875 | | | | | 880 |
| Lys | Ala | His | Gly | Ile | Asp | Pro | Asn | Ile | Arg | Thr | Gly | Val | Arg | Thr | Ile |
| | | | | 885 | | | | | 890 | | | | | 895 | |
| Thr | Thr | Gly | Ala | Pro | Val | Thr | Tyr | Ser | Thr | Tyr | Gly | Lys | Phe | Leu | Ala |
| | | | 900 | | | | | 905 | | | | | 910 | | |
| Asp | Gly | Gly | Cys | Ser | Gly | Gly | Ala | Tyr | Asp | Ile | Ile | Ile | Cys | Asp | Glu |
| | | 915 | | | | | 920 | | | | | 925 | | | |
| Cys | His | Ser | Thr | Asp | Ser | Thr | Thr | Ile | Leu | Gly | Ile | Gly | Thr | Val | Leu |

```
              930                   935                   940
Asp Gln Ala Glu Thr Ala Gly Ala Arg Leu Val Val Leu Ala Thr Ala
945                 950                 955                 960

Thr Pro Pro Gly Ser Val Thr Val Pro His Pro Asn Ile Glu Glu Val
                965                 970                 975

Ala Leu Ser Asn Thr Gly Glu Ile Pro Phe Tyr Gly Lys Ala Ile Pro
                980                 985                 990

Ile Glu Ala Ile Arg Gly Gly Arg His Leu Ile Phe Cys His Ser Lys
            995                 1000                1005

Lys Lys Cys Asp Glu Leu Ala Ala Lys Leu Ser Gly Leu Gly Ile Asn
    1010                1015                1020

Ala Val Ala Tyr Tyr Arg Gly Leu Asp Val Ser Val Ile Pro Thr Ile
1025                1030                1035                1040

Gly Asp Val Val Val Ala Thr Asp Ala Leu Met Thr Gly Tyr Thr
                1045                1050                1055

Gly Asp Phe Asp Ser Val Ile Asp Cys Asn Thr Cys Val Thr Gln Thr
                1060                1065                1070

Val Asp Phe Ser Leu Asp Pro Thr Phe Thr Ile Glu Thr Thr Thr Val
            1075                1080                1085

Pro Gln Asp Ala Val Ser Arg Ser Gln Arg Arg Gly Arg Thr Gly Arg
        1090                1095                1100

Gly Arg Arg Gly Ile Tyr Arg Phe Val Thr Pro Gly Glu Arg Pro Ser
1105                1110                1115                1120

Gly Met Phe Asp Ser Ser Val Leu Cys Glu Cys Tyr Asp Ala Gly Cys
                1125                1130                1135

Ala Trp Tyr Glu Leu Thr Pro Ala Glu Thr Ser Val Arg Leu Arg Ala
            1140                1145                1150

Tyr Leu Asn Thr Pro Gly Leu Pro Val Cys Gln Asp His Leu Glu Phe
            1155                1160                1165

Trp Glu Ser Val Phe Thr Gly Leu Thr His Ile Asp Ala His Phe Leu
            1170                1175                1180

Ser Gln Thr Lys Gln Ala Gly Asp Asn Phe Pro Tyr Leu Val Ala Tyr
1185                1190                1195                1200

Gln Ala Thr Val Cys Ala Arg Ala Gln Ala Pro Pro Ser Trp Asp
                1205                1210                1215

Gln Met Trp Lys Cys Leu Ile Arg Leu Lys Pro Thr Leu His Gly Pro
        1220                1225                1230

Thr Pro Leu Leu Tyr Arg Leu Gly Ala Val Gln Asn Glu Val Thr Leu
            1235                1240                1245

Thr His Pro Ile Thr Lys Tyr Ile Met Ala Cys Met Ser Ala Asp Leu
        1250                1255                1260

Glu Val Val Thr Ser Thr Trp Val Leu Val Gly Gly Val Leu Ala Ala
1265                1270                1275                1280

Leu Ala Ala Tyr Cys Leu Thr Thr Gly Ser Val Val Ile Val Gly Arg
                1285                1290                1295

Ile Ile Leu Ser Gly Arg Pro Ala Ile Val Pro Asp Arg Glu Leu Leu
            1300                1305                1310

Tyr Gln Glu Phe Asp Glu Met Glu Glu Cys Ala Ser His Leu Pro Tyr
        1315                1320                1325

Ile Glu Gln Gly Met Gln Leu Ala Glu Gln Phe Lys Gln Lys Ala Leu
    1330                1335                1340

Gly Leu Leu Gln Thr Ala Thr Lys Gln Ala Glu Ala Ala Ala Pro Val
1345                1350                1355                1360
```

```
Val Glu Ser Lys Trp Arg Ala Leu Glu Thr Phe Trp Ala Lys His Met
              1365            1370            1375

Trp Asn Phe Ile Ser Gly Ile Gln Tyr Leu Ala Gly Leu Ser Thr Leu
        1380            1385            1390

Pro Gly Asn Pro Ala Ile Ala Ser Leu Met Ala Phe Thr Ala Ser Ile
        1395            1400            1405

Thr Ser Pro Leu Thr Thr Gln Ser Thr Leu Leu Phe Asn Ile Leu Gly
    1410            1415            1420

Gly Trp Val Ala Ala Gln Leu Ala Pro Pro Ser Ala Ala Ser Ala Phe
1425            1430            1435            1440

Val Gly Ala Gly Ile Ala Gly Ala Ala Val Gly Ser Ile Gly Leu Gly
            1445            1450            1455

Lys Val Leu Val Asp Ile Leu Ala Gly Tyr Gly Ala Gly Val Ala Gly
            1460            1465            1470

Ala Leu Val Ala Phe Lys Val Met Ser Gly Glu Met Pro Ser Thr Glu
        1475            1480            1485

Asp Leu Val Asn Leu Leu Pro Ala Ile Leu Ser Pro Gly Ala Leu Val
        1490            1495            1500

Val Gly Val Val Cys Ala Ala Ile Leu Arg Arg His Val Gly Pro Gly
1505            1510            1515            1520

Glu Gly Ala Val Gln Trp Met Asn Arg Leu Ile Ala Phe Ala Ser Arg
            1525            1530            1535

Gly Asn His Val Ser Pro Thr His Tyr Val Pro Glu Ser Asp Ala Ala
            1540            1545            1550

Ala Arg Val Thr Gln Ile Leu Ser Ser Leu Thr Ile Thr Gln Leu Leu
    1555            1560            1565

Lys Arg Leu His Gln Trp Ile Asn Glu Asp Cys Ser Thr Pro Cys Ser
    1570            1575            1580

Gly Ser Trp Leu Arg Asp Val Trp Asp Trp Ile Cys Thr Val Leu Thr
1585            1590            1595            1600

Asp Phe Lys Thr Trp Leu Gln Ser Lys Leu Leu Pro Gln Leu Pro Gly
            1605            1610            1615

Val Pro Phe Phe Ser Cys Gln Arg Gly Tyr Lys Gly Val Trp Arg Gly
            1620            1625            1630

Asp Gly Ile Met Gln Thr Thr Cys Pro Cys Gly Ala Gln Ile Thr Gly
            1635            1640            1645

His Val Lys Asn Gly Ser Met Arg Ile Val Gly Pro Lys Thr Cys Ser
    1650            1655            1660

Asn Thr Trp His Gly Thr Phe Pro Ile Asn Ala Tyr Thr Thr Gly Pro
1665            1670            1675            1680

Cys Thr Pro Ser Pro Ala Pro Asn Tyr Ser Arg Ala Leu Trp Arg Val
            1685            1690            1695

Ala Ala Glu Glu Tyr Val Glu Val Thr Arg Val Gly Asp Phe His Tyr
            1700            1705            1710

Val Thr Gly Met Thr Thr Asp Asn Val Lys Cys Pro Cys Gln Val Pro
        1715            1720            1725

Ala Pro Glu Phe Phe Ser Glu Val Asp Gly Val Arg Leu His Arg Tyr
    1730            1735            1740

Ala Pro Ala Cys Arg Pro Leu Leu Arg Glu Glu Val Thr Phe Gln Val
1745            1750            1755            1760

Gly Leu Asn Gln Tyr Leu Val Gly Ser Gln Leu Pro Cys Glu Pro Glu
            1765            1770            1775

Pro Asp Val Ala Val Leu Thr Ser Met Leu Thr Asp Pro Ser His Ile
            1780            1785            1790
```

Thr Ala Glu Thr Ala Lys Arg Arg Leu Ala Arg Gly Ser Pro Pro Ser
                1795                1800                1805

Leu Ala Ser Ser Ser Ala Ser Gln Leu Ser Ala Pro Ser Leu Lys Ala
        1810                1815                1820

Thr Cys Thr Thr His His Val Ser Pro Asp Ala Asp Leu Ile Glu Ala
1825                1830                1835                1840

Asn Leu Leu Trp Arg Gln Glu Met Gly Gly Asn Ile Thr Arg Val Glu
                1845                1850                1855

Ser Glu Asn Lys Val Val Val Leu Asp Ser Phe Asp Pro Leu Arg Ala
                1860                1865                1870

Glu Glu Asp Glu Arg Glu Val Ser Val Pro Ala Glu Ile Leu Arg Lys
                1875                1880                1885

Ser Lys Lys Phe Pro Ala Ala Met Pro Ile Trp Ala Arg Pro Asp Tyr
        1890                1895                1900

Asn Pro Pro Leu Leu Glu Ser Trp Lys Asp Pro Asp Tyr Val Pro Pro
1905                1910                1915                1920

Val Val His Gly Cys Pro Leu Pro Pro Ile Lys Ala Pro Pro Ile Pro
                1925                1930                1935

Pro Pro Arg Arg Lys Arg Thr Val Val Leu Thr Glu Ser Ser Val Ser
                1940                1945                1950

Ser Ala Leu Ala Glu Leu Ala Thr Lys Thr Phe Gly Ser Ser Glu Ser
        1955                1960                1965

Ser Ala Val Asp Ser Gly Thr Ala Thr Ala Leu Pro Asp Gln Ala Ser
        1970                1975                1980

Asp Asp Gly Asp Lys Gly Ser Asp Val Glu Ser Tyr Ser Ser Met Pro
1985                1990                1995                2000

Pro Leu Glu Gly Glu Pro Gly Asp Pro Asp Leu Ser Asp Gly Ser Trp
                2005                2010                2015

Ser Thr Val Ser Glu Glu Ala Ser Glu Asp Val Val Cys Cys Ser Met
                2020                2025                2030

Ser Tyr Thr Trp Thr Gly Ala Leu Ile Thr Pro Cys Ala Ala Glu Glu
        2035                2040                2045

Ser Lys Leu Pro Ile Asn Ala Leu Ser Asn Ser Leu Leu Arg His His
        2050                2055                2060

Asn Met Val Tyr Ala Thr Thr Ser Arg Ser Ala Gly Leu Arg Gln Lys
2065                2070                2075                2080

Lys Val Thr Phe Asp Arg Leu Gln Val Leu Asp Asp His Tyr Arg Asp
                2085                2090                2095

Val Leu Lys Glu Met Lys Ala Lys Ala Ser Thr Val Lys Ala Lys Leu
                2100                2105                2110

Leu Ser Val Glu Glu Ala Cys Lys Leu Thr Pro Pro His Ser Ala Lys
                2115                2120                2125

Ser Lys Phe Gly Tyr Gly Ala Lys Asp Val Arg Asn Leu Ser Ser Lys
        2130                2135                2140

Ala Val Asn His Ile His Ser Val Trp Lys Asp Leu Leu Glu Asp Thr
2145                2150                2155                2160

Val Thr Pro Ile Asp Thr Thr Ile Met Ala Lys Asn Glu Val Phe Cys
                2165                2170                2175

Val Gln Pro Glu Lys Gly Gly Arg Lys Pro Ala Arg Leu Ile Val Phe
                2180                2185                2190

Pro Asp Leu Gly Val Arg Val Cys Glu Lys Met Ala Leu Tyr Asp Val
        2195                2200                2205

Val Ser Thr Leu Pro Gln Val Val Met Gly Ser Ser Tyr Gly Phe Gln

```
                    2210                    2215                         2220
Tyr  Ser  Pro  Gly  Gln  Arg  Val  Glu  Phe  Leu  Val  Asn  Thr  Trp  Lys  Ser
2225                2230                    2235                         2240

Lys  Lys  Asn  Pro  Met  Gly  Phe  Ser  Tyr  Asp  Thr  Arg  Cys  Phe  Asp  Ser
                    2245                    2250                         2255

Thr  Val  Thr  Glu  Asn  Asp  Ile  Arg  Val  Glu  Glu  Ser  Ile  Tyr  Gln  Cys
                    2260                    2265                         2270

Cys  Asp  Leu  Ala  Pro  Glu  Ala  Arg  Gln  Ala  Ile  Lys  Ser  Leu  Thr  Glu
                    2275                    2280                         2285

Arg  Leu  Tyr  Ile  Gly  Gly  Pro  Leu  Thr  Asn  Ser  Lys  Gly  Gln  Asn  Cys
                    2290                    2295                         2300

Gly  Tyr  Arg  Arg  Cys  Arg  Ala  Ser  Gly  Val  Leu  Thr  Thr  Ser  Cys  Gly
2305                2310                    2315                         2320

Asn  Thr  Leu  Thr  Cys  Tyr  Leu  Lys  Ala  Ser  Ala  Ala  Cys  Arg  Ala  Ala
                    2325                    2330                         2335

Lys  Leu  Gln  Asp  Cys  Thr  Met  Leu  Val  Asn  Gly  Asp  Asp  Leu  Val  Val
                    2340                    2345                         2350

Ile  Cys  Glu  Ser  Ala  Gly  Thr  Gln  Glu  Asp  Ala  Ala  Ser  Leu  Arg  Val
                    2355                    2360                         2365

Phe  Thr  Glu  Ala  Met  Thr  Arg  Tyr  Ser  Ala  Pro  Pro  Gly  Asp  Pro  Pro
                    2370                    2375                         2380

Gln  Pro  Glu  Tyr  Asp  Leu  Glu  Leu  Ile  Thr  Ser  Cys  Ser  Ser  Asn  Val
2385                2390                    2395                         2400

Ser  Val  Ala  His  Asp  Ala  Ser  Gly  Lys  Arg  Val  Tyr  Tyr  Leu  Thr  Arg
                    2405                    2410                         2415

Asp  Pro  Thr  Thr  Pro  Leu  Ala  Arg  Ala  Ala  Trp  Glu  Thr  Ala  Arg  His
                    2420                    2425                         2430

Thr  Pro  Val  Asn  Ser  Trp  Leu  Gly  Asn  Ile  Ile  Met  Tyr  Ala  Pro  Thr
                    2435                    2440                         2445

Leu  Trp  Ala  Arg  Met  Ile  Leu  Met  Thr  His  Phe  Phe  Ser  Ile  Leu  Leu
                    2450                    2455                         2460

Ala  Gln  Glu  Gln  Leu  Glu  Lys  Ala  Leu  Asp  Cys  Gln  Ile  Tyr  Gly  Ala
2465                2470                    2475                         2480

Cys  Tyr  Ser  Ile  Glu  Pro  Leu  Asp  Leu  Pro  Gln  Ile  Ile  Glu  Arg  Leu
                    2485                    2490                         2495

His  Gly  Leu  Ser  Ala  Phe  Ser  Leu  His  Ser  Tyr  Ser  Pro  Gly  Glu  Ile
                    2500                    2505                         2510

Asn  Arg  Val  Ala  Ser  Cys  Leu  Arg  Lys  Leu  Gly  Val  Pro  Pro  Leu  Arg
                    2515                    2520                         2525

Val  Trp  Arg  His  Arg  Ala  Arg  Ser  Val  Arg  Ala  Arg  Leu  Leu  Ser  Gln
                    2530                    2535                         2540

Gly  Gly  Arg  Ala  Ala  Thr  Cys  Gly  Lys  Tyr  Leu  Phe  Asn  Trp  Ala  Val
2545                2550                    2555                         2560

Lys  Thr  Lys  Leu  Lys  Leu  Thr  Pro  Ile  Pro  Ala  Ala  Ser  Arg  Leu  Asp
                    2565                    2570                         2575

Leu  Ser  Gly  Trp  Phe  Val  Ala  Gly  Tyr  Ser  Gly  Gly  Asp  Ile  Tyr  His
                    2580                    2585                         2590

Ser  Leu  Ser  Arg  Ala  Arg  Pro  Arg  Trp  Phe  Met  Leu  Cys  Leu  Leu  Leu
                    2595                    2600                         2605

Leu  Ser  Val  Gly  Val  Gly  Ile  Tyr  Leu  Leu  Pro  Asn
                    2610                    2615                         2620
```

( 2 ) INFORMATION FOR SEQ ID NO:33:

( i ) SEQUENCE CHARACTERISTICS:
   ( A ) LENGTH: 1020 base pairs
   ( B ) TYPE: nucleic acid
   ( C ) STRANDEDNESS: single
   ( D ) TOPOLOGY: linear ( i i ) MOLECULE TYPE: cDNA from genomic RNA ( i x ) FEATURE:
   ( A ) NAME/KEY: misc_feature
   ( B ) LOCATION: 1..1020
   ( D ) OTHER INFORMATION: /note: "sequence = 1500 - 2519 of SEQ ID NO: 1"

( i x ) FEATURE:
   ( A ) NAME/KEY: CDS
   ( B ) LOCATION: 1..1020

( x i ) SEQUENCE DESCRIPTION: SEQ ID NO:33:

| | | | | | | | | | | | | | | | | |
|---|---|---|---|---|---|---|---|---|---|---|---|---|---|---|---|---|
| GGG | GCG | CAA | GCC | AAA | ACC | ACC | AAC | AGG | CTC | GTG | TCC | ATG | TTC | GCA | AGT | 48 |
| Gly | Ala | Gln | Ala | Lys | Thr | Thr | Asn | Arg | Leu | Val | Ser | Met | Phe | Ala | Ser | |
| 1 | | | | 5 | | | | | 10 | | | | | 15 | | |
| GGG | CCG | TCT | CAG | AAA | ATC | CAG | CTT | ATA | AAC | ACC | AAT | GGG | AGT | TGG | CAC | 96 |
| Gly | Pro | Ser | Gln | Lys | Ile | Gln | Leu | Ile | Asn | Thr | Asn | Gly | Ser | Trp | His | |
| | | | 20 | | | | | 25 | | | | | 30 | | | |
| ATC | AAC | AGG | ACT | GCC | CTG | AAC | TGC | AAT | GAC | TCT | CTC | CAG | ACT | GGG | TTT | 144 |
| Ile | Asn | Arg | Thr | Ala | Leu | Asn | Cys | Asn | Asp | Ser | Leu | Gln | Thr | Gly | Phe | |
| | | 35 | | | | | 40 | | | | | 45 | | | | |
| CTT | GCC | GCG | CTG | TTC | TAC | ACA | CAT | AGT | TTC | AAC | TCG | TCC | GGG | TGC | CCA | 192 |
| Leu | Ala | Ala | Leu | Phe | Tyr | Thr | His | Ser | Phe | Asn | Ser | Ser | Gly | Cys | Pro | |
| | 50 | | | | | 55 | | | | | 60 | | | | | |
| GAG | CGC | ATG | GCC | CAG | TGC | CGC | ACC | ATT | GAC | AAG | TTC | GAC | CAG | GGA | TGG | 240 |
| Glu | Arg | Met | Ala | Gln | Cys | Arg | Thr | Ile | Asp | Lys | Phe | Asp | Gln | Gly | Trp | |
| 65 | | | | | 70 | | | | | 75 | | | | | 80 | |
| GGT | CCC | ATT | ACT | TAT | GCT | GAG | TCT | AGC | AGA | TCA | GAC | CAG | AGG | CCA | TAT | 288 |
| Gly | Pro | Ile | Thr | Tyr | Ala | Glu | Ser | Ser | Arg | Ser | Asp | Gln | Arg | Pro | Tyr | |
| | | | | 85 | | | | | 90 | | | | | 95 | | |
| TGC | TGG | CAC | TAC | CCA | CCT | CCA | CAA | TGT | ACC | ATC | GTA | CCT | GCG | TCG | GAG | 336 |
| Cys | Trp | His | Tyr | Pro | Pro | Pro | Gln | Cys | Thr | Ile | Val | Pro | Ala | Ser | Glu | |
| | | | 100 | | | | | 105 | | | | | 110 | | | |
| GTG | TGC | GGC | CCA | GTG | TAC | TGC | TTC | ACC | CCA | AGC | CCT | GTC | GTC | GTG | GGG | 384 |
| Val | Cys | Gly | Pro | Val | Tyr | Cys | Phe | Thr | Pro | Ser | Pro | Val | Val | Val | Gly | |
| | | 115 | | | | | 120 | | | | | 125 | | | | |
| ACG | ACC | GAT | CGT | TTC | GGT | GTC | CCT | ACG | TAT | AGA | TGG | GGG | GAG | AAC | GAG | 432 |
| Thr | Thr | Asp | Arg | Phe | Gly | Val | Pro | Thr | Tyr | Arg | Trp | Gly | Glu | Asn | Glu | |
| | 130 | | | | | 135 | | | | | 140 | | | | | |
| ACT | GAC | GTG | CTG | CTG | CTC | AAC | AAC | ACG | CGG | CCG | CCG | CAA | GGC | AAC | TGG | 480 |
| Thr | Asp | Val | Leu | Leu | Leu | Asn | Asn | Thr | Arg | Pro | Pro | Gln | Gly | Asn | Trp | |
| 145 | | | | | 150 | | | | | 155 | | | | | 160 | |
| TTC | GGC | TGC | ACA | TGG | ATG | AAT | AGC | ACC | GGG | TTC | ACC | AAG | ACA | TGT | GGG | 528 |
| Phe | Gly | Cys | Thr | Trp | Met | Asn | Ser | Thr | Gly | Phe | Thr | Lys | Thr | Cys | Gly | |
| | | | | 165 | | | | | 170 | | | | | 175 | | |
| GGG | CCC | CCG | TGT | AAC | ATC | GGG | GGG | GTC | GGC | AAC | AAC | ACC | CTG | ACC | TGC | 576 |
| Gly | Pro | Pro | Cys | Asn | Ile | Gly | Gly | Val | Gly | Asn | Asn | Thr | Leu | Thr | Cys | |
| | | | 180 | | | | | 185 | | | | | 190 | | | |
| CCC | ACG | GAC | TGC | TTC | CGG | AAG | CAC | CCC | GAG | GCT | ACC | TAC | ACA | AAA | TGT | 624 |
| Pro | Thr | Asp | Cys | Phe | Arg | Lys | His | Pro | Glu | Ala | Thr | Tyr | Thr | Lys | Cys | |
| | | 195 | | | | | 200 | | | | | 205 | | | | |
| GGT | TCG | GGG | CCT | TGG | CTG | ACA | CCT | AGG | TGC | ATG | GTT | GAC | TAT | CCA | TAC | 672 |
| Gly | Ser | Gly | Pro | Trp | Leu | Thr | Pro | Arg | Cys | Met | Val | Asp | Tyr | Pro | Tyr | |
| | 210 | | | | | 215 | | | | | 220 | | | | | |
| AGG | CTC | TGG | CAT | TAC | CCC | TGC | ACT | GTT | AAC | TTT | ACC | ATC | TTC | AAG | GTT | 720 |
| Arg | Leu | Trp | His | Tyr | Pro | Cys | Thr | Val | Asn | Phe | Thr | Ile | Phe | Lys | Val | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| AGG | ATG | TAT | GTG | GGG | GGG | GTG | GAG | CAC | AGG | CTC | AAT | GCT | GCA | TGC | AAT | 768 |
| Arg | Met | Tyr | Val | Gly | Gly | Val | Glu | His | Arg | Leu | Asn | Ala | Ala | Cys | Asn | |
| | | | 245 | | | | 250 | | | | | 255 | | | | |
| TGG | ACC | CGA | GGA | GAG | CGT | TGT | GAC | TTG | GAG | GAC | AGG | GAT | AGG | CCG | GAG | 816 |
| Trp | Thr | Arg | Gly | Glu | Arg | Cys | Asp | Leu | Glu | Asp | Arg | Asp | Arg | Pro | Glu | |
| | | | 260 | | | | 265 | | | | | 270 | | | | |
| CTC | AGC | CCG | CTG | CTG | CTG | TCT | ACA | ACA | GAG | TGG | CAG | GTA | CTG | CCC | TGT | 864 |
| Leu | Ser | Pro | Leu | Leu | Leu | Ser | Thr | Thr | Glu | Trp | Gln | Val | Leu | Pro | Cys | |
| | | 275 | | | | | 280 | | | | | 285 | | | | |
| TCC | TTC | ACC | ACC | CTA | CCA | GCT | CTG | TCC | ACT | GGC | TTG | ATT | CAC | CTC | CAT | 912 |
| Ser | Phe | Thr | Thr | Leu | Pro | Ala | Leu | Ser | Thr | Gly | Leu | Ile | His | Leu | His | |
| | | 290 | | | | | 295 | | | | | 300 | | | | |
| CAG | AAC | ATC | GTG | GAC | GTG | CAA | TAC | CTA | TAC | GGT | ATA | GGG | TCA | GCG | GTT | 960 |
| Gln | Asn | Ile | Val | Asp | Val | Gln | Tyr | Leu | Tyr | Gly | Ile | Gly | Ser | Ala | Val | |
| 305 | | | | | 310 | | | | | 315 | | | | | 320 | |
| GTC | TCC | TTT | GCA | ATC | AAA | TGG | GAG | TAT | GTC | CTG | TTG | CTT | TTC | CTT | CTC | 1008 |
| Val | Ser | Phe | Ala | Ile | Lys | Trp | Glu | Tyr | Val | Leu | Leu | Leu | Phe | Leu | Leu | |
| | | | | 325 | | | | | 330 | | | | | 335 | | |
| CTA | GCG | GAC | GCA | | | | | | | | | | | | | 1020 |
| Leu | Ala | Asp | Ala | | | | | | | | | | | | | |
| | | | 340 | | | | | | | | | | | | | |

(2) INFORMATION FOR SEQ ID NO:34:

(i) SEQUENCE CHARACTERISTICS:
    (A) LENGTH: 340 amino acids
    (B) TYPE: amino acid
    (D) TOPOLOGY: linear (ii) MOLECULE TYPE: protein (xi) SEQUENCE DESCRIPTION: SEQ ID NO:34:

| | | | | | | | | | | | | | | |
|---|---|---|---|---|---|---|---|---|---|---|---|---|---|---|
| Gly | Ala | Gln | Ala | Lys | Thr | Thr | Asn | Arg | Leu | Val | Ser | Met | Phe | Ala | Ser |
| 1 | | | | 5 | | | | | 10 | | | | | 15 | |
| Gly | Pro | Ser | Gln | Lys | Ile | Gln | Leu | Ile | Asn | Thr | Asn | Gly | Ser | Trp | His |
| | | | 20 | | | | | 25 | | | | | 30 | | |
| Ile | Asn | Arg | Thr | Ala | Leu | Asn | Cys | Asn | Asp | Ser | Leu | Gln | Thr | Gly | Phe |
| | | | 35 | | | | 40 | | | | | 45 | | | |
| Leu | Ala | Ala | Leu | Phe | Tyr | Thr | His | Ser | Phe | Asn | Ser | Ser | Gly | Cys | Pro |
| | 50 | | | | | 55 | | | | | 60 | | | | |
| Glu | Arg | Met | Ala | Gln | Cys | Arg | Thr | Ile | Asp | Lys | Phe | Asp | Gln | Gly | Trp |
| 65 | | | | | 70 | | | | | 75 | | | | | 80 |
| Gly | Pro | Ile | Thr | Tyr | Ala | Glu | Ser | Ser | Arg | Ser | Asp | Gln | Arg | Pro | Tyr |
| | | | | 85 | | | | | 90 | | | | | 95 | |
| Cys | Trp | His | Tyr | Pro | Pro | Pro | Gln | Cys | Thr | Ile | Val | Pro | Ala | Ser | Glu |
| | | | 100 | | | | | 105 | | | | | 110 | | |
| Val | Cys | Gly | Pro | Val | Tyr | Cys | Phe | Thr | Pro | Ser | Pro | Val | Val | Val | Gly |
| | | | 115 | | | | | 120 | | | | | 125 | | |
| Thr | Thr | Asp | Arg | Phe | Gly | Val | Pro | Thr | Tyr | Arg | Trp | Gly | Glu | Asn | Glu |
| | 130 | | | | | 135 | | | | | 140 | | | | |
| Thr | Asp | Val | Leu | Leu | Leu | Asn | Asn | Thr | Arg | Pro | Pro | Gln | Gly | Asn | Trp |
| 145 | | | | | 150 | | | | | 155 | | | | | 160 |
| Phe | Gly | Cys | Thr | Trp | Met | Asn | Ser | Thr | Gly | Phe | Thr | Lys | Thr | Cys | Gly |
| | | | | 165 | | | | | 170 | | | | | 175 | |
| Gly | Pro | Pro | Cys | Asn | Ile | Gly | Gly | Val | Gly | Asn | Asn | Thr | Leu | Thr | Cys |
| | | | 180 | | | | | 185 | | | | | 190 | | |
| Pro | Thr | Asp | Cys | Phe | Arg | Lys | His | Pro | Glu | Ala | Thr | Tyr | Thr | Lys | Cys |
| | | 195 | | | | | 200 | | | | | 205 | | | |
| Gly | Ser | Gly | Pro | Trp | Leu | Thr | Pro | Arg | Cys | Met | Val | Asp | Tyr | Pro | Tyr |

```
        210                  215                  220
Arg Leu Trp His Tyr Pro Cys Thr Val Asn Phe Thr Ile Phe Lys Val
225                 230                 235                 240

Arg Met Tyr Val Gly Gly Val Glu His Arg Leu Asn Ala Ala Cys Asn
            245                 250                 255

Trp Thr Arg Gly Glu Arg Cys Asp Leu Glu Asp Arg Asp Arg Pro Glu
            260                 265                 270

Leu Ser Pro Leu Leu Leu Ser Thr Glu Trp Gln Val Leu Pro Cys
        275                 280                 285

Ser Phe Thr Thr Leu Pro Ala Leu Ser Thr Gly Leu Ile His Leu His
    290                 295                 300

Gln Asn Ile Val Asp Val Gln Tyr Leu Tyr Gly Ile Gly Ser Ala Val
305                 310                 315                 320

Val Ser Phe Ala Ile Lys Trp Glu Tyr Val Leu Leu Leu Phe Leu Leu
                325                 330                 335

Leu Ala Asp Ala
            340
```

( 2 ) INFORMATION FOR SEQ ID NO:35:

( i ) SEQUENCE CHARACTERISTICS:
        ( A ) LENGTH: 7863 base pairs
        ( B ) TYPE: nucleic acid
        ( C ) STRANDEDNESS: single
        ( D ) TOPOLOGY: linear ( i i ) MOLECULE TYPE: cDNA from genomic RNA ( i x ) FEATURE:
        ( A ) NAME/KEY: CDS
        ( B ) LOCATION: 1..7863

( i x ) FEATURE:
        ( A ) NAME/KEY: misc_feature
        ( B ) LOCATION: 1..7863
        ( D ) OTHER INFORMATION: /note= "sequence = 1500 - 9362 of SEQ ID NO: 1"

( x i ) SEQUENCE DESCRIPTION: SEQ ID NO:35:

```
GGG GCG CAA GCC AAA ACC ACC AAC AGG CTC GTG TCC ATG TTC GCA AGT        48
Gly Ala Gln Ala Lys Thr Thr Asn Arg Leu Val Ser Met Phe Ala Ser
1               5                   10                  15

GGG CCG TCT CAG AAA ATC CAG CTT ATA AAC ACC AAT GGG AGT TGG CAC        96
Gly Pro Ser Gln Lys Ile Gln Leu Ile Asn Thr Asn Gly Ser Trp His
            20                  25                  30

ATC AAC AGG ACT GCC CTG AAC TGC AAT GAC TCT CTC CAG ACT GGG TTT       144
Ile Asn Arg Thr Ala Leu Asn Cys Asn Asp Ser Leu Gln Thr Gly Phe
        35                  40                  45

CTT GCC GCG CTG TTC TAC ACA CAT AGT TTC AAC TCG TCC GGG TGC CCA       192
Leu Ala Ala Leu Phe Tyr Thr His Ser Phe Asn Ser Ser Gly Cys Pro
    50                  55                  60

GAG CGC ATG GCC CAG TGC CGC ACC ATT GAC AAG TTC GAC CAG GGA TGG       240
Glu Arg Met Ala Gln Cys Arg Thr Ile Asp Lys Phe Asp Gln Gly Trp
65                  70                  75                  80

GGT CCC ATT ACT TAT GCT GAG TCT AGC AGA TCA GAC CAG AGG CCA TAT       288
Gly Pro Ile Thr Tyr Ala Glu Ser Ser Arg Ser Asp Gln Arg Pro Tyr
                85                  90                  95

TGC TGG CAC TAC CCA CCT CCA CAA TGT ACC ATC GTA CCT GCG TCG GAG       336
Cys Trp His Tyr Pro Pro Pro Gln Cys Thr Ile Val Pro Ala Ser Glu
            100                 105                 110

GTG TGC GGC CCA GTG TAC TGC TTC ACC CCA AGC CCT GTC GTC GTG GGG       384
Val Cys Gly Pro Val Tyr Cys Phe Thr Pro Ser Pro Val Val Val Gly
        115                 120                 125
```

| | | | | | | | | | | | | | | | | |
|---|---|---|---|---|---|---|---|---|---|---|---|---|---|---|---|---|
| ACG | ACC | GAT | CGT | TTC | GGT | GTC | CCT | ACG | TAT | AGA | TGG | GGG | GAG | AAC | GAG | 432 |
| Thr | Thr | Asp | Arg | Phe | Gly | Val | Pro | Thr | Tyr | Arg | Trp | Gly | Glu | Asn | Glu | |
| | | 130 | | | | 135 | | | | | 140 | | | | | |
| ACT | GAC | GTG | CTG | CTG | CTC | AAC | AAC | ACG | CGG | CCG | CCG | CAA | GGC | AAC | TGG | 480 |
| Thr | Asp | Val | Leu | Leu | Leu | Asn | Asn | Thr | Arg | Pro | Pro | Gln | Gly | Asn | Trp | |
| 145 | | | | | 150 | | | | | 155 | | | | | 160 | |
| TTC | GGC | TGC | ACA | TGG | ATG | AAT | AGC | ACC | GGG | TTC | ACC | AAG | ACA | TGT | GGG | 528 |
| Phe | Gly | Cys | Thr | Trp | Met | Asn | Ser | Thr | Gly | Phe | Thr | Lys | Thr | Cys | Gly | |
| | | | | 165 | | | | | 170 | | | | | 175 | | |
| GGG | CCC | CCG | TGT | AAC | ATC | GGG | GGG | GTC | GGC | AAC | AAC | ACC | CTG | ACC | TGC | 576 |
| Gly | Pro | Pro | Cys | Asn | Ile | Gly | Gly | Val | Gly | Asn | Asn | Thr | Leu | Thr | Cys | |
| | | | | 180 | | | | | 185 | | | | | 190 | | |
| CCC | ACG | GAC | TGC | TTC | CGG | AAG | CAC | CCC | GAG | GCT | ACC | TAC | ACA | AAA | TGT | 624 |
| Pro | Thr | Asp | Cys | Phe | Arg | Lys | His | Pro | Glu | Ala | Thr | Tyr | Thr | Lys | Cys | |
| | | | 195 | | | | 200 | | | | | 205 | | | | |
| GGT | TCG | GGG | CCT | TGG | CTG | ACA | CCT | AGG | TGC | ATG | GTT | GAC | TAT | CCA | TAC | 672 |
| Gly | Ser | Gly | Pro | Trp | Leu | Thr | Pro | Arg | Cys | Met | Val | Asp | Tyr | Pro | Tyr | |
| | 210 | | | | | 215 | | | | | 220 | | | | | |
| AGG | CTC | TGG | CAT | TAC | CCC | TGC | ACT | GTT | AAC | TTT | ACC | ATC | TTC | AAG | GTT | 720 |
| Arg | Leu | Trp | His | Tyr | Pro | Cys | Thr | Val | Asn | Phe | Thr | Ile | Phe | Lys | Val | |
| 225 | | | | | 230 | | | | | 235 | | | | | 240 | |
| AGG | ATG | TAT | GTG | GGG | GGG | GTG | GAG | CAC | AGG | CTC | AAT | GCT | GCA | TGC | AAT | 768 |
| Arg | Met | Tyr | Val | Gly | Gly | Val | Glu | His | Arg | Leu | Asn | Ala | Ala | Cys | Asn | |
| | | | | 245 | | | | | 250 | | | | | 255 | | |
| TGG | ACC | CGA | GGA | GAG | CGT | TGT | GAC | TTG | GAG | GAC | AGG | GAT | AGG | CCG | GAG | 816 |
| Trp | Thr | Arg | Gly | Glu | Arg | Cys | Asp | Leu | Glu | Asp | Arg | Asp | Arg | Pro | Glu | |
| | | | 260 | | | | | 265 | | | | | 270 | | | |
| CTC | AGC | CCG | CTG | CTG | CTG | TCT | ACA | ACA | GAG | TGG | CAG | GTA | CTG | CCC | TGT | 864 |
| Leu | Ser | Pro | Leu | Leu | Leu | Ser | Thr | Thr | Glu | Trp | Gln | Val | Leu | Pro | Cys | |
| | | 275 | | | | | 280 | | | | | 285 | | | | |
| TCC | TTC | ACC | ACC | CTA | CCA | GCT | CTG | TCC | ACT | GGC | TTG | ATT | CAC | CTC | CAT | 912 |
| Ser | Phe | Thr | Thr | Leu | Pro | Ala | Leu | Ser | Thr | Gly | Leu | Ile | His | Leu | His | |
| | 290 | | | | | 295 | | | | | 300 | | | | | |
| CAG | AAC | ATC | GTG | GAC | GTG | CAA | TAC | CTA | TAC | GGT | ATA | GGG | TCA | GCG | GTT | 960 |
| Gln | Asn | Ile | Val | Asp | Val | Gln | Tyr | Leu | Tyr | Gly | Ile | Gly | Ser | Ala | Val | |
| 305 | | | | | 310 | | | | | 315 | | | | | 320 | |
| GTC | TCC | TTT | GCA | ATC | AAA | TGG | GAG | TAT | GTC | CTG | TTG | CTT | TTC | CTT | CTC | 1008 |
| Val | Ser | Phe | Ala | Ile | Lys | Trp | Glu | Tyr | Val | Leu | Leu | Leu | Phe | Leu | Leu | |
| | | | | 325 | | | | | 330 | | | | | 335 | | |
| CTA | GCG | GAC | GCA | CGT | GTC | TGT | GCC | TGC | TTG | TGG | ATG | ATG | CTG | CTG | ATA | 1056 |
| Leu | Ala | Asp | Ala | Arg | Val | Cys | Ala | Cys | Leu | Trp | Met | Met | Leu | Leu | Ile | |
| | | | 340 | | | | | 345 | | | | | 350 | | | |
| GCC | CAG | GCC | GAG | GCC | GCC | TTG | GAG | AAC | CTG | GTG | GTC | CTC | AAT | TCG | GCG | 1104 |
| Ala | Gln | Ala | Glu | Ala | Ala | Leu | Glu | Asn | Leu | Val | Val | Leu | Asn | Ser | Ala | |
| | | 355 | | | | | 360 | | | | | 365 | | | | |
| TCT | GTG | GCC | GGC | GCA | CAT | GGC | ATC | CTC | TCC | TTC | CTT | GTG | TTC | TTC | TGT | 1152 |
| Ser | Val | Ala | Gly | Ala | His | Gly | Ile | Leu | Ser | Phe | Leu | Val | Phe | Phe | Cys | |
| | 370 | | | | | 375 | | | | | 380 | | | | | |
| GCC | GCC | TGG | TAC | ATC | AAA | GGC | AGG | CTG | GTC | CCT | GGG | GCG | ACA | TAT | GCT | 1200 |
| Ala | Ala | Trp | Tyr | Ile | Lys | Gly | Arg | Leu | Val | Pro | Gly | Ala | Thr | Tyr | Ala | |
| 385 | | | | | 390 | | | | | 395 | | | | | 400 | |
| CTT | TAT | GGC | GTG | TGG | CCG | CTG | CTC | CTG | TTG | CTG | GCA | TTA | CCA | CCG | | 1248 |
| Leu | Tyr | Gly | Val | Trp | Pro | Leu | Leu | Leu | Leu | Leu | Ala | Leu | Pro | Pro | | |
| | | | | 405 | | | | | 410 | | | | | 415 | | |
| CGA | GCT | TAC | GCC | ATG | GAC | CGG | GAG | ATG | GCT | GCA | TCG | TGC | GGA | GGC | GCG | 1296 |
| Arg | Ala | Tyr | Ala | Met | Asp | Arg | Glu | Met | Ala | Ala | Ser | Cys | Gly | Gly | Ala | |
| | | | | 420 | | | | | 425 | | | | | 430 | | |
| GTT | TTT | GTG | GGT | CTG | GTA | CTC | CTG | ACT | TTG | TCA | CCA | TAC | TAC | AAG | GTG | 1344 |
| Val | Phe | Val | Gly | Leu | Val | Leu | Leu | Thr | Leu | Ser | Pro | Tyr | Tyr | Lys | Val | |
| | | | 435 | | | | | 440 | | | | | 445 | | | |

| | | | | | | | | | | | | | | | | |
|---|---|---|---|---|---|---|---|---|---|---|---|---|---|---|---|---|
| TTC | CTC | GCT | AGG | CTC | ATA | TGG | TGG | TTA | CAA | TAT | TTT | ACC | ACC | AGA | GCC | 1392 |
| Phe | Leu | Ala | Arg | Leu | Ile | Trp | Trp | Leu | Gln | Tyr | Phe | Thr | Thr | Arg | Ala | |
| | 450 | | | | 455 | | | | | | 460 | | | | | |
| GAG | GCG | GAC | TTA | CAT | GTG | TGG | ATC | CCC | CCC | CTC | AAC | GCT | CGG | GGA | GGC | 1440 |
| Glu | Ala | Asp | Leu | His | Val | Trp | Ile | Pro | Pro | Leu | Asn | Ala | Arg | Gly | Gly | |
| 465 | | | | | 470 | | | | | 475 | | | | | 480 | |
| CGC | GAT | GCC | ATC | ATC | CTC | CTC | ATG | TGC | GCA | GTC | CAT | CCA | GAG | CTA | ATC | 1488 |
| Arg | Asp | Ala | Ile | Ile | Leu | Leu | Met | Cys | Ala | Val | His | Pro | Glu | Leu | Ile | |
| | | | | 485 | | | | | 490 | | | | | 495 | | |
| TTT | GAC | ATC | ACC | AAA | CTT | CTA | ATT | GCC | ATA | CTC | GGT | CCG | CTC | ATG | GTG | 1536 |
| Phe | Asp | Ile | Thr | Lys | Leu | Leu | Ile | Ala | Ile | Leu | Gly | Pro | Leu | Met | Val | |
| | | | 500 | | | | | 505 | | | | | 510 | | | |
| CTC | CAA | GCT | GGC | ATA | ACC | AGA | GTG | CCG | TAC | TTC | GTG | CGC | GCT | CAA | GGG | 1584 |
| Leu | Gln | Ala | Gly | Ile | Thr | Arg | Val | Pro | Tyr | Phe | Val | Arg | Ala | Gln | Gly | |
| | | | 515 | | | | 520 | | | | | 525 | | | | |
| CTC | ATT | CAT | GCA | TGC | ATG | TTA | GTG | CGG | AAG | GTC | GCT | GGG | GGT | CAT | TAT | 1632 |
| Leu | Ile | His | Ala | Cys | Met | Leu | Val | Arg | Lys | Val | Ala | Gly | Gly | His | Tyr | |
| | 530 | | | | | 535 | | | | | 540 | | | | | |
| GTC | CAA | ATG | GCC | TTC | ATG | AAG | CTG | GGC | GCG | CTG | ACA | GGC | ACG | TAC | ATT | 1680 |
| Val | Gln | Met | Ala | Phe | Met | Lys | Leu | Gly | Ala | Leu | Thr | Gly | Thr | Tyr | Ile | |
| 545 | | | | | 550 | | | | | 555 | | | | | 560 | |
| TAC | AAC | CAT | CTT | ACC | CCG | CTA | CGG | GAT | TGG | CCA | CGC | GCG | GGC | CTA | CGA | 1728 |
| Tyr | Asn | His | Leu | Thr | Pro | Leu | Arg | Asp | Trp | Pro | Arg | Ala | Gly | Leu | Arg | |
| | | | | 565 | | | | | 570 | | | | | 575 | | |
| GAC | CTT | GCG | GTG | GCA | GTG | GAG | CCC | GTC | GTC | TTC | TCC | GAC | ATG | GAG | ACC | 1776 |
| Asp | Leu | Ala | Val | Ala | Val | Glu | Pro | Val | Val | Phe | Ser | Asp | Met | Glu | Thr | |
| | | | 580 | | | | | 585 | | | | | 590 | | | |
| AAG | ATC | ATC | ACC | TGG | GGA | GCA | GAC | ACC | GCG | GCG | TGT | GGG | GAC | ATC | ATC | 1824 |
| Lys | Ile | Ile | Thr | Trp | Gly | Ala | Asp | Thr | Ala | Ala | Cys | Gly | Asp | Ile | Ile | |
| | | | 595 | | | | | 600 | | | | | 605 | | | |
| TTG | GGT | CTG | CCC | GTC | TCC | GCC | CGA | AGG | GGA | AAG | GAG | ATA | CTC | CTG | GGC | 1872 |
| Leu | Gly | Leu | Pro | Val | Ser | Ala | Arg | Arg | Gly | Lys | Glu | Ile | Leu | Leu | Gly | |
| | 610 | | | | | 615 | | | | | 620 | | | | | |
| CCG | GCC | GAT | AGT | CTT | GAA | GGG | CGG | GGG | TTG | CGA | CTC | CTC | GCG | CCC | ATC | 1920 |
| Pro | Ala | Asp | Ser | Leu | Glu | Gly | Arg | Gly | Leu | Arg | Leu | Leu | Ala | Pro | Ile | |
| 625 | | | | | 630 | | | | | 635 | | | | | 640 | |
| ACG | GCC | TAC | TCC | CAA | CAG | ACG | CGG | GGC | CTA | CTT | GGT | TGC | ATC | ATC | ACT | 1968 |
| Thr | Ala | Tyr | Ser | Gln | Gln | Thr | Arg | Gly | Leu | Leu | Gly | Cys | Ile | Ile | Thr | |
| | | | | 645 | | | | | 650 | | | | | 655 | | |
| AGC | CTT | ACA | GGC | CGG | GAC | AAG | AAC | CAG | GTC | GAG | GGA | GAG | GTT | CAG | GTG | 2016 |
| Ser | Leu | Thr | Gly | Arg | Asp | Lys | Asn | Gln | Val | Glu | Gly | Glu | Val | Gln | Val | |
| | | | 660 | | | | | 665 | | | | | 670 | | | |
| GTT | TCC | ACC | GCA | ACA | CAA | TCC | TTC | CTG | GCG | ACC | TGC | GTC | AAC | GGC | GTG | 2064 |
| Val | Ser | Thr | Ala | Thr | Gln | Ser | Phe | Leu | Ala | Thr | Cys | Val | Asn | Gly | Val | |
| | | 675 | | | | | 680 | | | | | 685 | | | | |
| TGT | TGG | ACC | GTT | TAC | CAT | GGT | GCT | GGC | TCA | AAG | ACC | TTA | GCC | GCG | CCA | 2112 |
| Cys | Trp | Thr | Val | Tyr | His | Gly | Ala | Gly | Ser | Lys | Thr | Leu | Ala | Ala | Pro | |
| | 690 | | | | | 695 | | | | | 700 | | | | | |
| AAG | GGG | CCA | ATC | ACC | CAG | ATG | TAC | ACT | AAT | GTG | GAC | CAG | GAC | CTC | GTC | 2160 |
| Lys | Gly | Pro | Ile | Thr | Gln | Met | Tyr | Thr | Asn | Val | Asp | Gln | Asp | Leu | Val | |
| 705 | | | | | 710 | | | | | 715 | | | | | 720 | |
| GGC | TGG | CCC | AAG | CCC | CCC | GGG | GCG | CGT | TCC | TTG | ACA | CCA | TGC | ACC | TGT | 2208 |
| Gly | Trp | Pro | Lys | Pro | Pro | Gly | Ala | Arg | Ser | Leu | Thr | Pro | Cys | Thr | Cys | |
| | | | | 725 | | | | | 730 | | | | | 735 | | |
| GGC | AGC | TCA | GAC | CTT | TAC | TTG | GTC | ACG | AGA | CAT | GCT | GAC | GTC | ATT | CCG | 2256 |
| Gly | Ser | Ser | Asp | Leu | Tyr | Leu | Val | Thr | Arg | His | Ala | Asp | Val | Ile | Pro | |
| | | | 740 | | | | | 745 | | | | | 750 | | | |
| GTG | CGC | CGG | CGG | GGC | GAC | AGT | AGG | GGG | AGC | CTG | CTC | TCC | CCC | AGG | CCT | 2304 |
| Val | Arg | Arg | Arg | Gly | Asp | Ser | Arg | Gly | Ser | Leu | Leu | Ser | Pro | Arg | Pro | |
| | | 755 | | | | | 760 | | | | | 765 | | | | |

| | | | | | | | | | | | | | | | |
|---|---|---|---|---|---|---|---|---|---|---|---|---|---|---|---|
| GTC | TCC | TAC | TTG | AAG | GGC | TCT | TCG | GGT | GGT | CCA | CTG | CTC | TGC | CCC | TTC |
| Val | Ser | Tyr | Leu | Lys | Gly | Ser | Ser | Gly | Gly | Pro | Leu | Leu | Cys | Pro | Phe |
| | | 770 | | | | 775 | | | | | 780 | | | | |

2352

| | | | | | | | | | | | | | | | |
|---|---|---|---|---|---|---|---|---|---|---|---|---|---|---|---|
| GGG | CAC | GCT | GTG | GGC | ATC | TTC | CGG | GCT | GCC | GTA | TGC | ACC | CGG | GGG | GTT |
| Gly | His | Ala | Val | Gly | Ile | Phe | Arg | Ala | Ala | Val | Cys | Thr | Arg | Gly | Val |
| 785 | | | | | 790 | | | | | 795 | | | | | 800 |

2400

| | | | | | | | | | | | | | | | |
|---|---|---|---|---|---|---|---|---|---|---|---|---|---|---|---|
| GCG | AAG | GCG | GTG | GAC | TTT | GTG | CCC | GTA | GAG | TCC | ATG | GAA | ACT | ACT | ATG |
| Ala | Lys | Ala | Val | Asp | Phe | Val | Pro | Val | Glu | Ser | Met | Glu | Thr | Thr | Met |
| | | | | 805 | | | | | 810 | | | | | 815 | |

2448

| | | | | | | | | | | | | | | | |
|---|---|---|---|---|---|---|---|---|---|---|---|---|---|---|---|
| CGG | TCT | CCG | GTC | TTC | ACG | GAC | AAC | TCA | TCC | CCC | CCG | GCC | GTA | CCG | CAG |
| Arg | Ser | Pro | Val | Phe | Thr | Asp | Asn | Ser | Ser | Pro | Pro | Ala | Val | Pro | Gln |
| | | | 820 | | | | | 825 | | | | | 830 | | |

2496

| | | | | | | | | | | | | | | | |
|---|---|---|---|---|---|---|---|---|---|---|---|---|---|---|---|
| TCA | TTT | CAA | GTG | GCC | CAC | CTA | CAC | GCT | CCC | ACT | GGC | AGC | GGC | AAG | AGT |
| Ser | Phe | Gln | Val | Ala | His | Leu | His | Ala | Pro | Thr | Gly | Ser | Gly | Lys | Ser |
| | | 835 | | | | | 840 | | | | | 845 | | | |

2544

| | | | | | | | | | | | | | | | |
|---|---|---|---|---|---|---|---|---|---|---|---|---|---|---|---|
| ACT | AAA | GTG | CCG | GCT | GCA | TAT | GCA | GCC | CAA | GGG | TAC | AAG | GTG | CTC | GTC |
| Thr | Lys | Val | Pro | Ala | Ala | Tyr | Ala | Ala | Gln | Gly | Tyr | Lys | Val | Leu | Val |
| 850 | | | | | 855 | | | | | 860 | | | | | |

2592

| | | | | | | | | | | | | | | | |
|---|---|---|---|---|---|---|---|---|---|---|---|---|---|---|---|
| CTC | AAT | CCG | TCC | GTT | GCC | GCT | ACC | TTA | GGG | TTT | GGG | GCG | TAT | ATG | TCT |
| Leu | Asn | Pro | Ser | Val | Ala | Ala | Thr | Leu | Gly | Phe | Gly | Ala | Tyr | Met | Ser |
| 865 | | | | | 870 | | | | | 875 | | | | | 880 |

2640

| | | | | | | | | | | | | | | | |
|---|---|---|---|---|---|---|---|---|---|---|---|---|---|---|---|
| AAG | GCA | CAC | GGT | ATT | GAC | CCC | AAC | ATC | AGA | ACT | GGG | GTA | AGG | ACC | ATT |
| Lys | Ala | His | Gly | Ile | Asp | Pro | Asn | Ile | Arg | Thr | Gly | Val | Arg | Thr | Ile |
| | | | | 885 | | | | | 890 | | | | | 895 | |

2688

| | | | | | | | | | | | | | | | |
|---|---|---|---|---|---|---|---|---|---|---|---|---|---|---|---|
| ACC | ACA | GGC | GCC | CCC | GTC | ACA | TAC | TCT | ACC | TAT | GGC | AAG | TTT | CTT | GCC |
| Thr | Thr | Gly | Ala | Pro | Val | Thr | Tyr | Ser | Thr | Tyr | Gly | Lys | Phe | Leu | Ala |
| | | | 900 | | | | | 905 | | | | | 910 | | |

2736

| | | | | | | | | | | | | | | | |
|---|---|---|---|---|---|---|---|---|---|---|---|---|---|---|---|
| GAT | GGT | GGT | TGC | TCT | GGG | GGC | GCT | TAT | GAC | ATC | ATA | ATA | TGT | GAT | GAG |
| Asp | Gly | Gly | Cys | Ser | Gly | Gly | Ala | Tyr | Asp | Ile | Ile | Ile | Cys | Asp | Glu |
| | | 915 | | | | | 920 | | | | | 925 | | | |

2784

| | | | | | | | | | | | | | | | |
|---|---|---|---|---|---|---|---|---|---|---|---|---|---|---|---|
| TGC | CAT | TCA | ACT | GAC | TCG | ACT | ACA | ATC | TTG | GGC | ATC | GGC | ACA | GTC | CTG |
| Cys | His | Ser | Thr | Asp | Ser | Thr | Thr | Ile | Leu | Gly | Ile | Gly | Thr | Val | Leu |
| 930 | | | | | 935 | | | | | 940 | | | | | |

2832

| | | | | | | | | | | | | | | | |
|---|---|---|---|---|---|---|---|---|---|---|---|---|---|---|---|
| GAC | CAA | GCG | GAG | ACG | GCT | GGA | GCG | CGG | CTT | GTC | GTG | CTC | GCC | ACC | GCT |
| Asp | Gln | Ala | Glu | Thr | Ala | Gly | Ala | Arg | Leu | Val | Val | Leu | Ala | Thr | Ala |
| 945 | | | | | 950 | | | | | 955 | | | | | 960 |

2880

| | | | | | | | | | | | | | | | |
|---|---|---|---|---|---|---|---|---|---|---|---|---|---|---|---|
| ACG | CCT | CCG | GGA | TCG | GTC | ACC | GTG | CCA | CAC | CCA | AAC | ATC | GAG | GAG | GTG |
| Thr | Pro | Pro | Gly | Ser | Val | Thr | Val | Pro | His | Pro | Asn | Ile | Glu | Glu | Val |
| | | | | 965 | | | | | 970 | | | | | 975 | |

2928

| | | | | | | | | | | | | | | | |
|---|---|---|---|---|---|---|---|---|---|---|---|---|---|---|---|
| GCC | CTG | TCT | AAT | ACT | GGA | GAG | ATC | CCC | TTC | TAT | GGC | AAA | GCC | ATC | CCC |
| Ala | Leu | Ser | Asn | Thr | Gly | Glu | Ile | Pro | Phe | Tyr | Gly | Lys | Ala | Ile | Pro |
| | | | 980 | | | | | 985 | | | | | 990 | | |

2976

| | | | | | | | | | | | | | | | |
|---|---|---|---|---|---|---|---|---|---|---|---|---|---|---|---|
| ATT | GAA | GCC | ATC | AGG | GGG | GGA | AGG | CAT | CTC | ATT | TTC | TGT | CAT | TCC | AAG |
| Ile | Glu | Ala | Ile | Arg | Gly | Gly | Arg | His | Leu | Ile | Phe | Cys | His | Ser | Lys |
| | | 995 | | | | | 1000 | | | | | 1005 | | | |

3024

| | | | | | | | | | | | | | | | |
|---|---|---|---|---|---|---|---|---|---|---|---|---|---|---|---|
| AAG | AAG | TGC | GAC | GAG | CTC | GCC | GCA | AAG | CTG | TCA | GGC | CTC | GGA | ATC | AAC |
| Lys | Lys | Cys | Asp | Glu | Leu | Ala | Ala | Lys | Leu | Ser | Gly | Leu | Gly | Ile | Asn |
| | | 1010 | | | | | 1015 | | | | | 1020 | | | |

3072

| | | | | | | | | | | | | | | | |
|---|---|---|---|---|---|---|---|---|---|---|---|---|---|---|---|
| GCT | GTG | GCG | TAT | TAC | CGG | GGG | CTC | GAT | GTG | TCC | GTC | ATA | CCA | ACT | ATC |
| Ala | Val | Ala | Tyr | Tyr | Arg | Gly | Leu | Asp | Val | Ser | Val | Ile | Pro | Thr | Ile |
| 1025 | | | | | 1030 | | | | | 1035 | | | | | 1040 |

3120

| | | | | | | | | | | | | | | | |
|---|---|---|---|---|---|---|---|---|---|---|---|---|---|---|---|
| GGA | GAC | GTC | GTT | GTC | GTG | GCA | ACA | GAC | GCT | CTG | ATG | ACG | GGC | TAT | ACG |
| Gly | Asp | Val | Val | Val | Val | Ala | Thr | Asp | Ala | Leu | Met | Thr | Gly | Tyr | Thr |
| | | | | 1045 | | | | | 1050 | | | | | 1055 | |

3168

| | | | | | | | | | | | | | | | |
|---|---|---|---|---|---|---|---|---|---|---|---|---|---|---|---|
| GGC | GAC | TTT | GAC | TCA | GTG | ATC | GAC | TGT | AAC | ACA | TGT | GTC | ACC | CAG | ACA |
| Gly | Asp | Phe | Asp | Ser | Val | Ile | Asp | Cys | Asn | Thr | Cys | Val | Thr | Gln | Thr |
| | | | 1060 | | | | | 1065 | | | | | 1070 | | |

3216

| | | | | | | | | | | | | | | | |
|---|---|---|---|---|---|---|---|---|---|---|---|---|---|---|---|
| GTC | GAC | TTC | AGC | TTG | GAT | CCC | ACC | TTC | ACC | ATT | GAG | ACG | ACG | ACC | GTG |
| Val | Asp | Phe | Ser | Leu | Asp | Pro | Thr | Phe | Thr | Ile | Glu | Thr | Thr | Thr | Val |
| | | | 1075 | | | | | 1080 | | | | | 1085 | | |

3264

```
CCT CAA GAC GCA GTG TCG CGC TCG CAG CGG CGG GGT AGG ACT GGC AGG        3312
Pro Gln Asp Ala Val Ser Arg Ser Gln Arg Arg Gly Arg Thr Gly Arg
        1090            1095                1100

GGT AGG AGA GGC ATC TAC AGG TTT GTG ACT CCG GGA GAA CGG CCC TCG        3360
Gly Arg Arg Gly Ile Tyr Arg Phe Val Thr Pro Gly Glu Arg Pro Ser
1105            1110                1115                    1120

GGC ATG TTC GAT TCC TCG GTC CTG TGT GAG TGC TAT GAC GCG GGC TGT        3408
Gly Met Phe Asp Ser Ser Val Leu Cys Glu Cys Tyr Asp Ala Gly Cys
                    1125                1130                1135

GCT TGG TAC GAG CTC ACC CCG GCC GAG ACC TCG GTT AGG TTG CGG GCC        3456
Ala Trp Tyr Glu Leu Thr Pro Ala Glu Thr Ser Val Arg Leu Arg Ala
        1140                1145                1150

TAC CTG AAC ACA CCA GGG TTG CCC GTT TGC CAG GAC CAC CTG GAG TTC        3504
Tyr Leu Asn Thr Pro Gly Leu Pro Val Cys Gln Asp His Leu Glu Phe
            1155                1160                1165

TGG GAG AGT GTC TTC ACA GGC CTC ACC CAT ATA GAT GCA CAC TTC TTG        3552
Trp Glu Ser Val Phe Thr Gly Leu Thr His Ile Asp Ala His Phe Leu
1170                1175                1180

TCC CAG ACC AAG CAG GCA GGA GAC AAC TTC CCC TAC CTG GTA GCA TAC        3600
Ser Gln Thr Lys Gln Ala Gly Asp Asn Phe Pro Tyr Leu Val Ala Tyr
1185                1190                1195                1200

CAA GCC ACG GTG TGC GCC AGG GCT CAG GCC CCA CCT CCA TCA TGG GAT        3648
Gln Ala Thr Val Cys Ala Arg Ala Gln Ala Pro Pro Pro Ser Trp Asp
                1205                1210                1215

CAA ATG TGG AAG TGT CTC ATA CGG CTG AAA CCT ACG CTG CAC GGG CCA        3696
Gln Met Trp Lys Cys Leu Ile Arg Leu Lys Pro Thr Leu His Gly Pro
        1220                1225                1230

ACA CCC TTG CTG TAC AGG CTG GGA GCC GTC CAG AAT GAG GTC ACC CTC        3744
Thr Pro Leu Leu Tyr Arg Leu Gly Ala Val Gln Asn Glu Val Thr Leu
    1235                1240                1245

ACC CAC CCC ATA ACC AAA TAC ATC ATG GCA TGC ATG TCG GCT GAC CTG        3792
Thr His Pro Ile Thr Lys Tyr Ile Met Ala Cys Met Ser Ala Asp Leu
1250                1255                1260

GAG GTC GTC ACT AGC ACC TGG GTG CTG GTG GGC GGA GTC CTT GCA GCT        3840
Glu Val Val Thr Ser Thr Trp Val Leu Val Gly Gly Val Leu Ala Ala
1265                1270                1275                1280

CTG GCC GCG TAT TGC CTG ACA ACA GGC AGT GTG GTC ATT GTG GGT AGG        3888
Leu Ala Ala Tyr Cys Leu Thr Thr Gly Ser Val Val Ile Val Gly Arg
                1285                1290                1295

ATT ATC TTG TCC GGG AGG CCG GCC ATT GTT CCC GAC AGG GAG CTT CTC        3936
Ile Ile Leu Ser Gly Arg Pro Ala Ile Val Pro Asp Arg Glu Leu Leu
        1300                1305                1310

TAC CAG GAG TTC GAT GAA ATG GAA GAG TGC GCC TCG CAC CTC CCT TAC        3984
Tyr Gln Glu Phe Asp Glu Met Glu Glu Cys Ala Ser His Leu Pro Tyr
    1315                1320                1325

ATC GAG CAG GGA ATG CAG CTC GCC GAG CAA TTC AAG CAG AAA GCG CTC        4032
Ile Glu Gln Gly Met Gln Leu Ala Glu Gln Phe Lys Gln Lys Ala Leu
1330                1335                1340

GGG TTA CTG CAA ACA GCC ACC AAA CAA GCG GAG GCT GCT GCT CCC GTG        4080
Gly Leu Leu Gln Thr Ala Thr Lys Gln Ala Glu Ala Ala Ala Pro Val
1345                1350                1355                1360

GTG GAG TCC AAG TGG CGA GCC CTT GAG ACA TTC TGG GCG AAG CAC ATG        4128
Val Glu Ser Lys Trp Arg Ala Leu Glu Thr Phe Trp Ala Lys His Met
                1365                1370                1375

TGG AAT TTC ATC AGC GGG ATA CAG TAC TTA GCA GGC TTA TCC ACT CTG        4176
Trp Asn Phe Ile Ser Gly Ile Gln Tyr Leu Ala Gly Leu Ser Thr Leu
        1380                1385                1390

CCT GGG AAC CCC GCA ATA GCA TCA TTG ATG GCA TTC ACA GCC TCT ATC        4224
Pro Gly Asn Pro Ala Ile Ala Ser Leu Met Ala Phe Thr Ala Ser Ile
    1395                1400                1405
```

```
ACC AGC CCG CTC ACC ACC CAA AGT ACC CTC CTG TTT AAC ATC TTG GGG         4272
Thr Ser Pro Leu Thr Thr Gln Ser Thr Leu Leu Phe Asn Ile Leu Gly
    1410                1415                    1420

GGG TGG GTG GCT GCC CAA CTC GCC CCC CCC AGC GCC GCT TCG GCT TTC         4320
Gly Trp Val Ala Ala Gln Leu Ala Pro Pro Ser Ala Ala Ser Ala Phe
1425                1430                1435                1440

GTG GGC GCC GGC ATC GCC GGT GCG GCT GTT GGC AGC ATA GGC CTT GGG         4368
Val Gly Ala Gly Ile Ala Gly Ala Ala Val Gly Ser Ile Gly Leu Gly
                1445                1450                1455

AAG GTG CTT GTG GAC ATT CTG GCG GGT TAT GGA GCA GGA GTG GCC GGC         4416
Lys Val Leu Val Asp Ile Leu Ala Gly Tyr Gly Ala Gly Val Ala Gly
                1460                1465                1470

GCG CTC GTG GCC TTT AAG GTC ATG AGC GGC GAG ATG CCC TCC ACC GAG         4464
Ala Leu Val Ala Phe Lys Val Met Ser Gly Glu Met Pro Ser Thr Glu
            1475                1480                1485

GAC CTG GTC AAT CTA CTT CCT GCC ATC CTC TCT CCT GGC GCC CTG GTC         4512
Asp Leu Val Asn Leu Leu Pro Ala Ile Leu Ser Pro Gly Ala Leu Val
        1490                1495                1500

GTC GGG GTC GTG TGT GCA GCA ATA CTG CGT CGA CAC GTG GGT CCG GGA         4560
Val Gly Val Val Cys Ala Ala Ile Leu Arg Arg His Val Gly Pro Gly
1505                1510                1515                1520

GAG GGG GCT GTG CAG TGG ATG AAC CGG CTG ATA GCG TTC GCC TCG CGG         4608
Glu Gly Ala Val Gln Trp Met Asn Arg Leu Ile Ala Phe Ala Ser Arg
                1525                1530                1535

GGT AAT CAT GTT TCC CCC ACG CAC TAT GTG CCT GAG AGC GAC GCC GCA         4656
Gly Asn His Val Ser Pro Thr His Tyr Val Pro Glu Ser Asp Ala Ala
            1540                1545                1550

GCG CGT GTT ACT CAG ATC CTC TCC AGC CTT ACC ATC ACT CAG CTG CTG         4704
Ala Arg Val Thr Gln Ile Leu Ser Ser Leu Thr Ile Thr Gln Leu Leu
            1555                1560                1565

AAA AGG CTC CAC CAG TGG ATT AAT GAA GAC TGC TCC ACA CCG TGT TCC         4752
Lys Arg Leu His Gln Trp Ile Asn Glu Asp Cys Ser Thr Pro Cys Ser
    1570                1575                1580

GGC TCG TGG CTA AGG GAT GTT TGG GAC TGG ATA TGC ACG GTG TTG ACT         4800
Gly Ser Trp Leu Arg Asp Val Trp Asp Trp Ile Cys Thr Val Leu Thr
1585                1590                1595                1600

GAC TTC AAG ACC TGG CTC CAG TCC AAG CTC CTG CCG CAG CTA CCT GGA         4848
Asp Phe Lys Thr Trp Leu Gln Ser Lys Leu Leu Pro Gln Leu Pro Gly
                1605                1610                1615

GTC CCT TTT TTC TCG TGC CAA CGC GGG TAC AAG GGA GTC TGG CGG GGA         4896
Val Pro Phe Phe Ser Cys Gln Arg Gly Tyr Lys Gly Val Trp Arg Gly
            1620                1625                1630

GAC GGC ATC ATG CAA ACC ACC TGC CCA TGT GGA GCA CAG ATC ACC GGA         4944
Asp Gly Ile Met Gln Thr Thr Cys Pro Cys Gly Ala Gln Ile Thr Gly
            1635                1640                1645

CAT GTC AAA AAC GGT TCC ATG AGG ATC GTC GGG CCT AAG ACC TGC AGC         4992
His Val Lys Asn Gly Ser Met Arg Ile Val Gly Pro Lys Thr Cys Ser
    1650                1655                1660

AAC ACG TGG CAT GGA ACA TTC CCC ATC AAC GCA TAC ACC ACG GGC CCC         5040
Asn Thr Trp His Gly Thr Phe Pro Ile Asn Ala Tyr Thr Thr Gly Pro
1665                1670                1675                1680

TGC ACA CCC TCT CCA GCG CCA AAC TAT CTT AGG GCG CTG TGG CGG GTG         5088
Cys Thr Pro Ser Pro Ala Pro Asn Tyr Ser Arg Ala Leu Trp Arg Val
                1685                1690                1695

GCC GCT GAG GAG TAC GTG GAG GTC ACG CGG GTG GGG GAT TTC CAC TAC         5136
Ala Ala Glu Glu Tyr Val Glu Val Thr Arg Val Gly Asp Phe His Tyr
                1700                1705                1710

GTG ACG GGC ATG ACC ACT GAC AAC GTA AAG TGC CCA TGC CAG GTT CCG         5184
Val Thr Gly Met Thr Thr Asp Asn Val Lys Cys Pro Cys Gln Val Pro
            1715                1720                1725
```

| | |
|---|---|
| GCT CCT GAA TTC TTC TCG GAG GTG GAC GGA GTG CGG TTG CAC AGG TAC<br>Ala Pro Glu Phe Phe Ser Glu Val Asp Gly Val Arg Leu His Arg Tyr<br>1730                                 1735                        1740 | 5232 |
| GCT CCG GCG TGC AGG CCT CTC CTA CGG GAG GAG GTT ACA TTC CAG GTC<br>Ala Pro Ala Cys Arg Pro Leu Leu Arg Glu Glu Val Thr Phe Gln Val<br>1745                               1750                     1755                      1760 | 5280 |
| GGG CTC AAC CAA TAC CTG GTT GGG TCA CAG CTA CCA TGC GAG CCC GAA<br>Gly Leu Asn Gln Tyr Leu Val Gly Ser Gln Leu Pro Cys Glu Pro Glu<br>                   1765                        1770                      1775 | 5328 |
| CCG GAT GTA GCA GTG CTC ACT TCC ATG CTC ACC GAC CCC TCC CAC ATC<br>Pro Asp Val Ala Val Leu Thr Ser Met Leu Thr Asp Pro Ser His Ile<br>                   1780                        1785                      1790 | 5376 |
| ACA GCA GAA ACG GCT AAG CGT AGG TTG GCC AGG GGT CTC CCC CCC TCC<br>Thr Ala Glu Thr Ala Lys Arg Arg Leu Ala Arg Gly Ser Pro Pro Ser<br>1795                               1800                           1805 | 5424 |
| TTG GCC AGC TCT TCA GCT AGC CAG TTG TCT GCG CCT TCC TTG AAG GCG<br>Leu Ala Ser Ser Ser Ala Ser Gln Leu Ser Ala Pro Ser Leu Lys Ala<br>1810                               1815                     1820 | 5472 |
| ACA TGC ACT ACC CAC CAT GTC TCT CCG GAC GCT GAC CTC ATC GAG GCC<br>Thr Cys Thr Thr His His Val Ser Pro Asp Ala Asp Leu Ile Glu Ala<br>1825                               1830                        1835                      1840 | 5520 |
| AAC CTC CTG TGG CGG CAG GAG ATG GGC GGG AAC ATC ACC CGC GTG GAG<br>Asn Leu Leu Trp Arg Gln Glu Met Gly Gly Asn Ile Thr Arg Val Glu<br>                   1845                        1850                      1855 | 5568 |
| TCG GAG AAC AAG GTG GTA GTC CTG GAC TCT TTC GAC CCG CTT CGA GCG<br>Ser Glu Asn Lys Val Val Val Leu Asp Ser Phe Asp Pro Leu Arg Ala<br>                   1860                        1865                      1870 | 5616 |
| GAG GAG GAT GAG AGG GAA GTA TCC GTT CCG GCG GAG ATC CTG CGG AAA<br>Glu Glu Asp Glu Arg Glu Val Ser Val Pro Ala Glu Ile Leu Arg Lys<br>                   1875                        1880                      1885 | 5664 |
| TCC AAG AAG TTC CCC GCA GCG ATG CCC ATC TGG GCG CGC CCG GAT TAC<br>Ser Lys Lys Phe Pro Ala Ala Met Pro Ile Trp Ala Arg Pro Asp Tyr<br>                   1890                        1895                      1900 | 5712 |
| AAC CCT CCA CTG TTA GAG TCC TGG AAG GAC CCG GAC TAC GTC CCT CCG<br>Asn Pro Pro Leu Leu Glu Ser Trp Lys Asp Pro Asp Tyr Val Pro Pro<br>1905                               1910                     1915                      1920 | 5760 |
| GTG GTG CAC GGG TGC CCG TTG CCA CCT ATC AAG GCC CCT CCA ATA CCA<br>Val Val His Gly Cys Pro Leu Pro Pro Ile Lys Ala Pro Pro Ile Pro<br>                   1925                        1930                      1935 | 5808 |
| CCT CCA CGG AGA AAG AGG ACG GTT GTC CTA ACA GAG TCC TCC GTG TCT<br>Pro Pro Arg Arg Lys Arg Thr Val Val Leu Thr Glu Ser Ser Val Ser<br>                   1940                        1945                      1950 | 5856 |
| TCT GCC TTA GCG GAG CTC GCT ACT AAG ACC TTC GGC AGC TCC GAA TCA<br>Ser Ala Leu Ala Glu Leu Ala Thr Lys Thr Phe Gly Ser Ser Glu Ser<br>                   1955                        1960                      1965 | 5904 |
| TCG GCC GTC GAC AGC GGC ACG GCG ACC GCC CTT CCT GAC CAG GCC TCC<br>Ser Ala Val Asp Ser Gly Thr Ala Thr Ala Leu Pro Asp Gln Ala Ser<br>1970                               1975                     1980 | 5952 |
| GAC GAC GGT GAC AAA GGA TCC GAC GTT GAG TCG TAC TCC TCC ATG CCC<br>Asp Asp Gly Asp Lys Gly Ser Asp Val Glu Ser Tyr Ser Ser Met Pro<br>1985                               1990                     1995                      2000 | 6000 |
| CCC CTT GAG GGG GAA CCG GGG GAC CCC GAT CTC AGT GAC GGG TCT TGG<br>Pro Leu Glu Gly Glu Pro Gly Asp Pro Asp Leu Ser Asp Gly Ser Trp<br>                   2005                        2010                      2015 | 6048 |
| TCT ACC GTG AGC GAG GAA GCT AGT GAG GAT GTC GTC TGC TGC TCA ATG<br>Ser Thr Val Ser Glu Glu Ala Ser Glu Asp Val Val Cys Cys Ser Met<br>                   2020                        2025                      2030 | 6096 |
| TCC TAC ACA TGG ACA GGC GCC TTG ATC ACG CCA TGC GCT GCG GAG GAA<br>Ser Tyr Thr Trp Thr Gly Ala Leu Ile Thr Pro Cys Ala Ala Glu Glu<br>                   2035                        2040                      2045 | 6144 |

```
AGC AAG CTG CCC ATC AAC GCG TTG AGC AAC TCT TTG CTG CGC CAC CAT    6192
Ser Lys Leu Pro Ile Asn Ala Leu Ser Asn Ser Leu Leu Arg His His
2050                2055                2060

AAC ATG GTT TAT GCC ACA ACA TCT CGC AGC GCA GGC CTG CGG CAG AAG    6240
Asn Met Val Tyr Ala Thr Thr Ser Arg Ser Ala Gly Leu Arg Gln Lys
2065                2070                2075                2080

AAG GTC ACC TTT GAC AGA CTG CAA GTC CTG GAC GAC CAC TAC CGG GAC    6288
Lys Val Thr Phe Asp Arg Leu Gln Val Leu Asp Asp His Tyr Arg Asp
                2085                2090                2095

GTG CTC AAG GAG ATG AAG GCG AAG GCG TCC ACA GTT AAG GCT AAA CTC    6336
Val Leu Lys Glu Met Lys Ala Lys Ala Ser Thr Val Lys Ala Lys Leu
2100                2105                2110

CTA TCC GTA GAG GAA GCC TGC AAG CTG ACG CCC CCA CAT TCG GCC AAA    6384
Leu Ser Val Glu Glu Ala Cys Lys Leu Thr Pro Pro His Ser Ala Lys
2115                2120                2125

TCC AAG TTT GGC TAT GGG GCA AAG GAC GTC CGG AAC CTA TCC AGC AAG    6432
Ser Lys Phe Gly Tyr Gly Ala Lys Asp Val Arg Asn Leu Ser Ser Lys
2130                2135                2140

GCC GTT AAC CAC ATC CAC TCC GTG TGG AAG GAC TTG CTG GAA GAC ACT    6480
Ala Val Asn His Ile His Ser Val Trp Lys Asp Leu Leu Glu Asp Thr
2145                2150                2155                2160

GTG ACA CCA ATT GAC ACC ACC ATC ATG GCA AAA AAT GAG GTT TTC TGT    6528
Val Thr Pro Ile Asp Thr Thr Ile Met Ala Lys Asn Glu Val Phe Cys
                2165                2170                2175

GTC CAA CCA GAG AAA GGA GGC CGT AAG CCA GCC CGC CTT ATC GTA TTC    6576
Val Gln Pro Glu Lys Gly Gly Arg Lys Pro Ala Arg Leu Ile Val Phe
2180                2185                2190

CCA GAT CTG GGA GTC CGT GTA TGC GAG AAG ATG GCC CTC TAT GAT GTG    6624
Pro Asp Leu Gly Val Arg Val Cys Glu Lys Met Ala Leu Tyr Asp Val
2195                2200                2205

GTC TCC ACC CTT CCT CAG GTC GTG ATG GGC TCC TCA TAC GGA TTC CAG    6672
Val Ser Thr Leu Pro Gln Val Val Met Gly Ser Ser Tyr Gly Phe Gln
2210                2215                2220

TAC TCT CCT GGG CAG CGA GTC GAG TTC CTG GTG AAT ACC TGG AAA TCA    6720
Tyr Ser Pro Gly Gln Arg Val Glu Phe Leu Val Asn Thr Trp Lys Ser
2225                2230                2235                2240

AAG AAA AAC CCC ATG GGC TTT TCA TAT GAC ACT CGC TGT TTC GAC TCA    6768
Lys Lys Asn Pro Met Gly Phe Ser Tyr Asp Thr Arg Cys Phe Asp Ser
                2245                2250                2255

ACG GTC ACC GAG AAC GAC ATC CGT GTT GAG GAG TCA ATT TAC CAA TGT    6816
Thr Val Thr Glu Asn Asp Ile Arg Val Glu Glu Ser Ile Tyr Gln Cys
                2260                2265                2270

TGT GAC TTG GCC CCC GAA GCC AGA CAG GCC ATA AAA TCG CTC ACA GAG    6864
Cys Asp Leu Ala Pro Glu Ala Arg Gln Ala Ile Lys Ser Leu Thr Glu
2275                2280                2285

CGG CTT TAT ATC GGG GGT CCT CTG ACT AAT TCA AAA GGG CAG AAC TGC    6912
Arg Leu Tyr Ile Gly Gly Pro Leu Thr Asn Ser Lys Gly Gln Asn Cys
2290                2295                2300

GGT TAT CGC CGG TGC CGC GCG AGC GGC GTG CTG ACG ACT AGC TGC GGT    6960
Gly Tyr Arg Arg Cys Arg Ala Ser Gly Val Leu Thr Thr Ser Cys Gly
2305                2310                2315                2320

AAC ACC CTC ACA TGT TAC TTG AAG GCC TCT GCA GCC TGT CGA GCT GCG    7008
Asn Thr Leu Thr Cys Tyr Leu Lys Ala Ser Ala Ala Cys Arg Ala Ala
                2325                2330                2335

AAG CTC CAG GAC TGC ACG ATG CTC GTG AAC GGA GAC GAC CTC GTC GTT    7056
Lys Leu Gln Asp Cys Thr Met Leu Val Asn Gly Asp Asp Leu Val Val
                2340                2345                2350

ATC TGT GAA AGC GCG GGA ACC CAA GAG GAC GCG GCG AGC CTA CGA GTC    7104
Ile Cys Glu Ser Ala Gly Thr Gln Glu Asp Ala Ala Ser Leu Arg Val
2355                2360                2365
```

```
TTC ACG GAG GCT ATG ACT AGG TAC TCC GCC CCC CCC GGG GAC CCG CCC    7152
Phe Thr Glu Ala Met Thr Arg Tyr Ser Ala Pro Pro Gly Asp Pro Pro
    2370            2375              2380

CAA CCA GAA TAC GAC TTG GAG CTG ATA ACA TCA TGT TCC TCC AAT GTG    7200
Gln Pro Glu Tyr Asp Leu Glu Leu Ile Thr Ser Cys Ser Ser Asn Val
2385              2390              2395                     2400

TCG GTC GCC CAC GAT GCA TCA GGC AAA AGG GTG TAC TAC CTC ACC CGT    7248
Ser Val Ala His Asp Ala Ser Gly Lys Arg Val Tyr Tyr Leu Thr Arg
                2405              2410                 2415

GAT CCC ACC ACC CCC CTA GCA CGG GCT GCG TGG GAG ACA GCT AGA CAC    7296
Asp Pro Thr Thr Pro Leu Ala Arg Ala Ala Trp Glu Thr Ala Arg His
            2420              2425              2430

ACT CCA GTT AAC TCC TGG CTA GGC AAC ATT ATT ATG TAT GCG CCC ACT    7344
Thr Pro Val Asn Ser Trp Leu Gly Asn Ile Ile Met Tyr Ala Pro Thr
        2435              2440              2445

TTG TGG GCA AGG ATG ATT CTG ATG ACT CAC TTC TTC TCC ATC CTT CTA    7392
Leu Trp Ala Arg Met Ile Leu Met Thr His Phe Phe Ser Ile Leu Leu
    2450              2455              2460

GCG CAG GAG CAA CTT GAA AAA GCC CTG GAC TGC CAG ATC TAC GGG GCC    7440
Ala Gln Glu Gln Leu Glu Lys Ala Leu Asp Cys Gln Ile Tyr Gly Ala
2465              2470              2475                     2480

TGT TAC TCC ATT GAG CCA CTT GAC CTA CCT CAG ATC ATT GAA CGA CTC    7488
Cys Tyr Ser Ile Glu Pro Leu Asp Leu Pro Gln Ile Ile Glu Arg Leu
                2485              2490              2495

CAT GGC CTT AGC GCA TTT TCA CTC CAT AGT TAC TCT CCA GGT GAG ATC    7536
His Gly Leu Ser Ala Phe Ser Leu His Ser Tyr Ser Pro Gly Glu Ile
            2500              2505              2510

AAT AGG GTG GCT TCA TGC CTC AGG AAA CTT GGG GTA CCA CCC TTG CGA    7584
Asn Arg Val Ala Ser Cys Leu Arg Lys Leu Gly Val Pro Pro Leu Arg
        2515              2520              2525

GTC TGG AGA CAT CGG GCC AGG AGC GTC CGC GCT AGG CTA CTG TCC CAG    7632
Val Trp Arg His Arg Ala Arg Ser Val Arg Ala Arg Leu Leu Ser Gln
    2530              2535              2540

GGA GGG AGG GCC GCC ACT TGT GGC AAA TAC CTC TTC AAC TGG GCA GTA    7680
Gly Gly Arg Ala Ala Thr Cys Gly Lys Tyr Leu Phe Asn Trp Ala Val
2545              2550              2555                     2560

AAA ACC AAA CTT AAA CTC ACT CCA ATC CCG GCT GCG TCC CGG CTG GAC    7728
Lys Thr Lys Leu Lys Leu Thr Pro Ile Pro Ala Ala Ser Arg Leu Asp
                2565              2570              2575

TTG TCC GGC TGG TTC GTT GCT GGT TAC AGC GGG GGA GAC ATA TAT CAC    7776
Leu Ser Gly Trp Phe Val Ala Gly Tyr Ser Gly Gly Asp Ile Tyr His
            2580              2585              2590

AGC CTG TCT CGT GCC CGA CCC CGT TGG TTC ATG CTG TGC CTA CTC CTA    7824
Ser Leu Ser Arg Ala Arg Pro Arg Trp Phe Met Leu Cys Leu Leu Leu
        2595              2600              2605

CTT TCT GTA GGG GTA GGC ATC TAC CTG CTC CCC AAC CGA                7863
Leu Ser Val Gly Val Gly Ile Tyr Leu Leu Pro Asn Arg
    2610              2615              2620
```

( 2 ) INFORMATION FOR SEQ ID NO:36:

( i ) SEQUENCE CHARACTERISTICS:
        ( A ) LENGTH: 2621 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

```
Gly Ala Gln Ala Lys Thr Thr Asn Arg Leu Val Ser Met Phe Ala Ser
1               5                   10                  15
```

| | | | | | | | | | | | | | | |
|---|---|---|---|---|---|---|---|---|---|---|---|---|---|---|
| Gly | Pro | Ser | Gln | Lys | Ile | Gln | Leu | Ile | Asn | Thr | Asn | Gly | Ser | Trp | His |
| | | | 20 | | | | 25 | | | | | | 30 | | |
| Ile | Asn | Arg | Thr | Ala | Leu | Asn | Cys | Asn | Asp | Ser | Leu | Gln | Thr | Gly | Phe |
| | | 35 | | | | 40 | | | | | 45 | | | | |
| Leu | Ala | Ala | Leu | Phe | Tyr | Thr | His | Ser | Phe | Asn | Ser | Ser | Gly | Cys | Pro |
| | 50 | | | | | 55 | | | | | 60 | | | | |
| Glu | Arg | Met | Ala | Gln | Cys | Arg | Thr | Ile | Asp | Lys | Phe | Asp | Gln | Gly | Trp |
| 65 | | | | | 70 | | | | | 75 | | | | | 80 |
| Gly | Pro | Ile | Thr | Tyr | Ala | Glu | Ser | Ser | Arg | Ser | Asp | Gln | Arg | Pro | Tyr |
| | | | | 85 | | | | | 90 | | | | | 95 | |
| Cys | Trp | His | Tyr | Pro | Pro | Pro | Gln | Cys | Thr | Ile | Val | Pro | Ala | Ser | Glu |
| | | | 100 | | | | | 105 | | | | | 110 | | |
| Val | Cys | Gly | Pro | Val | Tyr | Cys | Phe | Thr | Pro | Ser | Pro | Val | Val | Val | Gly |
| | | 115 | | | | | 120 | | | | | 125 | | | |
| Thr | Thr | Asp | Arg | Phe | Gly | Val | Pro | Thr | Tyr | Arg | Trp | Gly | Glu | Asn | Glu |
| | 130 | | | | | 135 | | | | | 140 | | | | |
| Thr | Asp | Val | Leu | Leu | Leu | Asn | Asn | Thr | Arg | Pro | Pro | Gln | Gly | Asn | Trp |
| 145 | | | | | 150 | | | | | 155 | | | | | 160 |
| Phe | Gly | Cys | Thr | Trp | Met | Asn | Ser | Thr | Gly | Phe | Thr | Lys | Thr | Cys | Gly |
| | | | | 165 | | | | | 170 | | | | | 175 | |
| Gly | Pro | Pro | Cys | Asn | Ile | Gly | Gly | Val | Gly | Asn | Asn | Thr | Leu | Thr | Cys |
| | | | 180 | | | | | 185 | | | | | 190 | | |
| Pro | Thr | Asp | Cys | Phe | Arg | Lys | His | Pro | Glu | Ala | Thr | Tyr | Thr | Lys | Cys |
| | | 195 | | | | | 200 | | | | | 205 | | | |
| Gly | Ser | Gly | Pro | Trp | Leu | Thr | Pro | Arg | Cys | Met | Val | Asp | Tyr | Pro | Tyr |
| | 210 | | | | | 215 | | | | | 220 | | | | |
| Arg | Leu | Trp | His | Tyr | Pro | Cys | Thr | Val | Asn | Phe | Thr | Ile | Phe | Lys | Val |
| 225 | | | | | 230 | | | | | 235 | | | | | 240 |
| Arg | Met | Tyr | Val | Gly | Gly | Val | Glu | His | Arg | Leu | Asn | Ala | Ala | Cys | Asn |
| | | | | 245 | | | | | 250 | | | | | 255 | |
| Trp | Thr | Arg | Gly | Glu | Arg | Cys | Asp | Leu | Glu | Asp | Arg | Asp | Arg | Pro | Glu |
| | | | 260 | | | | | 265 | | | | | 270 | | |
| Leu | Ser | Pro | Leu | Leu | Leu | Ser | Thr | Thr | Glu | Trp | Gln | Val | Leu | Pro | Cys |
| | | 275 | | | | | 280 | | | | | 285 | | | |
| Ser | Phe | Thr | Thr | Leu | Pro | Ala | Leu | Ser | Thr | Gly | Leu | Ile | His | Leu | His |
| | 290 | | | | | 295 | | | | | 300 | | | | |
| Gln | Asn | Ile | Val | Asp | Val | Gln | Tyr | Leu | Tyr | Gly | Ile | Gly | Ser | Ala | Val |
| 305 | | | | | 310 | | | | | 315 | | | | | 320 |
| Val | Ser | Phe | Ala | Ile | Lys | Trp | Glu | Tyr | Val | Leu | Leu | Leu | Phe | Leu | Leu |
| | | | | 325 | | | | | 330 | | | | | 335 | |
| Leu | Ala | Asp | Ala | Arg | Val | Cys | Ala | Cys | Leu | Trp | Met | Met | Leu | Leu | Ile |
| | | | 340 | | | | | 345 | | | | | 350 | | |
| Ala | Gln | Ala | Glu | Ala | Ala | Leu | Glu | Asn | Leu | Val | Val | Leu | Asn | Ser | Ala |
| | | 355 | | | | | 360 | | | | | 365 | | | |
| Ser | Val | Ala | Gly | Ala | His | Gly | Ile | Leu | Ser | Phe | Leu | Val | Phe | Phe | Cys |
| | 370 | | | | | 375 | | | | | 380 | | | | |
| Ala | Ala | Trp | Tyr | Ile | Lys | Gly | Arg | Leu | Val | Pro | Gly | Ala | Thr | Tyr | Ala |
| 385 | | | | | 390 | | | | | 395 | | | | | 400 |
| Leu | Tyr | Gly | Val | Trp | Pro | Leu | Leu | Leu | Leu | Leu | Leu | Ala | Leu | Pro | Pro |
| | | | | 405 | | | | | 410 | | | | | 415 | |
| Arg | Ala | Tyr | Ala | Met | Asp | Arg | Glu | Met | Ala | Ala | Ser | Cys | Gly | Gly | Ala |
| | | | 420 | | | | | 425 | | | | | 430 | | |
| Val | Phe | Val | Gly | Leu | Val | Leu | Leu | Thr | Leu | Ser | Pro | Tyr | Tyr | Lys | Val |
| | | 435 | | | | | 440 | | | | | 445 | | | |

```
Phe Leu Ala Arg Leu Ile Trp Trp Leu Gln Tyr Phe Thr Thr Arg Ala
    450             455                 460

Glu Ala Asp Leu His Val Trp Ile Pro Pro Leu Asn Ala Arg Gly Gly
465             470             475                         480

Arg Asp Ala Ile Ile Leu Leu Met Cys Ala Val His Pro Glu Leu Ile
                485             490                     495

Phe Asp Ile Thr Lys Leu Leu Ile Ala Ile Leu Gly Pro Leu Met Val
            500             505                     510

Leu Gln Ala Gly Ile Thr Arg Val Pro Tyr Phe Val Arg Ala Gln Gly
        515             520                 525

Leu Ile His Ala Cys Met Leu Val Arg Lys Val Ala Gly Gly His Tyr
    530             535                 540

Val Gln Met Ala Phe Met Lys Leu Gly Ala Leu Thr Gly Thr Tyr Ile
545             550             555                         560

Tyr Asn His Leu Thr Pro Leu Arg Asp Trp Pro Arg Ala Gly Leu Arg
            565             570                     575

Asp Leu Ala Val Ala Val Glu Pro Val Phe Ser Asp Met Glu Thr
        580             585             590

Lys Ile Ile Thr Trp Gly Ala Asp Thr Ala Ala Cys Gly Asp Ile Ile
    595             600             605

Leu Gly Leu Pro Val Ser Ala Arg Arg Gly Lys Glu Ile Leu Leu Gly
    610             615             620

Pro Ala Asp Ser Leu Glu Gly Arg Gly Leu Arg Leu Leu Ala Pro Ile
625             630             635                         640

Thr Ala Tyr Ser Gln Gln Thr Arg Gly Leu Leu Gly Cys Ile Ile Thr
            645             650             655

Ser Leu Thr Gly Arg Asp Lys Asn Gln Val Glu Gly Glu Val Gln Val
            660             665             670

Val Ser Thr Ala Thr Gln Ser Phe Leu Ala Thr Cys Val Asn Gly Val
        675             680             685

Cys Trp Thr Val Tyr His Gly Ala Gly Ser Lys Thr Leu Ala Ala Pro
    690             695             700

Lys Gly Pro Ile Thr Gln Met Tyr Thr Asn Val Asp Gln Asp Leu Val
705             710             715                         720

Gly Trp Pro Lys Pro Pro Gly Ala Arg Ser Leu Thr Pro Cys Thr Cys
            725             730             735

Gly Ser Ser Asp Leu Tyr Leu Val Thr Arg His Ala Asp Val Ile Pro
            740             745             750

Val Arg Arg Arg Gly Asp Ser Arg Gly Ser Leu Leu Ser Pro Arg Pro
        755             760             765

Val Ser Tyr Leu Lys Gly Ser Ser Gly Gly Pro Leu Leu Cys Pro Phe
    770             775             780

Gly His Ala Val Gly Ile Phe Arg Ala Ala Val Cys Thr Arg Gly Val
785             790             795                         800

Ala Lys Ala Val Asp Phe Val Pro Val Glu Ser Met Glu Thr Thr Met
            805             810                     815

Arg Ser Pro Val Phe Thr Asp Asn Ser Ser Pro Pro Ala Val Pro Gln
            820             825             830

Ser Phe Gln Val Ala His Leu His Ala Pro Thr Gly Ser Gly Lys Ser
        835             840             845

Thr Lys Val Pro Ala Ala Tyr Ala Ala Gln Gly Tyr Lys Val Leu Val
    850             855             860

Leu Asn Pro Ser Val Ala Ala Thr Leu Gly Phe Gly Ala Tyr Met Ser
```

-continued

```
865                    870                    875                    880
Lys Ala His Gly Ile Asp Pro Asn Ile Arg Thr Gly Val Arg Thr Ile
                885                    890                    895
Thr Thr Gly Ala Pro Val Thr Tyr Ser Thr Tyr Gly Lys Phe Leu Ala
                900                    905                    910
Asp Gly Gly Cys Ser Gly Gly Ala Tyr Asp Ile Ile Ile Cys Asp Glu
                915                    920                    925
Cys His Ser Thr Asp Ser Thr Thr Ile Leu Gly Ile Gly Thr Val Leu
                930                    935                    940
Asp Gln Ala Glu Thr Ala Gly Ala Arg Leu Val Leu Ala Thr Ala
945                    950                    955                    960
Thr Pro Pro Gly Ser Val Thr Val Pro His Pro Asn Ile Glu Glu Val
                965                    970                    975
Ala Leu Ser Asn Thr Gly Glu Ile Pro Phe Tyr Gly Lys Ala Ile Pro
                980                    985                    990
Ile Glu Ala Ile Arg Gly Gly Arg His Leu Ile Phe Cys His Ser Lys
                995                    1000                   1005
Lys Lys Cys Asp Glu Leu Ala Ala Lys Leu Ser Gly Leu Gly Ile Asn
                1010                   1015                   1020
Ala Val Ala Tyr Tyr Arg Gly Leu Asp Val Ser Val Ile Pro Thr Ile
1025                   1030                   1035                   1040
Gly Asp Val Val Val Ala Thr Asp Ala Leu Met Thr Gly Tyr Thr
                1045                   1050                   1055
Gly Asp Phe Asp Ser Val Ile Asp Cys Asn Thr Cys Val Thr Gln Thr
                1060                   1065                   1070
Val Asp Phe Ser Leu Asp Pro Thr Phe Thr Ile Glu Thr Thr Thr Val
                1075                   1080                   1085
Pro Gln Asp Ala Val Ser Arg Ser Gln Arg Arg Gly Arg Thr Gly Arg
                1090                   1095                   1100
Gly Arg Gly Ile Tyr Arg Phe Val Thr Pro Gly Glu Arg Pro Ser
1105                   1110                   1115                   1120
Gly Met Phe Asp Ser Ser Val Leu Cys Glu Cys Tyr Asp Ala Gly Cys
                1125                   1130                   1135
Ala Trp Tyr Glu Leu Thr Pro Ala Glu Thr Ser Val Arg Leu Arg Ala
                1140                   1145                   1150
Tyr Leu Asn Thr Pro Gly Leu Pro Val Cys Gln Asp His Leu Glu Phe
                1155                   1160                   1165
Trp Glu Ser Val Phe Thr Gly Leu Thr His Ile Asp Ala His Phe Leu
                1170                   1175                   1180
Ser Gln Thr Lys Gln Ala Gly Asp Asn Phe Pro Tyr Leu Val Ala Tyr
1185                   1190                   1195                   1200
Gln Ala Thr Val Cys Ala Arg Ala Gln Ala Pro Pro Ser Trp Asp
                1205                   1210                   1215
Gln Met Trp Lys Cys Leu Ile Arg Leu Lys Pro Thr Leu His Gly Pro
                1220                   1225                   1230
Thr Pro Leu Leu Tyr Arg Leu Gly Ala Val Gln Asn Glu Val Thr Leu
                1235                   1240                   1245
Thr His Pro Ile Thr Lys Tyr Ile Met Ala Cys Met Ser Ala Asp Leu
                1250                   1255                   1260
Glu Val Val Thr Ser Thr Trp Val Leu Val Gly Gly Val Leu Ala Ala
1265                   1270                   1275                   1280
Leu Ala Ala Tyr Cys Leu Thr Thr Gly Ser Val Val Ile Val Gly Arg
                1285                   1290                   1295
```

| | | | | | | | | | | | | | | |
|---|---|---|---|---|---|---|---|---|---|---|---|---|---|---|
| Ile | Ile | Leu | Ser | Gly | Arg | Pro | Ala | Ile | Val | Pro | Asp | Arg | Glu | Leu | Leu |
| | | | 1300 | | | | 1305 | | | | | 1310 | | |
| Tyr | Gln | Glu | Phe | Asp | Glu | Met | Glu | Glu | Cys | Ala | Ser | His | Leu | Pro | Tyr |
| 1315 | | | | | 1320 | | | | | | 1325 | | | |
| Ile | Glu | Gln | Gly | Met | Gln | Leu | Ala | Glu | Gln | Phe | Lys | Gln | Lys | Ala | Leu |
| | 1330 | | | | | 1335 | | | | | | 1340 | | | |
| Gly | Leu | Leu | Gln | Thr | Ala | Thr | Lys | Gln | Ala | Glu | Ala | Ala | Ala | Pro | Val |
| 1345 | | | | | 1350 | | | | | 1355 | | | | | 1360 |
| Val | Glu | Ser | Lys | Trp | Arg | Ala | Leu | Glu | Thr | Phe | Trp | Ala | Lys | His | Met |
| | | | | 1365 | | | | | 1370 | | | | | 1375 | |
| Trp | Asn | Phe | Ile | Ser | Gly | Ile | Gln | Tyr | Leu | Ala | Gly | Leu | Ser | Thr | Leu |
| | | | | 1380 | | | | | 1385 | | | | | 1390 | |
| Pro | Gly | Asn | Pro | Ala | Ile | Ala | Ser | Leu | Met | Ala | Phe | Thr | Ala | Ser | Ile |
| | | | 1395 | | | | | 1400 | | | | | 1405 | | |
| Thr | Ser | Pro | Leu | Thr | Thr | Gln | Ser | Thr | Leu | Leu | Phe | Asn | Ile | Leu | Gly |
| | 1410 | | | | | 1415 | | | | | | 1420 | | | |
| Gly | Trp | Val | Ala | Ala | Gln | Leu | Ala | Pro | Pro | Ser | Ala | Ala | Ser | Ala | Phe |
| 1425 | | | | | 1430 | | | | | 1435 | | | | | 1440 |
| Val | Gly | Ala | Gly | Ile | Ala | Gly | Ala | Ala | Val | Gly | Ser | Ile | Gly | Leu | Gly |
| | | | | 1445 | | | | | 1450 | | | | | 1455 | |
| Lys | Val | Leu | Val | Asp | Ile | Leu | Ala | Gly | Tyr | Gly | Ala | Gly | Val | Ala | Gly |
| | | | | 1460 | | | | | 1465 | | | | | 1470 | |
| Ala | Leu | Val | Ala | Phe | Lys | Val | Met | Ser | Gly | Glu | Met | Pro | Ser | Thr | Glu |
| | | | 1475 | | | | | 1480 | | | | | 1485 | | |
| Asp | Leu | Val | Asn | Leu | Leu | Pro | Ala | Ile | Leu | Ser | Pro | Gly | Ala | Leu | Val |
| | 1490 | | | | | 1495 | | | | | | 1500 | | | |
| Val | Gly | Val | Val | Cys | Ala | Ala | Ile | Leu | Arg | Arg | His | Val | Gly | Pro | Gly |
| 1505 | | | | | 1510 | | | | | 1515 | | | | | 1520 |
| Glu | Gly | Ala | Val | Gln | Trp | Met | Asn | Arg | Leu | Ile | Ala | Phe | Ala | Ser | Arg |
| | | | | 1525 | | | | | 1530 | | | | | 1535 | |
| Gly | Asn | His | Val | Ser | Pro | Thr | His | Tyr | Val | Pro | Glu | Ser | Asp | Ala | Ala |
| | | | | 1540 | | | | | 1545 | | | | | 1550 | |
| Ala | Arg | Val | Thr | Gln | Ile | Leu | Ser | Ser | Leu | Thr | Ile | Thr | Gln | Leu | Leu |
| | | 1555 | | | | | 1560 | | | | | 1565 | | | |
| Lys | Arg | Leu | His | Gln | Trp | Ile | Asn | Glu | Asp | Cys | Ser | Thr | Pro | Cys | Ser |
| | 1570 | | | | | 1575 | | | | | 1580 | | | | |
| Gly | Ser | Trp | Leu | Arg | Asp | Val | Trp | Asp | Trp | Ile | Cys | Thr | Val | Leu | Thr |
| 1585 | | | | | 1590 | | | | | 1595 | | | | | 1600 |
| Asp | Phe | Lys | Thr | Trp | Leu | Gln | Ser | Lys | Leu | Leu | Pro | Gln | Leu | Pro | Gly |
| | | | | 1605 | | | | | 1610 | | | | | 1615 | |
| Val | Pro | Phe | Phe | Ser | Cys | Gln | Arg | Gly | Tyr | Lys | Gly | Val | Trp | Arg | Gly |
| | | | 1620 | | | | | 1625 | | | | | 1630 | | |
| Asp | Gly | Ile | Met | Gln | Thr | Thr | Cys | Pro | Cys | Gly | Ala | Gln | Ile | Thr | Gly |
| | | | 1635 | | | | | 1640 | | | | | 1645 | | |
| His | Val | Lys | Asn | Gly | Ser | Met | Arg | Ile | Val | Gly | Pro | Lys | Thr | Cys | Ser |
| | 1650 | | | | | 1655 | | | | | 1660 | | | | |
| Asn | Thr | Trp | His | Gly | Thr | Phe | Pro | Ile | Asn | Ala | Tyr | Thr | Thr | Gly | Pro |
| 1665 | | | | | 1670 | | | | | 1675 | | | | | 1680 |
| Cys | Thr | Pro | Ser | Pro | Ala | Pro | Asn | Tyr | Ser | Arg | Ala | Leu | Trp | Arg | Val |
| | | | | 1685 | | | | | 1690 | | | | | 1695 | |
| Ala | Ala | Glu | Glu | Tyr | Val | Glu | Val | Thr | Arg | Val | Gly | Asp | Phe | His | Tyr |
| | | | | 1700 | | | | | 1705 | | | | | 1710 | |
| Val | Thr | Gly | Met | Thr | Thr | Asp | Asn | Val | Lys | Cys | Pro | Cys | Gln | Val | Pro |
| | | 1715 | | | | | 1720 | | | | | 1725 | | | |

```
Ala Pro Glu Phe Phe Ser Glu Val Asp Gly Val Arg Leu His Arg Tyr
    1730                1735                1740
Ala Pro Ala Cys Arg Pro Leu Leu Arg Glu Glu Val Thr Phe Gln Val
1745                1750                1755                1760
Gly Leu Asn Gln Tyr Leu Val Gly Ser Gln Leu Pro Cys Glu Pro Glu
                1765                1770                1775
Pro Asp Val Ala Val Leu Thr Ser Met Leu Thr Asp Pro Ser His Ile
                1780                1785                1790
Thr Ala Glu Thr Ala Lys Arg Arg Leu Ala Arg Gly Ser Pro Pro Ser
            1795                1800                1805
Leu Ala Ser Ser Ser Ala Ser Gln Leu Ser Ala Pro Ser Leu Lys Ala
        1810                1815                1820
Thr Cys Thr Thr His His Val Ser Pro Asp Ala Asp Leu Ile Glu Ala
1825                1830                1835                1840
Asn Leu Leu Trp Arg Gln Glu Met Gly Gly Asn Ile Thr Arg Val Glu
                1845                1850                1855
Ser Glu Asn Lys Val Val Val Leu Asp Ser Phe Asp Pro Leu Arg Ala
            1860                1865                1870
Glu Glu Asp Glu Arg Glu Val Ser Val Pro Ala Glu Ile Leu Arg Lys
            1875                1880                1885
Ser Lys Lys Phe Pro Ala Ala Met Pro Ile Trp Ala Arg Pro Asp Tyr
    1890                1895                1900
Asn Pro Pro Leu Leu Glu Ser Trp Lys Asp Pro Asp Tyr Val Pro Pro
1905                1910                1915                1920
Val Val His Gly Cys Pro Leu Pro Pro Ile Lys Ala Pro Pro Ile Pro
                1925                1930                1935
Pro Pro Arg Arg Lys Arg Thr Val Val Leu Thr Glu Ser Ser Val Ser
            1940                1945                1950
Ser Ala Leu Ala Glu Leu Ala Thr Lys Thr Phe Gly Ser Ser Glu Ser
        1955                1960                1965
Ser Ala Val Asp Ser Gly Thr Ala Thr Ala Leu Pro Asp Gln Ala Ser
    1970                1975                1980
Asp Asp Gly Asp Lys Gly Ser Asp Val Glu Ser Tyr Ser Ser Met Pro
1985                1990                1995                2000
Pro Leu Glu Gly Glu Pro Gly Asp Pro Asp Leu Ser Asp Gly Ser Trp
                2005                2010                2015
Ser Thr Val Ser Glu Glu Ala Ser Glu Asp Val Val Cys Cys Ser Met
            2020                2025                2030
Ser Tyr Thr Trp Thr Gly Ala Leu Ile Thr Pro Cys Ala Ala Glu Glu
        2035                2040                2045
Ser Lys Leu Pro Ile Asn Ala Leu Ser Asn Ser Leu Leu Arg His His
    2050                2055                2060
Asn Met Val Tyr Ala Thr Thr Ser Arg Ser Ala Gly Leu Arg Gln Lys
2065                2070                2075                2080
Lys Val Thr Phe Asp Arg Leu Gln Val Leu Asp Asp His Tyr Arg Asp
                2085                2090                2095
Val Leu Lys Glu Met Lys Ala Lys Ala Ser Thr Val Lys Ala Lys Leu
            2100                2105                2110
Leu Ser Val Glu Glu Ala Cys Lys Leu Thr Pro Pro His Ser Ala Lys
        2115                2120                2125
Ser Lys Phe Gly Tyr Gly Ala Lys Asp Val Arg Asn Leu Ser Ser Lys
    2130                2135                2140
Ala Val Asn His Ile His Ser Val Trp Lys Asp Leu Leu Glu Asp Thr
```

```
2145                2150                2155                2160
Val Thr Pro Ile Asp Thr Thr Ile Met Ala Lys Asn Glu Val Phe Cys
                2165                2170                2175
Val Gln Pro Glu Lys Gly Gly Arg Lys Pro Ala Arg Leu Ile Val Phe
                2180                2185                2190
Pro Asp Leu Gly Val Arg Val Cys Glu Lys Met Ala Leu Tyr Asp Val
                2195                2200                2205
Val Ser Thr Leu Pro Gln Val Val Met Gly Ser Ser Tyr Gly Phe Gln
                2210                2215                2220
Tyr Ser Pro Gly Gln Arg Val Glu Phe Leu Val Asn Thr Trp Lys Ser
2225                2230                2235                2240
Lys Lys Asn Pro Met Gly Phe Ser Tyr Asp Thr Arg Cys Phe Asp Ser
                2245                2250                2255
Thr Val Thr Glu Asn Asp Ile Arg Val Glu Glu Ser Ile Tyr Gln Cys
                2260                2265                2270
Cys Asp Leu Ala Pro Glu Ala Arg Gln Ala Ile Lys Ser Leu Thr Glu
                2275                2280                2285
Arg Leu Tyr Ile Gly Gly Pro Leu Thr Asn Ser Lys Gly Gln Asn Cys
                2290                2295                2300
Gly Tyr Arg Arg Cys Arg Ala Ser Gly Val Leu Thr Thr Ser Cys Gly
2305                2310                2315                2320
Asn Thr Leu Thr Cys Tyr Leu Lys Ala Ser Ala Ala Cys Arg Ala Ala
                2325                2330                2335
Lys Leu Gln Asp Cys Thr Met Leu Val Asn Gly Asp Asp Leu Val Val
                2340                2345                2350
Ile Cys Glu Ser Ala Gly Thr Gln Glu Asp Ala Ala Ser Leu Arg Val
                2355                2360                2365
Phe Thr Glu Ala Met Thr Arg Tyr Ser Ala Pro Pro Gly Asp Pro Pro
                2370                2375                2380
Gln Pro Glu Tyr Asp Leu Glu Leu Ile Thr Ser Cys Ser Ser Asn Val
2385                2390                2395                2400
Ser Val Ala His Asp Ala Ser Gly Lys Arg Val Tyr Tyr Leu Thr Arg
                2405                2410                2415
Asp Pro Thr Thr Pro Leu Ala Arg Ala Ala Trp Glu Thr Ala Arg His
                2420                2425                2430
Thr Pro Val Asn Ser Trp Leu Gly Asn Ile Ile Met Tyr Ala Pro Thr
                2435                2440                2445
Leu Trp Ala Arg Met Ile Leu Met Thr His Phe Phe Ser Ile Leu Leu
                2450                2455                2460
Ala Gln Glu Gln Leu Glu Lys Ala Leu Asp Cys Gln Ile Tyr Gly Ala
2465                2470                2475                2480
Cys Tyr Ser Ile Glu Pro Leu Asp Leu Pro Gln Ile Ile Glu Arg Leu
                2485                2490                2495
His Gly Leu Ser Ala Phe Ser Leu His Ser Tyr Ser Pro Gly Glu Ile
                2500                2505                2510
Asn Arg Val Ala Ser Cys Leu Arg Lys Leu Gly Val Pro Pro Leu Arg
                2515                2520                2525
Val Trp Arg His Arg Ala Arg Ser Val Arg Ala Arg Leu Leu Ser Gln
                2530                2535                2540
Gly Gly Arg Ala Ala Thr Cys Gly Lys Tyr Leu Phe Asn Trp Ala Val
2545                2550                2555                2560
Lys Thr Lys Leu Lys Leu Thr Pro Ile Pro Ala Ala Ser Arg Leu Asp
                2565                2570                2575
```

```
Leu  Ser  Gly  Trp  Phe  Val  Ala  Gly  Tyr  Ser  Gly  Gly  Asp  Ile  Tyr  His
          2580                    2585                    2590

Ser  Leu  Ser  Arg  Ala  Arg  Pro  Arg  Trp  Phe  Met  Leu  Cys  Leu  Leu  Leu
          2595                    2600                    2605

Leu  Ser  Val  Gly  Val  Gly  Ile  Tyr  Leu  Leu  Pro  Asn  Arg
          2610                    2615                    2620
```

( 2 ) INFORMATION FOR SEQ ID NO:37:

( i ) SEQUENCE CHARACTERISTICS:
        ( A ) LENGTH: 831 base pairs
        ( B ) TYPE: nucleic acid
        ( C ) STRANDEDNESS: single
        ( D ) TOPOLOGY: linear ( i i ) MOLECULE TYPE: cDNA from genomic RNA ( i x ) FEATURE:
        ( A ) NAME/KEY: misc_feature
        ( B ) LOCATION: 1..831
        ( D ) OTHER INFORMATION: /note: "sequence = 2520 - 3350 of
            SEQ ID NO: 1"

( i x ) FEATURE:
        ( A ) NAME/KEY: CDS
        ( B ) LOCATION: 1..831

( x i ) SEQUENCE DESCRIPTION: SEQ ID NO:37:

```
CGT  GTC  TGT  GCC  TGC  TTG  TGG  ATG  ATG  CTG  CTG  ATA  GCC  CAG  GCC  GAG        48
Arg  Val  Cys  Ala  Cys  Leu  Trp  Met  Met  Leu  Leu  Ile  Ala  Gln  Ala  Glu
 1                   5                        10                       15

GCC  GCC  TTG  GAG  AAC  CTG  GTG  GTC  CTC  AAT  TCG  GCG  TCT  GTG  GCC  GGC        96
Ala  Ala  Leu  Glu  Asn  Leu  Val  Val  Leu  Asn  Ser  Ala  Ser  Val  Ala  Gly
               20                        25                       30

GCA  CAT  GGC  ATC  CTC  TCC  TTC  CTT  GTG  TTC  TTC  TGT  GCC  GCC  TGG  TAC       144
Ala  His  Gly  Ile  Leu  Ser  Phe  Leu  Val  Phe  Phe  Cys  Ala  Ala  Trp  Tyr
          35                        40                       45

ATC  AAA  GGC  AGG  CTG  GTC  CCT  GGG  GCG  ACA  TAT  GCT  CTT  TAT  GGC  GTG       192
Ile  Lys  Gly  Arg  Leu  Val  Pro  Gly  Ala  Thr  Tyr  Ala  Leu  Tyr  Gly  Val
     50                        55                       60

TGG  CCG  CTG  CTC  CTG  CTC  TTG  CTG  GCA  TTA  CCA  CCG  CGA  GCT  TAC  GCC       240
Trp  Pro  Leu  Leu  Leu  Leu  Leu  Leu  Ala  Leu  Pro  Pro  Arg  Ala  Tyr  Ala
 65                       70                        75                       80

ATG  GAC  CGG  GAG  ATG  GCT  GCA  TCG  TGC  GGA  GGC  GCG  GTT  TTT  GTG  GGT       288
Met  Asp  Arg  Glu  Met  Ala  Ala  Ser  Cys  Gly  Gly  Ala  Val  Phe  Val  Gly
                    85                        90                       95

CTG  GTA  CTG  CTG  ACT  TTG  TCA  CCA  TAC  TAC  AAG  GTG  TTC  CTC  GCT  AGG       336
Leu  Val  Leu  Leu  Thr  Leu  Ser  Pro  Tyr  Tyr  Lys  Val  Phe  Leu  Ala  Arg
               100                       105                      110

CTC  ATA  TGG  TGG  TTA  CAA  TAT  TTT  ACC  ACC  AGA  GCC  GAG  GCG  GAC  TTA       384
Leu  Ile  Trp  Trp  Leu  Gln  Tyr  Phe  Thr  Thr  Arg  Ala  Glu  Ala  Asp  Leu
          115                       120                      125

CAT  GTG  TGG  ATC  CCC  CCC  CTC  AAC  GCT  CGG  GGA  GGC  CGC  GAT  GCC  ATC       432
His  Val  Trp  Ile  Pro  Pro  Leu  Asn  Ala  Arg  Gly  Gly  Arg  Asp  Ala  Ile
     130                       135                      140

ATC  CTC  CTC  ATG  TGC  GCA  GTC  CAT  CCA  GAG  CTA  ATC  TTT  GAC  ATC  ACC       480
Ile  Leu  Leu  Met  Cys  Ala  Val  His  Pro  Glu  Leu  Ile  Phe  Asp  Ile  Thr
145                       150                      155                      160

AAA  CTT  CTA  ATT  GCC  ATA  CTC  GGT  CCG  CTC  ATG  GTG  CTC  CAA  GCT  GGC       528
Lys  Leu  Leu  Ile  Ala  Ile  Leu  Gly  Pro  Leu  Met  Val  Leu  Gln  Ala  Gly
                    165                      170                      175

ATA  ACC  AGA  GTG  CCG  TAC  TTC  GTG  CGC  GCT  CAA  GGG  CTC  ATT  CAT  GCA       576
Ile  Thr  Arg  Val  Pro  Tyr  Phe  Val  Arg  Ala  Gln  Gly  Leu  Ile  His  Ala
               180                       185                     190
```

```
TGC ATG TTA GTG CGG AAG GTC GCT GGG GGT CAT TAT GTC CAA ATG GCC        624
Cys Met Leu Val Arg Lys Val Ala Gly Gly His Tyr Val Gln Met Ala
        195                 200                 205

TTC ATG AAG CTG GGC GCG CTG ACA GGC ACG TAC ATT TAC AAC CAT CTT        672
Phe Met Lys Leu Gly Ala Leu Thr Gly Thr Tyr Ile Tyr Asn His Leu
        210                 215                 220

ACC CCG CTA CGG GAT TGG CCA CGC GCG GGC CTA CGA GAC CTT GCG GTG        720
Thr Pro Leu Arg Asp Trp Pro Arg Ala Gly Leu Arg Asp Leu Ala Val
225                 230                 235                 240

GCA GTG GAG CCC GTC GTC TTC TCC GAC ATG GAG ACC AAG ATC ATC ACC        768
Ala Val Glu Pro Val Val Phe Ser Asp Met Glu Thr Lys Ile Ile Thr
                    245                 250                 255

TGG GGA GCA GAC ACC GCG GCG TGT GGG GAC ATC ATC TTG GGT CTG CCC        816
Trp Gly Ala Asp Thr Ala Ala Cys Gly Asp Ile Ile Leu Gly Leu Pro
                260                 265                 270

GTC TCC GCC CGA AGG                                                    831
Val Ser Ala Arg Arg
        275
```

(2) INFORMATION FOR SEQ ID NO:38:

(i) SEQUENCE CHARACTERISTICS:
        (A) LENGTH: 277 amino acids
        (B) TYPE: amino acid
        (D) TOPOLOGY: linear (ii) MOLECULE TYPE: protein (xi) SEQUENCE DESCRIPTION: SEQ ID NO:38:

```
Arg Val Cys Ala Cys Leu Trp Met Met Leu Leu Ile Ala Gln Ala Glu
 1               5                  10                  15

Ala Ala Leu Glu Asn Leu Val Val Leu Asn Ser Ala Ser Val Ala Gly
                20                  25                  30

Ala His Gly Ile Leu Ser Phe Leu Val Phe Phe Cys Ala Ala Trp Tyr
            35                  40                  45

Ile Lys Gly Arg Leu Val Pro Gly Ala Thr Tyr Ala Leu Tyr Gly Val
        50                  55                  60

Trp Pro Leu Leu Leu Leu Leu Leu Ala Leu Pro Pro Arg Ala Tyr Ala
65                  70                  75                  80

Met Asp Arg Glu Met Ala Ala Ser Cys Gly Gly Ala Val Phe Val Gly
                85                  90                  95

Leu Val Leu Leu Thr Leu Ser Pro Tyr Tyr Lys Val Phe Leu Ala Arg
                100                 105                 110

Leu Ile Trp Trp Leu Gln Tyr Phe Thr Thr Arg Ala Glu Ala Asp Leu
            115                 120                 125

His Val Trp Ile Pro Pro Leu Asn Ala Arg Gly Gly Arg Asp Ala Ile
        130                 135                 140

Ile Leu Leu Met Cys Ala Val His Pro Glu Leu Ile Phe Asp Ile Thr
145                 150                 155                 160

Lys Leu Leu Ile Ala Ile Leu Gly Pro Leu Met Val Leu Gln Ala Gly
                165                 170                 175

Ile Thr Arg Val Pro Tyr Phe Val Arg Ala Gln Gly Leu Ile His Ala
                180                 185                 190

Cys Met Leu Val Arg Lys Val Ala Gly Gly His Tyr Val Gln Met Ala
            195                 200                 205

Phe Met Lys Leu Gly Ala Leu Thr Gly Thr Tyr Ile Tyr Asn His Leu
        210                 215                 220

Thr Pro Leu Arg Asp Trp Pro Arg Ala Gly Leu Arg Asp Leu Ala Val
225                 230                 235                 240
```

| | | | | | | | | | | | | | | | |
|---|---|---|---|---|---|---|---|---|---|---|---|---|---|---|---|
| Ala | Val | Glu | Pro | Val | Val | Phe | Ser | Asp | Met | Glu | Thr | Lys | Ile | Ile | Thr |
| | | | | 245 | | | | | 250 | | | | | 255 | |
| Trp | Gly | Ala | Asp | Thr | Ala | Ala | Cys | Gly | Asp | Ile | Ile | Leu | Gly | Leu | Pro |
| | | | 260 | | | | | 265 | | | | | 270 | | |
| Val | Ser | Ala | Arg | Arg | | | | | | | | | | | |
| | | 275 | | | | | | | | | | | | | |

( 2 ) INFORMATION FOR SEQ ID NO:39:

( i ) SEQUENCE CHARACTERISTICS:
( A ) LENGTH: 1827 base pairs
( B ) TYPE: nucleic acid
( C ) STRANDEDNESS: single
( D ) TOPOLOGY: linear ( i i ) MOLECULE TYPE: cDNA from genomic RNA ( i x ) FEATURE:
( A ) NAME/KEY: misc_feature
( B ) LOCATION: 1..1827
( D ) OTHER INFORMATION: /note= "sequence = 3351 - 5177 of SEQ ID NO: 1"

( i x ) FEATURE:
( A ) NAME/KEY: CDS
( B ) LOCATION: 1..1827

( x i ) SEQUENCE DESCRIPTION: SEQ ID NO:39:

| | | | | | | | | | | | | | | | | |
|---|---|---|---|---|---|---|---|---|---|---|---|---|---|---|---|---|
| GGA | AAG | GAG | ATA | CTC | CTG | GGC | CCG | GCC | GAT | AGT | CTT | GAA | GGG | CGG | GGG | 48 |
| Gly | Lys | Glu | Ile | Leu | Leu | Gly | Pro | Ala | Asp | Ser | Leu | Glu | Gly | Arg | Gly | |
| 1 | | | | 5 | | | | | 10 | | | | | 15 | | |
| TTG | CGA | CTC | CTC | GCG | CCC | ATC | ACG | GCC | TAC | TCC | CAA | CAG | ACG | CGG | GGC | 96 |
| Leu | Arg | Leu | Leu | Ala | Pro | Ile | Thr | Ala | Tyr | Ser | Gln | Gln | Thr | Arg | Gly | |
| | | | 20 | | | | | 25 | | | | | 30 | | | |
| CTA | CTT | GGT | TGC | ATC | ATC | ACT | AGC | CTT | ACA | GGC | CGG | GAC | AAG | AAC | CAG | 144 |
| Leu | Leu | Gly | Cys | Ile | Ile | Thr | Ser | Leu | Thr | Gly | Arg | Asp | Lys | Asn | Gln | |
| | | 35 | | | | | 40 | | | | | 45 | | | | |
| GTC | GAG | GGA | GAG | GTT | CAG | GTG | GTT | TCC | ACC | GCA | ACA | CAA | TCC | TTC | CTG | 192 |
| Val | Glu | Gly | Glu | Val | Gln | Val | Val | Ser | Thr | Ala | Thr | Gln | Ser | Phe | Leu | |
| | 50 | | | | | 55 | | | | | 60 | | | | | |
| GCG | ACC | TGC | GTC | AAC | GGC | GTG | TGT | TGG | ACC | GTT | TAC | CAT | GGT | GCT | GGC | 240 |
| Ala | Thr | Cys | Val | Asn | Gly | Val | Cys | Trp | Thr | Val | Tyr | His | Gly | Ala | Gly | |
| 65 | | | | | 70 | | | | | 75 | | | | | 80 | |
| TCA | AAG | ACC | TTA | GCC | GCG | CCA | AAG | GGG | CCA | ATC | ACC | CAG | ATG | TAC | ACT | 288 |
| Ser | Lys | Thr | Leu | Ala | Ala | Pro | Lys | Gly | Pro | Ile | Thr | Gln | Met | Tyr | Thr | |
| | | | | 85 | | | | | 90 | | | | | 95 | | |
| AAT | GTG | GAC | CAG | GAC | CTC | GTC | GGC | TGG | CCC | AAG | CCC | CCC | GGG | GCG | CGT | 336 |
| Asn | Val | Asp | Gln | Asp | Leu | Val | Gly | Trp | Pro | Lys | Pro | Pro | Gly | Ala | Arg | |
| | | | 100 | | | | | 105 | | | | | 110 | | | |
| TCC | TTG | ACA | CCA | TGC | ACC | TGT | GGC | AGC | TCA | GAC | CTT | TAC | TTG | GTC | ACG | 384 |
| Ser | Leu | Thr | Pro | Cys | Thr | Cys | Gly | Ser | Ser | Asp | Leu | Tyr | Leu | Val | Thr | |
| | | 115 | | | | | 120 | | | | | 125 | | | | |
| AGA | CAT | GCT | GAC | GTC | ATT | CCG | GTG | CGC | CGG | CGG | GGC | GAC | AGT | AGG | GGG | 432 |
| Arg | His | Ala | Asp | Val | Ile | Pro | Val | Arg | Arg | Arg | Gly | Asp | Ser | Arg | Gly | |
| | 130 | | | | | 135 | | | | | 140 | | | | | |
| AGC | CTG | CTC | TCC | CCC | AGG | CCT | GTC | TCC | TAC | TTG | AAG | GGC | TCT | TCG | GGT | 480 |
| Ser | Leu | Leu | Ser | Pro | Arg | Pro | Val | Ser | Tyr | Leu | Lys | Gly | Ser | Ser | Gly | |
| 145 | | | | | 150 | | | | | 155 | | | | | 160 | |
| GGT | CCA | CTG | CTC | TGC | CCC | TTC | GGG | CAC | GCT | GTG | GGC | ATC | TTC | CGG | GCT | 528 |
| Gly | Pro | Leu | Leu | Cys | Pro | Phe | Gly | His | Ala | Val | Gly | Ile | Phe | Arg | Ala | |
| | | | | 165 | | | | | 170 | | | | | 175 | | |
| GCC | GTA | TGC | ACC | CGG | GGG | GTT | GCG | AAG | GCG | GTG | GAC | TTT | GTG | CCC | GTA | 576 |
| Ala | Val | Cys | Thr | Arg | Gly | Val | Ala | Lys | Ala | Val | Asp | Phe | Val | Pro | Val | |
| | | | 180 | | | | | 185 | | | | | 190 | | | |

```
GAG TCC ATG GAA ACT ACT ATG CGG TCT CCG GTC TTC ACG GAC AAC TCA      624
Glu Ser Met Glu Thr Thr Met Arg Ser Pro Val Phe Thr Asp Asn Ser
        195             200                 205

TCC CCC CCG GCC GTA CCG CAG TCA TTT CAA GTG GCC CAC CTA CAC GCT      672
Ser Pro Pro Ala Val Pro Gln Ser Phe Gln Val Ala His Leu His Ala
    210             215                 220

CCC ACT GGC AGC GGC AAG AGT ACT AAA GTG CCG GCT GCA TAT GCA GCC      720
Pro Thr Gly Ser Gly Lys Ser Thr Lys Val Pro Ala Ala Tyr Ala Ala
225             230                 235                 240

CAA GGG TAC AAG GTG CTC GTC CTC AAT CCG TCC GTT GCC GCT ACC TTA      768
Gln Gly Tyr Lys Val Leu Val Leu Asn Pro Ser Val Ala Ala Thr Leu
                245                 250                 255

GGG TTT GGG GCG TAT ATG TCT AAG GCA CAC GGT ATT GAC CCC AAC ATC      816
Gly Phe Gly Ala Tyr Met Ser Lys Ala His Gly Ile Asp Pro Asn Ile
            260                 265                 270

AGA ACT GGG GTA AGG ACC ATT ACC ACA GGC GCC CCC GTC ACA TAC TCT      864
Arg Thr Gly Val Arg Thr Ile Thr Thr Gly Ala Pro Val Thr Tyr Ser
        275                 280                 285

ACC TAT GGC AAG TTT CTT GCC GAT GGT GGT TGC TCT GGG GGC GCT TAT      912
Thr Tyr Gly Lys Phe Leu Ala Asp Gly Gly Cys Ser Gly Gly Ala Tyr
    290                 295                 300

GAC ATC ATA ATA TGT GAT GAG TGC CAT TCA ACT GAC TCG ACT ACA ATC      960
Asp Ile Ile Ile Cys Asp Glu Cys His Ser Thr Asp Ser Thr Thr Ile
305             310                 315                 320

TTG GGC ATC GGC ACA GTC CTG GAC CAA GCG GAG ACG GCT GGA GCG CGG     1008
Leu Gly Ile Gly Thr Val Leu Asp Gln Ala Glu Thr Ala Gly Ala Arg
                325                 330                 335

CTT GTC GTG CTC GCC ACC GCT ACG CCT CCG GGA TCG GTC ACC GTG CCA     1056
Leu Val Val Leu Ala Thr Ala Thr Pro Pro Gly Ser Val Thr Val Pro
            340                 345                 350

CAC CCA AAC ATC GAG GAG GTG GCC CTG TCT AAT ACT GGA GAG ATC CCC     1104
His Pro Asn Ile Glu Glu Val Ala Leu Ser Asn Thr Gly Glu Ile Pro
        355                 360                 365

TTC TAT GGC AAA GCC ATC CCC ATT GAA GCC ATC AGG GGG GGA AGG CAT     1152
Phe Tyr Gly Lys Ala Ile Pro Ile Glu Ala Ile Arg Gly Gly Arg His
    370                 375                 380

CTC ATT TTC TGT CAT TCC AAG AAG AAG TGC GAC GAG CTC GCC GCA AAG     1200
Leu Ile Phe Cys His Ser Lys Lys Lys Cys Asp Glu Leu Ala Ala Lys
385             390                 395                 400

CTG TCA GGC CTC GGA ATC AAC GCT GTG GCG TAT TAC CGG GGG CTC GAT     1248
Leu Ser Gly Leu Gly Ile Asn Ala Val Ala Tyr Tyr Arg Gly Leu Asp
                405                 410                 415

GTG TCC GTC ATA CCA ACT ATC GGA GAC GTC GTT GTC GTG GCA ACA GAC     1296
Val Ser Val Ile Pro Thr Ile Gly Asp Val Val Val Val Ala Thr Asp
            420                 425                 430

GCT CTG ATG ACG GGC TAT ACG GGC GAC TTT GAC TCA GTG ATC GAC TGT     1344
Ala Leu Met Thr Gly Tyr Thr Gly Asp Phe Asp Ser Val Ile Asp Cys
        435                 440                 445

AAC ACA TGT GTC ACC CAG ACA GTC GAC TTC AGC TTG GAT CCC ACC TTC     1392
Asn Thr Cys Val Thr Gln Thr Val Asp Phe Ser Leu Asp Pro Thr Phe
    450                 455                 460

ACC ATT GAG ACG ACG ACC GTG CCT CAA GAC GCA GTG TCG CGC TCG CAG     1440
Thr Ile Glu Thr Thr Thr Val Pro Gln Asp Ala Val Ser Arg Ser Gln
465                 470                 475                 480

CGG CGG GGT AGG ACT GGC AGG GGT AGG AGA GGC ATC TAC AGG TTT GTG     1488
Arg Arg Gly Arg Thr Gly Arg Gly Arg Arg Gly Ile Tyr Arg Phe Val
                485                 490                 495

ACT CCG GGA GAA CGG CCC TCG GGC ATG TTC GAT TCC TCG GTC CTG TGT     1536
Thr Pro Gly Glu Arg Pro Ser Gly Met Phe Asp Ser Ser Val Leu Cys
            500                 505                 510
```

| | | | | | | | | | | | | | | | | |
|---|---|---|---|---|---|---|---|---|---|---|---|---|---|---|---|---|
| GAG | TGC | TAT | GAC | GCG | GGC | TGT | GCT | TGG | TAC | GAG | CTC | ACC | CCG | GCC | GAG | 1584 |
| Glu | Cys | Tyr | Asp | Ala | Gly | Cys | Ala | Trp | Tyr | Glu | Leu | Thr | Pro | Ala | Glu | |
| | 515 | | | | 520 | | | | | 525 | | | | | | |
| ACC | TCG | GTT | AGG | TTG | CGG | GCC | TAC | CTG | AAC | ACA | CCA | GGG | TTG | CCC | GTT | 1632 |
| Thr | Ser | Val | Arg | Leu | Arg | Ala | Tyr | Leu | Asn | Thr | Pro | Gly | Leu | Pro | Val | |
| | 530 | | | | 535 | | | | | 540 | | | | | | |
| TGC | CAG | GAC | CAC | CTG | GAG | TTC | TGG | GAG | AGT | GTC | TTC | ACA | GGC | CTC | ACC | 1680 |
| Cys | Gln | Asp | His | Leu | Glu | Phe | Trp | Glu | Ser | Val | Phe | Thr | Gly | Leu | Thr | |
| 545 | | | | 550 | | | | | 555 | | | | | 560 | | |
| CAT | ATA | GAT | GCA | CAC | TTC | TTG | TCC | CAG | ACC | AAG | CAG | GCA | GGA | GAC | AAC | 1728 |
| His | Ile | Asp | Ala | His | Phe | Leu | Ser | Gln | Thr | Lys | Gln | Ala | Gly | Asp | Asn | |
| | | | | 565 | | | | | 570 | | | | | 575 | | |
| TTC | CCC | TAC | CTG | GTA | GCA | TAC | CAA | GCC | ACG | GTG | TGC | GCC | AGG | GCT | CAG | 1776 |
| Phe | Pro | Tyr | Leu | Val | Ala | Tyr | Gln | Ala | Thr | Val | Cys | Ala | Arg | Ala | Gln | |
| | | | 580 | | | | | 585 | | | | | 590 | | | |
| GCC | CCA | CCT | CCA | TCA | TGG | GAT | CAA | ATG | TGG | AAG | TGT | CTC | ATA | CGG | CTG | 1824 |
| Ala | Pro | Pro | Pro | Ser | Trp | Asp | Gln | Met | Trp | Lys | Cys | Leu | Ile | Arg | Leu | |
| | | 595 | | | | | 600 | | | | | 605 | | | | |
| AAA | | | | | | | | | | | | | | | | 1827 |
| Lys | | | | | | | | | | | | | | | | |

(2) INFORMATION FOR SEQ ID NO:40:

(i) SEQUENCE CHARACTERISTICS:
        (A) LENGTH: 609 amino acids
        (B) TYPE: amino acid
        (D) TOPOLOGY: linear (ii) MOLECULE TYPE: protein (xi) SEQUENCE DESCRIPTION: SEQ ID NO:40:

| | | | | | | | | | | | | | | |
|---|---|---|---|---|---|---|---|---|---|---|---|---|---|---|
| Gly | Lys | Glu | Ile | Leu | Leu | Gly | Pro | Ala | Asp | Ser | Leu | Glu | Gly | Arg | Gly |
| 1 | | | | 5 | | | | | 10 | | | | | 15 | |
| Leu | Arg | Leu | Leu | Ala | Pro | Ile | Thr | Ala | Tyr | Ser | Gln | Gln | Thr | Arg | Gly |
| | | | 20 | | | | | 25 | | | | | 30 | | |
| Leu | Leu | Gly | Cys | Ile | Ile | Thr | Ser | Leu | Thr | Gly | Arg | Asp | Lys | Asn | Gln |
| | | 35 | | | | | 40 | | | | | 45 | | | |
| Val | Glu | Gly | Glu | Val | Gln | Val | Val | Ser | Thr | Ala | Thr | Gln | Ser | Phe | Leu |
| | 50 | | | | | 55 | | | | | 60 | | | | |
| Ala | Thr | Cys | Val | Asn | Gly | Val | Cys | Trp | Thr | Val | Tyr | His | Gly | Ala | Gly |
| 65 | | | | | 70 | | | | | 75 | | | | | 80 |
| Ser | Lys | Thr | Leu | Ala | Ala | Pro | Lys | Gly | Pro | Ile | Thr | Gln | Met | Tyr | Thr |
| | | | | 85 | | | | | 90 | | | | | 95 | |
| Asn | Val | Asp | Gln | Asp | Leu | Val | Gly | Trp | Pro | Lys | Pro | Pro | Gly | Ala | Arg |
| | | | | 100 | | | | | 105 | | | | | 110 | |
| Ser | Leu | Thr | Pro | Cys | Thr | Cys | Gly | Ser | Ser | Asp | Leu | Tyr | Leu | Val | Thr |
| | | | 115 | | | | | 120 | | | | | 125 | | |
| Arg | His | Ala | Asp | Val | Ile | Pro | Val | Arg | Arg | Arg | Gly | Asp | Ser | Arg | Gly |
| | | | 130 | | | | | 135 | | | | | 140 | | |
| Ser | Leu | Leu | Ser | Pro | Arg | Pro | Val | Ser | Tyr | Leu | Lys | Gly | Ser | Ser | Gly |
| 145 | | | | | 150 | | | | | 155 | | | | | 160 |
| Gly | Pro | Leu | Leu | Cys | Pro | Phe | Gly | His | Ala | Val | Gly | Ile | Phe | Arg | Ala |
| | | | | 165 | | | | | 170 | | | | | 175 | |
| Ala | Val | Cys | Thr | Arg | Gly | Val | Ala | Lys | Ala | Val | Asp | Phe | Val | Pro | Val |
| | | | 180 | | | | | 185 | | | | | 190 | | |
| Glu | Ser | Met | Glu | Thr | Thr | Met | Arg | Ser | Pro | Val | Phe | Thr | Asp | Asn | Ser |
| | | 195 | | | | | 200 | | | | | 205 | | | |
| Ser | Pro | Pro | Ala | Val | Pro | Gln | Ser | Phe | Gln | Val | Ala | His | Leu | His | Ala |

```
            210                 215                    220
Pro Thr Gly Ser Gly Lys Ser Thr Lys Val Pro Ala Ala Tyr Ala Ala
225                 230                 235                 240

Gln Gly Tyr Lys Val Leu Val Leu Asn Pro Ser Val Ala Ala Thr Leu
                245                 250                 255

Gly Phe Gly Ala Tyr Met Ser Lys Ala His Gly Ile Asp Pro Asn Ile
            260                 265                 270

Arg Thr Gly Val Arg Thr Ile Thr Thr Gly Ala Pro Val Thr Tyr Ser
        275                 280                 285

Thr Tyr Gly Lys Phe Leu Ala Asp Gly Gly Cys Ser Gly Gly Ala Tyr
    290                 295                 300

Asp Ile Ile Ile Cys Asp Glu Cys His Ser Thr Asp Ser Thr Thr Ile
305                 310                 315                 320

Leu Gly Ile Gly Thr Val Leu Asp Gln Ala Glu Thr Ala Gly Ala Arg
                325                 330                 335

Leu Val Val Leu Ala Thr Ala Thr Pro Pro Gly Ser Val Thr Val Pro
            340                 345                 350

His Pro Asn Ile Glu Glu Val Ala Leu Ser Asn Thr Gly Glu Ile Pro
        355                 360                 365

Phe Tyr Gly Lys Ala Ile Pro Ile Glu Ala Ile Arg Gly Gly Arg His
    370                 375                 380

Leu Ile Phe Cys His Ser Lys Lys Lys Cys Asp Glu Leu Ala Ala Lys
385                 390                 395                 400

Leu Ser Gly Leu Gly Ile Asn Ala Val Ala Tyr Tyr Arg Gly Leu Asp
                405                 410                 415

Val Ser Val Ile Pro Thr Ile Gly Asp Val Val Val Ala Thr Asp
            420                 425                 430

Ala Leu Met Thr Gly Tyr Thr Gly Asp Phe Asp Ser Val Ile Asp Cys
        435                 440                 445

Asn Thr Cys Val Thr Gln Thr Val Asp Phe Ser Leu Asp Pro Thr Phe
    450                 455                 460

Thr Ile Glu Thr Thr Thr Val Pro Gln Asp Ala Val Ser Arg Ser Gln
465                 470                 475                 480

Arg Arg Gly Arg Thr Gly Arg Gly Arg Gly Ile Tyr Arg Phe Val
                485                 490                 495

Thr Pro Gly Glu Arg Pro Ser Gly Met Phe Asp Ser Ser Val Leu Cys
            500                 505                 510

Glu Cys Tyr Asp Ala Gly Cys Ala Trp Tyr Glu Leu Thr Pro Ala Glu
        515                 520                 525

Thr Ser Val Arg Leu Arg Ala Tyr Leu Asn Thr Pro Gly Leu Pro Val
    530                 535                 540

Cys Gln Asp His Leu Glu Phe Trp Glu Ser Val Phe Thr Gly Leu Thr
545                 550                 555                 560

His Ile Asp Ala His Phe Leu Ser Gln Thr Lys Gln Ala Gly Asp Asn
                565                 570                 575

Phe Pro Tyr Leu Val Ala Tyr Gln Ala Thr Val Cys Ala Arg Ala Gln
            580                 585                 590

Ala Pro Pro Pro Ser Trp Asp Gln Met Trp Lys Cys Leu Ile Arg Leu
        595                 600                 605

Lys
```

( 2 ) INFORMATION FOR SEQ ID NO:41:

( i ) SEQUENCE CHARACTERISTICS:

(A) LENGTH: 90 base pairs
(B) TYPE: nucleic acid
(C) STRANDEDNESS: single
(D) TOPOLOGY: linear (ii) MOLECULE TYPE: cDNA from genomic RNA (ix) FEATURE:
(A) NAME/KEY: misc_feature
(B) LOCATION: 1..90
(D) OTHER INFORMATION: /note: "sequence = 4485 - 4574 of SEQ ID NO: 1"

(ix) FEATURE:
(A) NAME/KEY: CDS
(B) LOCATION: 1..90

(xi) SEQUENCE DESCRIPTION: SEQ ID NO:41:

| ATC | AGG | GGG | GGA | AGG | CAT | CTC | ATT | TTC | TGT | CAT | TCC | AAG | AAG | AAG | TGC | 48 |
|-----|-----|-----|-----|-----|-----|-----|-----|-----|-----|-----|-----|-----|-----|-----|-----|----|
| Ile | Arg | Gly | Gly | Arg | His | Leu | Ile | Phe | Cys | His | Ser | Lys | Lys | Lys | Cys |    |
| 1   |     |     |     | 5   |     |     |     |     | 10  |     |     |     |     | 15  |     |    |

| GAC | GAG | CTC | GCC | GCA | AAG | CTG | TCA | GGC | CTC | GGA | ATC | AAC | GCT | 90 |
|-----|-----|-----|-----|-----|-----|-----|-----|-----|-----|-----|-----|-----|-----|----|
| Asp | Glu | Leu | Ala | Ala | Lys | Leu | Ser | Gly | Leu | Gly | Ile | Asn | Ala |    |
|     |     |     | 20  |     |     |     |     | 25  |     |     |     |     | 30  |    |

(2) INFORMATION FOR SEQ ID NO:42:

(i) SEQUENCE CHARACTERISTICS:
(A) LENGTH: 30 amino acids
(B) TYPE: amino acid
(D) TOPOLOGY: linear (ii) MOLECULE TYPE: protein (xi) SEQUENCE DESCRIPTION: SEQ ID NO:42:

| Ile | Arg | Gly | Gly | Arg | His | Leu | Ile | Phe | Cys | His | Ser | Lys | Lys | Lys | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Glu | Leu | Ala | Ala | Lys | Leu | Ser | Gly | Leu | Gly | Ile | Asn | Ala |
|-----|-----|-----|-----|-----|-----|-----|-----|-----|-----|-----|-----|-----|-----|
|     |     |     | 20  |     |     |     |     | 25  |     |     |     |     | 30  |

(2) INFORMATION FOR SEQ ID NO:43:

(i) SEQUENCE CHARACTERISTICS:
(A) LENGTH: 741 base pairs
(B) TYPE: nucleic acid
(C) STRANDEDNESS: single
(D) TOPOLOGY: linear (ii) MOLECULE TYPE: cDNA from genomic RNA (ix) FEATURE:
(A) NAME/KEY: misc_feature
(B) LOCATION: 1..741
(D) OTHER INFORMATION: /note: "sequence = 5178 - 5918 of SEQ ID NO: 1"

(ix) FEATURE:
(A) NAME/KEY: CDS
(B) LOCATION: 1..741

(xi) SEQUENCE DESCRIPTION: SEQ ID NO:43:

| CCT | ACG | CTG | CAC | GGG | CCA | ACA | CCC | TTG | CTG | TAC | AGG | CTG | GGA | GCC | GTC | 48 |
|-----|-----|-----|-----|-----|-----|-----|-----|-----|-----|-----|-----|-----|-----|-----|-----|----|
| Pro | Thr | Leu | His | Gly | Pro | Thr | Pro | Leu | Leu | Tyr | Arg | Leu | Gly | Ala | Val |    |
| 1   |     |     |     | 5   |     |     |     |     | 10  |     |     |     |     | 15  |     |    |

| CAG | AAT | GAG | GTC | ACC | CTC | ACC | CAC | CCC | ATA | ACC | AAA | TAC | ATC | ATG | GCA | 96 |
|-----|-----|-----|-----|-----|-----|-----|-----|-----|-----|-----|-----|-----|-----|-----|-----|----|
| Gln | Asn | Glu | Val | Thr | Leu | Thr | His | Pro | Ile | Thr | Lys | Tyr | Ile | Met | Ala |    |
|     |     |     | 20  |     |     |     |     | 25  |     |     |     |     | 30  |     |     |    |

| TGC | ATG | TCG | GCT | GAC | CTG | GAG | GTC | GTC | ACT | AGC | ACC | TGG | GTG | CTG | GTG | 144 |
|-----|-----|-----|-----|-----|-----|-----|-----|-----|-----|-----|-----|-----|-----|-----|-----|-----|
| Cys | Met | Ser | Ala | Asp | Leu | Glu | Val | Val | Thr | Ser | Thr | Trp | Val | Leu | Val |     |
|     |     |     | 35  |     |     |     |     | 40  |     |     |     |     | 45  |     |     |     |

| | | | | | | | | | | | | | | | | |
|---|---|---|---|---|---|---|---|---|---|---|---|---|---|---|---|---|
| GGC | GGA | GTC | CTT | GCA | GCT | CTG | GCC | GCG | TAT | TGC | CTG | ACA | ACA | GGC | AGT | 192 |
| Gly | Gly | Val | Leu | Ala | Ala | Leu | Ala | Ala | Tyr | Cys | Leu | Thr | Thr | Gly | Ser | |
| | 50 | | | | 55 | | | | | 60 | | | | | | |
| GTG | GTC | ATT | GTG | GGT | AGG | ATT | ATC | TTG | TCC | GGG | AGG | CCG | GCC | ATT | GTT | 240 |
| Val | Val | Ile | Val | Gly | Arg | Ile | Ile | Leu | Ser | Gly | Arg | Pro | Ala | Ile | Val | |
| 65 | | | | | 70 | | | | 75 | | | | | | 80 | |
| CCC | GAC | AGG | GAG | CTT | CTC | TAC | CAG | GAG | TTC | GAT | GAA | ATG | GAA | GAG | TGC | 288 |
| Pro | Asp | Arg | Glu | Leu | Leu | Tyr | Gln | Glu | Phe | Asp | Glu | Met | Glu | Glu | Cys | |
| | | | | 85 | | | | | 90 | | | | | 95 | | |
| GCC | TCG | CAC | CTC | CCT | TAC | ATC | GAG | CAG | GGA | ATG | CAG | CTC | GCC | GAG | CAA | 336 |
| Ala | Ser | His | Leu | Pro | Tyr | Ile | Glu | Gln | Gly | Met | Gln | Leu | Ala | Glu | Gln | |
| | | | 100 | | | | | 105 | | | | | 110 | | | |
| TTC | AAG | CAG | AAA | GCG | CTC | GGG | TTA | CTG | CAA | ACA | GCC | ACC | AAA | CAA | GCG | 384 |
| Phe | Lys | Gln | Lys | Ala | Leu | Gly | Leu | Leu | Gln | Thr | Ala | Thr | Lys | Gln | Ala | |
| | | 115 | | | | | 120 | | | | | 125 | | | | |
| GAG | GCT | GCT | GCT | CCC | GTG | GTG | GAG | TCC | AAG | TGG | CGA | GCC | CTT | GAG | ACA | 432 |
| Glu | Ala | Ala | Ala | Pro | Val | Val | Glu | Ser | Lys | Trp | Arg | Ala | Leu | Glu | Thr | |
| | 130 | | | | | 135 | | | | | 140 | | | | | |
| TTC | TGG | GCG | AAG | CAC | ATG | TGG | AAT | TTC | ATC | AGC | GGG | ATA | CAG | TAC | TTA | 480 |
| Phe | Trp | Ala | Lys | His | Met | Trp | Asn | Phe | Ile | Ser | Gly | Ile | Gln | Tyr | Leu | |
| 145 | | | | | 150 | | | | | 155 | | | | | 160 | |
| GCA | GGC | TTA | TCC | ACT | CTG | CCT | GGG | AAC | CCC | GCA | ATA | GCA | TCA | TTG | ATG | 528 |
| Ala | Gly | Leu | Ser | Thr | Leu | Pro | Gly | Asn | Pro | Ala | Ile | Ala | Ser | Leu | Met | |
| | | | | 165 | | | | | 170 | | | | | 175 | | |
| GCA | TTC | ACA | GCC | TCT | ATC | ACC | AGC | CCG | CTC | ACC | ACC | CAA | AGT | ACC | CTC | 576 |
| Ala | Phe | Thr | Ala | Ser | Ile | Thr | Ser | Pro | Leu | Thr | Thr | Gln | Ser | Thr | Leu | |
| | | | 180 | | | | | 185 | | | | | 190 | | | |
| CTG | TTT | AAC | ATC | TTG | GGG | GGG | TGG | GTG | GCT | GCC | CAA | CTC | GCC | CCC | CCC | 624 |
| Leu | Phe | Asn | Ile | Leu | Gly | Gly | Trp | Val | Ala | Ala | Gln | Leu | Ala | Pro | Pro | |
| | | 195 | | | | | 200 | | | | | 205 | | | | |
| AGC | GCC | GCT | TCG | GCT | TTC | GTG | GGC | GCC | GGC | ATC | GCC | GGT | GCG | GCT | GTT | 672 |
| Ser | Ala | Ala | Ser | Ala | Phe | Val | Gly | Ala | Gly | Ile | Ala | Gly | Ala | Ala | Val | |
| | 210 | | | | | 215 | | | | | 220 | | | | | |
| GGC | AGC | ATA | GGC | CTT | GGG | AAG | GTG | CTT | GTG | GAC | ATT | CTG | GCG | GGT | TAT | 720 |
| Gly | Ser | Ile | Gly | Leu | Gly | Lys | Val | Leu | Val | Asp | Ile | Leu | Ala | Gly | Tyr | |
| 225 | | | | | 230 | | | | | 235 | | | | | 240 | |
| GGA | GCA | GGA | GTG | GCC | GGC | GCG | | | | | | | | | | 741 |
| Gly | Ala | Gly | Val | Ala | Gly | Ala | | | | | | | | | | |
| | | | 245 | | | | | | | | | | | | | |

( 2 ) INFORMATION FOR SEQ ID NO:44:

( i ) SEQUENCE CHARACTERISTICS:
( A ) LENGTH: 247 amino acids
( B ) TYPE: amino acid
( D ) TOPOLOGY: linear ( i i ) MOLECULE TYPE: protein ( x i ) SEQUENCE DESCRIPTION: SEQ ID NO:44:

| | | | | | | | | | | | | | | |
|---|---|---|---|---|---|---|---|---|---|---|---|---|---|---|
| Pro | Thr | Leu | His | Gly | Pro | Thr | Pro | Leu | Leu | Tyr | Arg | Leu | Gly | Ala | Val |
| 1 | | | | 5 | | | | | 10 | | | | | 15 | |
| Gln | Asn | Glu | Val | Thr | Leu | Thr | His | Pro | Ile | Thr | Lys | Tyr | Ile | Met | Ala |
| | | | 20 | | | | | 25 | | | | | 30 | | |
| Cys | Met | Ser | Ala | Asp | Leu | Glu | Val | Val | Thr | Ser | Thr | Trp | Val | Leu | Val |
| | | 35 | | | | | 40 | | | | | 45 | | | |
| Gly | Gly | Val | Leu | Ala | Ala | Leu | Ala | Ala | Tyr | Cys | Leu | Thr | Thr | Gly | Ser |
| | 50 | | | | | 55 | | | | | 60 | | | | |
| Val | Val | Ile | Val | Gly | Arg | Ile | Ile | Leu | Ser | Gly | Arg | Pro | Ala | Ile | Val |
| 65 | | | | | 70 | | | | | 75 | | | | | 80 |
| Pro | Asp | Arg | Glu | Leu | Leu | Tyr | Gln | Glu | Phe | Asp | Glu | Met | Glu | Glu | Cys |

```
                              85                          90                          95
Ala  Ser  His  Leu  Pro  Tyr  Ile  Glu  Gln  Gly  Met  Gln  Leu  Ala  Glu  Gln
               100                         105                         110

Phe  Lys  Gln  Lys  Ala  Leu  Gly  Leu  Leu  Gln  Thr  Ala  Thr  Lys  Gln  Ala
          115                         120                         125

Glu  Ala  Ala  Ala  Pro  Val  Val  Glu  Ser  Lys  Trp  Arg  Ala  Leu  Glu  Thr
     130                         135                         140

Phe  Trp  Ala  Lys  His  Met  Trp  Asn  Phe  Ile  Ser  Gly  Ile  Gln  Tyr  Leu
145                           150                         155                         160

Ala  Gly  Leu  Ser  Thr  Leu  Pro  Gly  Asn  Pro  Ala  Ile  Ala  Ser  Leu  Met
                    165                         170                         175

Ala  Phe  Thr  Ala  Ser  Ile  Thr  Ser  Pro  Leu  Thr  Thr  Gln  Ser  Thr  Leu
               180                         185                         190

Leu  Phe  Asn  Ile  Leu  Gly  Gly  Trp  Val  Ala  Ala  Gln  Leu  Ala  Pro  Pro
          195                         200                         205

Ser  Ala  Ala  Ser  Ala  Phe  Val  Gly  Ala  Gly  Ile  Ala  Gly  Ala  Ala  Val
     210                         215                         220

Gly  Ser  Ile  Gly  Leu  Gly  Lys  Val  Leu  Val  Asp  Ile  Leu  Ala  Gly  Tyr
225                           230                         235                         240

Gly  Ala  Gly  Val  Ala  Gly  Ala
                    245
```

( 2 ) INFORMATION FOR SEQ ID NO:45:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( i i ) MOLECULE TYPE: cDNA from genomic RNA ( i x ) FEATURE:
        ( A ) NAME/KEY: misc_feature
        ( B ) LOCATION: 1..90
        ( D ) OTHER INFORMATION: /note: "sequence = 5544 - 5633 of SEQ ID NO: 1"

( i x ) FEATURE:
        ( A ) NAME/KEY: CDS
        ( B ) LOCATION: 1..90

( x i ) SEQUENCE DESCRIPTION: SEQ ID NO:45:

```
ACA  GCC  ACC  AAA  CAA  GCG  GAG  GCT  GCT  GCT  CCC  GTG  GTG  GAG  TCC  AAG      48
Thr  Ala  Thr  Lys  Gln  Ala  Glu  Ala  Ala  Ala  Pro  Val  Val  Glu  Ser  Lys
  1                    5                         10                        15

TGG  CGA  GCC  CTT  GAG  ACA  TTC  TGG  GCG  AAG  CAC  ATG  TGG  AAT                90
Trp  Arg  Ala  Leu  Glu  Thr  Phe  Trp  Ala  Lys  His  Met  Trp  Asn
               20                        25                        30
```

( 2 ) INFORMATION FOR SEQ ID NO:46:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: protein ( x i ) SEQUENCE DESCRIPTION: SEQ ID NO:46:

```
Thr  Ala  Thr  Lys  Gln  Ala  Glu  Ala  Ala  Ala  Pro  Val  Val  Glu  Ser  Lys
  1                    5                         10                        15

Trp  Arg  Ala  Leu  Glu  Thr  Phe  Trp  Ala  Lys  His  Met  Trp  Asn
               20                        25                        30
```

( 2 ) INFORMATION FOR SEQ ID NO:47:

( i ) SEQUENCE CHARACTERISTICS:
        ( A ) LENGTH: 453 base pairs
        ( B ) TYPE: nucleic acid
        ( C ) STRANDEDNESS: single
        ( D ) TOPOLOGY: linear ( i i ) MOLECULE TYPE: cDNA from genomic RNA ( i x ) FEATURE:
        ( A ) NAME/KEY: misc_feature
        ( B ) LOCATION: 1..453
        ( D ) OTHER INFORMATION: /note: "sequence = 5919 - 6371 of
        SEQ ID NO: 1"

( i x ) FEATURE:
        ( A ) NAME/KEY: CDS
        ( B ) LOCATION: 1..453

( x i ) SEQUENCE DESCRIPTION: SEQ ID NO:47:

```
CTC  GTG  GCC  TTT  AAG  GTC  ATG  AGC  GGC  GAG  ATG  CCC  TCC  ACC  GAG  GAC      48
Leu  Val  Ala  Phe  Lys  Val  Met  Ser  Gly  Glu  Met  Pro  Ser  Thr  Glu  Asp
 1              5                        10                       15

CTG  GTC  AAT  CTA  CTT  CCT  GCC  ATC  CTC  TCT  CCT  GGC  GCC  CTG  GTC  GTC      96
Leu  Val  Asn  Leu  Leu  Pro  Ala  Ile  Leu  Ser  Pro  Gly  Ala  Leu  Val  Val
              20                        25                       30

GGG  GTC  GTG  TGT  GCA  GCA  ATA  CTG  CGT  CGA  CAC  GTG  GGT  CCG  GGA  GAG     144
Gly  Val  Val  Cys  Ala  Ala  Ile  Leu  Arg  Arg  His  Val  Gly  Pro  Gly  Glu
         35                        40                       45

GGG  GCT  GTG  CAG  TGG  ATG  AAC  CGG  CTG  ATA  GCG  TTC  GCC  TCG  CGG  GGT     192
Gly  Ala  Val  Gln  Trp  Met  Asn  Arg  Leu  Ile  Ala  Phe  Ala  Ser  Arg  Gly
         50                        55                       60

AAT  CAT  GTT  TCC  CCC  ACG  CAC  TAT  GTG  CCT  GAG  AGC  GAC  GCC  GCA  GCG     240
Asn  His  Val  Ser  Pro  Thr  His  Tyr  Val  Pro  Glu  Ser  Asp  Ala  Ala  Ala
 65                       70                       75                       80

CGT  GTT  ACT  CAG  ATC  CTC  TCC  AGC  CTT  ACC  ATC  ACT  CAG  CTG  CTG  AAA     288
Arg  Val  Thr  Gln  Ile  Leu  Ser  Ser  Leu  Thr  Ile  Thr  Gln  Leu  Leu  Lys
                   85                        90                       95

AGG  CTC  CAC  CAG  TGG  ATT  AAT  GAA  GAC  TGC  TCC  ACA  CCG  TGT  TCC  GGC     336
Arg  Leu  His  Gln  Trp  Ile  Asn  Glu  Asp  Cys  Ser  Thr  Pro  Cys  Ser  Gly
              100                       105                      110

TCG  TGG  CTA  AGG  GAT  GTT  TGG  GAC  TGG  ATA  TGC  ACG  GTG  TTG  ACT  GAC     384
Ser  Trp  Leu  Arg  Asp  Val  Trp  Asp  Trp  Ile  Cys  Thr  Val  Leu  Thr  Asp
              115                       120                      125

TTC  AAG  ACC  TGG  CTC  CAG  TCC  AAG  CTC  CTG  CCG  CAG  CTA  CCT  GGA  GTC     432
Phe  Lys  Thr  Trp  Leu  Gln  Ser  Lys  Leu  Leu  Pro  Gln  Leu  Pro  Gly  Val
         130                       135                      140

CCT  TTT  TTC  TCG  TGC  CAA  CGC                                                   453
Pro  Phe  Phe  Ser  Cys  Gln  Arg
145                       150
```

( 2 ) INFORMATION FOR SEQ ID NO:48:

( i ) SEQUENCE CHARACTERISTICS:
        ( A ) LENGTH: 151 amino acids
        ( B ) TYPE: amino acid
        ( D ) TOPOLOGY: linear ( i i ) MOLECULE TYPE: protein ( x i ) SEQUENCE DESCRIPTION: SEQ ID NO:48:

```
Leu  Val  Ala  Phe  Lys  Val  Met  Ser  Gly  Glu  Met  Pro  Ser  Thr  Glu  Asp
 1              5                        10                       15

Leu  Val  Asn  Leu  Leu  Pro  Ala  Ile  Leu  Ser  Pro  Gly  Ala  Leu  Val  Val
```

```
                    20                         25                              30
Gly Val Val Cys Ala Ala Ile Leu Arg Arg His Val Gly Pro Gly Glu
        35                      40                  45
Gly Ala Val Gln Trp Met Asn Arg Leu Ile Ala Phe Ala Ser Arg Gly
    50                      55                  60
Asn His Val Ser Pro Thr His Tyr Val Pro Glu Ser Asp Ala Ala Ala
65                      70                  75                      80
Arg Val Thr Gln Ile Leu Ser Ser Leu Thr Ile Thr Gln Leu Leu Lys
                85                      90                  95
Arg Leu His Gln Trp Ile Asn Glu Asp Cys Ser Thr Pro Cys Ser Gly
            100                     105                 110
Ser Trp Leu Arg Asp Val Trp Asp Trp Ile Cys Thr Val Leu Thr Asp
        115                     120                 125
Phe Lys Thr Trp Leu Gln Ser Lys Leu Leu Pro Gln Leu Pro Gly Val
        130                     135                 140
Pro Phe Phe Ser Cys Gln Arg
145                 150
```

(2) INFORMATION FOR SEQ ID NO:49:

(i) SEQUENCE CHARACTERISTICS:
      (A) LENGTH: 2991 base pairs
      (B) TYPE: nucleic acid
      (C) STRANDEDNESS: single
      (D) TOPOLOGY: linear (ii) MOLECULE TYPE: cDNA from genomic RNA (ix) FEATURE:
      (A) NAME/KEY: misc_feature
      (B) LOCATION: 1..2991
      (D) OTHER INFORMATION: /note="sequence = 6372 - 9362 of SEQ ID NO: 1"

(ix) FEATURE:
      (A) NAME/KEY: CDS
      (B) LOCATION: 1..2991

(xi) SEQUENCE DESCRIPTION: SEQ ID NO:49:

```
GGG TAC AAG GGA GTC TGG CGG GGA GAC GGC ATC ATG CAA ACC ACC TGC     48
Gly Tyr Lys Gly Val Trp Arg Gly Asp Gly Ile Met Gln Thr Thr Cys
 1               5                  10                  15

CCA TGT GGA GCA CAG ATC ACC GGA CAT GTC AAA AAC GGT TCC ATG AGG     96
Pro Cys Gly Ala Gln Ile Thr Gly His Val Lys Asn Gly Ser Met Arg
                20                  25                  30

ATC GTC GGG CCT AAG ACC TGC AGC AAC ACG TGG CAT GGA ACA TTC CCC    144
Ile Val Gly Pro Lys Thr Cys Ser Asn Thr Trp His Gly Thr Phe Pro
            35                  40                  45

ATC AAC GCA TAC ACC ACG GGC CCC TGC ACA CCC TCT CCA GCG CCA AAC    192
Ile Asn Ala Tyr Thr Thr Gly Pro Cys Thr Pro Ser Pro Ala Pro Asn
        50                  55                  60

TAT TCT AGG GCG CTG TGG CGG GTG GCC GCT GAG GAG TAC GTG GAG GTC    240
Tyr Ser Arg Ala Leu Trp Arg Val Ala Ala Glu Glu Tyr Val Glu Val
 65                 70                  75                  80

ACG CGG GTG GGG GAT TTC CAC TAC GTG ACG GGC ATG ACC ACT GAC AAC    288
Thr Arg Val Gly Asp Phe His Tyr Val Thr Gly Met Thr Thr Asp Asn
                85                  90                  95

GTA AAG TGC CCA TGC CAG GTT CCG GCT CCT GAA TTC TTC TCG GAG GTG    336
Val Lys Cys Pro Cys Gln Val Pro Ala Pro Glu Phe Phe Ser Glu Val
            100                 105                 110

GAC GGA GTG CGG TTG CAC AGG TAC GCT CCG GCG TGC AGG CCT CTC CTA    384
Asp Gly Val Arg Leu His Arg Tyr Ala Pro Ala Cys Arg Pro Leu Leu
        115                 120                 125
```

```
CGG GAG GAG GTT ACA TTC CAG GTC GGG CTC AAC CAA TAC CTG GTT GGG        432
Arg Glu Glu Val Thr Phe Gln Val Gly Leu Asn Gln Tyr Leu Val Gly
    130             135                 140

TCA CAG CTA CCA TGC GAG CCC GAA CCG GAT GTA GCA GTG CTC ACT TCC        480
Ser Gln Leu Pro Cys Glu Pro Glu Pro Asp Val Ala Val Leu Thr Ser
145             150                 155                 160

ATG CTC ACC GAC CCC TCC CAC ATC ACA GCA GAA ACG GCT AAG CGT AGG        528
Met Leu Thr Asp Pro Ser His Ile Thr Ala Glu Thr Ala Lys Arg Arg
                165                 170                 175

TTG GCC AGG GGG TCT CCC CCC TCC TTG GCC AGC TCT TCA GCT AGC CAG        576
Leu Ala Arg Gly Ser Pro Pro Ser Leu Ala Ser Ser Ser Ala Ser Gln
            180                 185                 190

TTG TCT GCG CCT TCC TTG AAG GCA ACA TGC ACT ACC CAC CAT GTC TCT        624
Leu Ser Ala Pro Ser Leu Lys Ala Thr Cys Thr Thr His His Val Ser
        195                 200                 205

CCG GAC GCT GAC CTC ATC GAG GCC AAC CTC CTG TGG CGG CAG GAG ATG        672
Pro Asp Ala Asp Leu Ile Glu Ala Asn Leu Leu Trp Arg Gln Glu Met
    210                 215                 220

GGC GGG AAC ATC ACC CGC GTG GAG TCG GAG AAC AAG GTG GTA GTC CTG        720
Gly Gly Asn Ile Thr Arg Val Glu Ser Glu Asn Lys Val Val Val Leu
225             230                 235                 240

GAC TCT TTC GAC CCG CTT CGA GCG GAG GAG GAT GAG AGG GAA GTA TCC        768
Asp Ser Phe Asp Pro Leu Arg Ala Glu Glu Asp Glu Arg Glu Val Ser
                245                 250                 255

GTT CCG GCG GAG ATC CTG CGG AAA TCC AAG AAG TTC CCC GCA GCG ATG        816
Val Pro Ala Glu Ile Leu Arg Lys Ser Lys Lys Phe Pro Ala Ala Met
            260                 265                 270

CCC ATC TGG GCG CGC CCG GAT TAC AAC CCT CCA CTG TTA GAG TCC TGG        864
Pro Ile Trp Ala Arg Pro Asp Tyr Asn Pro Pro Leu Leu Glu Ser Trp
        275                 280                 285

AAG GAC CCG GAC TAC GTC CCT CCG GTG GTG CAC GGG TGC CCG TTG CCA        912
Lys Asp Pro Asp Tyr Val Pro Pro Val Val His Gly Cys Pro Leu Pro
    290                 295                 300

CCT ATC AAG GCC CCT CCA ATA CCA CCT CCA CGG AGA AAG AGG ACG GTT        960
Pro Ile Lys Ala Pro Pro Ile Pro Pro Pro Arg Arg Lys Arg Thr Val
305             310                 315                 320

GTC CTA ACA GAG TCC TCC GTG TCT TCT GCC TTA GCG GAG CTC GCT ACT       1008
Val Leu Thr Glu Ser Ser Val Ser Ser Ala Leu Ala Glu Leu Ala Thr
                325                 330                 335

AAG ACC TTC GGC AGC TCC GAA TCA TCG GCC GTC GAC AGC GGC ACG GCG       1056
Lys Thr Phe Gly Ser Ser Glu Ser Ser Ala Val Asp Ser Gly Thr Ala
            340                 345                 350

ACC GCC CTT CCT GAC CAG GCC TCC GAC GAC GGT GAC AAA GGA TCC GAC       1104
Thr Ala Leu Pro Asp Gln Ala Ser Asp Asp Gly Asp Lys Gly Ser Asp
        355                 360                 365

GTT GAG TCG TAC TCC TCC ATG CCC CCC CTT GAG GGG GAA CCG GGG GAC       1152
Val Glu Ser Tyr Ser Ser Met Pro Pro Leu Glu Gly Glu Pro Gly Asp
    370                 375                 380

CCC GAT CTC AGT GAC GGG TCT TGG TCT ACC GTG AGC GAG GAA GCT AGT       1200
Pro Asp Leu Ser Asp Gly Ser Trp Ser Thr Val Ser Glu Glu Ala Ser
385             390                 395                 400

GAG GAT GTC GTC TGC TGC TCA ATG TCC TAC ACA TGG ACA GGC GCC TTG       1248
Glu Asp Val Val Cys Cys Ser Met Ser Tyr Thr Trp Thr Gly Ala Leu
                405                 410                 415

ATC ACG CCA TGC GCT GCG GAG GAA AGC AAG CTG CCC ATC AAC GCG TTG       1296
Ile Thr Pro Cys Ala Ala Glu Glu Ser Lys Leu Pro Ile Asn Ala Leu
            420                 425                 430

AGC AAC TCT TTG CTG CGC CAC CAT AAC ATG GTT TAT GCC ACA ACA TCT       1344
Ser Asn Ser Leu Leu Arg His His Asn Met Val Tyr Ala Thr Thr Ser
        435                 440                 445
```

| | | | | | | | | | | | | | | | | |
|---|---|---|---|---|---|---|---|---|---|---|---|---|---|---|---|---|
| CGC | AGC | GCA | GGC | CTG | CGG | CAG | AAG | AAG | GTC | ACC | TTT | GAC | AGA | CTG | CAA | 1392 |
| Arg | Ser | Ala | Gly | Leu | Arg | Gln | Lys | Lys | Val | Thr | Phe | Asp | Arg | Leu | Gln | |
| | 450 | | | | | 455 | | | | | 460 | | | | | |
| GTC | CTG | GAC | GAC | CAC | TAC | CGG | GAC | GTG | CTC | AAG | GAG | ATG | AAG | GCG | AAG | 1440 |
| Val | Leu | Asp | Asp | His | Tyr | Arg | Asp | Val | Leu | Lys | Glu | Met | Lys | Ala | Lys | |
| 465 | | | | | 470 | | | | | 475 | | | | | 480 | |
| GCG | TCC | ACA | GTT | AAG | GCT | AAA | CTC | CTA | TCC | GTA | GAG | GAA | GCC | TGC | AAG | 1488 |
| Ala | Ser | Thr | Val | Lys | Ala | Lys | Leu | Leu | Ser | Val | Glu | Glu | Ala | Cys | Lys | |
| | | | | 485 | | | | | 490 | | | | | 495 | | |
| CTG | ACG | CCC | CCA | CAT | TCG | GCC | AAA | TCC | AAG | TTT | GGC | TAT | GGG | GCA | AAG | 1536 |
| Leu | Thr | Pro | Pro | His | Ser | Ala | Lys | Ser | Lys | Phe | Gly | Tyr | Gly | Ala | Lys | |
| | | | 500 | | | | | 505 | | | | | 510 | | | |
| GAC | GTC | CGG | AAC | CTA | TCC | AGC | AAG | GCC | GTT | AAC | CAC | ATC | CAC | TCC | GTG | 1584 |
| Asp | Val | Arg | Asn | Leu | Ser | Ser | Lys | Ala | Val | Asn | His | Ile | His | Ser | Val | |
| | | 515 | | | | | 520 | | | | | 525 | | | | |
| TGG | AAG | GAC | TTG | CTG | GAA | GAC | ACT | GTG | ACA | CCA | ATT | GAC | ACC | ACC | ATC | 1632 |
| Trp | Lys | Asp | Leu | Leu | Glu | Asp | Thr | Val | Thr | Pro | Ile | Asp | Thr | Thr | Ile | |
| | 530 | | | | | 535 | | | | | 540 | | | | | |
| ATG | GCA | AAA | AAT | GAG | GTT | TTC | TGT | GTC | CAA | CCA | GAG | AAA | GGA | GGC | CGT | 1680 |
| Met | Ala | Lys | Asn | Glu | Val | Phe | Cys | Val | Gln | Pro | Glu | Lys | Gly | Gly | Arg | |
| 545 | | | | | 550 | | | | | 555 | | | | | 560 | |
| AAG | CCA | GCC | CGC | CTT | ATC | GTA | TTC | CCA | GAT | CTG | GGA | GTC | CGT | GTA | TGC | 1728 |
| Lys | Pro | Ala | Arg | Leu | Ile | Val | Phe | Pro | Asp | Leu | Gly | Val | Arg | Val | Cys | |
| | | | | 565 | | | | | 570 | | | | | 575 | | |
| GAG | AAG | ATG | GCC | CTC | TAT | GAT | GTG | GTC | TCC | ACC | CTT | CCT | CAG | GTC | GTG | 1776 |
| Glu | Lys | Met | Ala | Leu | Tyr | Asp | Val | Val | Ser | Thr | Leu | Pro | Gln | Val | Val | |
| | | | 580 | | | | | 585 | | | | | 590 | | | |
| ATG | GGC | TCC | TCA | TAC | GGA | TTC | CAG | TAC | TCT | CCT | GGG | CAG | CGA | GTC | GAG | 1824 |
| Met | Gly | Ser | Ser | Tyr | Gly | Phe | Gln | Tyr | Ser | Pro | Gly | Gln | Arg | Val | Glu | |
| | | 595 | | | | | 600 | | | | | 605 | | | | |
| TTC | CTG | GTG | AAT | ACC | TGG | AAA | TCA | AAG | AAA | AAC | CCC | ATG | GGC | TTT | TCA | 1872 |
| Phe | Leu | Val | Asn | Thr | Trp | Lys | Ser | Lys | Lys | Asn | Pro | Met | Gly | Phe | Ser | |
| | 610 | | | | | 615 | | | | | 620 | | | | | |
| TAT | GAC | ACT | CGC | TGT | TTC | GAC | TCA | ACG | GTC | ACC | GAG | AAC | GAC | ATC | CGT | 1920 |
| Tyr | Asp | Thr | Arg | Cys | Phe | Asp | Ser | Thr | Val | Thr | Glu | Asn | Asp | Ile | Arg | |
| 625 | | | | | 630 | | | | | 635 | | | | | 640 | |
| GTT | GAG | GAG | TCA | ATT | TAC | CAA | TGT | TGT | GAC | TTG | GCC | CCC | GAA | GCC | AGA | 1968 |
| Val | Glu | Glu | Ser | Ile | Tyr | Gln | Cys | Cys | Asp | Leu | Ala | Pro | Glu | Ala | Arg | |
| | | | | 645 | | | | | 650 | | | | | 655 | | |
| CAG | GCC | ATA | AAA | TCG | CTC | ACA | GAG | CGG | CTT | TAT | ATC | GGG | GGT | CCT | CTG | 2016 |
| Gln | Ala | Ile | Lys | Ser | Leu | Thr | Glu | Arg | Leu | Tyr | Ile | Gly | Gly | Pro | Leu | |
| | | | 660 | | | | | 665 | | | | | 670 | | | |
| ACT | AAT | TCA | AAA | GGG | CAG | AAC | TGC | GGT | TAT | CGC | CGG | TGC | CGC | GCG | AGC | 2064 |
| Thr | Asn | Ser | Lys | Gly | Gln | Asn | Cys | Gly | Tyr | Arg | Arg | Cys | Arg | Ala | Ser | |
| | | 675 | | | | | 680 | | | | | 685 | | | | |
| GGC | GTG | CTG | ACG | ACT | AGC | TGC | GGT | AAC | ACC | CTC | ACA | TGT | TAC | TTG | AAG | 2112 |
| Gly | Val | Leu | Thr | Thr | Ser | Cys | Gly | Asn | Thr | Leu | Thr | Cys | Tyr | Leu | Lys | |
| | 690 | | | | | 695 | | | | | 700 | | | | | |
| GCC | TCT | GCA | GCC | TGT | CGA | GCT | GCG | AAG | CTC | CAG | GAC | TGC | ACG | ATG | CTC | 2160 |
| Ala | Ser | Ala | Ala | Cys | Arg | Ala | Ala | Lys | Leu | Gln | Asp | Cys | Thr | Met | Leu | |
| 705 | | | | | 710 | | | | | 715 | | | | | 720 | |
| GTG | AAC | GGA | GAC | GAC | CTC | GTC | GTT | ATC | TGT | GAA | AGC | GCG | GGA | ACC | CAA | 2208 |
| Val | Asn | Gly | Asp | Asp | Leu | Val | Val | Ile | Cys | Glu | Ser | Ala | Gly | Thr | Gln | |
| | | | | 725 | | | | | 730 | | | | | 735 | | |
| GAG | GAC | GCG | GCG | AGC | CTA | CGA | GTC | TTC | ACG | GAG | GCT | ATG | ACT | AGG | TAC | 2256 |
| Glu | Asp | Ala | Ala | Ser | Leu | Arg | Val | Phe | Thr | Glu | Ala | Met | Thr | Arg | Tyr | |
| | | | 740 | | | | | 745 | | | | | 750 | | | |
| TCC | GCC | CCC | CCC | GGG | GAC | CCG | CCC | CAA | CCA | GAA | TAC | GAC | TTG | GAG | CTG | 2304 |
| Ser | Ala | Pro | Pro | Gly | Asp | Pro | Pro | Gln | Pro | Glu | Tyr | Asp | Leu | Glu | Leu | |
| | | 755 | | | | | 760 | | | | | 765 | | | | |

| | | | | | | | | | | | | | | | | |
|---|---|---|---|---|---|---|---|---|---|---|---|---|---|---|---|---|
| ATA | ACA | TCA | TGT | TCC | TCC | AAT | GTG | TCG | GTC | GCC | CAC | GAT | GCA | TCA | GGC | 2352 |
| Ile | Thr | Ser | Cys | Ser | Ser | Asn | Val | Ser | Val | Ala | His | Asp | Ala | Ser | Gly | |
| 770 | | | | | 775 | | | | | 780 | | | | | | |
| AAA | AGG | GTG | TAC | TAC | CTC | ACC | CGT | GAT | CCC | ACC | ACC | CCC | CTA | GCA | CGG | 2400 |
| Lys | Arg | Val | Tyr | Tyr | Leu | Thr | Arg | Asp | Pro | Thr | Thr | Pro | Leu | Ala | Arg | |
| 785 | | | | | 790 | | | | | 795 | | | | | 800 | |
| GCT | GCG | TGG | GAG | ACA | GCT | AGA | CAC | ACT | CCA | GTT | AAC | TCC | TGG | CTA | GGC | 2448 |
| Ala | Ala | Trp | Glu | Thr | Ala | Arg | His | Thr | Pro | Val | Asn | Ser | Trp | Leu | Gly | |
| | | | | 805 | | | | | 810 | | | | | 815 | | |
| AAC | ATT | ATT | ATG | TAT | GCG | CCC | ACT | TTG | TGG | GCA | AGG | ATG | ATT | CTG | ATG | 2496 |
| Asn | Ile | Ile | Met | Tyr | Ala | Pro | Thr | Leu | Trp | Ala | Arg | Met | Ile | Leu | Met | |
| | | | 820 | | | | | 825 | | | | | 830 | | | |
| ACT | CAC | TTC | TTC | TCC | ATC | CTT | CTA | GCG | CAG | GAG | CAA | CTT | GAA | AAA | GCC | 2544 |
| Thr | His | Phe | Phe | Ser | Ile | Leu | Leu | Ala | Gln | Glu | Gln | Leu | Glu | Lys | Ala | |
| | | 835 | | | | | 840 | | | | | 845 | | | | |
| CTG | GAC | TGC | CAG | ATC | TAC | GGG | GCC | TGT | TAC | TCC | ATT | GAG | CCA | CTT | GAC | 2592 |
| Leu | Asp | Cys | Gln | Ile | Tyr | Gly | Ala | Cys | Tyr | Ser | Ile | Glu | Pro | Leu | Asp | |
| | 850 | | | | | 855 | | | | | 860 | | | | | |
| CTA | CCT | CAG | ATC | ATT | GAA | CGA | CTC | CAT | GGC | CTT | AGC | GCA | TTT | TCA | CTC | 2640 |
| Leu | Pro | Gln | Ile | Ile | Glu | Arg | Leu | His | Gly | Leu | Ser | Ala | Phe | Ser | Leu | |
| 865 | | | | | 870 | | | | | 875 | | | | | 880 | |
| CAT | AGT | TAC | TCT | CCA | GGT | GAG | ATC | AAT | AGG | GTG | GCT | TCA | TGC | CTC | AGG | 2688 |
| His | Ser | Tyr | Ser | Pro | Gly | Glu | Ile | Asn | Arg | Val | Ala | Ser | Cys | Leu | Arg | |
| | | | | 885 | | | | | 890 | | | | | 895 | | |
| AAA | CTT | GGG | GTA | CCA | CCC | TTG | CGA | GTC | TGG | AGA | CAT | CGG | GCC | AGG | AGC | 2736 |
| Lys | Leu | Gly | Val | Pro | Pro | Leu | Arg | Val | Trp | Arg | His | Arg | Ala | Arg | Ser | |
| | | | 900 | | | | | 905 | | | | | 910 | | | |
| GTC | CGC | GCT | AGG | CTA | CTG | TCC | CAG | GGA | GGG | AGG | GCC | GCC | ACT | TGT | GGC | 2784 |
| Val | Arg | Ala | Arg | Leu | Leu | Ser | Gln | Gly | Gly | Arg | Ala | Ala | Thr | Cys | Gly | |
| | | 915 | | | | | 920 | | | | | 925 | | | | |
| AAA | TAC | CTC | TTC | AAC | TGG | GCA | GTA | AAA | ACC | AAA | CTT | AAA | CTC | ACT | CCA | 2832 |
| Lys | Tyr | Leu | Phe | Asn | Trp | Ala | Val | Lys | Thr | Lys | Leu | Lys | Leu | Thr | Pro | |
| 930 | | | | | 935 | | | | | 940 | | | | | | |
| ATC | CCG | GCT | GCG | TCC | CGG | CTG | GAC | TTG | TCC | GGC | TGG | TTC | GTT | GCT | GGT | 2880 |
| Ile | Pro | Ala | Ala | Ser | Arg | Leu | Asp | Leu | Ser | Gly | Trp | Phe | Val | Ala | Gly | |
| 945 | | | | | 950 | | | | | 955 | | | | | 960 | |
| TAC | AGC | GGG | GGA | GAC | ATA | TAT | CAC | AGC | CTG | TCT | CGT | GCC | CGA | CCC | CGT | 2928 |
| Tyr | Ser | Gly | Gly | Asp | Ile | Tyr | His | Ser | Leu | Ser | Arg | Ala | Arg | Pro | Arg | |
| | | | | 965 | | | | | 970 | | | | | 975 | | |
| TGG | TTC | ATG | CTG | TGC | CTA | CTC | CTA | CTT | TCT | GTA | GGG | GTA | GGC | ATC | TAC | 2976 |
| Trp | Phe | Met | Leu | Cys | Leu | Leu | Leu | Leu | Ser | Val | Gly | Val | Gly | Ile | Tyr | |
| | | | 980 | | | | | 985 | | | | | 990 | | | |
| CTG | CTC | CCC | AAC | CGA | | | | | | | | | | | | 2991 |
| Leu | Leu | Pro | Asn | Arg | | | | | | | | | | | | |
| | | 995 | | | | | | | | | | | | | | |

( 2 ) INFORMATION FOR SEQ ID NO:50:

( i ) SEQUENCE CHARACTERISTICS:
        ( A ) LENGTH: 997 amino acids
        ( B ) TYPE: amino acid
        ( D ) TOPOLOGY: linear ( i i ) MOLECULE TYPE: protein ( x i ) SEQUENCE DESCRIPTION: SEQ ID NO:50:

| | | | | | | | | | | | | | | |
|---|---|---|---|---|---|---|---|---|---|---|---|---|---|---|
| Gly | Tyr | Lys | Gly | Val | Trp | Arg | Gly | Asp | Gly | Ile | Met | Gln | Thr | Thr | Cys |
| 1 | | | | 5 | | | | | 10 | | | | | 15 | |
| Pro | Cys | Gly | Ala | Gln | Ile | Thr | Gly | His | Val | Lys | Asn | Gly | Ser | Met | Arg |
| | | | 20 | | | | | 25 | | | | | 30 | | |
| Ile | Val | Gly | Pro | Lys | Thr | Cys | Ser | Asn | Thr | Trp | His | Gly | Thr | Phe | Pro |

|  | 35 |  |  |  | 40 |  |  |  | 45 |  |  |  |
|---|---|---|---|---|---|---|---|---|---|---|---|---|

Ile Asn Ala Tyr Thr Thr Gly Pro Cys Thr Pro Ser Pro Ala Pro Asn
                50                      55                      60

Tyr Ser Arg Ala Leu Trp Arg Val Ala Ala Glu Glu Tyr Val Glu Val
 65                      70                      75                      80

Thr Arg Val Gly Asp Phe His Tyr Val Thr Gly Met Thr Thr Asp Asn
                85                      90                      95

Val Lys Cys Pro Cys Gln Val Pro Ala Pro Glu Phe Phe Ser Glu Val
                100                     105                     110

Asp Gly Val Arg Leu His Arg Tyr Ala Pro Ala Cys Arg Pro Leu Leu
                115                     120                     125

Arg Glu Glu Val Thr Phe Gln Val Gly Leu Asn Gln Tyr Leu Val Gly
 130                     135                     140

Ser Gln Leu Pro Cys Glu Pro Glu Pro Asp Val Ala Val Leu Thr Ser
 145                     150                     155                     160

Met Leu Thr Asp Pro Ser His Ile Thr Ala Glu Thr Ala Lys Arg Arg
                165                     170                     175

Leu Ala Arg Gly Ser Pro Pro Ser Leu Ala Ser Ser Ser Ala Ser Gln
                180                     185                     190

Leu Ser Ala Pro Ser Leu Lys Ala Thr Cys Thr Thr His His Val Ser
                195                     200                     205

Pro Asp Ala Asp Leu Ile Glu Ala Asn Leu Leu Trp Arg Gln Glu Met
 210                     215                     220

Gly Gly Asn Ile Thr Arg Val Glu Ser Glu Asn Lys Val Val Val Leu
 225                     230                     235                     240

Asp Ser Phe Asp Pro Leu Arg Ala Glu Glu Asp Glu Arg Glu Val Ser
                245                     250                     255

Val Pro Ala Glu Ile Leu Arg Lys Ser Lys Lys Phe Pro Ala Ala Met
                260                     265                     270

Pro Ile Trp Ala Arg Pro Asp Tyr Asn Pro Pro Leu Leu Glu Ser Trp
                275                     280                     285

Lys Asp Pro Asp Tyr Val Pro Pro Val Val His Gly Cys Pro Leu Pro
                290                     295                     300

Pro Ile Lys Ala Pro Pro Ile Pro Pro Pro Arg Arg Lys Arg Thr Val
 305                     310                     315                     320

Val Leu Thr Glu Ser Ser Val Ser Ser Ala Leu Ala Glu Leu Ala Thr
                325                     330                     335

Lys Thr Phe Gly Ser Ser Glu Ser Ser Ala Val Asp Ser Gly Thr Ala
                340                     345                     350

Thr Ala Leu Pro Asp Gln Ala Ser Asp Asp Gly Asp Lys Gly Ser Asp
                355                     360                     365

Val Glu Ser Tyr Ser Ser Met Pro Pro Leu Glu Gly Glu Pro Gly Asp
 370                     375                     380

Pro Asp Leu Ser Asp Gly Ser Trp Ser Thr Val Ser Glu Glu Ala Ser
 385                     390                     395                     400

Glu Asp Val Val Cys Cys Ser Met Ser Tyr Thr Trp Thr Gly Ala Leu
                405                     410                     415

Ile Thr Pro Cys Ala Ala Glu Glu Ser Lys Leu Pro Ile Asn Ala Leu
                420                     425                     430

Ser Asn Ser Leu Leu Arg His His Asn Met Val Tyr Ala Thr Thr Ser
                435                     440                     445

Arg Ser Ala Gly Leu Arg Gln Lys Lys Val Thr Phe Asp Arg Leu Gln
 450                     455                     460

```
Val Leu Asp Asp His Tyr Arg Asp Val Leu Lys Glu Met Lys Ala Lys
465                 470                 475                 480

Ala Ser Thr Val Lys Ala Lys Leu Leu Ser Val Glu Glu Ala Cys Lys
                485                 490                 495

Leu Thr Pro Pro His Ser Ala Lys Ser Lys Phe Gly Tyr Gly Ala Lys
            500                 505                 510

Asp Val Arg Asn Leu Ser Ser Lys Ala Val Asn His Ile His Ser Val
            515                 520                 525

Trp Lys Asp Leu Leu Glu Asp Thr Val Thr Pro Ile Asp Thr Thr Ile
    530                 535                 540

Met Ala Lys Asn Glu Val Phe Cys Val Gln Pro Glu Lys Gly Gly Arg
545                 550                 555                 560

Lys Pro Ala Arg Leu Ile Val Phe Pro Asp Leu Gly Val Arg Val Cys
                565                 570                 575

Glu Lys Met Ala Leu Tyr Asp Val Val Ser Thr Leu Pro Gln Val Val
            580                 585                 590

Met Gly Ser Ser Tyr Gly Phe Gln Tyr Ser Pro Gly Gln Arg Val Glu
        595                 600                 605

Phe Leu Val Asn Thr Trp Lys Ser Lys Lys Asn Pro Met Gly Phe Ser
    610                 615                 620

Tyr Asp Thr Arg Cys Phe Asp Ser Thr Val Thr Glu Asn Asp Ile Arg
625                 630                 635                 640

Val Glu Glu Ser Ile Tyr Gln Cys Cys Asp Leu Ala Pro Glu Ala Arg
                645                 650                 655

Gln Ala Ile Lys Ser Leu Thr Glu Arg Leu Tyr Ile Gly Gly Pro Leu
            660                 665                 670

Thr Asn Ser Lys Gly Gln Asn Cys Gly Tyr Arg Arg Cys Arg Ala Ser
            675                 680                 685

Gly Val Leu Thr Thr Ser Cys Gly Asn Thr Leu Thr Cys Tyr Leu Lys
    690                 695                 700

Ala Ser Ala Ala Cys Arg Ala Ala Lys Leu Gln Asp Cys Thr Met Leu
705                 710                 715                 720

Val Asn Gly Asp Asp Leu Val Val Ile Cys Glu Ser Ala Gly Thr Gln
                725                 730                 735

Glu Asp Ala Ala Ser Leu Arg Val Phe Thr Glu Ala Met Thr Arg Tyr
            740                 745                 750

Ser Ala Pro Pro Gly Asp Pro Pro Gln Pro Glu Tyr Asp Leu Glu Leu
            755                 760                 765

Ile Thr Ser Cys Ser Ser Asn Val Ser Val Ala His Asp Ala Ser Gly
    770                 775                 780

Lys Arg Val Tyr Tyr Leu Thr Arg Asp Pro Thr Thr Pro Leu Ala Arg
785                 790                 795                 800

Ala Ala Trp Glu Thr Ala Arg His Thr Pro Val Asn Ser Trp Leu Gly
            805                 810                 815

Asn Ile Ile Met Tyr Ala Pro Thr Leu Trp Ala Arg Met Ile Leu Met
            820                 825                 830

Thr His Phe Phe Ser Ile Leu Leu Ala Gln Glu Gln Leu Glu Lys Ala
        835                 840                 845

Leu Asp Cys Gln Ile Tyr Gly Ala Cys Tyr Ser Ile Glu Pro Leu Asp
    850                 855                 860

Leu Pro Gln Ile Ile Glu Arg Leu His Gly Leu Ser Ala Phe Ser Leu
865                 870                 875                 880

His Ser Tyr Ser Pro Gly Glu Ile Asn Arg Val Ala Ser Cys Leu Arg
                885                 890                 895
```

-continued

| | | | | | | | | | | | | | | | |
|---|---|---|---|---|---|---|---|---|---|---|---|---|---|---|---|
| Lys | Leu | Gly | Val<br>900 | Pro | Pro | Leu | Arg | Val<br>905 | Trp | Arg | His | Arg | Ala<br>910 | Arg | Ser |
| Val | Arg | Ala<br>915 | Arg | Leu | Leu | Ser | Gln<br>920 | Gly | Gly | Arg | Ala | Ala<br>925 | Thr | Cys | Gly |
| Lys | Tyr<br>930 | Leu | Phe | Asn | Trp | Ala<br>935 | Val | Lys | Thr | Lys | Leu<br>940 | Lys | Leu | Thr | Pro |
| Ile<br>945 | Pro | Ala | Ala | Ser | Arg<br>950 | Leu | Asp | Leu | Ser | Gly<br>955 | Trp | Phe | Val | Ala | Gly<br>960 |
| Tyr | Ser | Gly | Gly | Asp<br>965 | Ile | Tyr | His | Ser | Leu<br>970 | Ser | Arg | Ala | Arg | Pro<br>975 | Arg |
| Trp | Phe | Met | Leu<br>980 | Cys | Leu | Leu | Leu | Leu<br>985 | Ser | Val | Gly | Val | Gly<br>990 | Ile | Tyr |
| Leu | Leu | Pro<br>995 | Asn | Arg | | | | | | | | | | | |

What is claim is:

1. An isolated polypeptide comprising an amino acid sequence coded for by the nucleotide sequence from nucleotide 2520 to nucleotide 3350 of SEQ ID NO: 1.

2. A diagnostic reagent for detection of non-A, non-B hepatitis by antigen-antibody reaction, comprising an isolated antigen polypeptide comprising an amino acid sequence coded for by the nucleotide sequence from nucleotide 2520 to nucleotide 3350 of SEQ ID NO: 1, and a buffer.

* * * * *